(12) United States Patent
Allen et al.

(10) Patent No.: US 11,802,127 B2
(45) Date of Patent: Oct. 31, 2023

(54) 3,4-DIHYDRO-2,7-NAPHTHYRIDINE-1,6(2H,7H)-DIONES AS MEK INHIBITORS

(71) Applicant: Pfizer Inc., New York, NY (US)

(72) Inventors: Shelley Allen, Niwot, CO (US); Patrick Michael Doerner Barbour, Westminster, CA (US); James Francis Blake, Longmont, CO (US); Mark Laurence Boys, Lyons, CO (US); Joshua Ryan Dahlke, Boulder, CO (US); Alex Andrew Kellum, Boulder, CO (US); David Austin Moreno, Centennial, CO (US); Jacob Matthew O'Leary, Denver, CO (US); Li Ren, Superior, CO (US)

(73) Assignee: Pfizer Inc., New York, NY (US)

( * ) Notice: Subject to any disclaimer, the term of this patent is extended or adjusted under 35 U.S.C. 154(b) by 49 days.

(21) Appl. No.: 17/708,072

(22) Filed: Mar. 30, 2022

(65) Prior Publication Data
US 2022/0324861 A1 Oct. 13, 2022

Related U.S. Application Data

(60) Provisional application No. 63/309,346, filed on Feb. 11, 2022, provisional application No. 63/168,456, filed on Mar. 31, 2021.

(51) Int. Cl.
| | | |
|---|---|---|
| *C07D 471/04* | (2006.01) | |
| *A61P 35/00* | (2006.01) | |
| *A61K 31/4375* | (2006.01) | |
| *A61K 45/06* | (2006.01) | |

(52) U.S. Cl.
CPC ........ *C07D 471/04* (2013.01); *A61K 31/4375* (2013.01); *A61K 45/06* (2013.01); *A61P 35/00* (2018.01)

(58) Field of Classification Search
CPC .................................................. C07D 471/04
See application file for complete search history.

(56) References Cited

U.S. PATENT DOCUMENTS

| 10,358,447 B2 | 7/2019 | Kakarla et al. |
| 2005/0222177 A1 | 10/2005 | Sim et al. |
| 2023/0013227 A1 | 1/2023 | Kincaid et al. |

FOREIGN PATENT DOCUMENTS

| EP | 1894932 A1 | 5/2008 | |
| WO | 2005/021533 | 3/2005 | |
| WO | 2005/051300 | 6/2005 | |
| WO | 2005/051301 | 6/2005 | |
| WO | 2005/051302 | 6/2005 | |
| WO | 2005/051906 | 6/2005 | |
| WO | 2005/063768 | 7/2005 | |
| WO | 2007/044084 | 4/2007 | |
| WO | 2007/109154 | 9/2007 | |
| WO | 2007/109160 | 9/2007 | |
| WO | 2007/109172 | 9/2007 | |
| WO | 2007/109182 | 9/2007 | |
| WO | 2007/109192 | 9/2007 | |
| WO | 2007/109201 | 9/2007 | |
| WO | 2008/079814 A2 | 7/2008 | |
| WO | 2008/112205 | 9/2008 | |
| WO | 2008/115890 A2 | 9/2008 | |
| WO | 2009/097287 | 8/2009 | |
| WO | 2009/099801 | 8/2009 | |
| WO | WO-2009097287 A1 * | 8/2009 | ........... C07D 471/04 |
| WO | 2009/146034 | 12/2009 | |
| WO | 2013/136249 A1 | 9/2013 | |
| WO | 2020/072492 | 4/2020 | |
| WO | 2013/033981 | 3/2023 | |

OTHER PUBLICATIONS

Current Development Status of MEK Inhibitors Cheng et al. Molecules 2017, 22, 1551; doi:10.3390/molecules22101551 (Year: 2017).*
International Search Report for PCT/IB2022/052952 completed on May 4, 2022.
Written Opinion for PCT/IB2022/052952 completed on May 4, 2022.
Braga, D., et al., Crystal Polymorphism and Multiple Crystal Forms, Struct Bond (2009), 132: 25-50.

* cited by examiner

*Primary Examiner* — Jeffrey S Lundgren
*Assistant Examiner* — Eric Tran
(74) *Attorney, Agent, or Firm* — Beau Burton

(57) ABSTRACT

The invention relates to a compound of Formula I

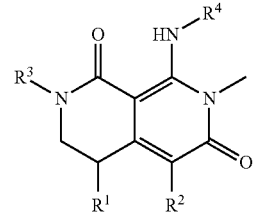

or a pharmaceutically acceptable salt thereof, wherein $R^1$, $R^2$, $R^3$ and $R^4$ are as defined herein. The invention further relates to pharmaceutical compositions comprising such compounds and salts, and to methods and uses of such compounds, salts and compositions for the treatment of abnormal cell growth, including cancer, in a subject in need thereof. The invention further relates to solid forms of 8-((2-fluoro-4-(methylthio)phenyl)amino)-2-(2-hydroxyethoxy)-7-methyl-3,4-dihydro-2,7-naphthyridine-1,6(2H,7H)-dione.

53 Claims, 5 Drawing Sheets

3,4-DIHYDRO-2,7-NAPHTHYRIDINE-1,6(2H,7H)-DIONES AS MEK INHIBITORS

FIELD OF THE INVENTION

The present invention relates to novel 3,4-dihydro-2,7-naphthyridine-1,6(2H,7H)-dione compounds, or pharmaceutically acceptable salts thereof, which act as MEK inhibitors and are useful for the treatment of abnormal cell growth, such as cancer, in patients. The present invention also relates to pharmaceutical compositions containing the compounds and to methods of using the compounds and compositions in the treatment of abnormal cell growth, such as cancer, in subject in need thereof. The present invention also relates to solid forms of 8-((2-fluoro-4-(methylthio)phenyl)amino)-2-(2-hydroxyethoxy)-7-methyl-3,4-dihydro-2,7-naphthyridine-1,6(2H,7H)-dione, to pharmaceutical compositions containing the solid forms, and to methods of using the solid forms and compositions thereof in the treatment of abnormal cell growth, such as cancer, in subject in need thereof.

BACKGROUND OF THE INVENTION

MEK kinase (Mitogen Activated Protein Kinase Kinase (MAPKK)) is an important component of the Ras-RAF-MEK-ERK cell survival pathway. The Ras pathway is activated by binding of growth factors, cytokines, and hormones to their cognate receptors. In cancer cells, this pathway is, however, constitutively activated and leads to increased cancer cell survival, cell proliferation, angiogenesis, and metastasis. The tumors that show constitutive activation of the pathway include, but are not limited to, those of the colon, pancreas, breast, brain, ovary, lungs, and skin. Activation of Ras (due to upstream signaling or as a result of activating point mutations in the Ras oncogene) lead to the phosphorylation and activation of Raf kinase that in turn phosphorylate and activate MEK1 and MEK2 (also known as MAPKK1 and MAPKK2). MEK1 and MEK2 are dual-specificity kinases that activate ERK1 and ERK2 by phosphorylating and activating the ERK1/2 kinase (also referred to as MAP Kinase) that further phosphorylates and regulates the function of proteins such as Mcl-1, Bim and Bad that are involved in cell survival and apoptosis. Thus, activation of this phosphorylation mediated cascade leads to enhanced cell proliferation, cell survival, and decreased cell death that are necessary for initiation and maintenance of the tumorigenic phenotype. Inhibition of this pathway, particularly inhibiting MEK activity, is known to be beneficial in treating hyperproliferative diseases. MEK inhibitors have shown variable degrees of activity in several settings, including BRAF V600-mutant melanoma, NRAS-mutant melanoma, low-grade serous ovarian cancer, plexiform neurofibromas, thyroid cancer, and low-grade gliomas, with more limited responses in KRAS-mutant pancreatic cancer or lung cancer.

Cancers that frequently metastasize to the brain, e.g., melanoma and non-small cell lung cancer, are known to carry MAPK pathway activating alterations such as the BRAF V600E and KRAS G12 mutation (Cancer Genome Atlas N., Cell 2015; 161:1681-96). Although activating mutations can occur at different levels in the canonical pathway, they all require signaling via mitogen/extracellular signal-regulated kinase (MEK) in order to increase proliferation and survival (Schubbert S, Shannon K, Bollag G., Nat Rev Cancer. 2007; 7:295-308). The common activation of the MAPK pathway in malignancies and the central and downstream location of MEK also render MEK inhibitors of potential interest for the treatment of intracranial tumors.

Blood-brain interfaces comprise the cerebral microvessel endothelium forming the blood-brain barrier (BBB) and the epithelium of the choroid plexuses forming the blood-CSF barrier (BCSFB). The blood brain barrier (BBB) is a highly selective physical, transport and metabolic barrier that divides the CNS from the blood. The BBB may prevent certain drugs from entering brain tissue and is therefore a limiting factor in the delivery of many peripherally-administered agents to the CNS. The efficacy of many molecularly targeted agents in central nervous system tumors is limited by penetration across the blood-brain barrier (BBB), which is composed of a monolayer of endothelial cells connected by tight junctions that serve as a physical barrier protecting the brain. In addition, these endothelial cells express multiple efflux transporters, including P-glycoprotein (P-gp) and breast cancer resistance protein (BCRP), which are known to exclude many anticancer agents from the brain (Ohtsuki and Terasaki, 2007, Pharm Res 24:1745-1758; Agarwal et al., 2011, Pharm Res 24:1745-1758). Similar to the blood-brain barrier, the blood-CSF barrier functions to prevent the passage of most blood-borne substances into the brain, while selectively permitting the passage specific substances into the brain and facilitating the removal of brain metabolites and metabolic products into the blood.

Thus, there remains a need for therapies for the treatment of tumors mediated by MEK, including therapies that can penetrate the BBB and/or BCSFB and target tumors in the CNS.

SUMMARY OF THE INVENTION

Provided herein, in part, are compounds of Formula I and Formula II and pharmaceutically acceptable salts thereof. Such compounds can inhibit the activity of MEK, thereby effecting biological functions, and may be useful for treating a subject having a MEK-associated tumor. Also provided herein are solid forms of 8-((2-fluoro-4-(methylthio)phenyl)amino)-2-(2-hydroxyethoxy)-7-methyl-3,4-dihydro-2,7-naphthyridine-1,6(2H,7H)-dione. Also provided are pharmaceutical compositions and medicaments comprising the compounds according to any of the formulae described herein, and pharmaceutically acceptable salts thereof, which may be useful for treating a subject having a MEK-associated tumor alone or in combination with additional anticancer therapies. Also provided herein are methods for preparing the compounds, pharmaceutically acceptable salts, and pharmaceutical compositions according to any of the formulae described herein and pharmaceutically acceptable salts thereof, and methods of using the foregoing. This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter.

According to an embodiment of the invention, provided herein is a compound of Formula I

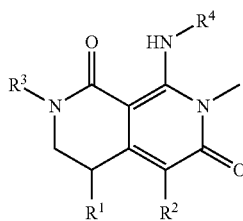

or a pharmaceutically acceptable salt thereof, wherein:
- $R^1$ is H, Br, C1-C6 alkyl or phenyl;
- $R^2$ is H, halogen or $CH_3$—;
- $R^3$ is H, hydroxyC1-C6 alkyl-, hydroxyC1-C6 alkoxy-, C1-C6 alkoxy, fluoroC1-C6 alkoxy, C3-C6 cycloalkyl, or (C3-C6 cycloalkyl)C1-C6 alkoxy-; and
- $R^4$ is phenyl substituted with 1, 2 or 3 substituents independently selected from halogen, C1-C6 alkyl, C1-C6 alkylthio, fluoroC1-C6 alkylthio, fluoroC1-C6 alkyl, C1-C6 alkoxy, fluoroC1-C6 alkoxy, C3-C6 cycloalkyl, and C1-C6 alkyl-C(=O)—.

Also provided herein is a compound of Formula II

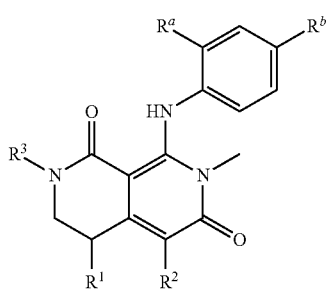

or a pharmaceutically acceptable salt thereof, wherein:
- $R^1$ is H, Br, C1-C6 alkyl or phenyl;
- $R^2$ is H, halogen or $CH_3$—;
- $R^3$ is H, hydroxyC1-C6 alkyl-, hydroxyC1-C6 alkoxy-, C1-C6 alkoxy, fluoroC1-C6 alkoxy, C3-C6 cycloalkyl, or (C3-C6 cycloalkyl)C1-C6 alkoxy-; and
- $R^a$ and $R^b$ are independently selected from halogen, C1-C6 alkyl, C1-C6 alkylthio, fluoroC1-C6 alkylthio, fluoroC1-C6 alkyl, C1-C6 alkoxy, fluoroC1-C6 alkoxy, C3-C6 cycloalkyl, and C1-C6 alkyl-C(=O)—.

In one embodiment, provided herein are solid forms of 8-((2-fluoro-4-(methylthio)phenyl)amino)-2-(2-hydroxyethoxy)-7-methyl-3,4-dihydro-2,7-naphthyrdine-1,6(2H,7H)-dione.

In one embodiment, provided herein is a pharmaceutical composition comprising a compound according to any of the formulae described herein, or a pharmaceutically acceptable salt thereof, and a pharmaceutically acceptable carrier or excipient. In some embodiments, the pharmaceutical composition comprises two or more pharmaceutically acceptable carriers and/or excipients.

In one embodiment, provided herein are therapeutic methods and uses comprising administering a compound according to any of the formulae described herein, or a pharmaceutically acceptable salt thereof, to a subject.

In one embodiment, provided herein is a method for the treatment of abnormal cell growth, for example a tumor, for example a MEK-associated tumor, in a subject in need thereof, comprising administering to the subject a therapeutically effective amount of a compound according to any of the formulae described herein, or a pharmaceutically acceptable salt thereof. Compounds according to any of the formulae described herein may be administered as single agents or may be administered in combination with one or more anticancer therapies.

In one embodiment, provided herein is a method for the treatment of abnormal cell growth, for example a tumor, for example a MEK-associated tumor, in a subject in need thereof, comprising administering to the subject an amount of a compound according to any of the formulae described herein, or a pharmaceutically acceptable salt thereof, in combination with an amount of an additional anticancer agent, which amounts are together effective in treating said abnormal cell growth.

In one embodiment, provided herein is a compound according to any of the formulae described herein, or a pharmaceutically acceptable salt thereof, for use as a medicament.

In one embodiment, provided herein is a compound according to any of the formulae described herein, or a pharmaceutically acceptable salt thereof, for use in the treatment of abnormal cell growth, for example a tumor, for example a MEK-associated tumor.

In one embodiment, provided herein is the use of a compound according to any of the formulae described herein, or a pharmaceutically acceptable salt thereof, for the manufacture of a medicament for the treatment of abnormal cell growth, for example a tumor, for example a MEK-associated tumor, in a subject.

In one embodiment, provided herein is a pharmaceutical composition comprising a compound according to any of the formulae described herein, or a pharmaceutically acceptable salt thereof, and at least one pharmaceutically acceptable carrier or excipient.

Each of the embodiments of the compounds according to any of the formulae described herein can be combined with one or more other embodiments of the compounds according to any of the formulae described herein not inconsistent with the embodiment(s) with which it is combined.

It is to be understood that both the foregoing general description and the following detailed description are exemplary and explanatory only and are not restrictive of the invention, as claimed.

DETAILED DESCRIPTION OF THE INVENTION

Figure 1:
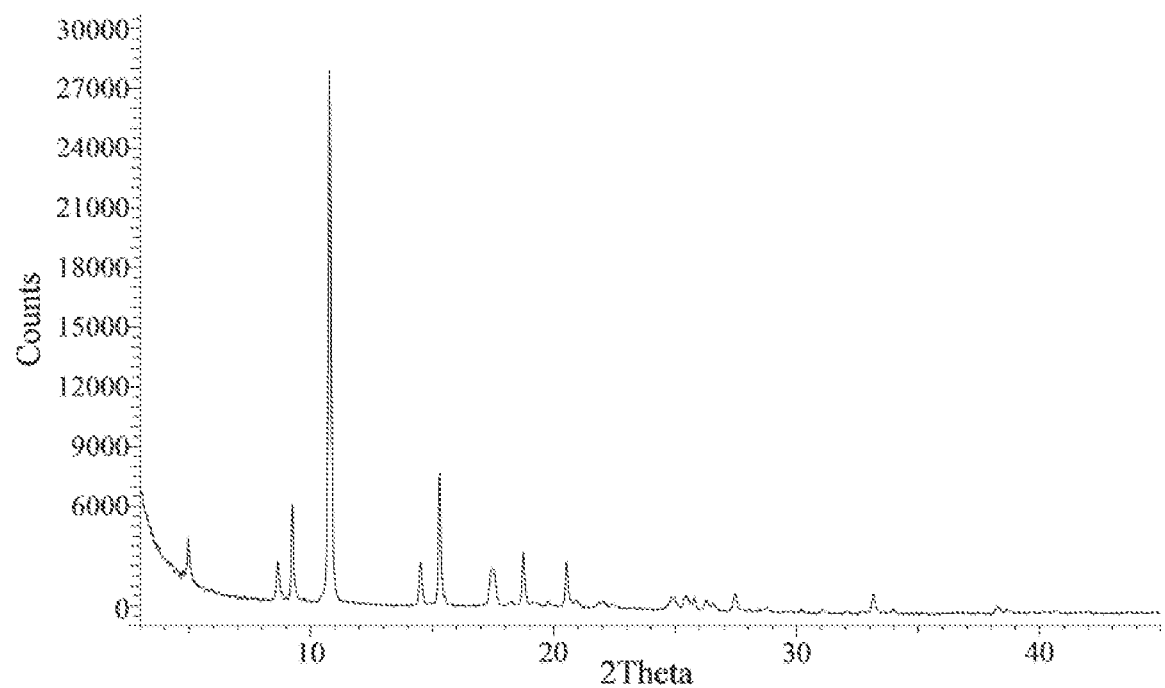
FIG. 1 depicts a powder X-ray diffraction pattern of crystalline anhydrous 8-((2-fluoro-4-(methylthio)phenyl)amino)-2-(2-hydroxyethoxy)-7-methyl-3,4-dihydro-2,7-naphthyridine-1,6(2H,7H)-dione, Form 1.

In one aspect, the invention provides a compound of the Formula I

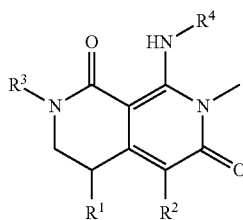

I or a pharmaceutically acceptable salt thereof, wherein:
$R^1$ is H, Br, C1-C6 alkyl or phenyl;
$R^2$ is H, halogen or $CH_3$—;
$R^3$ is H, hydroxyC1-C6 alkyl-, hydroxyC1-C6 alkoxy-, C1-C6 alkoxy, fluoroC1-C6 alkoxy, C3-C6 cycloalkyl, or (C3-C6 cycloalkyl)C1-C6 alkoxy-; and
$R^4$ is phenyl substituted with 1, 2 or 3 substituents independently selected from halogen, C1-C6 alkyl, C1-C6 alkylthio, fluoroC1-C6 alkylthio, fluoroC1-C6 alkyl, C1-C6 alkoxy, fluoroC1-C6 alkoxy, C3-C6 cycloalkyl, and C1-C6 alkyl-C(=O)—.

As used herein, the singular forms "a", "an", and "the" when referring to substituents include plural references unless indicated otherwise. For example, "a" substituent includes one or more substituents.

For complex chemical names employed herein, a substituent group is typically named before the group to which it attaches. For example, methoxyethyl comprises an ethyl backbone with a methoxy substituent.

The term "halogen" means —F (sometimes referred to herein as "fluoro" or "fluoros"), —Cl, —Br and —I.

The term "C1-C6 alkyl" as used herein refers to a saturated linear or branched-chain monovalent hydrocarbon radical of one to six carbon atoms. Examples of alkyl groups include, but are not limited to, methyl, ethyl, 1-propyl, isopropyl, 1-butyl, isobutyl, sec-butyl, tert-butyl, 2-methyl-2-propyl, pentyl, neopentyl, and hexyl.

The term "hydroxyC1-C6 alkyl-" as used herein refers to refers to a C1-C6 alkyl radical as defined herein, wherein one of the hydrogen atoms is replaced with a hydroxy group.

The term "hydroxy" refers to an —OH group.

The term "C3-C6 cycloalkyl" means a fully saturated carbocyclic ring having from 3-6 ring carbon atoms. Examples include cyclopropyl, cyclobutyl, cyclopentyl and cyclohexyl.

The term "fluoroC1-C6 alkyl" as used herein refers to a C1-C6 alkyl radical as defined herein, wherein one, two or three hydrogen atoms is replaced with one, two or three fluoro atoms, respectively. Examples include, but are not limited to, fluoromethyl, difluoromethyl, trifluoromethyl, 2-fluoroethyl, 2,2-difluoroethyl, and 2,2,2-trifluoroethyl.

The term "C1-C6 alkoxy" as used herein refers to a C1-C6 alkyl radical as defined herein that is single bonded to an oxygen atom, wherein the radical is on the oxygen atom (i.e., C1-C6-O—). Examples of alkoxy groups include, but are not limited to, methoxy, ethoxy, propoxy, and isopropoxy.

The term "fluoroC1-C6 alkoxy" as used herein refers to a C1-C6 alkoxy as defined herein, wherein one, two or three hydrogen atoms is replaced with one, two or three fluoro atoms, respectively. An example includes, but is not limited to, trifluoromethoxy.

The term "(C3-C6 cycloalkyl)C1-C6 alkoxy-" refers to a C1-C6 alkoxy- as defined herein, wherein one of the hydrogen atoms is replaced with a C3-C6 cycloalkyl group as defined herein.

The term "C1-C6 alkylthio" as used herein refers to a (C1-C6 alkyl)S— radical wherein the C1-C6 alkyl portion is as defined herein.

The term "fluoroC1-C6 alkylthio" as used herein refers to a C1-C6 alkylthio group as defined herein, wherein one, two or three hydrogen atoms is replaced with one, two or three fluoro atoms, respectively.

In one embodiment of Formula I, $R^1$ is H.
In one embodiment of Formula I, $R^1$ is Br.
In one embodiment of Formula I, $R^1$ is C1-C6 alkyl. In one embodiment of Formula I, $R^1$ is methyl.
In one embodiment of Formula I, $R^1$ is phenyl.
In one embodiment of Formula I, $R^2$ is H.
In one embodiment, $R^2$ is halogen.
In one embodiment of Formula I, $R^2$ is F.
In one embodiment of Formula I, $R^2$ is Cl.
In one embodiment of Formula I, $R^2$ is Br.
In one embodiment of Formula I, $R^2$ is I.
In one embodiment of Formula I, $R^2$ is $CH_3$—.
In one embodiment of Formula I, $R^1$ is H and $R^2$ is H.
In one embodiment of Formula I, $R^3$ is H.
In one embodiment of Formula I, $R^3$ is hydroxyC1-C6 alkyl-. Nonlimiting examples include 2-hydroxyethyl.
In one embodiment of Formula I, $R^3$ is hydroxyC1-C6 alkoxy-. Nonlimiting examples include 2-hydroxyethoxy and 2-hydroxypropoxy having the structures:

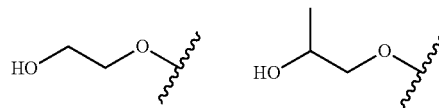

respectively.

In one embodiment of Formula I, $R^3$ is C1-C6 alkoxy. Nonlimiting examples include methoxy, ethoxy, 1-methylethoxy, and 2,2-dimethylethoxy.

In one embodiment of Formula I, $R^3$ is fluoroC1-C6 alkoxy. A nonlimiting example includes 2,2-difluoroethoxy.

In one embodiment of Formula I, $R^3$ is C3-C6 cycloalkyl. A nonlimiting example is cyclopropyl.

In one embodiment of Formula I, $R^3$ is (C3-C6 cycloalkyl)C1-C6 alkoxy-. A nonlimiting example is cyclopropylmethoxy.

In one embodiment of Formula I, $R^4$ is phenyl substituted with 1, 2 or 3 substituents independently selected from fluoro, chloro, bromo, iodo, ethyl, propyl, isopropyl, methylthio, difluoromethylthio, trifluoromethyl, methoxy, difluoromethoxy, cyclopropyl, and C1-C6 alkyl-C(=O)—.

In one embodiment of Formula I, $R^4$ is phenyl substituted with 1 or 2 substituents independently selected from halogen, C1-C6 alkyl, C1-C6 alkylthio, fluoroC1-C6 alkylthio, fluoroC1-C6 alkyl, C1-C6 alkoxy, fluoroC1-C6 alkoxy, C3-C6 cycloalkyl, and C1-C6 alkyl-C(=O)—.

In one embodiment of Formula I, $R^4$ is phenyl substituted with 1 or 2 substituents independently selected from fluoro, chloro, bromo, iodo, ethyl, propyl, isopropyl, methylthio, difluoromethylthio, trifluoromethyl, methoxy, difluoromethoxy, cyclopropyl, and C1-C6 alkyl-C(=O)—.

In one embodiment of Formula I, $R^4$ is phenyl substituted with 1 substituent selected from halogen, C1-C6 alkyl, C1-C6 alkylthio, fluoroC1-C6 alkylthio, fluoroC1-C6 alkyl, C1-C6 alkoxy, fluoroC1-C6 alkoxy, C3-C6 cycloalkyl, and C1-C6 alkyl-C(=O)—.

In one embodiment of Formula I, $R^4$ is phenyl substituted with 1 substituent selected from fluoro, chloro, bromo, iodo, ethyl, propyl, isopropyl, methylthio, difluoromethylthio, trifluoromethyl, methoxy, difluoromethoxy, cyclopropyl, and C1-C6 alkyl-C(=O)—.

In one embodiment of Formula I, $R^4$ is selected from the structures:

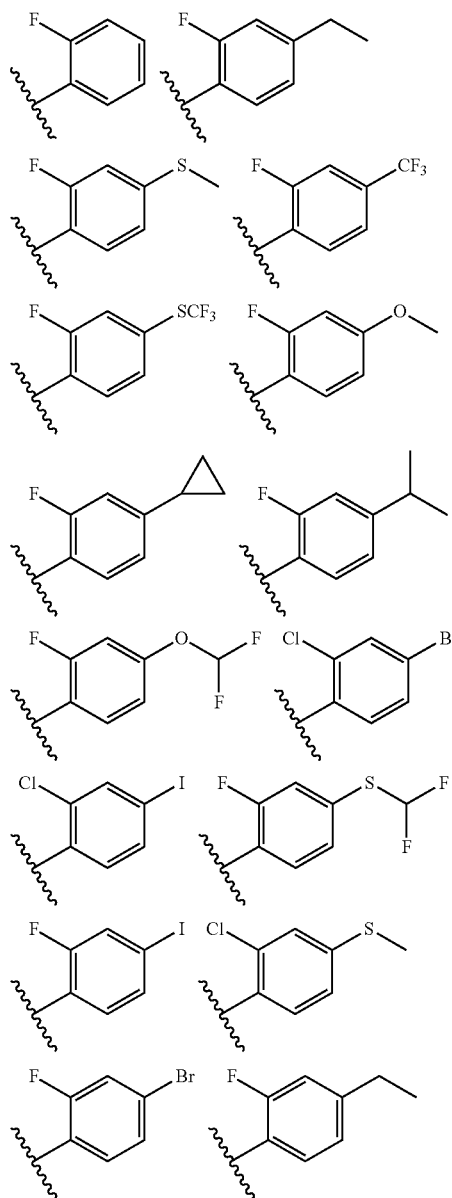

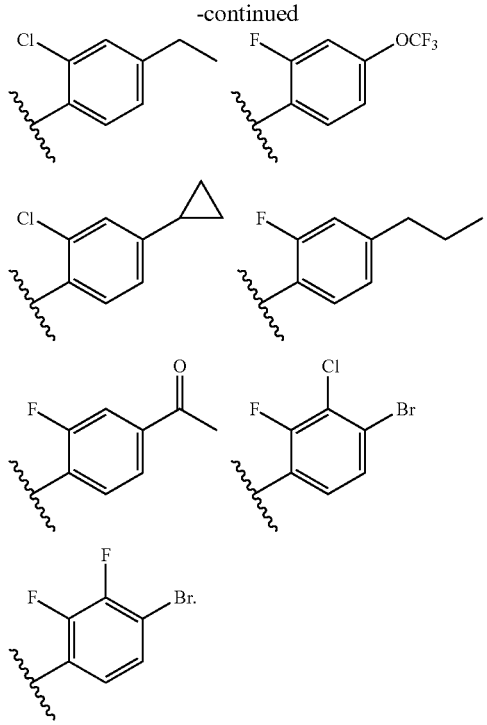

In one embodiment of Formula I, $R^4$ is

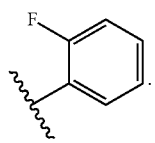

In one embodiment of Formula I, $R^4$ is

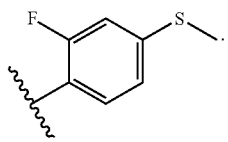 [SMILES: *c1ccc(SC)cc1F]

In one embodiment of Formula I, $R^4$ is selected from the structures:

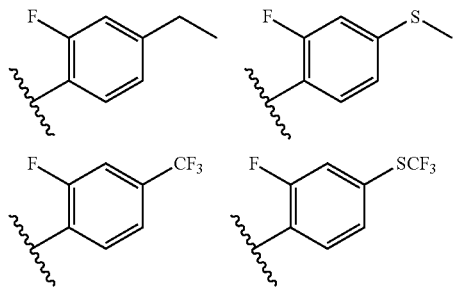

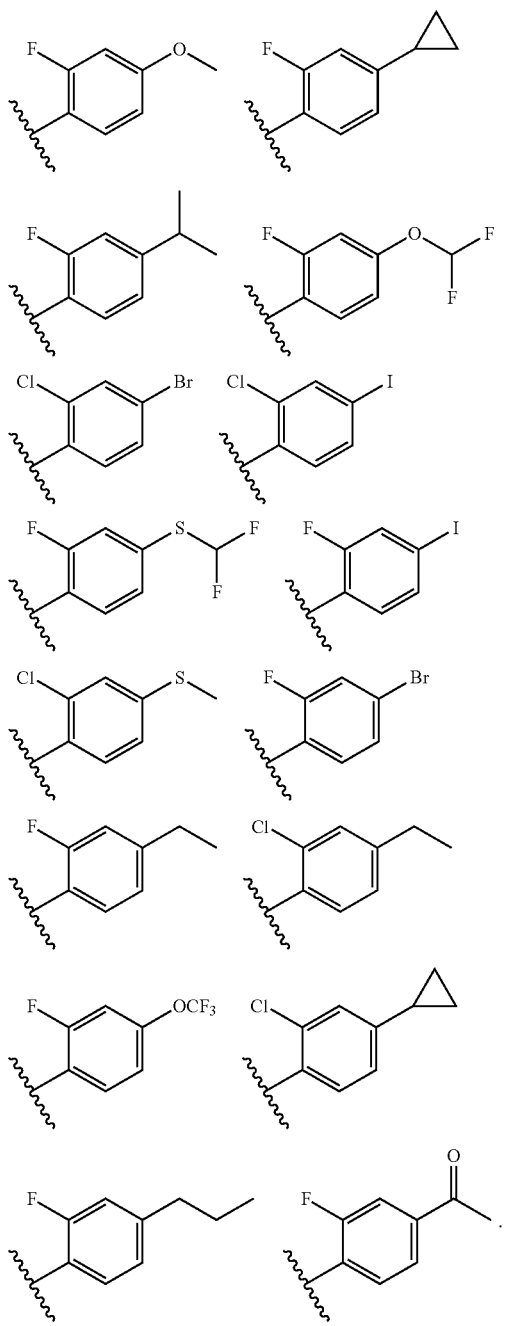

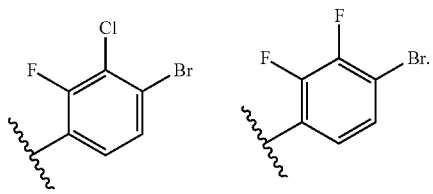 [SMILES: *c1ccc(Br)c(Cl)c1F ; *c1ccc(Br)c(F)c1F]

In one embodiment of Formula I, R⁴ is selected from the structures:

In one embodiment, $R^4$ has the structure:

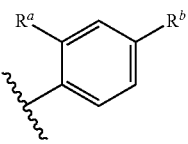

wherein $R^a$ and $R^b$ are independently selected from halogen, C1-C6 alkyl, C1-C6 alkylthio, fluoroC1-C6 alkylthio, fluoroC1-C6 alkyl, C1-C6 alkoxy, fluoroC1-C6 alkoxy, C3-C6 cycloalkyl, and C1-C6 alkyl-C(=O)—. In one embodiment, wherein $R^a$ is halogen. In one embodiment, $R^b$ is halogen, C1-C6 alkyl, C1-C6 alkylthio, or fluoroC1-C6 alkoxy. In one embodiment, wherein $R^a$ is halogen and $R^b$ is halogen, C1-C6 alkyl, C1-C6 alkylthio, or fluoroC1-C6 alkoxy.

In one embodiment, provided herein is a compound of Formula II:

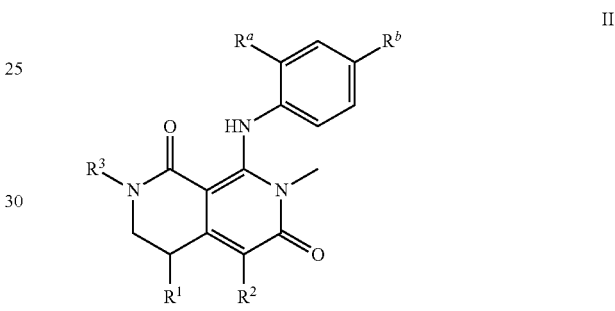

or a pharmaceutically acceptable salt thereof, wherein:
$R^1$ is H, Br, C1-C6 alkyl or phenyl;
$R^2$ is H, halogen or $CH_3$—;
$R^3$ is H, hydroxyC1-C6 alkyl-, hydroxyC1-C6 alkoxy-, C1-C6 alkoxy, fluoroC1-C6 alkoxy, C3-C6 cycloalkyl, or (C3-C6 cycloalkyl)C1-C6 alkoxy-; and
$R^a$ and $R^b$ are independently selected from halogen, C1-C6 alkyl, C1-C6 alkylthio, fluoroC1-C6 alkylthio, fluoroC1-C6 alkyl, C1-C6 alkoxy, fluoroC1-C6 alkoxy, C3-C6 cycloalkyl, and C1-C6 alkyl-C(=O)—.

In one embodiment of Formula II, $R^1$ is H.
In one embodiment of Formula II, $R^1$ is Br.
In one embodiment of Formula II, $R^1$ is C1-C6 alkyl. In one embodiment of Formula II, $R^1$ is methyl.
In one embodiment of Formula II, $R^1$ is phenyl.
In one embodiment of Formula II, $R^2$ is H.
In one embodiment of Formula II, $R^2$ is halogen.
In one embodiment of Formula II, $R^2$ is F.
In one embodiment of Formula II, $R^2$ is Cl.
In one embodiment of Formula II, $R^2$ is Br.
In one embodiment of Formula II, $R^2$ is I.
In one embodiment of Formula II, $R^2$ is CH—.
In one embodiment of Formula II, $R^2$ is H or $CH_3$—.
In one embodiment of Formula II, $R^1$ is H and $R^2$ is H or $CH_3$—.
In one embodiment of Formula II, $R^1$ is H and $R^2$ is H.
In one embodiment of Formula II, $R^3$ is H.
In one embodiment of Formula II, $R^3$ is hydroxyC1-C6 alkyl-. Nonlimiting examples include 2-hydroxyethyl.
In one embodiment of Formula II, $R^3$ is hydroxyC1-C6 alkoxy-. Nonlimiting examples include 2-hydroxyethoxy and 2-hydroxypropoxy having the structures:

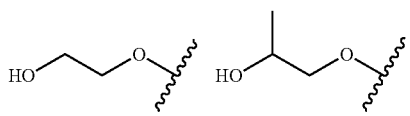

respectively.

In one embodiment of Formula II, $R^3$ is C1-C6 alkoxy. Nonlimiting examples include methoxy, ethoxy, 1-methylethoxy, and 2,2-dimethylethoxy.

In one embodiment of Formula II, $R^3$ is fluoroC1-C6 alkoxy. A nonlimiting example includes 2,2-difluoroethoxy.

In one embodiment of Formula II, $R^3$ is C3-C6 cycloalkyl. A nonlimiting example is cyclopropyl.

In one embodiment of Formula II, $R^3$ is (C3-C6 cycloalkyl)C1-C6 alkoxy-. A nonlimiting example is cyclopropylmethoxy.

In one embodiment of Formula II, $R^3$ is H or hydroxyC1-C6 alkoxy-.

In one embodiment of Formula II, $R^a$ is halogen. In one embodiment of Formula II, $R^a$ is fluoro or chloro. In one embodiment of Formula II, $R^a$ is fluoro.

In one embodiment of Formula II, $R^b$ is fluoro, chloro, bromo, iodo, ethyl, propyl, isopropyl, methylthio, difluoromethylthio, trifluoromethyl, methoxy, difluoromethoxy, cyclopropyl, or $CH_3C(=O)$—.

In one embodiment of Formula II, $R^b$ is halogen, C1-C6 alkyl, C1-C6 alkylthio, or fluoroC1-C6 alkoxy.

In one embodiment of Formula II, $R^b$ is bromo, iodo, ethyl, methylthio, or difluoromethoxy. In one embodiment of Formula II, $R^b$ is methylthio.

In one embodiment of Formula II, $R^a$ is fluoro and $R^b$ is methylthio.

In one embodiment of Formula II, $R^a$ is halogen and $R^b$ is halogen, C1-C6 alkyl, C1-C6 alkylthio, fluoroC1-C6 alkylthio, fluoroC1-C6 alkyl, C1-C6 alkoxy, fluoroC1-C6 alkoxy, C3-C6 cycloalkyl, or C1-C6 alkyl-C(=O)—.

In one embodiment of Formula II, $R^a$ is halogen and $R^b$ is halogen, C1-C6 alkyl, C1-C6 alkylthio, or fluoroC1-C6 alkoxy.

In one embodiment of Formula II, $R^1$ is halogen and $R^b$ is halogen. In one embodiment of Formula II, $R^a$ is halogen, $R^b$ is halogen, $R^1$ is H and $R^2$ is H.

In one embodiment of Formula II, $R^a$ is halogen and $R^b$ is C1-C6 alkyl. In one embodiment of Formula II, $R^a$ is halogen, $R^b$ is C1-C6 alkyl, $R^1$ is H and $R^2$ is H.

In one embodiment of Formula II, $R^a$ is halogen and $R^b$ is C1-C6 alkylthio. In one embodiment of Formula II, $R^a$ is halogen, $R^b$ is C1-C6 alkylthio, $R^1$ is H and $R^2$ is H.

In one embodiment of Formula II, $R^a$ is halogen and $R^b$ is fluoroC1-C6 alkylthio. In one embodiment of Formula II, $R^a$ is halogen, $R^b$ is fluoroC1-C6 alkylthio, $R^1$ is H and $R^2$ is H.

In one embodiment of Formula II, $R^a$ is fluoro, $R^b$ is methylthio, $R^1$ is H and $R^2$ is H.

In one embodiment of Formula II, $R^1$ is halogen and $R^b$ is fluoroC1-C6 alkyl. In one embodiment of Formula II, $R^a$ is halogen, $R^b$ is fluoroC1-C6 alkyl, $R^1$ is H and $R^2$ is H.

In one embodiment of Formula II, $R^a$ is halogen and $R^b$ is C1-C6 alkoxy. In one embodiment of Formula II, $R^a$ is halogen, $R^b$ is C1-C6 alkoxy, $R^1$ is H and $R^2$ is H.

In one embodiment of Formula II, $R^a$ is halogen and $R^b$ is fluoroC1-C6 alkoxy. In one embodiment of Formula II, $R^a$ is halogen, $R^b$ is fluoroC1-C6 alkoxy, $R^1$ is H and $R^2$ is H.

In one embodiment of Formula II, $R^a$ is halogen and $R^b$ is C3-C6 cycloalkyl. In one embodiment of Formula II, $R^a$ is halogen, $R^b$ is C3-C6 cycloalkyl, $R^1$ is H and $R^2$ is H.

In one embodiment of Formula II, $R^a$ is halogen and $R^b$ is C1-C6 alkyl-C(=O)—. In one embodiment of Formula II, $R^a$ is halogen, $R^b$ is C1-C6 alkyl-C(=O)—, $R^1$ is H and $R^2$ is H.

In one embodiment of Formula II, $R^1$ is H, $R^2$ is H or $CH_3$—, $R^3$ is H or hydroxyC1-C6 alkoxy-, $R^a$ is halogen and $R^b$ is halogen, C1-C6 alkyl, C1-C6 alkylthio, fluoroC1-C6 alkylthio, fluoroC1-C6 alkyl, C1-C6 alkoxy, fluoroC1-C6 alkoxy, C3-C6 cycloalkyl, or C1-C6 alkyl-C(=O)—.

In one embodiment of Formula II, $R^1$ is H, $R^2$ is H or $CH_3$—, $R^3$ is H or hydroxyC1-C6 alkoxy-, $R^a$ is halogen, and $R^b$ is halogen, C1-C6 alkyl, C1-C6 alkylthio, or fluoroC1-C6 alkoxy.

In one embodiment of any of the above described embodiments of Formula II, the group

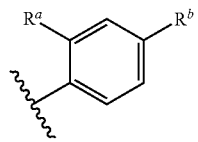

is selected from the structures:

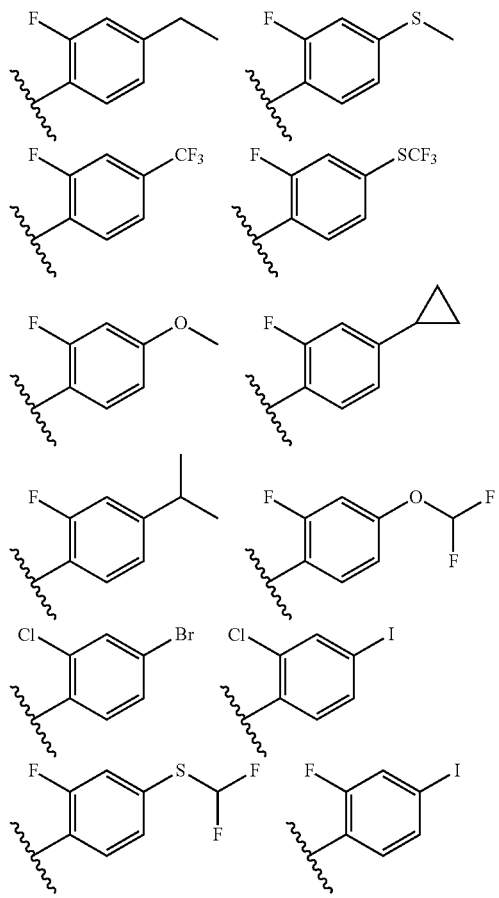

-continued

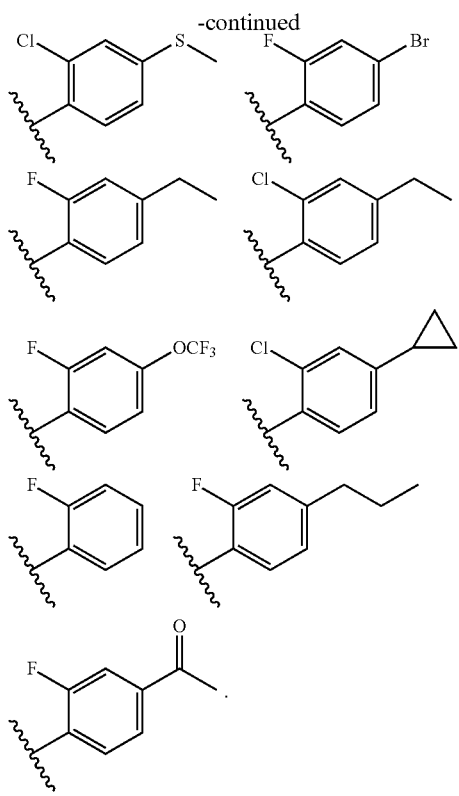

The term "compound," as used herein is meant to include all stereoisomers, geometric isomers, tautomers, and isotopes of the structures depicted. Compounds herein identified by name or structure as one particular tautomeric form are intended to include other tautomeric forms unless otherwise specified.

The compounds of the formulae provided herein may have asymmetric carbon atoms. The carbon carbon bonds of the compounds of the invention may be depicted herein using a solid line (-), a solid wedge ( ▬▬▬ ), or a dotted wedge ( ·······⊪ ). The use of a solid line to depict bonds to asymmetric carbon atoms is meant to indicate that all possible stereoisomers (e.g. specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of the invention may contain more than one asymmetric carbon atom. In those compounds, the use of a solid line to depict bonds to asymmetric carbon atoms is meant to indicate that all possible stereoisomers are meant to be included and the attached stereocenter. For example, unless stated otherwise, it is intended that the compounds of the invention can exist as enantiomers and diastereomers or as racemates and mixtures thereof. The use of a solid line to depict bonds to one or more asymmetric carbon atoms in a compound of the invention and the use of a solid or dotted wedge to depict bonds to other asymmetric carbon atoms in the same compound is meant to indicate that a mixture of diastereomers is present.

Compounds of the invention that have chiral centers may exist as stereoisomers, such as racemates, enantiomers, or diastereomers.

Stereoisomers of the compounds of the formulae herein can include cis and trans isomers, optical isomers such as (R) and (S) enantiomers, diastereomers, geometric isomers, rotational isomers, atropisomers, conformational isomers, and tautomers of the compounds of the invention, including compounds exhibiting more than one type of isomerism; and mixtures thereof (such as racemates and diastereomeric pairs).

Also included are acid addition salts or base addition salts, wherein the counterion is optically active, for example, d-lactate or l-lysine, or racemic, for example, dl-tartrate or dl-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

Conventional techniques for the preparation/isolation of individual enantiomers include chiral synthesis from a suitable optically pure precursor or resolution of the racemate (or the racemate of a salt or derivative) using, for example, chiral high-pressure liquid chromatography (HPLC) or superfluid critical chromatography (SFC).

Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art.

Chiral compounds of the invention (and chiral precursors thereof) may be obtained in enantiomerically enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluent affords the enriched mixture.

Stereoisomeric conglomerates may be separated by conventional techniques known to those skilled in the art; see, for example, "Stereochemistry of Organic Compounds" by E L Eliel (Wiley, New York, 1994), the disclosure of which is incorporated herein by reference in its entirety.

The enantiomeric purity of compounds described herein may be described in terms of enantiomeric excess (ee), which indicates the degree to which a sample contains one enantiomer in greater amounts than the other. A racemic mixture has an ee of 0%, while a single completely pure enantiomer has an ee of 100%. Similarly, diastereomeric purity may be described in terms of diastereomeric excess (de).

The compounds of the invention may exhibit the phenomena of tautomerism and structural isomerism. For example, the compounds may exist in several tautomeric forms, including the enol and imine form, and the keto and enamine form and geometric isomers and mixtures thereof. All such tautomeric forms are included within the scope of compounds of the invention. Tautomers exist as mixtures of a tautomeric set in solution. In solid form, usually one tautomer predominates. Even though one tautomer may be described, the present invention includes all tautomers of the compounds of the formulae provided. A tautomer of a compound of Formula I may occur, for example, when $R^3$ is hydrogen, that is:

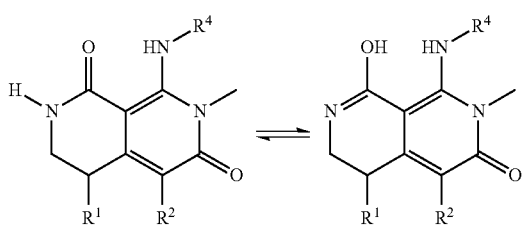

In addition, some of the compounds of the invention may form atropisomers (e.g., substituted biaryls). Atropisomers are conformational stereoisomers which occur when rotation about a single bond in the molecule is prevented, or greatly slowed, as a result of steric interactions with other parts of the molecule and the substituents at both ends of the single bond are unsymmetrical. The interconversion of atropisomers is slow enough to allow separation and isolation under predetermined conditions. The energy barrier to thermal racemization may be determined by the steric hindrance to free rotation of one or more bonds forming a chiral axis.

The present invention also includes pharmaceutically acceptable isotopically labeled compounds, which are identical to those recited in one of the formulae provided, but for the fact that one or more atoms are replaced by an atom having an atomic mass or mass number different from the atomic mass or mass number usually found in nature.

Isotopically labeled compounds of the invention can generally be prepared by conventional techniques known to those skilled in the art or by processes analogous to those described herein, using an appropriate isotopically labeled reagent in place of the nonlabeled reagent otherwise employed.

Examples of isotopes that may be incorporated into compounds of the invention include isotopes of hydrogen, carbon, nitrogen, oxygen, phosphorus, sulfur, fluorine and chlorine, such as, but not limited to, $^2H$, $^3H$, $^{13}C$, $^{14}C$, $^{15}N$, $^{18}O$, $^{17}O$, $^{32}P$, $^{35}S$, $^{18}F$ and $^{36}Cl$. Certain isotopically labeled compounds of the invention, for example those into which radioactive isotopes such as $^2H$, $^3H$ or $^{14}C$ are incorporated, are useful in one or both of drug or substrate tissue distribution assays. Tritiated, i.e., $^3H$, and carbon 14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Substitution with positron emitting isotopes, such as $^{11}C$, $^{18}F$, $^{15}O$ and $^{13}N$, may be useful in Positron Emission Topography (PET) studies for examining substrate receptor occupancy. Isotopically labeled compounds of the invention may generally be prepared by carrying out the procedures disclosed in the Schemes and/or in the Examples and Preparations below, by substituting an isotopically labeled reagent for a non-isotopically labeled reagent.

Pharmaceutically acceptable solvates in accordance with the invention include those wherein the solvent of crystallization may be isotopically substituted, e.g., $D_2O$, $d^6$-acetone, $d^6$-DMSO.

Unless indicated otherwise, all references herein to the inventive compounds include references to salts, solvates, hydrates and complexes thereof, and to solvates, hydrates and complexes of salts thereof, including polymorphs, stereoisomers, and isotopically labelled versions thereof.

Compounds of the invention may exist in the form of pharmaceutically acceptable salts such as, e.g., acid addition salts and base addition salts of the compounds of one of the formulae provided herein. As used herein, the term "pharmaceutically acceptable salt" refers to those salts which retain the biological effectiveness and properties of the parent compound. The phrase "pharmaceutically acceptable salt(s)", as used herein, unless otherwise indicated, includes salts of acidic or basic groups which may be present in the compounds of the formulae disclosed herein.

For example, the compounds of the invention that are basic in nature are capable of forming a wide variety of salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention can be prepared by treating the base compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

The acids that may be used to prepare pharmaceutically acceptable acid addition salts of such basic compounds of those that form nontoxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate salts.

Examples of salts include, but are not limited to, acetate, acrylate, benzenesulfonate, benzoate (such as chlorobenzoate, methylbenzoate, dinitrobenzoate, hydroxybenzoate, and methoxybenzoate), bicarbonate, bisulfate, bisulfite, bitartrate, borate, bromide, butyne-1,4-dioate, calcium edetate, camsylate, carbonate, chloride, caproate, caprylate, clavulanate, citrate, decanoate, dihydrochloride, dihydrogenphosphate, edetate, edislyate, estolate, esylate, ethylsuccinate, formate, fumarate, gluceptate, gluconate, glutamate, glycollate, glycollylarsanilate, heptanoate, hexyne-1,6-dioate, hexylresorcinate, hydrabamine, hydrobromide, hydrochloride, g hydroxy butyrate, iodide, isobutyrate, isothionate, lactate, lactobionate, laurate, malate, maleate, malonate, mandelate, mesylate, metaphosphate, methane sulfonate, methylsulfate, monohydrogenphosphate, mucate, napsylate, naphthalene-1-sulfonate, naphthalene-2-sulfonate, nitrate, oleate, oxalate, pamoate (embonate), palmitate, pantothenate, phenylacetates, phenylbutyrate, phenylpropionate, phthalate, phosphate/diphosphate, polygalacturonate, propanesulfonate, propionate, propiolate, pyrophosphate, pyrosulfate, salicylate, stearate, subacetate, suberate, succinate, sulfate, sulfonate, sulfite, tannate, tartrate, teoclate, tosylate and valerate salts.

Illustrative examples of suitable salts include organic salts derived from amino acids, such as glycine and arginine, ammonia, primary, secondary, and tertiary amines and cyclic amines, such as piperidine, morpholine and piperazine, and inorganic salts derived from sodium, calcium, potassium, magnesium, manganese, iron, copper, zinc, aluminum and lithium.

The compounds of the invention that include a basic moiety, such as an amino group, may form pharmaceutically acceptable salts with various amino acids, in addition to the acids mentioned above.

Alternatively, the compounds useful that are acidic in nature may be capable of forming base salts with various pharmacologically acceptable cations. Examples of such salts include the alkali metal or alkaline earth metal salts and particularly, the sodium and potassium salts. These salts are all prepared by conventional techniques. The chemical bases which are used as reagents to prepare the pharmaceutically acceptable base salts of this invention are those which form nontoxic base salts with the acidic compounds herein. These salts may be prepared by any suitable method, for example, treatment of the free acid with an inorganic or organic base, such as an amine (primary, secondary or tertiary), an alkali metal hydroxide or alkaline earth metal hydroxide, or the like. These salts can also be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The chemical bases that may be used as reagents to prepare pharmaceutically acceptable base salts of the compounds of the invention that are acidic in nature are those that form nontoxic base salts with such compounds. Such nontoxic base salts include, but are not limited to, those derived from such pharmacologically acceptable cations such as alkali metal cations (e.g., potassium and sodium) and alkaline earth metal cations (e.g., calcium and magnesium), ammonium or water soluble amine addition salts such as N-methylglucamine (meglumine), and the lower alkanolammonium and other base salts of pharmaceutically acceptable organic amines.

Hemisalts of acids and bases may also be formed, for example, hemisulphate and hemicalcium salts.

For a review on suitable salts, see Handbook of Pharmaceutical Salts: Properties, Selection, and Use by Stahl and Wermuth (Wiley VCH, 2002). Methods for making pharmaceutically acceptable salts of compounds of the invention, and of interconverting salt and free base forms, are known to one of skill in the art.

Salts of the present invention can be prepared according to methods known to those of skill in the art. A pharmaceutically acceptable salt of the inventive compounds can be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost nonionized.

It will be understood by those of skill in the art that the compounds of the invention in free base form having a basic functionality may be converted to the acid addition salts by treating with a stoichiometric excess of the appropriate acid. The acid addition salts of the compounds of the invention may be reconverted to the corresponding free base by treating with a stoichiometric excess of a suitable base, such as potassium carbonate or sodium hydroxide, typically in the presence of aqueous solvent, and at a temperature of between about 0° C. and 100° C. The free base form may be isolated by conventional means, such as extraction with an organic solvent. In addition, acid addition salts of the compounds of the invention may be interchanged by taking advantage of differential solubilities of the salts, volatilities or acidities of the acids, or by treating with the appropriately loaded ion exchange resin. For example, the interchange may be affected by the reaction of a salt of the compounds of the invention with a slight stoichiometric excess of an acid of a lower pK than the acid component of the starting salt. This conversion is typically carried out at a temperature between about 0° C. and the boiling point of the solvent being used as the medium for the procedure. Similar exchanges are possible with base addition salts, typically via the intermediacy of the free base form.

The compounds of the invention may exist in both unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm. The term 'solvate' is used herein to describe a molecular complex comprising the compound of the invention and one or more pharmaceutically acceptable solvent molecules, for example, ethanol. The term 'hydrate' is employed when the solvent is water. Pharmaceutically acceptable solvates in accordance with the invention include hydrates and solvates wherein the solvent of crystallization may be isotopically substituted, e.g. $D_2O$, d6-acetone, d6-DMSO.

The invention also relates to prodrugs of the compounds of the formulae provided herein. Thus, certain derivatives of compounds of the invention which may have little or no pharmacological activity themselves can, when administered to a patient, be converted into the inventive compounds, for example, by hydrolytic cleavage. Such derivatives are referred to as 'prodrugs'. Further information on the use of prodrugs may be found in 'Prodrugs as Novel Delivery Systems, Vol. 14, ACS Symposium Series (T Higuchi and W Stella); 'Bioreversible Carriers in Drug Design', Pergamon Press, 1987 (ed. E B Roche, American Pharmaceutical Association); Guarino, V. R; Stella, V. J.: Biotech Pharm. Aspects 2007 5 (Pt2) 133-187; and J. Rautio et al. Nature Reviews Drug Discovery, 17, 559-587 (2018) the disclosures of which are incorporated herein by reference in their entireties.

Prodrugs in accordance with the invention can, for example, be produced by replacing appropriate functionalities present in the inventive compounds with certain moieties known to those skilled in the art as 'promoieties' as described, for example, in "Design of Prodrugs" by H Bundgaard (Elsevier, 1985), the disclosure of which is incorporated herein by reference in its entirety.

Some non-limiting examples of prodrugs in accordance with the invention include:
  (i) when a compound contains a carboxylic acid functionality (—COOH), an ester thereof, for example, replacement of the hydrogen with (C1-C6)alkyl;
  (ii) when a compound contains an alcohol functionality (—OH), an ether thereof, for example, replacement of the hydrogen with (C1-C6)alkanoyloxymethyl, or with a phosphate ether group; and (iii) when a compound contains a primary or secondary amino functionality (NH$_2$ or NHR where R is not H), an amide thereof, for example, replacement of one or both hydrogens with a suitably metabolically labile group, such as an amide, carbamate, urea, phosphonate, sulfonate, etc.

Further examples of replacement groups in accordance with the foregoing examples and examples of other prodrug types may be found in the aforementioned references.

Finally, certain inventive compounds may themselves act as prodrugs of other of the inventive compounds.

Also included within the scope of the invention are metabolites of compounds of the formulae described herein, i.e., compounds formed in vivo upon administration of the drug, often by oxidation or dealkylation. Some examples of metabolites in accordance with the invention include, but are not limited to, (i) where the compound of the invention contains an alkyl group, a hydroxyalkyl derivative thereof (—CH>—COH):
(ii) where the compound of the invention contains an alkoxy group, a hydroxy derivative thereof (—OR→—OH);
(iii) where the compound of the invention contains a tertiary amino group, a secondary amino derivative thereof (—NRR'→—NHR or —NHR');
(iv) where the compound of the invention contains a secondary amino group, a primary derivative thereof (—NHR→—NH$_2$);
(v) where the compound of the invention contains a phenyl moiety, a phenol derivative thereof (-Ph→-PhOH);
(vi) where the compound of the invention contains an amide group, a carboxylic acid derivative thereof (—CONH$_2$→COOH); and
(vii) where the compound contains a hydroxy or carboxylic acid group, the compound may be metabolized by conjugation, for example with glucuronic acid to form a glucuronide. Other routes of conjugative metabolism exist. These pathways are frequently known as Phase 2 metabolism and include, for example, sulfation or acetylation. Other functional groups, such as NH groups, may also be subject to conjugation.

In one embodiment, provided herein are solid forms of 8-((2-fluoro-4-(methylthio)phenyl)amino)-2-(2-hydroxyethoxy)-7-methyl-3,4-dihydro-2,7-naphthyridine-1,6(2H,7H)-dione. In one embodiment, the solid form is a crystalline form. In one embodiment, the solid form is an amorphous form.

The terms "crystalline" as used herein, means having a regularly repeating arrangement of molecules or external face planes. A single compound may give rise to a variety of crystalline forms where each form has different and distinct solid state physical properties, such as different solubility profiles, dissolution rates, melting point temperatures, flowability, and/or different X-ray diffraction peaks. The differences in physical properties may affect pharmaceutical parameters such as storage stability, compressibility and density (which can be important in formulation and product manufacturing), and dissolution rate (which can be an important factor in bioavailability).

The term 'amorphous' refers to a state in which the material lacks long range order at the molecular level and, depending upon temperature, may exhibit the physical properties of a solid or a liquid. Typically, such materials do not give distinctive X-ray diffraction patterns and, while exhibiting the properties of a solid, are more formally described as a liquid. Upon heating, a change from solid to liquid properties occurs which is characterized by a change of state, typically second order ('glass transition').

There are a number of analytical methods one of ordinary skill in the art in solid-state chemistry can use to analyze solid forms. Powder X-ray diffraction may also be suitable for quantifying the amount of a crystalline solid form (or forms) in a mixture. In powder X-ray diffraction, X-rays are directed onto a crystalline powder and the intensity of the diffracted X-rays is measured as a function of the angle between the X-ray source and the beam diffracted by the sample. The intensity of these diffracted X-rays can be plotted on a graph as peaks with the x-axis being the angle (this is known as the "2-theta" angle) between the X-ray source and the diffracted X-rays and with the y-axis being the intensity of the diffracted X-rays. This graph is called a powder X-ray diffraction pattern or powder pattern. Different crystalline solid forms exhibit different powder patterns because the location of the peaks on the x-axis is a property of the solid-state structure of the crystal.

One of ordinary skill in the art will appreciate that a typical precision of the 2-theta x-axis value of a peak in a powder pattern is on the order of plus or minus 0.2 degrees 2-theta (±0.2 degrees 2 theta). Thus, for example, a diffraction peak that appears at "about 18.0 degrees 2-theta" means that the peak appears at 18.0 degrees±0.2 degrees 2-theta, i.e., it could be between 17.8 degrees 2-theta and 18.2 degrees 2-theta when measured on most X-ray diffractometers under most conditions. Further, one skilled in the art will appreciate that the relative peak intensities will show inter-apparatus variability as well as variability due to degree of crystallinity, preferred orientation, prepared sample surface, and other factors known to those skilled in the art and should be taken as qualitative measures only. Accordingly, as used herein, the term "essentially the same" with reference to powder X-ray diffraction peak positions, means that typical variability in peak position and intensity are on the order of ±0.2 degrees 2 theta.

Powder X-ray diffraction is just one of several analytical techniques one may use to characterize and/or identify crystalline solid forms. Spectroscopic techniques such as Raman (including microscopic Raman), infrared, and solid state NMR spectroscopies may be used to characterize and/or identify crystalline solid forms. These techniques may also be used to quantify the amount of one or more crystalline solid forms in a mixture and peak values can also be reported with the modifier "about" in front of the peak values.

The term "anhydrous" as used herein, refers to a crystalline form without any solvent or water molecules in the crystal lattice The term "hydrate" refers to a solvate comprising the compound and a stoichiometric or non-stoichiometric amount of water. The term "monohydrate" refers to a hydrate comprising one molecule of water per molecule of compound (i.e., a 1:1 stoichiometry of water to compound).

In one embodiment, the invention provides crystalline anhydrous 8-((2-fluoro-4-(methylthio)phenyl)amino)-2-(2-hydroxyethoxy)-7-methyl-3,4-dihydro-2,7-naphthyrdine-1,6(2H,7H)-dione, Form 1.

In one embodiment, crystalline anhydrous 8-((2-fluoro-4-(methylthio)phenyl)amino)-2-(2-hydroxyethoxy)-7-methyl-3,4-dihydro-2,7-naphthyridine-1,6(2H,7H)-dione, Form 1 is characterized by powder X-ray diffraction (PXRD) (2-theta).

Table X provides a PXRD peak list for crystalline anhydrous 8-((2-fluoro-4-(methylthio)phenyl)amino)-2-(2-hydroxyethoxy)-7-methyl-3,4-dihydro-2,7-naphthyrdine-1,6 (2H,7H)-dione, Form 1 in degrees 2-theta (±0.2 degrees 2-theta).

TABLE X

| Angle (degrees 2-Theta) | Rel. Intensity (%) |
| --- | --- |
| 5.0 | 8.1 |
| 8.7 | 7.5 |
| 9.3 | 18.3 |
| 10.8 | 100.0 |
| 14.5 | 8.1 |
| 15.3 | 17.4 |
| 18.8 | 9.9 |
| 20.5 | 8.4 |

In one embodiment, the invention provides crystalline anhydrous 8-((2-fluoro-4-(methylthio)phenyl)amino)-2-(2-hydroxyethoxy)-7-methyl-3,4-dihydro-2,7-naphthyridine-1,6(2H,7H)-dione, Form 1 having a PXRD pattern comprising characterizing peaks at 5.0, 8.7, 9.3, 10.8, 14.5, 15.3, 18.8 and 20.5 degrees 2-theta (±0.2 degrees 2-theta).

In one embodiment, the invention provides crystalline anhydrous 8-((2-fluoro-4-(methylthio)phenyl)amino)-2-(2-hydroxyethoxy)-7-methyl-3,4-dihydro-2,7-naphthyridine-1,6(2H,7H)-dione, Form 1 having a PXRD pattern comprising peaks at 2-theta values essentially the same as shown in FIG. 1.

In one embodiment, the invention provides crystalline anhydrous 8-((2-fluoro-4-(methylthio)phenyl)amino)-2-(2-hydroxyethoxy)-7-methyl-3,4-dihydro-2,7-naphthyridine-1,6(2H,7H)-dione, Form 2.

In one embodiment, crystalline anhydrous 8-((2-fluoro-4-(methylthio)phenyl)amino)-2-(2-hydroxyethoxy)-7-methyl-3,4-dihydro-2,7-naphthyridine-1,6(2H,7H)-dione, Form 2 is characterized by powder X-ray diffraction (PXRD) (2-theta). In one embodiment, PXRD analysis of crystalline anhydrous 8-((2-fluoro-4-(methylthio)phenyl)amino)-2-(2-hydroxyethoxy)-7-methyl-3,4-dihydro-2,7-naphthyridine-1,6(2H,7H)-dione, Form 2 is conducted at 25° C. and at a relative humidity below 10%, for example as described in Example 77.

Table Y provides a PXRD peak list for crystalline anhydrous 8-((2-fluoro-4-(methylthio)phenyl)amino)-2-(2-hydroxyethoxy)-7-methyl-3,4-dihydro-2,7-naphthyridine-1,6 (2H,7H)-dione, Form 2 in degrees 2-theta (±0.2 degrees 2-theta).

TABLE Y

| Angle (degrees 2-Theta) | Rel. Intensity (%) |
| --- | --- |
| 7.1 | 5.2 |
| 9.4 | 100.0 |
| 12.4 | 8.8 |
| 12.8 | 5.1 |
| 14.3 | 14.2 |
| 15.6 | 14.8 |
| 16.4 | 3.9 |
| 17.4 | 5.3 |
| 18.5 | 7.3 |
| 18.9 | 43.4 |
| 19.5 | 17.7 |
| 19.9 | 35.2 |
| 21.1 | 20.7 |
| 21.4 | 7.9 |
| 23.2 | 12.1 |
| 23.7 | 9.1 |

TABLE Y-continued

| Angle (degrees 2-Theta) | Rel. Intensity (%) |
| --- | --- |
| 24.8 | 6.2 |
| 25.6 | 31.2 |
| 27.6 | 8.5 |
| 30.3 | 4.6 |
| 33.2 | 5.5 |
| 33.5 | 5.3 |
| 37.5 | 6.6 |

In one embodiment, the invention provides crystalline anhydrous 8-((2-fluoro-4-(methylthio)phenyl)amino)-2-(2-hydroxyethoxy)-7-methyl-3,4-dihydro-2,7-naphthyridine-1,6(2H,7H)-dione, Form 2 having a PXRD pattern comprising characterizing peaks at 7.1, 9.4, 12.4, 12.8, 14.3, 15.6, 16.4, 17.4, 18.5, 18.9, 19.5, 19.9, 21.1, 21.4, 23.2, 23.7, 24.8, 25.6, 27.6, 30.3, 33.2, 33.5, and 37.5 degrees 2-theta (±0.2 degrees 2-theta).

Figure 2:
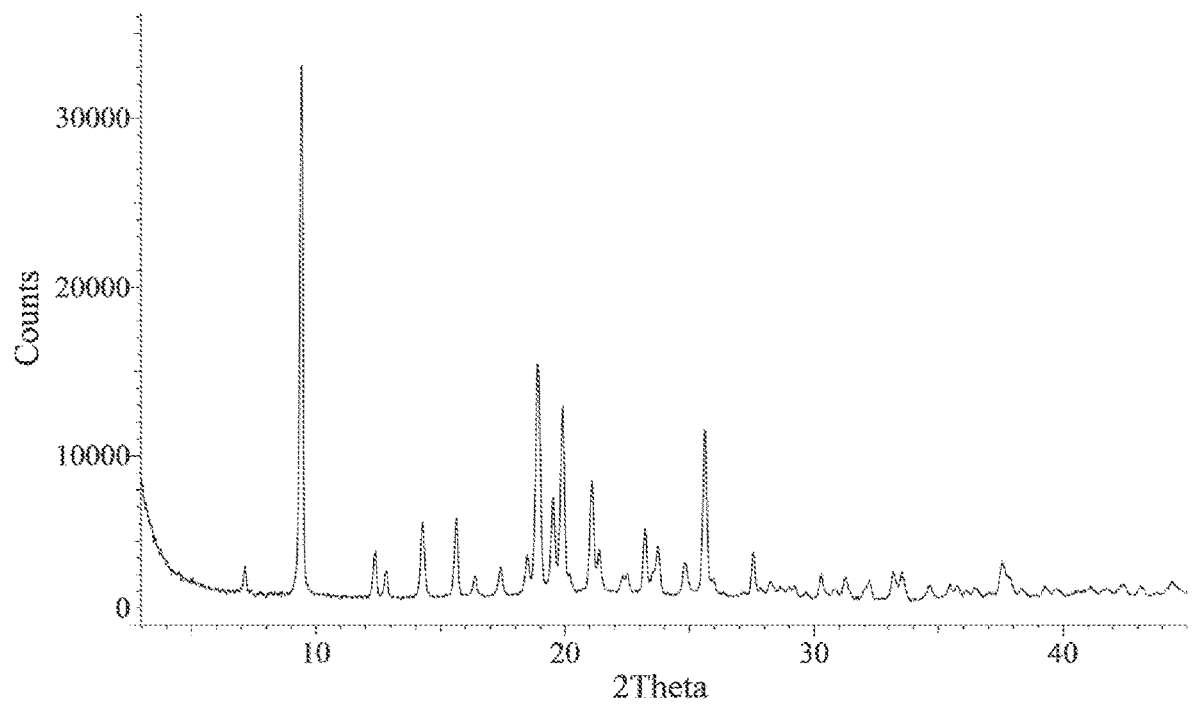
FIG. 2. depicts a powder X-ray diffraction pattern of crystalline anhydrous 8-((2-fluoro-4-(methylthio)phenyl)amino)-2-(2-hydroxyethoxy)-7-methyl-3,4-dihydro-2,7-naphthyridine-1,6(2H,7H)-dione, Form 2.

In one embodiment, the invention provides crystalline anhydrous 8-((2-fluoro-4-(methylthio)phenyl)amino)-2-(2-hydroxyethoxy)-7-methyl-3,4-dihydro-2,7-naphthyrdine-1,6(2H,7H)-dione, Form 2 having a PXRD pattern comprising peaks at 2-theta values essentially the same as shown in FIG. 2.

In one embodiment, the invention provides crystalline monohydrate 8-((2-fluoro-4-(methylthio)phenyl)amino)-2-(2-hydroxyethoxy)-7-methyl-3,4-dihydro-2,7-naphthyridine-1,6(2H, 7H)-dione, Form 3.

In one embodiment, crystalline monohydrate 8-((2-fluoro-4-(methylthio)phenyl)amino)-2-(2-hydroxyethoxy)-7-methyl-3,4-dihydro-2,7-naphthyridine-1,6(2H,7H)-dione, Form 3 is characterized by powder X-ray diffraction (PXRD) (2-theta). In one embodiment, PXRD analysis of crystalline monohydrate 8-((2-fluoro-4-(methylthio)phenyl)amino)-2-(2-hydroxyethoxy)-7-methyl-3,4-dihydro-2,7-naphthyridine-1,6(2H,7H)-dione, Form 3 is conducted at 25° C. and at relative humidity above 30%.

Table Z provides a PXRD peak list for crystalline monohydrate 8-((2-fluoro-4-(methylthio)phenyl)amino)-2-(2-hydroxyethoxy)-7-methyl-3,4-dihydro-2,7-naphthyridine-1,6 (2H, 7H)-dione, Form 3 in degrees 2-theta (±0.2 degrees 2-theta).

TABLE Z

| Angle (degrees 2-Theta) | Rel. Intensity (%) |
| --- | --- |
| 6.9 | 10.0 |
| 9.1 | 100.0 |
| 11.8 | 6.0 |
| 12.0 | 21.1 |
| 13.7 | 11.6 |
| 14.0 | 18.1 |
| 15.2 | 31.2 |
| 15.8 | 4.3 |
| 18.0 | 72.2 |
| 18.3 | 19.3 |
| 19.0 | 27.7 |
| 19.3 | 7.6 |
| 20.2 | 37.2 |
| 20.9 | 8.8 |
| 21.6 | 49.2 |
| 22.6 | 19.2 |
| 23.6 | 30.5 |
| 24.0 | 27.9 |
| 24.9 | 18.1 |

TABLE Z-continued

| Angle (degrees 2-Theta) | Rel. Intensity (%) |
|---|---|
| 25.2 | 12.3 |
| 25.8 | 69.7 |
| 27.5 | 32.0 |
| 28.1 | 11.5 |
| 28.4 | 5.9 |
| 29.8 | 15.0 |
| 30.9 | 11.2 |
| 31.7 | 6.2 |
| 32.3 | 7.3 |
| 36.5 | 13.2 |

In one embodiment, the invention provides crystalline monohydrate 8-((2-fluoro-4-(methylthio)phenyl)amino)-2-(2-hydroxyethoxy)-7-methyl-3,4-dihydro-2,7-naphthyridine-1,6(2H,7H)-dione, Form 3 having a PXRD pattern comprising characterizing peaks at 13.7, 18.0 and 18.3 degrees 2-theta (±0.2 degrees 2-theta).

In one embodiment, the invention provides crystalline monohydrate 8-((2-fluoro-4-(methylthio)phenyl)amino)-2-(2-hydroxyethoxy)-7-methyl-3,4-dihydro-2,7-naphthyridine-1,6(2H,7H)-dione, Form 3 having a PXRD pattern comprising characterizing peaks at 6.9, 9.1, 13.7, 18.0 and 18.3 degrees 2-theta (±0.2 degrees 2-theta).

In one embodiment, the invention provides crystalline monohydrate 8-((2-fluoro-4-(methylthio)phenyl)amino)-2-(2-hydroxyethoxy)-7-methyl-3,4-dihydro-2,7-naphthyridine-1,6(2H,7H)-dione, Form 3 having a PXRD pattern comprising characterizing peaks at 6.9, 9.1, 11.8, 12.0, 13.7, 14.0, 15.2, 15.8, 18.0, 18.3, 19.0, 19.3, 20.2, 20.9, 21.6, 22.6, 23.6, 24.0, 24.9, 25.2, 25.8, 27.5, 28.1, 28.4, 29.8, 30.9, 31.7, 32.3 and 36.5 degrees 2-theta (±0.2 degrees 2-theta).

Figure 3:
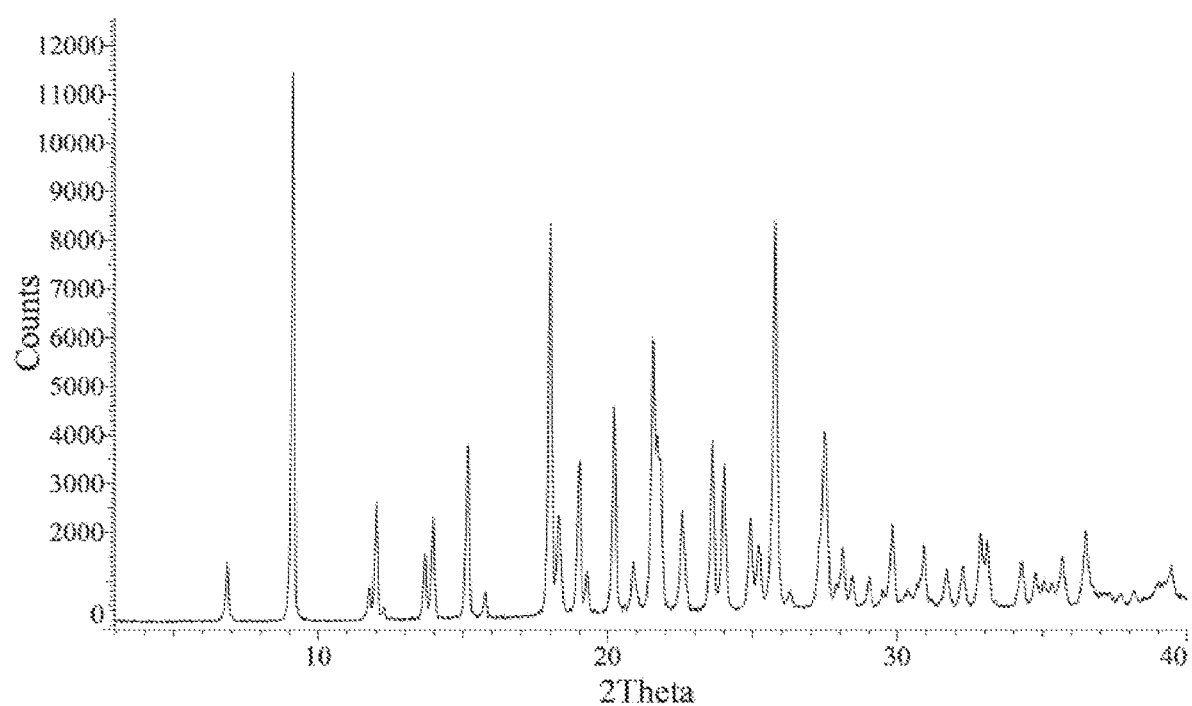
FIG. 3. depicts a powder X-ray diffraction pattern of crystalline monohydrate 8-((2-fluoro-4-(methylthio)phenyl)amino)-2-(2-hydroxyethoxy)-7-methyl-3,4-dihydro-2,7-naphthyridine-1,6(2H,7H)-dione, Form 3.

In one embodiment, the invention provides crystalline monohydrate 8-((2-fluoro-4-(methylthio)phenyl)amino)-2-(2-hydroxyethoxy)-7-methyl-3,4-dihydro-2,7-naphthyridine-1,6(2H,7H)-dione, Form 3 having a PXRD pattern comprising peaks at 2-theta values essentially the same as shown in FIG. 3.

In one embodiment, the invention provides amorphous 8-((2-fluoro-4-(methylthio)phenyl)amino)-2-(2-hydroxyethoxy)-7-methyl-3,4-dihydro-2,7-naphthyridine-1,6(2H,7H)-dione, Form 4.

In one embodiment, amorphous 8-((2-fluoro-4-(methylthio)phenyl)amino)-2-(2-hydroxyethoxy)-7-methyl-3,4-dihydro-2,7-naphthyridine-1,6(2H,7H)-dione, Form 4 is characterized by powder X-ray diffraction (PXRD) (2-theta).

Figure 4:
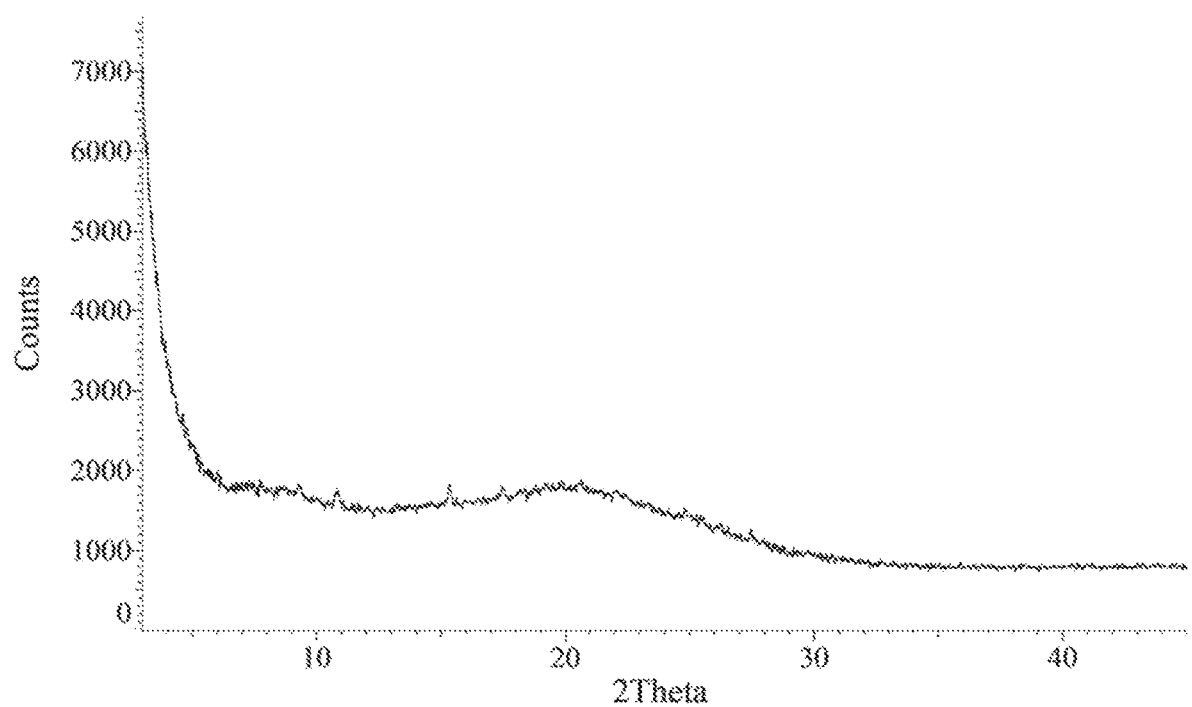
FIG. 4. depicts a powder X-ray diffraction pattern of amorphous 8-((2-fluoro-4-(methylthio)phenyl)amino)-2-(2-hydroxyethoxy)-7-methyl-3,4-dihydro-2,7-naphthyridine-1,6(2H,7H)-dione, Form 4.

In one embodiment, the invention provides amorphous 8-((2-fluoro-4-(methylthio)phenyl)amino)-2-(2-hydroxyethoxy)-7-methyl-3,4-dihydro-2,7-naphthyridine-1,6(2H,7H)-dione, Form 4 having a PXRD pattern comprising peaks at 2-theta values essentially the same as shown in FIG. 4.

The invention further provides therapeutic methods and uses comprising administering the compounds of the invention, or pharmaceutically acceptable salts thereof, alone or in combination with other therapeutic agents or palliative agents.

Compounds of Formula I and Formula II, and pharmaceutically acceptable salts thereof are useful for treating diseases and disorders which can be treated with a MEK kinase inhibitor, such as MEK-associated diseases and disorders, e.g., for the treatment of abnormal cell growth, such tumors, for example MEK-associated tumors. The ability of compounds of Formula I and Formula II, and pharmaceutically acceptable salts thereof, to act as MEK inhibitors may be demonstrated by the assay described in Example A. $IC_{50}$ values are shown in Table A.

Accordingly, in one embodiment, provided herein is a method of treating a tumor, comprising administering to a subject in need thereof a therapeutically effective amount of a compound of Formula I or a pharmaceutically acceptable salt thereof, or a compound of Formula II or a pharmaceutically acceptable salt thereof. In one embodiment, the tumor is a MEK-associated tumor.

As used herein, the terms "MEK kinase inhibitor" and "MEK inhibitor" are used interchangeably and refer to a compound that inhibits the mitogen-activated protein kinase kinase enzymes MEK1 and/or MEK2.

The terms "MEK-associated" and "MEK-mediated" are used interchangeably and refer to a disease or disorder having constitutive activation of a MEK kinase which can be treated with a MEK inhibitor. Examples include a MEK-associated abnormal cell growth such as MEK-associated tumors, e.g., MEK-associated cancers. In one embodiment, the term "MEK-associated" refers to a disease or disorder having a dysregulation of the expression or activity of a MEK kinase, or a dysregulation of a BRAF gene or a BRAF kinase.

The phrase "dysregulation of the expression or activity of a MEK kinase" refers to gene amplification that results in overexpression of a MEK protein or an autocrine activity resulting from the overexpression of a MEK gene in a cell that results in a pathogenic increase in the activity of a kinase domain of a MEK protein (e.g., a constitutively active kinase domain of a MEK protein) in a cell.

The phrase "dysregulation of a BRAF gene or a BRAF kinase" refers to a genetic mutation (e.g., a BRAF gene translocation that results in the expression of a fusion protein, a deletion in a BRAF gene that results in the expression of a BRAF protein that includes a deletion of at least one amino acid as compared to the wild-type BRAF protein, or a mutation in a BRAF gene that results in the expression of a BRAF protein with one or more point mutations as compared to a wild-type BRAF protein). As another example, a dysregulation of a BRAF gene, a BRAF protein, or expression or activity, or level of any of the same, can be a mutation in a BRAF gene that encodes a BRAF protein that is constitutively active or has increased activity as compared to a protein encoded by a BRAF gene that does not include the mutation. For example, a dysregulation of a BRAF gene, a BRAF protein, or expression or activity, or level of any of the same, can be the result of a gene or chromosome translocation which results in the expression of a fusion protein that contains a first portion of BRAF that includes a functional kinase domain, and a second portion of a partner protein (i.e., that is not BRAF).

In one embodiment, the MEK-associated disease or disorder has an activating BRAF mutation. In one embodiment, the MEK-associated disease or disorder is a MEK-associated cancer having an activating BRAF mutation. Non-limiting examples of BRAF mutations include BRAF V600 mutations, e.g., V600E, V600D, V600K, V600R and V600S. In one embodiment, the BRAF mutation is a V600E mutation. In one embodiment, the BRAF mutation is a V600K mutation.

In one embodiment, the MEK-associated disease or disorder is a MEK-associated tumor has one or more BRAF fusions that lead to constitutive kinase activation and transformation, including but not limited to KIAA11549-BRAF, MKRN1-BRAF, TRIM24-BRAF, AGAP3-BRAF, ZC3HAV1-BRAF, AKAP9-BRAF, CCDC6-BRAF, AGK- BRAF, EPS15-BRAF, NUP214-BRAF, ARMC10-BRAF, BTF3L4-BRAF, GHR-BRAF, ZC3HAV1-BRAF, ZNF767-BRAF, CCDC91-BRAF, DYNC112-BRAF, ZKSCAN1-BRAF, GTF2I-BRAF, MZT1-BRAF, RAD18-BRAF, CUX1-BRAF, SLC12A7-BRAF, MYRIP-BRAF, SND1-BRAF, NUB1-BRAF, KLHL7-BRAF, TANK-BRAF, RBMS3-BRAF, STRN3-BRAF, STK35-BRAF, ETFA-BRAF, SVOPL-BRAF, JHDM1D-BRAF, or BCAP29-BRAF.

In one embodiment, the MEK-associated disease or disorder is a MEK-associated tumor having a BRAF-fusion protein, wherein the tumor is breast carcinoma (e.g., breast invasive ductal carcinoma) colorectal carcinoma (e.g., colon adenocarcinoma), esophageal carcinoma (e.g., esophagus adenocarcinoma), glioma (e.g., brain desmoplastic infantile ganglioglioma, brain pilocytic astrocytoma, brain pleomorphic xanthoastrocytoma, spinal cord low-grade glioma (NOS), anaplastic oligodendroglioma, anaplastic ganglioglioma), head & neck carcinoma (e.g., head and neck neuroendocrine carcinoma), lung carcinoma (e.g., lung adenocarcinoma, lung non-small-cell lung cancer (NOS)), melanoma (e.g., cutaneous melanoma Spitzoid, mucosal melanoma non-Spitzoid, cutaneous melanoma Spitzoid, unknown primary melanoma, cutaneous melanoma non-Spitzoid), pancreatic carcinoma (e.g., adenocarcinoma, pancreas acinar cell carcinoma), prostatic carcinoma (e.g., prostate acinar adenocarcinoma), sarcoma (malignant solid fibrous tumor), thyroid carcinoma (thyroid papillary carcinoma), unknown primary carcinoma (e.g., unknown primary, adenocarcinoma), pleura mesothelioma, rectum adenocarcinoma, uterus endometrial carcinoma (e.g., uterus endometrial adenocarcinoma (NOS)) or ovary serous carcinoma.

In one embodiment, the MEK-associated cancer is selected from the cancers having the BRAF-fusion proteins described in Table 1 (J. S. Ross, et al., Int. J. Cancer 138, 881-890 (2016)).

TABLE 1

Exemplary BRAF Fusion Partners and Cancers

| Tumor group | histology | tumor type | fusion |
| --- | --- | --- | --- |
| breast carcinoma | | | BCAP29-BRAF |
| breast carcinoma | breast carcinoma | metastatic | KIAA11549-BRAF |
| colorectal carcinoma | colon adenocarcinoma | primary | MKRN1-BRAF |
| colorectal carcinoma | colon adenocarcinoma | metastatic | TRIM24-BRAF |
| colorectal carcinoma | coion adenocarcinoma | primary | AGAP3-BRAF |
| esophageal carcinoma | esophagus adenocarcinoma | primary | ZC3HAV1-BRAF |
| glioma | brain desmoplastic infantile ganglioglioma | primary | KIAA11549-BRAF |
| glioma | brain pilocytic astrocytoma | primary | KIAA11549-BRAF |
| glioma | brain pleomorphic xanthoastrocytoma | primary | KIAA11549-BRAF |
| glioma | spinal cord low-grade glioma (NOS) | primary | KIAA11549-BRAF |
| glioma | brain pilocytic astrocytoma | primary | AKAP9-BRAF |
| glioma | brain pleomorphic xanthoastrocytoma | primary | CCDC6-BRAF |
| glioma | brain pleomorphic xanthoastrocytoma | primary | AGK-BRAF |
| glioma | not pilocytic; anaplastic oligodendroglioma | primary | AGK-BRAF |
| glioma | not pilocytic; anaplastic ganglioglioma | primary | KIAA11549-BRAF |
| head & neck carcinoma | head and neck neuroendocrine carcinoma | primary | MKRN1-BRAF |
| lung carcinoma | lung adenocarcinoma | metastatic | EPS15-BRAF |
| lung carcinoma | lung non-small cell lung cancer (NOS) | primary | NUP214-BRAF |
| lung carcinoma | lung adenocarcinoma | primary | ARMC10-BRAF |
| lung carcinoma | lung adenocarcinoma | primary | BTF3L4-BRAF |
| lung carcinoma | lung adenocarcinoma | primary | AGK-BRAF |
| lung carcinoma | lung adenocarcinoma | metastatic | GHR-BRAF |
| lung carcinoma | lung adenocarcinoma | primary | ZC3HAV1-BRAF |
| lung carcinoma | lung non-small cell lung cancer (NOS) | primary | TRIM224-BRAF |
| melanoma | cutaneous melanoma Spitzoid | primary | TRIM24-BRAF |
| melanoma | mucosal melanoma non-Spitzoid | metastatic | ZNF767-BRAF |
| melanoma | cutaneious melanoma non-Spitzoid | metastatic | CCDC91-BRAF |
| melanoma | cutaneous melanoma Spitzoid | primary | DYNC112-BRAF |
| melanoma | cutaneous melanoma Spitzoid | metastatic | AKAP9-BRAF |
| melanoma | cutaneous melanoma Spitzoid | metastatic | ZKSCAN1-BRAF |
| melanoma | unknown primary melanoma | metastatic | GTF2I-BRAF |
| melanoma | cutaneous melanoma non-Spitzoid | metastatic | AGAP3-BRAF |
| melanoma | cutaneous melanoma Spitzoid | metastatic | AGK-BRAF |
| melanoma | cutaneous melanoma Spitzoid | metastatic | MZT1-BRAF |
| melanoma | cutaneious melanoma non-Spitzoid | primary | RAD18-BRAF |
| melanoma | cutaneous melanoma Spitzoid | metastatic | CUX1-BRAF |
| melanoma | cutaneous melanoma Spitzoid | metastatic | SLC12A7-BRAF |

TABLE 1-continued

Exemplary BRAF Fusion Partners and Cancers

| Tumor group | histology | tumor type | fusion |
|---|---|---|---|
| pancreatic carcinoma | pancreas ductal adenocarcinoma | primary | MYRIP-BRAF |
| pancreatic carcinoma | pancreas acinar cell carcinoma | metastatic | SND1-BRAF |
| prostatic carcinoma | prostate acinar adenocarcinoma | metastatic | NUB1-BRAF |
| sarcoma | malignant solid fibrous tumor | primary | KIAA1549-BRAF |
| thyroid carcinoma | thyroid papillary carcinoma | primary | KLHL7-BRAF |
| thyroid carcinoma | thyroid papillary carcinoma | primary | TANK-BRAF |
| thyroid carcinoma | thyroid papillary carcinoma | metastatic | RBMS3-BRAF |
| unknown primary carcinoma | unknown primary, adenocarcinoma | metastatic | STRN3-BRAF |
| unknown primary carcinoma | unknown primary, carcinoma (NOS) | metastatic | SND1-BRAF |
| pleura mesothelioma | pleura mesothelioma | primary | STK35-BRAF |
| rectum adenocarcinoma | rectum adenocarcinoma | metastatic | ETFA-BRAF |
| uterus endometrial carcinoma | uterus endometrial adenocarcinoma (NOS) | metastatic | SVOPL-BRAF |
| ovary serous carcinoma | ovary serous carcinoma | metastatic | JHDM1D-BRAF |

In one embodiment, the MEK-associated tumor is a BRAF wild-type tumor.

The term "wild-type" describes a nucleic acid (e.g., a BRAF gene or a BRAF mRNA) that is typically found in a subject that does not have a disease or disorder related to the reference nucleic acid or protein.

The term "wild-type BRAF" describes a BRAF nucleic acid (e.g., a BRAF gene or a BRAF mRNA) or a BRAF protein that is found in a subject that does not have an activating BRAF-mutation.

"Abnormal cell growth", as used herein, unless otherwise indicated, refers to cell growth that is independent of normal regulatory mechanisms (e.g., loss of contact inhibition), for example, a tumor. Abnormal cell growth may be benign (not cancerous), or malignant (cancerous).

The terms "cancer" or "cancerous" refers to any malignant and/or invasive growth or tumor caused by abnormal cell growth. Cancer includes primary cancer that originates at a specific site in the body, a metastatic cancer that has spread from the place in which it started to other parts of the body, a recurrence from the original primary cancer after remission, and a second primary cancer that is a new primary cancer in a patient with a history of previous cancer of a different type from the second primary cancer. Cancer includes solid tumors named for the type of cells that form them, cancer of blood, bone marrow, or the lymphatic system. A solid tumor is an abnormal growth or mass of tissue that usually does not contain cysts or liquid areas. Examples of solid tumors are sarcomas, carcinomas, and lymphomas. Leukemias (cancers of the blood) generally do not form solid tumors (National Cancer Institute, Dictionary of Cancer Terms).

As used herein, terms "treat" or "treatment" refer to therapeutic or palliative measures. Beneficial or desired clinical results include, but are not limited to, alleviation, in whole or in part, of symptoms associated with a disease or disorder or condition, diminishment of the extent of disease, stabilized (i.e., not worsening) state of disease, delay or slowing of disease progression, amelioration or palliation of the disease state (e.g., one or more symptoms of the disease), and remission (whether partial or total), whether detectable or undetectable.

The term "treat" or "treating" a cancer as used herein means to administer a compound of the present invention to a subject having cancer, or diagnosed with cancer, to achieve at least one positive therapeutic effect, such as, for example, reduced number of cancer cells, reduced tumor size, reduced rate of cancer cell infiltration into peripheral organs, or reduced rate of tumor metastases or tumor growth, reversing, alleviating, or inhibiting the progress of, the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

For the purposes of this invention, beneficial or desired clinical results include, but are not limited to, one or more of the following: reducing the proliferation of (or destroying) neoplastic or cancerous cell; inhibiting metastasis or neoplastic cells; shrinking or decreasing the size of a tumor; an increase in the period of remission for a subject (e.g., as compared to the one or more metric(s) in a subject having a similar cancer receiving no treatment or a different treatment, or as compared to the one or more metric(s) in the same subject prior to treatment); decreasing symptoms resulting from the cancer; increasing the quality of life of those suffering from the cancer; decreasing the dose of other medications required to treat the cancer; delaying the progression of the cancer; curing the cancer; overcoming one or more resistance mechanisms of the cancer; and/or prolonging survival of patients the cancer. Positive therapeutic effects in cancer can be measured in several ways (see, for example, W. A. Weber, Assessing tumor response to therapy, J. Nucl. Med. 50 Suppl. 1:1 S-10S (2009). For example, with respect to tumor growth inhibition (T/C), according to the National Cancer Institute (NCI) standards, a T/C less than or equal to 42% is the minimum level of anti-tumor activity. A T/C<10% is considered a high anti-tumor activity level, with T/C (%)=median tumor volume of the treated/median tumor volume of the control×100.

In one embodiment, the treatment achieved by administration of a compound of the invention is defined by reference to any of the following: partial response (PR), complete response (CR), overall response (OR), progression free survival (PFS), disease free survival (DFS) and overall survival (OS). PFS, also referred to as "Time to Tumor Progression" indicates the length of time during and after treatment that the cancer does not grow and includes the amount of time patients have experienced a CR or PR, as well as the amount of time patients have experienced stable disease (SD). DFS refers to the length of time during and after treatment that the patient remains free of disease. OS refers to a prolongation in life expectancy as compared to naive or untreated subjects or patients. In one embodiment, response to treatment with a compound of the invention is any of PR, CR, OR, PFS, DFS, or OS that is assessed using Response Evaluation Criteria in Solid Tumors (RECIST) 1.1 response criteria.

The treatment regimen for a compound of the invention that is effective to treat a cancer patient may vary according to factors such as the disease state, age, and weight of the patient, and the ability of the therapy to elicit an anti-cancer response in the subject. While an embodiment of any of the aspects of the invention may not be effective in achieving a positive therapeutic effect in every subject, it should do so in a statistically significant number of subjects as determined by any statistical test known in the art such as the Student's t-test, the chi2-test the U-test according to Mann and Whitney, the Kruskal-Wallis test (H-test), Jonckheere-Terpstrattesty and the Wilcon on-test.

The terms "treatment regimen", "dosing protocol" and "dosing regimen" are used interchangeably to refer to the dose and timing of administration of a compound of the invention, alone or in combination with another therapeutic agent.

"Ameliorating" means a lessening or improvement of one or more symptoms upon treatment with a combination described herein, as compared to not administering the combination. "Ameliorating" also includes shortening or reduction in duration of a symptom.

As used herein, the term "subject" refers to any animal, including mammals such as humans. In one embodiment, the subject has experienced and/or exhibited at least one symptom of the disease or disorder to be treated and/or prevented. In one embodiment, the subject has been identified or diagnosed as having a MEK-associated tumor (e.g., as determined using a regulatory agency-approved, e.g., FDA-approved, assay or kit). In one embodiment, the subject has a MEK-associated tumor that is positive for a BRAF mutation (e.g., as determined using a regulatory agency-approved assay or kit). The subject can be a subject whose tumors have a MEK mutation (e.g., where the tumor is identified as such using a regulatory agency-approved, e.g., FDA-approved, kit or assay). In one embodiment, the subject is suspected of having a MEK-associated tumor. In one embodiment, the subject has a clinical record indicating that the subject has a MEK-associated tumor that has a BRAF mutation (and optionally the clinical record indicates that the subject should be treated with any of the compositions provided herein). In one embodiment, the subject is a human. In one embodiment, the human subject is a pediatric subject.

The term "pediatric subject" as used herein refers to a subject under the age of 21 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E, Nelson *Textbook of Pediatrics,* 15th Ed. Philadelphia: W.B. Saunders Company, 1996: Rudolph A M, et al. *Rudolph's Pediatrics,* 21st Ed. New York: McGraw-Hill, 2002; and Avery M D, First L R. *Pediatric Medicine,* 2nd Ed. Baltimore: Williams & Wilkins; 1994. In one embodiment, a pediatric subject is from birth through the first 28 days of life, from 29 days of age to less than two years of age, from two years of age to less than 12 years of age, or 12 years of age through 21 years of age (up to, but not including, the twenty-second birthday). In one embodiment, a pediatric subject is from birth through the first 28 days of life, from 29 days of age to less than 1 year of age, from one month of age to less than four months of age, from three months of age to less than seven months of age, from six months of age to less than 1 year of age, from 1 year of age to less than 2 years of age, from 2 years of age to less than 3 years of age, from 2 years of age to less than seven years of age, from 3 years of age to less than 5 years of age, from 5 years of age to less than 10 years of age, from 6 years of age to less than 13 years of age, from 10 years of age to less than 15 years of age, or from 15 years of age to less than 22 years of age.

In one embodiment, provided herein is a method of treating a tumor, the method comprising administering to a subject in need thereof a therapeutically effective amount of a compound of Formula I or a pharmaceutically acceptable salt thereof or a compound of Formula II or a pharmaceutically acceptable salt thereof. In one embodiment, the tumor is a MEK-associated tumor. In one embodiment, the MEK-associated tumor has a BRAF mutation. In one embodiment, the BRAF mutation is V600E and/or V600K and/or V600D and/or V600R and/or V600S. In one embodiment, the BRAF mutation is V600E. In one embodiment, the BRAF mutation is V600K. In one embodiment, the MEK-associated tumor has a BRAF fusion, e.g., a BRAF fusion disclosed herein. In one embodiment, the MEK-associated tumor is a BRAF wild-type tumor.

In one embodiment of any of the methods of use described herein, the tumor is a solid tumor. In one embodiment of any of the methods disclosed herein, the solid tumor is a MEK-associated tumor. In one embodiment, the tumor is intracranial. In one embodiment, the tumor is extracranial. In one embodiment of any of the methods of uses described herein, the tumor (e.g., a MEK-associated tumor) is a malignant tumor (i.e., cancer) e.g., a MEK-associated cancer. In one embodiment of any of the methods of use described herein, the MEK-associated cancer is melanoma, colon cancer, colorectal cancer, lung cancer (e.g., small cell lung carcinoma or non-small cell lung carcinoma), thyroid cancer (e.g., papillary thyroid cancer, medullary thyroid cancer, differentiated thyroid cancer, recurrent thyroid cancer, or refractory differentiated thyroid cancer), breast cancer, ovarian cancer, cancer of the CNS, bone cancer, cancer of the anus, anal canal, or anorectum, cancer of the eye, bile duct cancer, ductal carcinoma in situ, liver cancer, gallbladder, or pleura, oral cancer, oral cavity cancer, lip cancer, oropharyngeal cancer, cancer of the nose, nasal cavity or middle ear, cancer of the vulva, esophageal cancer, cervical cancer, gastrointestinal carcinoid tumor, hypopharynx cancer, kidney cancer, larynx cancer, liver cancer, lung cancer, melanoma, nasopharynx cancer, peripheral nervous system cancers (e.g., neuroblastoma), ovarian cancer, pancreatic cancer, peritoneum, omentum, and mesentery cancer, pharynx cancer, prostate cancer, renal cancer (e.g., renal cell carcinoma (RCC)), small intestine cancer, soft tissue cancer, stomach cancer, testicular cancer, uterine cancer, ureter cancer, or urinary bladder cancer.

In one embodiment of any of the methods of use described herein, the MEK-associated cancer is an extracranial cancer (i.e., an extracranial tumor). In one embodiment, the extracranial cancer is selected from melanoma, colorectal cancer, thyroid cancer, non-small cell lung cancer, ovarian cancer, and neuroblastoma. In one embodiment, the MEK-associated cancer is melanoma. In one embodiment, the MEK-associated cancer is colorectal cancer. In one embodiment, the MEK-associated cancer is thyroid cancer. In one embodiment, the MEK-associated cancer is non-small cell lung cancer. In one embodiment, the MEK-associated cancer is ovarian cancer. In one embodiment, the MEK-associated cancer is neuroblastoma.

In one embodiment of any of the methods of use described herein, the MEK-associated cancer is a CNS cancer.

In one embodiment of any of the methods of use described herein, the MEK-associated cancer is an intracranial cancer (brain cancer).

In one embodiment of any of the methods of use described herein, the cancer is a metastatic cancer.

The term "metastasis" is an art known term that refers to the spread of cancer cells from the place where they first formed (the primary site) to one or more other sites in a subject (one or more secondary sites). In metastasis, cancer cells break away from the original (primary) tumor, travel through the blood or lymph system, and form a new tumor (a metastatic tumor) in other organs or tissues of the body. The new, metastatic tumor includes the same or similar cancer cells as the primary tumor. At the secondary site, the tumor cell may proliferate and begin the growth or colonization of a secondary tumor at this distant site.

The term "metastatic cancer" (also known as "secondary cancer") as used herein refers to a type of cancer that originates in one tissue type, but then spreads to one or more tissues outside of the (primary) cancer's origin. Metastatic brain cancer refers to cancer in the brain, i.e., cancer which originated in a tissue other than the brain and has metastasized to the brain.

In one embodiment, compounds of Formula I or a pharmaceutically acceptable salts thereof and compounds of Formula II or a pharmaceutically acceptable salts thereof exhibit surprising brain and/or CNS penetrance. Such compounds are capable of crossing the BBB and inhibiting a MEK kinase in the brain and/or other CNS structures. Accordingly, in one embodiment, compounds provided herein are useful for treating a CNS tumor such as a CNS cancer.

In one embodiment, the MEK-associated tumor is a malignant CNS tumor (i.e., a MEK-associated CNS cancer). In one embodiment, the MEK-associated CNS cancer has a BRAF mutation. In one embodiment the MEK-associated CNS cancer is has a BRAF V600 mutation. In one embodiment, the BRAF mutation is V600E and/or V600K and/or V600D and/or V600R and/or V600S. In one embodiment the MEK-associated CNS cancer is has a BRAF V600E mutation. In one embodiment the MEK-associated CNS cancer is has a BRAF V600K mutation. In one embodiment, the MEK-associated tumor has a BRAF fusion. In one embodiment, the MEK-associated tumor is a BRAF wild-type tumor.

The term "CNS cancer" or "cancer of the CNS" as used interchangeably herein refers to a cancer (i.e., a malignant tumor) of the CNS, including cancers of the brain (also known as intracranial tumors), cancers of the spinal cord, and cancers of the meninges surrounding the brain and spinal cord. Cancers of the brain include metastatic brain cancers (i.e., metastatic intracranial cancers) and malignant primary brain tumors.

In one embodiment, the MEK-associated CNS cancer is a MEK-associated metastatic brain cancer. The MEK-associated metastatic brain cancer may be the result of any cancer described herein, wherein the subject has developed at least one brain metastasis. In one embodiment, the metastatic brain cancer is melanoma, colorectal cancer, thyroid cancer, non-small cell lung cancer, ovarian cancer, or neuroblastoma. In one embodiment, the MEK-associated metastatic brain cancer is metastatic melanoma, metastatic colorectal cancer, or metastatic non-small cell lung cancer. In one embodiment, the MEK-associated metastatic brain cancer is metastatic melanoma. In one embodiment, the MEK-associated metastatic brain cancer is metastatic colorectal cancer. In one embodiment, the MEK-associated metastatic brain cancer is metastatic non-small cell lung cancer. In one embodiment, the MEK-associated metastatic brain cancer is metastatic ovarian cancer. In one embodiment, the metastatic brain cancer is metastatic thyroid cancer. In one embodiment, the MEK-associated metastatic brain cancer is kidney cancer. In one embodiment, the cancer is MEK-associated metastatic cancer with at least one brain metastasis (i.e., a metastatic brain cancer). In one embodiment, the cancer is MEK-associated metastatic melanoma with at least one brain metastasis. In one embodiment, the cancer is MEK-associated metastatic colorectal cancer with at least one brain metastasis. In one embodiment, the cancer is MEK-associated metastatic non-small cell lung cancer with at least one brain metastasis. In one embodiment, the cancer is MEK-associated metastatic ovarian cancer with at least one brain metastasis. In one embodiment, the cancer is MEK-associated metastatic thyroid cancer with at least one brain metastasis. In one embodiment, the cancer is MEK-associated neuroblastoma with at least one brain metastasis. In one embodiment of any of said MEK-associated metastatic brain cancers, the cancer has a BRAF mutation. In one embodiment the cancer has a BRAF V600 mutation. In one embodiment, the BRAF mutation is V600E and/or V600K and/or V600D and/or V600R and/or V600S. In one embodiment the cancer is has a BRAF V600E mutation. In one embodiment the cancer is has a BRAF V600K mutation. In one embodiment, the MEK-associated tumor has a BRAF fusion. In one embodiment, the MEK-associated tumor is a BRAF wild-type tumor.

In one embodiment, the MEK-associated cancer is leptomeningeal metastases (leptomeningeal disease (LMD)). LMD represents a subset of CNS metastases that grow in the lining of the brain or spine and/or in the cerebrospinal fluid (CSF), or leptomeningeal carcinomatosis. In mammals, the meninges are the dura mater, the arachnoid mater, and the pia mater. CSF is located in the subarachnoid space between the arachnoid mater and the pia mater. The arachnoid and pia mater together are sometimes called the leptomeninges. When LMD occurs in the leptomeninges and/or CSF surrounding the spinal cord, it may be referred to as "extracranial LMD". When LMD occurs in the leptomeninges and/or CSF of the brain, it may be referred to as "intracranial LMD". Since LMD cancer cells can be suspended in the CSF, they can quickly spread throughout the CNS. As a result, LMD has a poor prognosis, with survival typically measured in months. In one embodiment, the metastatic cancer is LMD. In one embodiment, the metastatic cancer is a MEK-associated LMD. In one embodiment, the metastatic cancer is a MEK-associated intracranial LMD. In one embodiment, the metastatic cancer is a MEK-associated extracranial LMD. In one embodiment the MEK-associated LMD is LMD derived from melanoma metastases (i.e., the LMD is metastatic melanoma). In one embodiment the MEK-associated LMD is LMD derived from colorectal cancer metastases (i.e., the LMD is metastatic colorectal cancer). In one embodiment the MEK-associated LMD is LMD derived from non-small cell lung cancer metastases (i.e., the LMD is metastatic non-small cell lung cancer). In one embodiment of any of said the MEK-associated LMD's, the LMD has a BRAF mutation. In one embodiment the MEK-associated LMD has a BRAF V600 mutation. In one embodiment, the BRAF mutation is V600E and/or V600K and/or V600D and/or V600R and/or V600S. In one embodiment the MEK-associated LMD is has a BRAF V600E mutation. In one embodiment the MEK-associated LMD is has a BRAF V600K mutation. In one embodiment, the MEK-associated LMD has a BRAF fusion. In one embodiment, the MEK-associated LMD is a BRAF wild-type tumor.

In one embodiment, the MEK-associated tumor is a cancer having a high risk of metastasis. In one embodiment, the tumor having a high risk of metastasis is a cancer having a BRAF V600E, V600D, V600K, V600R and/or V600S mutation. In one embodiment, the cancer having a high risk of metastasis has a BRAF fusion, e.g., any of the BRAF fusions disclosed herein. In one embodiment, the cancer having a high risk of metastasis is a BRAF wild-type tumor. In one embodiment, the cancer having a high risk of metastasis is melanoma, colorectal cancer, thyroid cancer, non-small cell lung cancer, ovarian cancer or neuroblastoma. In one embodiment, the cancer having a high risk of metastasis is melanoma, colorectal cancer, thyroid cancer, non-small cell lung cancer, ovarian cancer or neuroblastoma. In one embodiment, the cancer having a high risk of metastasis is melanoma. In one embodiment, the cancer having a high risk of metastasis is melanoma having a BRAF V600E mutation or BRAF V600K mutation. In one embodiment, the cancer having a high risk of metastasis is colorectal cancer. In one embodiment, the cancer having a high risk of metastasis is colorectal cancer having a BRAF V600E mutation or BRAF V600K mutation. In one embodiment, the cancer having a high risk of metastasis is thyroid cancer. In one embodiment, the cancer having a high risk of metastasis is thyroid cancer having a BRAF V600E mutation or BRAF V600K mutation. In one embodiment, the cancer having a high risk of metastasis is non-small cell lung cancer. In one embodiment, the cancer having a high risk of metastasis is non-small cell lung cancer having a BRAF V600E mutation or BRAF V600K mutation. In one embodiment, the cancer having a high risk of metastasis is ovarian cancer. In one embodiment, the cancer having a high risk of metastasis is ovarian cancer having a BRAF V600E mutation or BRAF V600K mutation. In one embodiment, the cancer having a high risk of metastasis is neuroblastoma. In one embodiment, the cancer having a high risk of metastasis is neuroblastoma having a BRAF V600E mutation or BRAF V600K mutation. In one embodiment, the cancer having a high risk of metastasis has a KIAA11549-BRAF fusion.

In one embodiment, the CNS tumor is a primary brain tumor. Primary brain tumors are tumors that start in the brain or spine and are known collectively as gliomas. The term "glioma" is used to describe tumors that originate in glial cells present in the CNS. According to the WHO classification of brain tumors, gliomas are graded by the cell activity and aggressiveness on a scale including Grade I (benign CNS tumors) and Grades II to IV (malignant CNS tumors):

Grade I glioma (Pilocytic astrocytoma): typically occurs in children in the cerebellum or brainstem, and occasionally in the cerebral hemispheres, and are slow growing. Grade I can occur in adults. Although they are benign (WHO grade 1), the difficulty in curing this disease makes their growth malignant in behavior with high morbidity rates (Rostami, Acta Neurochir (Wien). 2017; 159(11): 2217-2221).

Grade II glioma (Low-grade gliomas): includes astrocytoma, oligodendroglioma, and mixed oligoastrocytoma. Grade II gliomas typically occur in young adults (e.g., ages 20-50) and are most often found in the cerebral hemispheres. Due to the infiltrative nature of these tumors, recurrences may occur. Some grade II gliomas recur and evolve into more aggressive tumors (grade III or IV).

Grade III glioma (Malignant glioma): includes anaplastic astrocytoma, anaplastic oligodendroglioma, and anaplastic mixed oligoastrocytoma. Grade III tumors are aggressive, high-grade cancers and invade nearby brain tissue with tentacle-like projections, making complete surgical removal more difficult.

Grade IV gliomas: includes Glioblastoma multiforme (GBM) and gliosarcoma; (GBM) is a malignant glioma. GBM is the most aggressive and most common primary brain tumor. Glioblastoma multiforme usually spreads quickly and invades other parts of the brain, with tentacle-like projections, making complete surgical removal more difficult. Gliosarcoma is a malignant cancer and is defined as a glioblastoma consisting of gliomatous and sarcomatous components.

In one embodiment, the primary brain tumor is a glioma. In one embodiment, the glioma is a low-grade glioma. In one embodiment, the glioma is a pediatric low-grade glioma.

In one embodiment, the primary brain tumor is a benign primary brain tumor. Benign primary brain tumors can cause severe pain, permanent brain damage and death, and in some cases, become malignant. Non-limiting examples of benign primary brain tumors include Grade I gliomas, papillary craniopharyngiomas, meningioma (including rhabdoid meningioma), atypical teratoid/rhabdoid tumors, and dysembryoplastic neuroepithelial tumor (DNT), pilocytic astrocytoma, oligodendroglioma, mixed oligoastrocytoma, anaplastic astrocytoma, anaplastic oligodendroglioma, anaplastic mixed oligoastrocytoma, diffuse astrocytoma, ependymoma, a pleomorphic xanthoastrocytoma (PXA), a ganglioglioma, a gliosarcoma, or an anaplastic ganglioglioma.

In one embodiment, the cancer is a peripheral nervous system cancer. In one embodiment, the peripheral nervous system cancer is neuroblastoma.

In one embodiment, provided herein is a method of treating a MEK-associated CNS tumor, comprising administering (e.g., oral administration) to a subject in need thereof a therapeutically effective amount of a compound of Formula I or a pharmaceutically acceptable salt thereof or a compound of Formula II or a pharmaceutically acceptable salt thereof to the subject in need thereof. In one embodiment, the MEK-associated CNS tumor has a BRAF V600 mutation. In one embodiment, the MEK-associated CNS tumor has a BRAF V600E and/or V600K and/or V600D and/or V600R mutation and/or V600S. In one embodiment, the MEK-associated CNS tumor has a BRAF V600E mutation. In one embodiment, the MEK-associated CNS tumor has a BRAF V600K mutation. In one embodiment, the MEK-associated CNS tumor has a BRAF fusion, e.g., any of the BRAF fusions disclosed herein, e.g., a KIAA11549-BRAF fusion. In one embodiment, the MEK-associated CNS tumor is a BRAF wild-type tumor. In one embodiment, the subject has been treated with one or more, anticancer therapies independently selected from anticancer agents, surgery and radiotherapy prior to administration of a compound of Formula I or a pharmaceutically acceptable salt thereof or a compound of Formula II or a pharmaceutically acceptable salt thereof, e.g., as described hereinbelow. In one embodiment, the subject is treated with a therapeutically effective amount compound of a compound of Formula I or a pharmaceutically acceptable salt thereof or a compound of Formula II or a pharmaceutically acceptable salt thereof in combination with one or more anticancer therapies independently selected from one or more anticancer agents, surgery and/or radiotherapy, e.g., as described hereinbelow. In one embodiment, the subject is treated with one or more anticancer therapies, independently selected from an anticancer agent, surgery, and radiotherapy after administration of a compound of Formula I or a pharmaceutically acceptable salt thereof or a compound of Formula II or a pharmaceutically acceptable salt thereof, e.g., as described hereinbelow. In one embodiment, the MEK-associated tumor is a CNS tumor. In one embodiment, the MEK-associated CNS tumor is a malignant CNS tumor (i.e., a CNS cancer). In one embodiment, the malignant CNS tumor is a metastatic CNS cancer. In one embodiment, the metastatic CNS cancer is selected from metastatic melanoma, metastatic colorectal cancer, metastatic non-small cell lung cancer, metastatic thyroid cancer, and metastatic ovarian cancer. In one embodiment, the metastatic CNS cancer is metastatic melanoma. In one embodiment, the metastatic CNS cancer is colorectal cancer. In one embodiment, the metastatic CNS cancer is metastatic non-small cell lung cancer. In one embodiment, the metastatic CNS cancer is metastatic thyroid cancer. In one embodiment, the metastatic CNS cancer is metastatic ovarian cancer. In one embodiment, the MEK-associated CNS cancer is LMD. In one embodiment, the LMD is intracranial. In one embodiment, the LMD is extracranial. In one embodiment, the LMD is metastatic melanoma. In one embodiment, the LMD is selected from metastatic melanoma, metastatic colorectal cancer, and metastatic non-small cell lung cancer. In one embodiment, the LMD is metastatic colorectal cancer. In one embodiment, the LMD is metastatic non-small cell lung cancer. In one embodiment, the MEK-associated CNS cancer is a primary brain tumor. In one embodiment, the primary brain tumor is a Grade 2 glioma. In one embodiment, the primary brain tumor is a Grade 3 glioma. In one embodiment, the primary brain tumor is a Grade 4 glioma. In one embodiment, the MEK-associated CNS tumor is a benign tumor. In one embodiment, the benign CNS tumor is a papillary craniopharyngioma, a meningioma (including rhabdoid meningioma), an atypical teratoid/rhabdoid tumor, or a dysembryoplastic neuroepithelial tumor (DNT). In one embodiment, the compound is a compound of Formula I or a pharmaceutically acceptable salt thereof. In one embodiment, the compound is a compound of Formula II or a pharmaceutically acceptable salt thereof. In one embodiment, the compound of is selected from a compound of Examples 1-69 or a pharmaceutically acceptable salt thereof.

The ability to determine whether a compound may be suitable for treating a CNS cancer may be determined, for example, by identifying if the compound is a substrate of an efflux transporter and/or measuring the cell permeability and/or measuring the free blood-to-free plasma ratio, as described herein.

In one embodiment, compounds of Formula I or pharmaceutically acceptable salts thereof and compounds of Formula II or pharmaceutically acceptable salt thereof, exhibit high cell permeability. Methods for determining the permeability of a compound of the invention can be determined according to the assay described in Example B, and permeability coefficients are provided in Table B1.

Compounds of the invention exhibit low efflux. In vitro methods of evaluating whether compounds of the invention are substrates for the efflux transporters P-glycoprotein (P-gp or Multi-drug Resistance 1 (MDR1) protein) and Breast cancer resistance protein (BCRP) are described in Example B, and efflux ratios of compounds of the invention are provided in Table B3.

In one embodiment, compounds of the invention exhibit medium-to-high brain (unbound)/plasma (unbound) ratios (i.e., medium-to-high free brain/plasma ratios). The ability of a compound of the invention to penetrate the BBB of a subject (e.g., a human) can be determined in a suitable animal model (e.g., a rodent, such as a mouse). For example, the ability of certain compounds to penetrate the BBB in mice was determined by evaluating the unbound brain-to-unbound plasma concentration (free B/P) ratio in mice e.g. as described in Example C, and the free brain-to-free plasma ratios are provided in Table C2. Calculating the free brain-to-free plasma ratio of compounds enables predictions of efficacious concentrations required to achieve efficacy in the periphery and the brain based upon dose-related exposure in animal models. These distribution data, along with the associated pharmacokinetic data, can be utilized to model and predict the dose required to achieve efficacy in human patients.

Accordingly, in one embodiment, the methods of the present invention include methods for treating a MEK-associated CNS cancer in a subject in need thereof, comprising administering a compound of Formula II or pharmaceutically acceptable salt, wherein at least a portion of the compound of Formula II penetrates the BBB, as demonstrated in a suitable animal model. In one embodiment, the brain/plasma ratio of total drug is at least about 0.3 after administration (e.g., oral or intravenous administration) to a subject. In one embodiment, the brain/plasma ratio of total drug is at least about 0.35 after administration (e.g., oral or intravenous administration) to a subject. In one embodiment, the brain/plasma ratio of total drug is at least about 0.4 after administration (e.g., oral or intravenous administration) to a subject. In one embodiment, the brain/plasma ratio of total drug is at least about 0.45 after administration (e.g., oral or intravenous administration) to a subject. In one embodiment, the brain/plasma ratio of total drug is at least about 0.5 after administration (e.g., oral or intravenous administration) to a subject. In one embodiment, the brain/plasma ratio of total drug is at least about 0.55 after administration (e.g. oral or intravenous administration) to a subject. In one embodiment, the brain/plasma ratio of total drug is at least about 0.6 after administration (e.g. oral or intravenous administration) to a subject. In one embodiment, the brain/plasma ratio of total drug is at least about 0.65 after administration (e.g. oral or intravenous administration) to a subject. In one embodiment, the brain/plasma ratio of total drug is at least about 0.7 after administration (e.g. oral or intravenous administration) to a subject. In one embodiment, the brain/plasma ratio of total drug is at least about 0.75 after administration (e.g. oral or intravenous administration) to a subject. In one embodiment, the brain/plasma ratio of total drug is at least about 0.8 after administration (e.g. oral or intravenous administration) to a subject. In one embodiment, the brain/plasma ratio of total drug is at least about 0.85 after administration (e.g. oral or intravenous administration) to a subject. In one embodiment, the brain/plasma ratio of total drug is at least about 0.9 after administration (e.g. oral or intravenous administration) to a subject. In one embodiment, the brain/plasma ratio of total drug is at least about 0.95 after administration (e.g. oral or intravenous administration) to a subject. In one embodiment, the brain/plasma ratio of total drug is at least about 1.0 after administration (e.g. oral or intravenous administration) to a subject. In one embodiment, the brain/plasma ratio of total drug is at least about 1.0 after administration (e.g. oral or intravenous administration) to a subject. In one embodiment, the brain/plasma ratio of total drug is at least about 1.1 after administration (e.g. oral or intravenous administration) to a subject. In one embodiment, the brain/plasma ratio of total drug is at least about 1.2 after administration (e.g. oral or intravenous administration) to a subject. In one embodiment, the brain/plasma ratio of total drug is at least about 1.3 after administration (e.g. oral or intravenous administration) to a subject. In one embodiment, the brain/plasma ratio of total drug is at least about 1.4 after administration (e.g. oral or intravenous administration) to a subject. In one embodiment, the brain/plasma ratio of total drug is at least about 1.5 after administration (e.g. oral or intravenous administration) to a subject. In one embodiment, the brain/plasma ratio of total drug is at least about 1.6 after administration (e.g. oral or intravenous administration) to a subject. In one embodiment, the brain/plasma ratio of total drug is at least about 1.7 after administration (e.g. oral or intravenous administration) to a subject. It is to be noted that the percentage of a compound that penetrates the BBB is calculated based upon the area under the concentration-time curve for a given time period ($AUC_{0-t}$) in the brain versus the plasma. Accordingly, the percentages represent a ratio of concentrations. That is, if ($AUC_{0-24\ h}$) for a compound is 20 ng/mL in the brain and 80 ng/mL in the plasma, then the percentage of the compound that penetrates the BBB is 20% (20 ng/mL in the brain divided by the total concentration of (20 ng/mL+80 ng/mL)) (i.e., a brain-to-plasma ratio of 0.20). In one embodiment, the percentages are calculated based upon the area under the concentration-time curve for the time period from t=0 (time of dosing) to the last quantifiable concentration point, i.e., ($AUC_{0-last}$).

Cancers that frequently metastasize to the brain are known to carry MAPK pathway activating alterations such as BRAF mutations, including the BRAF mutations disclosed herein, or BRAF fusions, including the BRAF fusions disclosed herein. Although activating mutations can occur at different levels in the canonical pathway, they all require signaling via mitogen/extracellular signal-regulated kinase (MEK) in order to increase proliferation and survival (Schubbert S, Shannon K, Bollag G. Nat Rev Cancer. 2007; 7:295-308). Mutations in the BRAF gene have been identified in malignant melanomas, papillary thyroid carcinomas, colorectal carcinomas, non-small cell lung carcinoma (NSCLC), and ovarian carcinomas and metastatic tumors thereof, and in primary brain tumors (Davies H., et al., Nature 417(6892):949-954, 2002). For example, BRAF mutations, such as BRAF V600 mutations, have been observed in numerous metastatic CNS tumors, including melanoma brain metastases (Flaherty K T, et al., Nat Rev Cancer (2012) 12(5):349-61), brain metastases of colorectal cancers and brain metastases of non-small cell lung cancer (Berghoff, A S, Preusser M., Curr Opin Neurol (2014) 27(6):689-696), papillary thyroid cancer (Kim, W W et al., J Otolaryngol Head Neck Surg. 2018; 47:4, 1-6), and ovarian cancer (Grisham R N., et al., Cancer, 2013; 119: 548-554).

BRAF mutations, e.g., the BRAF mutations disclosed herein, and BRAF fusions, e.g., the BRAF fusions disclosed herein, have also been observed in malignant primary brain tumors, including Grade IV gliomas, e.g., glioblastomas and gliosarcomas, anaplastic astrocytomas (high-grade tumors) and WHO grade III anaplastic gangliogliomas (Berghoff, A S, Preusser M., Curr Opin Neurol (2014) 27(6):689-696); Schindler et al. (Acta Neuropathol 121(3):397-405, 2011); Behling et al. (Diagn Pathol 11(1):55, 2016); K. C. Schreck, et al., Cancers, 2019, 11, 1262)) in pediatric and adult populations.

BRAF mutations, e.g., the BRAF mutations disclosed herein, and BRAF fusions, e.g., the BRAF fusions disclosed herein, have also been observed in benign primary brain tumors, for example in WHO Grade II astrocytomas, WHO grade II pleomorphic xanthoastrocytomas (PXAs), pleomorphic xanthoastrocytomas with anaplasia, Pilocytic astrocytoma (PA), papillary craniopharyngiomas, gangliogliomas, astroblastomas, pilocytic astrocytomas, atypical teratoid/rhabdoid tumors, rhabdoid meningiomas (Berghoff, A S, Preusser M., Curr Opin Neurol (2014) 27(6):689-696; Schindler et al. (Acta Neuropathol 121(3):397-405, 2011); Behling et al. (Diagn Pathol 11(1):55, 2016); (Behling et al., Diagn Pathol 11(1):55, 2016; Brastianos et al., Nat Genet 46(2):161-165, 2014; Dougherty et al., Neuro Oncol 12(7): 621-630, 2010; Lehman et al., Neuro Oncol 19(1):31-42, 2017; Mordechai et al., Pediatr Hematol Oncol 32(3):207-211, 2015; Myung et al., Transl Oncol 5(6):430-436, 2012; Schindler et al., Acta Neuropathol 121(3):397-405, 2011)), in pediatric and adult populations.

BRAF mutations have also been detected in relapsed neuroblastomas (Eleveld, T F, et al., Nat Genet 47(8):864-871, 2015). Neuroblastoma is a pediatric tumor of the peripheral nervous system. The majority of neuroblastoma subjects have tumors that initially respond to chemotherapy, but a large proportion of subjects will experience therapy-resistant relapses.

Accordingly, also provided herein is a method for treating a subject diagnosed with or identified as having a MEK-associated tumor, e.g., any of the exemplary MEK-associated tumors disclosed herein, comprising administering to the subject a therapeutically effective amount of a compound of Formula I or a pharmaceutically acceptable salt thereof or a compound of Formula II or a pharmaceutically acceptable salt thereof, wherein the subject that has been identified or diagnosed as having a tumor having a BRAF mutation of BRAF fusion, e.g., through the use of a regulatory agency-approved, e.g., FDA-approved test or assay for identifying BRAF mutation or fusion in a subject or a biopsy sample from the subject or by performing any of the non-limiting examples of assays described herein. In one embodiment, the test or assay is provided as a kit. In one embodiment, the assay utilizes next generation sequencing, pyrosequencing, immunohistochemistry, fluorescence microscopy, break apart FISH analysis, Southern blotting, Western blotting, FACS analysis, Northern blotting, or PCR-based amplification (e.g., RT-PCR and quantitative real-time RT-PCR). In one embodiment, the assay is a regulatory agency-approved assay, e.g., FDA-approved kit.

In one embodiment, the biopsy is a tumor biopsy (e.g., a tumor sample obtained during traditional surgery or a stereotactic needle biopsy, e.g., a stereotactic need biopsy guided by CT or MRI scanning). Tissue biopsy methods can be used to detect total tumor burden and/or the BRAF mutation and/or the BRAF fusion.

In one embodiment, the BRAF mutation or fusion can be identified using a liquid biopsy (variously referred to as a fluid biopsy or fluid phase biopsy). See, e.g., Karachialiou et al., "Real-time liquid biopsies become a reality in cancer treatment", Ann. Transl. Med., 3(3):36, 2016. Liquid biopsy methods can be used to detect total tumor burden and/or the BRAF mutation. Liquid biopsies can be performed on biological samples obtained relatively easily from a subject (e.g., via a simple blood draw) and are generally less invasive than traditional methods used to detect tumor burden and/or BRAF mutation. In one embodiment, liquid biopsies can be used to detect the presence of a BRAF mutation at an earlier stage than traditional methods. In one embodiment, the biological sample to be used in a liquid biopsy can include CSF, blood, plasma, urine, saliva, sputum, broncho-alveolar lavage, bile, lymphatic fluid, cyst fluid, stool, ascites, and combinations thereof. In one embodiment, a liquid biopsy can be used to detect circulating tumor cells (CTCs). In one embodiment, a liquid biopsy can be used to detect cell-free DNA. In one embodiment, the cell-free DNA detected using a liquid biopsy is circulating tumor DNA (ctDNA) that is derived from tumor cells. Analysis of ctDNA (e.g., using sensitive detection techniques such as, without limitation, next-generation sequencing (NGS), traditional PCR, digital PCR, or microarray analysis) can be used to identify a BRAF mutation or BRAF fusion.

In one embodiment, a BRAF mutation or BRAF fusion identified using a liquid biopsy is also present in a cancer cell that is present in the subject (e.g., in a tumor). In one embodiment, any of the types of BRAF mutations or fusions can be detected using a liquid biopsy. In one embodiment, a genetic mutation identified via a liquid biopsy can be used to identify the subject as a candidate for a particular treatment.

"Tumor burden" also referred to as "tumor load", refers to the total amount of tumor material distributed throughout the body. Tumor burden refers to the total number of cancer cells or the total size of tumor(s), throughout the body, including lymph nodes and bone narrow. Tumor burden can be determined by a variety of methods known in the art, such as, e.g. by measuring the dimensions of tumor(s) upon removal from the subject, e.g., using calipers, or while in the body using imaging techniques, e.g., magnetic resonance imaging (MRI) scans, computed tomography (CT), multi-detector CT (MDCT), positron emission tomography (PET), X-ray, ultrasound, or bone scan.

The term "tumor size" refers to the total size of the tumor which can be measured as the length and width of a tumor. Tumor size may be determined by a variety of methods known in the art, such as, e.g., by measuring the dimensions of tumor(s) upon removal from the subject, e.g., using calipers, or while in the body using imaging techniques, e.g., MRI scans, bone scan, ultrasound, or CT.

Liquid biopsies can be performed at multiple times during a course of diagnosis, a course of monitoring, and/or a course of treatment to determine one or more clinically relevant parameters including, without limitation, progression of the disease or efficacy of a treatment, after administering a treatment to the subject. For example, a first liquid biopsy can be performed at a first time point and a second liquid biopsy can be performed at a second time point during a course of diagnosis, a course of monitoring, and/or a course of treatment. In one embodiment, the first time point can be a time point prior to diagnosing a subject with a disease (e.g., when the subject is healthy), and the second time point can be a time point after subject has developed the disease (e.g., the second time point can be used to diagnose the subject with the disease). In one embodiment, the first time point can be a time point prior to diagnosing a subject with a disease (e.g., when the subject is healthy), after which the subject is monitored, and the second time point can be a time point after monitoring the subject. In one embodiment, the first time point can be a time point after diagnosing a subject with a disease, after which a treatment is administered to the subject, and the second time point can be a time point after the treatment is administered; in such cases, the second time point can be used to assess the efficacy of the treatment (e.g., if the genetic mutation(s) detected at the first time point are reduced in abundance or are undetectable).

A compound of Formula I or a pharmaceutically acceptable salt thereof or a compound of Formula II or a pharmaceutically acceptable salt thereof may be used alone or in combination with one or more different forms of treatment to treat a subject with an abnormal cell growth, such as a MEK-associated tumor, for example a MEK-associated cancer.

In one embodiment, a compound of Formula I or a pharmaceutically acceptable salt thereof or a compound of Formula II or a pharmaceutically acceptable salt thereof may be used in combination with one or more, e.g., one or more additional anticancer therapies, for example one or more therapies independently selected from surgery, radiotherapy and anticancer agents that work by the same or by a different mechanism of action. In one embodiment, treatment of a subject having a MEK-associated cancer with a compound of Formula I or a pharmaceutically acceptable salt thereof or a compound of Formula II or a pharmaceutically acceptable salt thereof in combination with one or more, e.g., one or more additional therapies, e.g., independently selected from one or more of surgery, radiotherapy, and anticancer agents (e.g., any of the anticancer agents described herein below, wherein the anticancer agent is other than a compound of Formula I or a pharmaceutically acceptable salt thereof or a compound of Formula II or a pharmaceutically acceptable salt thereof), can have increased therapeutic efficacy as compared to treatment of the same subject or a similar subject with a compound of Formula I or a pharmaceutically acceptable salt thereof or a compound of Formula II or a pharmaceutically acceptable salt thereof as a monotherapy. When a combination therapy is used and the one or more, e.g., one two or three anticancer therapies are independently selected from one or more anticancer agents such as any of the anticancer agents disclosed herein, the anticancer agent(s) may be administered simultaneously or separately with variable intervening time limits and in any order with a compound of the invention in any order and using varying dosing schedules. In one embodiment, the anticancer agent(s) is administered to the subject prior to administration of the compound of the invention. In another embodiment, the anticancer agent(s) is administered to the subject after administration of the compound of the invention. In another embodiment, the anticancer agent(s) is administered to the subject simultaneously with the administration of the compound of the invention. In one embodiment, a compound of Formula I or a pharmaceutically acceptable salt thereof or a compound of Formula II or a pharmaceutically acceptable salt thereof is used in combination with one additional anticancer therapy which is surgery, radiotherapy, or an anticancer agent that work by the same or by a different mechanism of action.

Accordingly, in one embodiment, provided herein are methods of treating a subject having a MEK-associated tumor (e.g., any of the MEK-associated tumors described herein) that comprise administering to the subject a therapeutically effective amount of a compound of Formula I or a pharmaceutically acceptable salt thereof or a compound of Formula II or a pharmaceutically acceptable salt thereof in combination with one or more additional anticancer therapies. In one embodiment, the anticancer therapy is one or more anticancer agents other than a compound of Formula I or a pharmaceutically acceptable salt thereof or a compound of Formula II or a pharmaceutically acceptable salt thereof. In one embodiment, the anticancer therapy is one anticancer agent other than a compound of Formula I or a pharmaceutically acceptable salt thereof or a compound of Formula II or a pharmaceutically acceptable salt thereof. In one embodiment, the additional anticancer therapy is surgery. In one embodiment, the additional anticancer therapy is radiotherapy.

Also provided herein is a compound of Formula I or a pharmaceutically acceptable salt thereof or a compound of Formula II or a pharmaceutically acceptable salt thereof for use in combination with one or more, e.g., one or more anticancer therapies. In one embodiment, the additional anticancer therapy is independently selected from one or more therapies independently selected from surgery, radiotherapy, and/or one or more anticancer agents that work by the same or by a different mechanism of action.

Also provided herein is one or more, e.g., one or more anticancer therapies for use in combination with a compound of Formula I or a pharmaceutically acceptable salt thereof or a compound of Formula II or a pharmaceutically acceptable salt thereof. In one embodiment, the additional anticancer therapy is independently selected from one or more therapies independently selected from surgery, radiotherapy, and/or one or more anticancer agents that work by the same or by a different mechanism of action.

Also provided herein is a compound of Formula I or a pharmaceutically acceptable salt thereof or a compound of Formula II or a pharmaceutically acceptable salt thereof for use in treating a MEK-associated tumor in combination with one or more, e.g., one or more additional anticancer therapies.

Also provided herein is one or more, e.g., one or more additional anticancer therapies, for use in treating a MEK-associated tumor by co-administration with a compound of a compound of Formula I or a pharmaceutically acceptable salt thereof or a compound of Formula II or a pharmaceutically acceptable salt thereof.

In one embodiment for treating a subject having a MEK-associated tumor, the subject is administered one or more anticancer therapies other than a compound of Formula I or a pharmaceutically acceptable salt thereof or a compound of Formula II or a pharmaceutically acceptable salt thereof, prior to administration of a compound of Formula I or a pharmaceutically acceptable salt thereof or a compound of Formula II or a pharmaceutically acceptable salt thereof. In one embodiment, the one or more anticancer therapies is selected from surgery, radiotherapy, and an anticancer agent that work by the same or by a different mechanism of action. For example, in one embodiment, a subject in need thereof may undergo at least partial resection of the tumor prior to administration of a compound of Formula I or a pharmaceutically acceptable salt thereof or a compound of Formula II or a pharmaceutically acceptable salt thereof. In one embodiment, the treatment by at least partial resection of the tumor reduces the size of the tumor (e.g., the tumor burden) occurs prior to administration of one or more doses of a compound of Formula I or a pharmaceutically acceptable salt thereof or a compound of Formula II or a pharmaceutically acceptable salt thereof. In one embodiment, a subject in need thereof may undergo radiotherapy prior to administration of a compound of Formula I or a pharmaceutically acceptable salt thereof or a compound of Formula II or a pharmaceutically acceptable salt thereof. In one embodiment, a subject in need thereof may undergo treatment with one or more anticancer agents other than a compound of Formula I or a pharmaceutically acceptable salt thereof or a compound of Formula II or a pharmaceutically acceptable salt thereof prior to administration of a compound of Formula I or a pharmaceutically acceptable salt thereof or a compound of Formula II or a pharmaceutically acceptable salt thereof. In one embodiment, a subject has a cancer that is refractory or intolerant to the previous therapy or therapies.

Accordingly, in one embodiment, provided herein are methods of treating a subject having a MEK-associated tumor, comprising (i) administering one or more, e.g., one or more anticancer therapies to said subject, and (ii) after (i), administering (a) a compound of Formula I or a pharmaceutically acceptable salt thereof or a compound of Formula II or a pharmaceutically acceptable salt thereof as monotherapy or (b) a compound of Formula I or a pharmaceutically acceptable salt thereof or a compound of Formula II or a pharmaceutically acceptable salt thereof in combination with one or more, e.g., one or more additional anticancer therapies. In one embodiment, the additional anticancer therapy is independently selected from one or more of surgery, radiotherapy, and/or one or more anticancer agents that work by the same or by a different mechanism of action. In one embodiment, the additional anticancer therapy is one or more anticancer agents that work by the same or by a different mechanism of action. In one embodiment, the additional anticancer therapy is one anticancer agent that works by the same or by a different mechanism of action. In one embodiment, the additional anticancer therapy is surgery. In one embodiment, the additional anticancer therapy is radiotherapy.

Non-limiting examples of additional anticancer agents that can be used in combination with a compound of Formula I or a pharmaceutically acceptable salt thereof or a compound of Formula II or a pharmaceutically acceptable salt thereof according to any of the combination therapy methods described herein include additional kinase inhibitors other than a compound of Formula I or a pharmaceutically acceptable salt thereof or a compound of Formula II or a pharmaceutically acceptable salt thereof, including MEK inhibitors, BRAF inhibitors, EGFR inhibitors, inhibitors of HER2 and/or HER3, SHP2 inhibitors, Axl inhibitors, PI3K inhibitors, SOS1 inhibitors, signal transduction pathway inhibitors, checkpoint inhibitors, modulators of the apoptosis pathway, cytotoxic chemotherapeutics, angiogenesis-targeted therapies, and immune-targeted agents including immunotherapy.

In one embodiment, the anticancer agent that can be used in combination with a compound of Formula I or a pharmaceutically acceptable salt thereof or a compound of Formula II or a pharmaceutically acceptable salt thereof according to any of the combination therapy methods described herein is a targeted therapeutic agent. A "targeted therapeutic agent" as used herein includes, refers to a molecule that blocks the growth of cancer cells by interfering with specific targeted molecules needed for carcinogenesis and tumor growth, rather than by simply interfering with all rapidly dividing cells (e.g., with traditional cytotoxic chemotherapy), and includes but is not limited to, receptor tyrosine kinase-targeted therapeutic agents, signal transduction pathway inhibitors (for example, Ras-Raf-MEK-ERK pathway inhibitors, PI3K-Akt-mTOR-S6K pathway inhibitors ("PI3K inhibitors")), and modulators of the apoptosis pathway.

In one embodiment, the anticancer agent that can be used in combination with a compound of Formula I or a pharmaceutically acceptable salt thereof or a compound of Formula II or a pharmaceutically acceptable salt thereof according to any of the combination therapy methods described herein is a BRAF inhibitor. Non-limiting examples of other BRAF inhibitors include encorafenib, dabrafenib, vemurafenib, N-[3-(5-chloro-1H-pyrrolo[2,3-b]pyridin-3-ylcarbonyl)-2,4-difluorophenyl]propane-1-sulfonamide (PLX4720), and (3R)—N-(3-[[5-(2-cyclopropylpyrmidin-5-yl)-1H-pyrrolo[2,3-b]pyridin-3-yl]carbonyl]-2,4-difluorophenyl)-3-fluoropyrrolidine-1-sulfonamide (PLX8394), and pharmaceutically acceptable salts thereof, the compounds disclosed in International Application No. PCT/IB2020/055992, published Dec. 30, 2020 as PCT Publication No. WO 2020/261156 A1, including, for example, a compound selected from:

N-(3-((3,5-dimethyl-4-oxo-3,4-dihydroquinazolin-6-yl)amino)-2,4-difluorophenyl)propane-1-sulfonamide;
N-(2-chloro-3-((3,5-dimethyl-4-oxo-3,4-dihydroquinazolin-6-yl)amino)phenyl)-3-fluoropropane-1-sulfonamide;
N-(2-chloro-3-((3,5-dimethyl-4-oxo-3,4-dihydroquinazolin-6-yl)amino)-4,5-difluorophenyl)propane-1-sulfonamide;
N-(2-chloro-3-((3,5-dimethyl-4-oxo-3,4-dihydroquinazolin-6-yl)amino)-4-fluorophenyl)propane-1-sulfonamide;
N-(2-chloro-3-((3,5-dimethyl-4-oxo-3,4-dihydroquinazolin-6-yl)amino)-4-fluorophenyl)-3-fluoropropane-1-sulfonamide;
N-(2-chloro-4-fluoro-3-((5-methyl-3-(methyl-d3)-4-oxo-3,4-dihydroquinazolin-6-yl)amino)-phenyl)-3-fluoropropane-1-sulfonamide;
N-{2-chloro-3-[(3,5-dimethyl-4-oxo-3,4-dihydroquinazolin-6-yl)oxy]-4-fluorophenyl}propane-1-sulfonamide;
N-(3-chloro-4-((3,5-dimethyl-4-oxo-3,4-dihydroquinazolin-6-yl)oxy)-5-fluoropyridin-2-yl)propane-1-sulfonamide; and
N-{2-chloro-3-[(3,5-dimethyl-4-oxo-3,4-dihydroquinazolin-6-yl)oxy]-4-fluorophenyl}-3-fluoropropane-1-sulfonamide;
or a pharmaceutically acceptable salt thereof;
and the compounds disclosed in PCT Publication No. WO2021/250521, published Dec. 16, 2021, including, for example, N-(2-chloro-4-fluoro-3-((5-fluoro-3-methyl-4-oxo-3,4-dihydroquinazolin-6-yl)amino)phenyl)-2-azabicyclo[2.1.1]hexane-2-sulfonamide, (R)—N-(2-chloro-4-fluoro-3-((5-fluoro-3-methyl-4-oxo-3,4-dihydroquinazolin-6-yl)amino)phenyl)-3-fluoropyrrolidine-1-sulfonamide, and N-(2-chloro-3-((5-chloro-3-methyl-4-oxo-3,4-dihydroquinazolin-6-yl)amino)-4-fluorophenyl)-3-fluoroazetidine-1-sulfonamide, or a pharmaceutically acceptable salt thereof.

In one embodiment, the BRAF inhibitor is selected from encorafenib or a pharmaceutically acceptable salt thereof, N-(2-chloro-3-((3,5-dimethyl-4-oxo-3,4-dihydroquinazolin-6-yl)amino)-4-fluorophenyl)-3-fluoropropane-1-sulfonamide or a pharmaceutically acceptable salt thereof, and N-(2-chloro-3-((5-chloro-3-methyl-4-oxo-3,4-dihydroquinazolin-6-yl)amino)-4-fluorophenyl)-3-fluoroazetidine-1-sulfonamide or a pharmaceutically acceptable salt thereof.

In one embodiment, the BRAF inhibitor is encorafenib or a pharmaceutically acceptable salt thereof. In one embodiment, the BRAF inhibitor is N-(2-chloro-3-((3,5-dimethyl-4-oxo-3,4-dihydroquinazolin-6-yl)amino)-4-fluorophenyl)-3-fluoropropane-1-sulfonamide or a pharmaceutically acceptable salt thereof. In one embodiment, the BRAF inhibitor is N-(2-chloro-3-((5-chloro-3-methyl-4-oxo-3,4-dihydroquinazolin-6-yl)amino)-4-fluorophenyl)-3-fluoroazetidine-1-sulfonamide or a pharmaceutically acceptable salt thereof.

Additional examples of BRAF inhibitors are known in the art.

In one embodiment, the anticancer agent that can be used in combination with a compound of Formula I or a pharmaceutically acceptable salt thereof or a compound of Formula II or a pharmaceutically acceptable salt thereof according to any of the combination therapy methods described herein is an EGFR inhibitor. Non-limiting examples of EGFR inhibitors include cetuximab (Erbitux®), panitumumab (Vectibix®), osimertinib (merelectinib, Tagrisso®), erlotinib (Tarceva®), gefitinib (Iressa®), necitumumab (Portrazza™), neratinib (Nerlynx®), lapatinib (Tykerb®), vandetanib (Caprelsa®), brigatinib (Alunbrig®) and inhibitors of EGFR disclosed in PCT Publication Nos. WO 2019/071351 and WO 2017/117680. Additional examples of EGFR inhibitors are known in the art.

In one embodiment, the anticancer agent that can be used in combination with a compound of Formula I or a pharmaceutically acceptable salt thereof or a compound of Formula II or a pharmaceutically acceptable salt thereof according to any of the combination therapy methods disclosed herein is a SHP2 inhibitor. Non-limiting examples of SHP2 inhibitors include 6-(4-amino-4-methylpiperidin-1-yl)-3-(2,3-dichlorophenyl)pyrazin-2-amine (SHP099), [3-[(3S,4S)-4-amino-3-methyl-2-oxa-8-azaspiro[4.5]decan-8-yl]-6-(2,3-dichlorophenyl)-5-methylpyrazin-2-yl]methanol (RMC-4550) RMC-4630, TNO155, and the compounds disclosed in WO 2020/081848, WO 2020/201991, WO 2015/107493, WO 2015/107494, WO 2015/107495 and WO 2019/075265. In one embodiment, the SHP2 inhibitor is a compound disclosed in WO 2020/201991. In one embodiment, the SHP2 inhibitor is (S)-1'-(6-((2-amino-3-chloropyridin-4-yl)thio)-1,2,4-triazin-3-yl)-1,3-dihydrospiro[indene-2,4'-piperidin]-1-amine or a pharmaceutically acceptable salt thereof.

In one embodiment, the anticancer agent that can be used in combination with a compound of Formula I or a pharmaceutically acceptable salt thereof or a compound of Formula II or a pharmaceutically acceptable salt thereof according to any of the combination therapy methods disclosed herein is a PI3K inhibitor. Non-limiting examples include buparlsib (BKM120), alpelisib (BYL719), samotolisib (LY3023414), 8-[(1R)-1-[(3,5-difluorophenyl)amino]ethyl]-N,N-dimethyl-2-(morpholin-4-yl)-4-oxo-4H-chromene-6-carboxamide (AZD8186), tenalisib (RP6530), voxtalisib hydrochloride (SAR-245409), gedatolisib (PF-05212384), panulisib (P-7170), taselisib (GDC-0032), trans-2-amino-8-[4-(2-hydroxyethoxy)cyclohexyl]-6-(6-methoxypyridin-3-yl)-4-methylpyrido[2,3-d]pyrimidin-7(8H)-one (PF-04691502), duvelisib (ABBV-954), N2-[4-oxo-4-[4-(4-oxo-8-phenyl-4H-1-benzopyran-2-yl)morpholin-4-ium-4-ylmethoxy]butyryl]-L-arginyl-glycyl-L-aspartyl-L-serine acetate (SF-1126), pictilisib (GDC-0941), 2-methyl-1-[2-methyl-3-(trifluoromethyl)benzyl]-6-(morpholin-4-yl)-1H-benzimidazole-4-carboxylic acid (GSK2636771), idelalisib (GS-1101), umbralisib tosylate (TGR-1202), pictilisib (GDC-0941), copanlisib hydrochloride (BAY 84-1236), dactolisib (BEZ-235), 1-(4-[5-[5-amino-6-(5-tert-butyl-1,3,4-oxadiazol-2-yl)pyrazin-2-yl]-1-ethyl-1H-1,2,4-triazol-3-yl]piperidin-1-yl)-3-hydroxypropan-1-one (AZD-8835), 5-[6,6-dimethyl-4-(morpholin-4-yl)-8,9-dihydro-6H-[1,4]oxazino[4,3-e]purin- 2-yl]pyrimidin-2-amine (GDC-0084) everolimus, rapamycin, perifosine, sirolimus, and temsirolimus.

In one embodiment, the anticancer agent that can be used in combination with a compound of Formula I or a pharmaceutically acceptable salt thereof or a compound of Formula II or a pharmaceutically acceptable salt thereof according to any of the combination therapy methods disclosed herein is an immunotherapy. The term "immunotherapy" refers to an agent that modulates the immune system. In one embodiment, an immunotherapy can increase the expression and/or activity of a regulator of the immune system. In one embodiment, an immunotherapy can decrease the expression and/or activity of a regulator of the immune system. In one embodiment, an immunotherapy can recruit and/or enhance the activity of an immune cell.

In one embodiment, the immunotherapy that can be used in combination with a compound of Formula I or a pharmaceutically acceptable salt thereof or a compound of Formula II or a pharmaceutically acceptable salt thereof according to any of the combination therapy methods disclosed herein is an antibody therapy (e.g., a monoclonal antibody, a conjugated antibody). In one embodiment, the antibody therapy is bevacizumab (Mvasti™, Avastin®), trastuzumab (Herceptin®), rituximab (MabThera™, Rituxan®), edrecolomab (Panorex), daratumuab (Darzalex®), olaratumab (Lartruvo™), ofatumumab (Arzerra®), alemtuzumab (Campath®), cetuximab (Erbitux®), oregovomab, pembrolizumab (Keytruda®), dinutiximab (Unituxin®), obinutuzumab (Gazyva®), tremelimumab (CP-675,206), ramucirumab (Cyramza®), ublituximab (TG-1101), panitumumab (Vectibix®), elotuzumab (Empliciti™), necitumumab (Portrazza™), cirmtuzumab (UC-961), ibritumomab (Zevalin®), isatuximab (SAR650984), nimotuzumab, fresolimumab (GC1008), lirilumab (INN), mogamulizumab (Poteligeo®), ficlatuzumab (AV-299), denosumab (Xgeva®), ganitumab, urelumab, pidilizumab, amatuximab, blinatumomab (AMG103; Blincyto®) or midostaurin (Rydapt).

In one embodiment, the immunotherapy that can be used in combination with a compound of Formula I or a pharmaceutically acceptable salt thereof or a compound of Formula II or a pharmaceutically acceptable salt thereof according to any of the combination therapy methods disclosed herein is an immune checkpoint inhibitor. In one embodiment, the immunotherapy includes one or more, e.g., one or two immune checkpoint inhibitors. In one embodiment, the immune checkpoint inhibitor is a CTLA-4 inhibitor, a PD-1 inhibitor or a PD-L1 inhibitor. In one embodiment, the CTLA-4 inhibitor is ipilimumab (Yervoy®) or tremelimumab (CP-675,206). In one embodiment, the PD-1 inhibitor is pembrolizumab (Keytruda®), nivolumab (Opdivo®) and sasanlimab (RN888). In one embodiment, the PD-L1 inhibitor is atezolizumab (Tecentriq®), or durvalumab (Imfinzi™).

In one embodiment, the anticancer therapy that can be used in combination with a compound of Formula I or a pharmaceutically acceptable salt thereof or a compound of Formula II or a pharmaceutically acceptable salt thereof according to any of the combination therapy methods disclosed herein is radiotherapy. Non-limiting examples of radiotherapy include external radiation beam therapy (e.g., external beam therapy using kilovoltage X-rays or megavoltage X-rays) or internal radiotherapy. Internal radiotherapy (also called brachytherapy) can include the use of, e.g., low-dose internal radiotherapy or high-dose internal radiotherapy. Low-dose internal radiotherapy includes, e.g., inserting small radioactive pellets into or proximal to a cancer tissue in the subject. High-dose internal radiotherapy includes, e.g., inserting a thin tube (e.g., a catheter) or an implant into or proximal to a cancer tissue in the subject, and delivering a high dose of radiation to the thin tube or implant using a radiation machine. Methods for performing radiotherapy on a subject having a cancer are known in the art. In embodiments wherein the tumor is a CNS tumor, the radiotherapy may include whole brain radiotherapy (WBRT) or stereotactic radiosurgery (SRS) such as Cyberknife®, XKnife®, Gamma Knife®, or ExacTrac®.

In one embodiment, the anticancer therapy that can be used in combination with a compound of Formula I or a pharmaceutically acceptable salt thereof or a compound of Formula II or a pharmaceutically acceptable salt thereof according to any of the combination therapy methods disclosed herein is surgery. Non-limiting examples of surgery include, e.g., open surgery or minimally invasive surgery. Surgery can include, e.g., at least a partial resection of the tumor, removing an entire tumor, debulking of a tumor, or removing a tumor that is causing pain or pressure in the subject. Methods for performing open surgery and minimally invasive surgery on a subject having a cancer are known in the art.

In one embodiment, provided herein is a method of treating a MEK-associated tumor (e.g., any of the MEK-associated tumors described herein) comprising administering to a subject in need thereof a therapeutically effective amounts of a compound of Formula I or a pharmaceutically acceptable salt thereof or a compound of Formula II or a pharmaceutically acceptable salt thereof and a BRAF inhibitor (e.g., any of the BRAF inhibitors disclosed herein) in any order, together or separately. In one embodiment, the compound of Formula I is a compound selected from Examples 1-69, or a pharmaceutically acceptable salt thereof.

In one embodiment, provided herein is a method of treating a MEK-associated tumor (e.g., any of the MEK-associated tumors described herein) comprising administering to a subject in need thereof a therapeutically effective amounts of a compound of Formula I or a pharmaceutically acceptable salt thereof or a compound of Formula II or a pharmaceutically acceptable salt thereof and an EGFR inhibitor (e.g., any of the EGFR inhibitors disclosed herein) in any order, together or separately. In one embodiment, the compound of Formula I is a compound selected from any one of Examples 1-69, or a pharmaceutically acceptable salt thereof.

In one embodiment, provided herein is a method of treating a MEK-associated tumor (e.g., any of the MEK-associated tumors described herein) comprising administering to a subject in need thereof a therapeutically effective amounts of a compound of Formula I or a pharmaceutically acceptable salt thereof or a compound of Formula II or a pharmaceutically acceptable salt thereof and a SHP2 inhibitor (e.g., any of the SHP2 inhibitors disclosed herein) in any order, together or separately. In one embodiment, the compound of Formula I is a compound selected from any one of Examples 1-69, or a pharmaceutically acceptable salt thereof.

In one embodiment, provided herein is a method of treating a MEK-associated tumor (e.g., any of the MEK-associated tumors described herein) comprising administering to a subject in need thereof a therapeutically effective amounts of a compound of Formula I or a pharmaceutically acceptable salt thereof or a compound of Formula II or a pharmaceutically acceptable salt thereof and a checkpoint inhibitor (e.g., any of the checkpoint inhibitors disclosed herein) in any order, together or separately. In one embodiment, the compound of Formula I is a compound selected from any one of Examples 1-69, or a pharmaceutically acceptable salt thereof.

Also provided herein is a pharmaceutical combination for treating a MEK-associated tumor in a subject in need thereof, which comprises (a) a compound of Formula I or a pharmaceutically acceptable salt thereof or a compound of Formula II or a pharmaceutically acceptable salt thereof and (b) at least one additional anticancer (e.g., any of the exemplary additional anticancer agents described herein or known in the art), wherein the compound of Formula I or a pharmaceutically acceptable salt thereof or the compound of Formula II or a pharmaceutically acceptable salt thereof and the one or more, e.g., one or more additional anticancer agents are formulated separately for simultaneous or separate use for the treatment of the tumor, wherein the amounts of the compound of Formula I or a pharmaceutically acceptable salt thereof or the compound of Formula II or a pharmaceutically acceptable salt thereof and of the additional anticancer agent(s) are together effective in treating the tumor; (ii) the use of such a combination for the preparation of a medicament for the treatment of the tumor; and (iii) a commercial package or product comprising such a combination as a combined preparation for simultaneous, separate or sequential use; and to a method of treatment of a tumor in a subject in need thereof.

The term "pharmaceutical combination", as used herein, refers to a non-fixed combination of the active ingredients. The term "non-fixed combination" means that a compound of Formula I or a pharmaceutically acceptable salt thereof or a compound of Formula II or a pharmaceutically acceptable salt thereof and one or more, e.g., one or more additional anticancer agents are formulated as separate compositions or dosages such that they may be administered to a subject in need thereof simultaneously or separately with variable intervening time limits and in any order, wherein such administration provides effective levels of the two or more compounds in the body of the subject. These also apply to cocktail therapies, e.g. the administration of three or more active ingredients. Similarly, the term "combination" when referring to a compound of Formula I or a pharmaceutically acceptable salt thereof or a compound of Formula II or a pharmaceutically acceptable salt thereof in use with a combination of one or more anticancer agents refers to a non-fixed combination.

Accordingly, also provided herein is a method of treating a MEK-associated tumor, comprising administering to a subject in need thereof a pharmaceutical combination for treating said tumor which comprises (a) a compound of Formula I or a pharmaceutically acceptable salt thereof or a compound of Formula II or a pharmaceutically acceptable salt thereof and (b) one or more, e.g., one or more additional anticancer agents for simultaneous, separate or sequential use for the treatment of the tumor, wherein the amounts of the compound of Formula I or a pharmaceutically acceptable salt thereof or the compound of Formula II or a pharmaceutically acceptable salt thereof and the additional anticancer agent(s) are together effective in treating the tumor.

In one embodiment, provided herein is a method of treating a MEK-associated tumor (e.g., a benign, malignant, or metastatic tumor) comprising administering to a subject in need thereof a therapeutically effective amount of a compound of Formula I or a pharmaceutically acceptable salt thereof or a compound of Formula II or a pharmaceutically acceptable salt thereof, wherein the subject has not received treatment with an anticancer therapy prior to administration of said compound of Formula I or a pharmaceutically acceptable salt thereof or a compound of Formula II or a pharmaceutically acceptable salt thereof, wherein the anticancer therapy is selected from one or more, e.g., one or more anticancer therapies independently selected from surgery, radiotherapy and an anticancer agent that works by the same or different mechanism of action. In one embodiment, patient has not been treated with an anticancer agent prior to administration of said compound of Formula I or a pharmaceutically acceptable salt thereof or a compound of Formula II or a pharmaceutically acceptable salt thereof. In one embodiment, patient has not been treated with surgery prior to administration of said compound of Formula I or a pharmaceutically acceptable salt thereof or a compound of Formula II or a pharmaceutically acceptable salt thereof. In one embodiment, patient has not been treated with radiotherapy prior to administration of said compound of Formula I or a pharmaceutically acceptable salt thereof or a compound of Formula II or a pharmaceutically acceptable salt thereof.

In one embodiment, provided herein is a method of treating a subject having a MEK-associated tumor (e.g., a benign, malignant, or metastatic tumor) comprising administering a therapeutically effective amount of a compound of Formula I or a pharmaceutically acceptable salt thereof or a compound of Formula II or a pharmaceutically acceptable salt thereof, wherein the subject has been treated with prior therapy or standard therapy (e.g., treatment with one or more anticancer agents other than a compound of Formula I or a pharmaceutically acceptable salt thereof and/or radiotherapy and/or surgery) wherein the MEK-associated tumor has become refractory or intolerant to said prior therapy. In one embodiment, the subject developed brain metastasis during said prior treatment.

In one embodiment of a method disclosed herein for of treating a subject having a MEK-associated tumor, a subject having metastatic melanoma (e.g., a metastatic melanoma having a BRAF V600 mutation or a BRAF fusion) has received treatment with a BRAF inhibitor prior to treatment with a compound of Formula I, or a pharmaceutically acceptable salt thereof, or a compound of Formula II, or a pharmaceutically acceptable salt thereof. In one embodiment, the subject was previously treated with a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide, (3R)—N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394). In one embodiment, the subject was previously treated with a BRAF inhibitor selected from encorafenib, dabrafenib and vemurafenib. In one embodiment, the subject became refractory to said prior treatment. In one embodiment, the subject developed brain metastasis during said prior treatment.

In one embodiment of a method disclosed herein for of treating a subject having a MEK-associated tumor, a subject having metastatic melanoma (e.g., metastatic melanoma having a BRAF V600 mutation or a BRAF fusion) has received treatment with a BRAF inhibitor and a MEK inhibitor prior to treatment with a compound of Formula I, or a pharmaceutically acceptable salt thereof, or a compound of Formula II, or a pharmaceutically acceptable salt thereof. In one embodiment, the subject was previously treated with a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide, and (3R)—N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394), and a MEK inhibitor selected from binimetinib, trametinib, cobimetinib, selumetinib, pimasertib, refametinib, N-[2(R),3-dihydroxypropoxy]-3,4-difluoro-2-(2-fluoro-4-iodophenylamino)benzamide (PD-325901), 2-(2-chloro-4-iodophenylamino)-N-(cyclopropylmethoxy)-3,4-difluorobenzamide (CI-1040), and 3-[2(R),3-dihydroxypropyl]-6-fluoro-5-(2-fluoro-4-iodophenylamino)-8-methylpyrido[2,3-d]pyrimidine-4,7(3H,8H)-dione (TAK-733). In one embodiment, the subject was previously treated with a BRAF inhibitor selected from encorafenib, dabrafenib and vemurafenib and a MEK inhibitor selected from binimetinib, trametinib, and cobimetinib. In one embodiment, the subject was previously treated with encorafenib and binimetinib. In one embodiment, the subject was previously treated with dabrafenib and trametinib. In one embodiment, the subject was previously treated with vemurafenib and cobimetinib. In one embodiment, the subject became refractory to said prior treatment. In one embodiment, the subject developed brain metastasis during said prior treatment.

In one embodiment of a method disclosed herein for of treating a subject having a MEK-associated tumor, a subject having metastatic melanoma (e.g., metastatic melanoma having a BRAF V600 mutation or a BRAF fusion) has received treatment with one or more, e.g., one or two checkpoint inhibitors (e.g., any of the checkpoint inhibitors disclosed herein, e.g., a CTLA-4 inhibitor, a PD-1 inhibitor, and/or a PD-L1 inhibitor) prior to treatment with a compound of Formula I, or a pharmaceutically acceptable salt thereof. In one embodiment, the subject was previously treated with one or more, e.g., one or two checkpoint inhibitors independently selected from ipilimumab, nivolumab, and pembrolizumab. In one embodiment, the subject became refractory to said prior treatment. In one embodiment, the subject developed brain metastasis during said prior treatment.

In one embodiment of a method disclosed herein for of treating a subject having a MEK-associated tumor, a subject having metastatic melanoma (e.g., metastatic melanoma having a BRAF V600 mutation or a BRAF fusion) has received treatment with one or more, e.g., one or two inhibitors of PI3K prior to treatment with a compound of Formula I, or a pharmaceutically acceptable salt thereof, or a compound of Formula I, or a pharmaceutically acceptable salt thereof. In one embodiment, the subject was previously treated with one or more, e.g., one or two PI3K inhibitors selected from buparlisib (BKM120), alpelisib (BYL719), samotolisib (LY3023414), 8-[(1R)-1-[(3,5-difluorophenyl)amino]ethyl]-N,N-dimethyl-2-(morpholin-4-yl)-4-oxo-4H-chromene-6-carboxamide (AZD8186), tenalisib (RP6530), voxtalisib hydrochloride (SAR-245409), gedatolisib (PF-05212384), panulisib (P-7170), taselisib (GDC-0032), trans-2-amino-8-[4-(2-hydroxyethoxy)cyclohexyl]-6-(6-methoxypyridin-3-yl)-4-methylpyrido[2,3-d]pyrimidin-7(8H)-one (PF-04691502), duvelisib (ABBV-954), N2-[4-oxo-4-[4-(4-oxo-8-phenyl-4H-1-benzopyran-2-yl)morpholin-4-ium-4-ylmethoxy]butyryl]-L-arginyl-glycyl-L-aspartyl-L-serine acetate (SF-1126), pictilisib (GDC-0941), 2-methyl-1-[2-methyl-3-(trifluoromethyl)benzyl]-6-(morpholin-4-yl)-1H-benzimidazole-4-carboxylic acid (GSK2636771), idelalisib (GS-1101), umbralisib tosylate (TGR-1202), pictilisib (GDC-0941), copanlisib hydrochloride (BAY 84-1236), dactolisib (BEZ-235), 1-(4-[5-[5-Amino-6-(5-tert-butyl-1,3,4-oxadiazol-2-yl)pyrazin-2-yl]-1-ethyl-1H-1,2,4-triazol-3-yl]piperidin-1-yl)-3-hydroxypropan-1-one (AZD-8835), 5-[6,6-Dimethyl-4-(morpholin-4-yl)-8,9-dihydro-6H-[1,4]oxazino[4,3-e]purin-2-yl]pyrimidin-2-amine (GDC-0084) everolimus, rapamycin, perifosine, sirolimus, and temsirolimus. In one embodiment, the subject was previously treated with buparlisib or alpelisib, alone or in combination. In one embodiment, the subject became refractory to said prior treatment. In one embodiment, the subject developed brain metastasis during said prior treatment. In one embodiment, the subject developed brain metastasis during said prior treatment.

In one embodiment of a method disclosed herein for of treating a subject having a MEK-associated tumor, a subject having metastatic melanoma (e.g., metastatic melanoma having a BRAF V600 mutation or a BRAF fusion) has received treatment with a BRAF inhibitor and one or more, e.g., one or two checkpoint inhibitors (e.g., any of the checkpoint inhibitors disclosed herein, e.g., a CTLA-4 inhibitor, a PD-1 inhibitor, and/or a PD-L1 inhibitor) prior to treatment with a compound of Formula I, or a pharmaceutically acceptable salt thereof, or a compound of Formula II, or a pharmaceutically acceptable salt thereof. In one embodiment, the subject was previously treated with a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide, and (3R)—N-(3-[[5-(2-cyclopropylpyrimidin-5-yl)-1H-pyrrolo[2,3-b]pyridin-3-yl]carbonyl]-2,4-difluorophenyl)-3-fluoro-pyrrolidine-1-sulfonamide (PLX8394), and one or more, e.g., one or two checkpoint inhibitors independently selected from ipilimumab, nivolumab and pembrolizumab. In one embodiment, the subject became refractory to said prior treatment. In one embodiment, the subject developed brain metastasis during said prior treatment.

In one embodiment of a method disclosed herein for of treating a subject having a MEK-associated tumor, a subject having metastatic melanoma (e.g., metastatic melanoma having a BRAF V600 mutation or a BRAF fusion) has received treatment with a BRAF inhibitor, a MEK inhibitor, and one or more, e.g., one or two checkpoint inhibitors (e.g., any of the checkpoint inhibitors disclosed herein, e.g., a CTLA-4 inhibitor, a PD-1 inhibitor, and/or a PD-L1 inhibitor) prior to treatment with a compound of Formula I, or a pharmaceutically acceptable salt thereof, or a compound of Formula II, or a pharmaceutically acceptable salt thereof. In one embodiment, the subject was previously treated with a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide (PLX4720), and (3R)—N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394), a MEK inhibitor selected from binimetinib, trametinib, cobimetinib, selumetinib, pimasertib, refametinib, N-[2(R),3-dihydroxypropoxy]-3,4-difluoro-2-(2-fluoro-4-iodophenylamino)benzamide (PD-325901), 2-(2-chloro-4-iodophenylamino)-N-(cyclopropylmethoxy)-3,4-difluorobenzamide (CI-1040), and 3-[2(R),3-dihydroxypropyl]-6-fluoro-5-(2-fluoro-4-iodophenylamino)-8-methylpyrido[2,3-d]pyrimidine-4,7(3H,8H)-dione (TAK-733), and one or checkpoint inhibitors (e.g., any of the checkpoint inhibitors disclosed herein, e.g., a CTLA-4 inhibitor, a PD-1 inhibitor, and/or a PD-L1 inhibitor). In one embodiment, the subject was previously treated with a BRAF inhibitor selected from encorafenib, dabrafenib and vemurafenib, a MEK inhibitor selected from binimetinib, trametinib and cobimetinib, and one or more, e.g., one or two checkpoint inhibitors independently selected from ipilimumab, nivolumab, and pembrolizumab. In one embodiment, the subject became refractory to said prior treatment. In one embodiment, the subject developed brain metastasis during said prior treatment.

In one embodiment of a method disclosed herein for of treating a subject having a MEK-associated tumor, a subject having metastatic melanoma (e.g., metastatic melanoma having a BRAF V600 mutation or a BRAF fusion) has received treatment with one or more, e.g., one or two alkylating agents prior to treatment with a compound of Formula I, or a pharmaceutically acceptable salt thereof, or a compound of Formula II, or a pharmaceutically acceptable salt thereof. In one embodiment, the subject was previously treated with s alkylating agents selected from temozolomide, fotemustine, lomustine and carmustine. In one embodiment, the subject was previously treated with temozolomide. In one embodiment, the subject became refractory to said prior treatment. In one embodiment, the subject developed brain metastasis during said prior treatment.

In one embodiment of a method disclosed herein for of treating a subject having a MEK-associated tumor, a subject having metastatic colorectal cancer (e.g., a metastatic colorectal cancer having a BRAF V600 mutation or a BRAF fusion) has received treatment with a MEK inhibitor and one or more, e.g., one or two checkpoint inhibitors (e.g., any of the checkpoint inhibitors disclosed herein, e.g., a CTLA-4 inhibitor, a PD-1 inhibitor, and/or a PD-L1 inhibitor) prior to treatment with a compound of Formula I, or a pharmaceutically acceptable salt thereof, or Formula II or a pharmaceutically acceptable salt thereof. In one embodiment, the subject was previously treated with a MEK inhibitor selected from binimetinib, trametinib, cobimetinib, selumetinib, pimasertib, refametinib, N-[2(R),3-dihydroxypropoxy]-3,4-difluoro-2-(2-fluoro-4-iodophenylamino)benzamide (PD-325901), 2-(2-chloro-4-iodophenylamino)-N-(cyclopropylmethoxy)-3,4-difluorobenzamide (CI-1040), and 3-[2(R),3-dihydroxypropyl]-6-fluoro-5-(2-fluoro-4-iodophenylamino)-8-methylpyrido[2,3-d]pyrimidine-4,7(3H,8H)-dione (TAK-733), and one or checkpoint inhibitors (e.g., any of the checkpoint inhibitors disclosed herein, e.g., a CTLA-4 inhibitor, a PD-1 inhibitor, and/or a PD-L1 inhibitor). In one embodiment, the subject was previously treated with a MEK inhibitor selected from binimetinib, trametinib and cobimetinib, and one or more, e.g., one or two checkpoint inhibitors independently selected from ipilimumab, nivolumab, and pembrolizumab. In one embodiment, the subject was previously treated with a MEK inhibitor which is binimetinib and a checkpoint inhibitor which is nivolumab, ipilimumab, or pembrolizumab. In one embodiment, the subject became refractory to said prior treatment. In one embodiment, the subject developed brain metastasis during said prior treatment.

In one embodiment of a method disclosed herein for of treating a subject having a MEK-associated tumor, a subject having metastatic colorectal cancer (e.g., a metastatic colorectal cancer having a BRAF V600 mutation or a BRAF fusion) has received treatment with one or more, e.g., one or two checkpoint inhibitors (e.g., any of the checkpoint inhibitors disclosed herein, e.g., a CTLA-4 inhibitor, a PD-1 inhibitor, and/or a PD-L1 inhibitor) prior to treatment with a compound of Formula I, or a pharmaceutically acceptable salt thereof, or a compound of Formula II, or a pharmaceutically acceptable salt thereof. In one embodiment, the subject was previously treated with one or more, e.g., one or two checkpoint inhibitors independently selected from ipilimumab, nivolumab, pembrolizumab, and sasanlimab. In one embodiment, the subject became refractory to said prior treatment. In one embodiment, the subject developed brain metastasis during said prior treatment.

In one embodiment of a method disclosed herein for of treating a subject having a MEK-associated tumor, a subject having a metastatic colorectal cancer (e.g., mutant metastatic colorectal cancer having a BRAF V600 mutation or a BRAF fusion) has received treatment with one or more cytotoxic chemotherapeutic agents prior to treatment with a compound of Formula I, or a pharmaceutically acceptable salt, thereof, or a compound of Formula II, or a pharmaceutically acceptable salt thereof. In one embodiment, the subject has received treatment with oxaliplatin, irinotecan, FOLFOXIRI (oxaliplatin, irinotecan and fluorouracil), FOLFIRI (folinic acid, fluorouracil and irinotecan) or CAPEOX (capecitabine and oxaliplatin) prior to treatment with a compound of Formula I, or a pharmaceutically acceptable salt, thereof. In one embodiment, the subject became refractory to said prior treatment. In one embodiment, the subject developed brain metastasis during said prior treatment.

In one embodiment of a method disclosed herein for of treating a subject having a MEK-associated tumor, a subject having a metastatic colorectal cancer (e.g., metastatic colorectal cancer having a BRAF V600 mutation or a BRAF fusion) has received treatment with an EGFR inhibitor, a BRAF inhibitor, and one or more cytotoxic chemotherapeutic agents prior to treatment with a compound of Formula I, or a pharmaceutically acceptable salt thereof, or a compound of Formula II, or a pharmaceutically acceptable salt thereof. In one embodiment, a subject having a metastatic colorectal cancer previously received treatment with an EGFR inhibitor selected from cetuximab, panitumumab, osimertinib, erlotinib, gefitinib, necitumumab, neratinib, lapatinib, vandetanib and brigatinib, a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide (PLX4720), and (3R)—N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394), and one or more cytotoxic chemotherapeutic agents. In one embodiment, the subject previously received treatment with an EGFR inhibitor selected from cetuximab, and panitumumab, a BRAF inhibitor which is vemurafenib, and a cytotoxic chemotherapeutic agent which is irinotecan. In one embodiment, the subject became refractory to said prior treatment. In one embodiment, the subject developed brain metastasis during said prior treatment.

In one embodiment of a method disclosed herein for of treating a subject having a MEK-associated tumor, a subject having a metastatic colorectal cancer (e.g., a metastatic colorectal cancer having a BRAF V600 mutation or a BRAF fusion) has received treatment with an EGFR inhibitor and one or more cytotoxic chemotherapeutic agents prior to treatment with a compound of Formula I, or a pharmaceutically acceptable salt thereof, a compound of Formula II, or a pharmaceutically acceptable salt thereof. In one embodiment, the subject has previously received treatment with an EGFR inhibitor selected from cetuximab, panitumumab, osimertinib, erlotinib, gefitinib, necitumumab, neratinib, lapatinib, vandetanib and brigatinib, and one or more chemotherapeutic agents. In one embodiment, the subject has previously received treatment with an EGFR inhibitor selected from cetuximab, and panitumumab, and a cytotoxic chemotherapeutic agent which is irinotecan or FOLFIRI (folinic acid, fluorouracil and irinotecan). In one embodiment, the subject became refractory to said prior treatment. In one embodiment, the subject developed brain metastasis during said prior treatment.

In one embodiment of a method disclosed herein for of treating a subject having a MEK-associated tumor, a subject having metastatic non-small cell lung cancer (e.g., a metastatic non-small cell lung cancer having a BRAF V600 mutation or a BRAF fusion) has received treatment with one or more, e.g., one or two EGFR inhibitors prior to treatment with a compound of Formula I, or a pharmaceutically acceptable salt thereof, a compound of Formula II, or a pharmaceutically acceptable salt thereof. In one embodiment, the subject was previously treated with one or more, e.g., one or two EGFR inhibitors independently selected from cetuximab, panitumumab, osimertinib, erlotinib, gefitinib, necitumumab, neratinib, lapatinib, vandetanib and brigatinib. In one embodiment, the subject was previously treated with erlotinib. In one embodiment, the subject was previously treated with gefitinib. In one embodiment, the subject was previously treated with erlotinib and gefitinib. In one embodiment, the subject became refractory to said prior treatment. In one embodiment, the subject developed brain metastasis during said prior treatment.

In one embodiment of a method disclosed herein for of treating a subject having a MEK-associated tumor, a subject having metastatic non-small cell lung cancer (e.g., metastatic non-small cell lung cancer having a BRAF mutation) previously received treatment with a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide (PLX4720), and (3R)—N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394), a MEK inhibitor selected from binimetinib, trametinib, cobimetinib, selumetinib, pimasertib, refametinib, N-[2(R),3-dihydroxypropoxy]-3,4-difluoro-2-(2-fluoro-4-iodophenylamino)benzamide (PD-325901), 2-(2-chloro-4-iodophenylamino)-N-(cyclopropylmethoxy)-3,4-difluorobenzamide (CI-1040), and 3-[2(R),3-dihydroxypropyl]-6-fluoro-5-(2-fluoro-4-iodophenylamino)-8-methylpyrido[2,3-d]pyrimidine-4,7(3H,8H)-dione (TAK-733), and an EGFR inhibitor selected from cetuximab, panitumumab, osimertinib, erlotinib, gefitinib, necitumumab, neratinib, lapatinib, vandetanib and brigatinib prior to treatment with a compound of Formula I or a pharmaceutically acceptable salt thereof or a compound of Formula II or a pharmaceutically acceptable salt thereof. In one embodiment, the subject was previously treated with a BRAF inhibitor selected from vemurafenib, dabrafenib and encorafenib and an EGFR inhibitor selected from cetuximab and panitumumab prior to treatment with a compound of Formula I, or a pharmaceutically acceptable salt thereof. In one embodiment, the subject became refractory to said prior treatment. In one embodiment, the subject developed brain metastasis during said prior treatment.

In one embodiment of a method disclosed herein for of treating a subject having a MEK-associated tumor, a subject having metastatic thyroid cancer (e.g., metastatic thyroid cancer having a BRAF V600 mutation or a BRAF fusion) previously received treatment with a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide (PLX4720), and (3R)—N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394), a MEK inhibitor selected from binimetinib, trametinib, cobimetinib, selumetinib, pimasertib, refametinib, N-[2(R),3-dihydroxypropoxy]-3,4-difluoro-2-(2-fluoro-4-iodophenylamino)benzamide (PD-325901), 2-(2-chloro-4-iodophenylamino)-N-(cyclopropylmethoxy)-3,4-difluorobenzamide (CI-1040), and 3-[2(R),3-dihydroxypropyl]-6-fluoro-5-(2-fluor-4-iodophenylamino)-8-methylpyrido[2,3-d]pyrimidine-4,7(3H,8H)-dione (TAK-733), and an EGFR inhibitor selected from cetuximab, panitumumab, osimertinib, erlotinib, gefitinib, necitumumab, neratinib, lapatinib, vandetanib and brigatinib prior to treatment with a compound of Formula I, or a pharmaceutically acceptable salt thereof, a compound of Formula II, or a pharmaceutically acceptable salt thereof. In one embodiment, the subject was previously treated with a BRAF inhibitor selected from vemurafenib, dabrafenib and encorafenib prior to treatment with a compound of Formula I, or a pharmaceutically acceptable salt thereof. In one embodiment, the subject became refractory to said prior treatment. In one embodiment, the subject developed brain metastasis during said prior treatment.

In one embodiment of a method disclosed herein for of treating a subject having a MEK-associated tumor, the subject has LMD and was previously treated with a BRAF inhibitor and one or more, e.g., one or two checkpoint inhibitors (e.g., any of the checkpoint inhibitors disclosed herein, e.g., a CTLA-4 inhibitor, a PD-1 inhibitor, and/or a PD-L1 inhibitor) prior to treatment with a compound of Formula I, or a pharmaceutically acceptable salt thereof, a compound of Formula II, or a pharmaceutically acceptable salt thereof. In one embodiment, the subject was previously treated with a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide (PLX4720), and (3R)—N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394), and one or more, e.g., one or two checkpoint inhibitors independently selected from ipilimumab, nivolumab, and pembrolizumab. In one embodiment, the subject became refractory to said prior treatment.

In one embodiment of a method disclosed herein for of treating a subject having a MEK-associated tumor, the subject has LMD and was previously treated with a BRAF inhibitor, a MEK inhibitor, and one or more, e.g., one or two checkpoint inhibitors (e.g., any of the checkpoint inhibitors disclosed herein, e.g., a CTLA-4 inhibitor, a PD-1 inhibitor, and/or a PD-L1 inhibitor) prior to treatment with a compound of Formula I, or a pharmaceutically acceptable salt thereof, a compound of Formula II, or a pharmaceutically acceptable salt thereof. In one embodiment, the subject was previously treated with a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide (PLX4720), and (3R)—N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394), a MEK inhibitor selected from binimetinib, trametinib, cobimetinib, selumetinib, pimasertib, refametinib, N-[2(R),3-dihydroxypropoxy]-3,4-difluoro-2-(2-fluoro-4-iodophenylamino)benzamide (PD-325901), 2-(2-chloro-4-iodophenylamino)-N-(cyclopropylmethoxy)-3,4-difluorobenzamide (CI-1040), and 3-[2(R),3-dihydroxypropyl]-6-fluoro-5-(2-fluoro-4-iodophenylamino)-8-methylpyrido[2,3-d]pyrimidine-4,7(3H,8H)-dione (TAK-733), and a checkpoint inhibitor (e.g., any of the checkpoint inhibitors disclosed herein, e.g., a CTLA-4 inhibitor, a PD-1 inhibitor, and/or a PD-L1 inhibitor). In one embodiment, the subject was previously treated with a BRAF inhibitor selected from encorafenib, dabrafenib and vemurafenib, a MEK inhibitor selected from binimetinib, trametinib and cobimetinib, and one or more, e.g., one or two checkpoint inhibitors independently selected from ipilimumab, nivolumab, and pembrolizumab. In one embodiment, the subject became refractory to said prior treatment.

In one embodiment of a method disclosed herein for of treating a subject having a MEK-associated tumor, the subject has LMD and was previously treated with one or more, e.g., one or two checkpoint inhibitors (e.g., any of the checkpoint inhibitors disclosed herein, e.g., a CTLA-4 inhibitor, a PD-1 inhibitor, and/or a PD-L1 inhibitor) prior to treatment with a compound of Formula I, or a pharmaceutically acceptable salt thereof, a compound of Formula II, or a pharmaceutically acceptable salt thereof. In one embodiment, the subject was previously treated with one or more, e.g., one or two checkpoint inhibitors independently selected from ipilimumab, nivolumab, and pembrolizumab. In one embodiment, the subject became refractory to said prior treatment.

In one embodiment of a method disclosed herein for of treating a subject having a MEK-associated tumor, the subject has a glioma and was previously treated with surgery prior to treatment with a compound of Formula I, or a pharmaceutically acceptable salt thereof, a compound of Formula II, or a pharmaceutically acceptable salt thereof. In one embodiment, the subject became refractory to said prior treatment. In one embodiment, the glioma is a Grade 2, Grade 3 or Grade 4 glioma.

In one embodiment of a method disclosed herein for of treating a subject having a MEK-associated tumor, the subject has a glioma and was previously treated with radiotherapy (e.g., whole brain radiotherapy or stereotactic radiosurgery) prior to treatment with a compound of Formula I, or a pharmaceutically acceptable salt thereof, a compound of Formula II, or a pharmaceutically acceptable salt thereof. In one embodiment, the subject became refractory to said prior treatment. In one embodiment, the glioma is a Grade 2, Grade 3 or Grade 4 glioma.

In one embodiment of a method disclosed herein for of treating a subject having a MEK-associated tumor, the subject has a glioma and was previously treated with one or more cytotoxic chemotherapy agents prior to treatment with a compound of Formula I, or a pharmaceutically acceptable salt thereof, a compound of Formula II, or a pharmaceutically acceptable salt thereof. In one embodiment, the subject was previously treated with and one or more cytotoxic chemotherapy agents independently selected from cisplatin, pemetrexed, vinorelbine and paclitaxel. In one embodiment, the subject became refractory to said prior treatment. In one embodiment, the glioma is a Grade 2, Grade 3 or Grade 4 glioma.

In one embodiment of a method disclosed herein for of treating a subject having a MEK-associated tumor, the subject has a MEK-associated glioma and was previously treated with an ornithine decarboxylase inhibitor prior to treatment with a compound of Formula I, or a pharmaceutically acceptable salt thereof, a compound of Formula II, or a pharmaceutically acceptable salt thereof. In one embodiment, the subject previously received treatment with an ornithine decarboxylase inhibitor which is eflornithine (as the racemate, or D or L enantiomer). In one embodiment, the subject became refractory to said prior treatment. In one embodiment, the glioma is a Grade 2, Grade 3 or Grade 4 glioma.

In one embodiment of a method disclosed herein for of treating a subject having a MEK-associated tumor, the subject has a MEK-associated glioma and was previously treated with an alkylating agent prior to treatment with a compound of Formula I, or a pharmaceutically acceptable salt thereof, or a pharmaceutically acceptable salt thereof, a compound of Formula II, or a pharmaceutically acceptable salt thereof. In one embodiment, the subject previously received treatment with an alkylating agent selected from temozolomide, lomustine, and carmustine. In one embodiment, the subject became refractory to said prior treatment. In one embodiment, the glioma is a Grade 2, Grade 3 or Grade 4 glioma.

In one embodiment of a method disclosed herein for of treating a subject having a MEK-associated tumor, the subject has a MEK-associated glioma and was previously treated with an alkylating agent and an ornithine decarboxylase inhibitor prior to treatment with a compound of Formula I, or a pharmaceutically acceptable salt thereof, a compound of Formula II, or a pharmaceutically acceptable salt thereof. In one embodiment, the subject previously received treatment with an alkylating agent selected from temozolomide, lomustine, and carmustine, and an ornithine decarboxylase inhibitor which is eflornithine (as the racemate, or D or L enantiomer). In one embodiment, the subject became refractory to said prior treatment. In one embodiment, the glioma is a Grade 2, Grade 3 or Grade 4 glioma.

In one embodiment of a method disclosed herein for of treating a subject having a MEK-associated tumor, the subject has a MEK-associated glioma and was previously treated with radiotherapy (e.g., whole brain radiotherapy or stereotactic radiosurgery) and an alkylating agent prior to treatment with a compound of Formula I, or a pharmaceutically acceptable salt thereof, a compound of Formula II, or a pharmaceutically acceptable salt thereof. In one embodiment, the subject previously received treatment with radiotherapy (e.g., whole brain radiotherapy or stereotactic radiosurgery) and an alkylating agent selected from temozolomide, lomustine, and carmustine. In one embodiment, the subject became refractory to said prior treatment. In one embodiment, the glioma is a Grade 2, Grade 3 or Grade 4 glioma.

In one embodiment of a method disclosed herein for of treating a subject having a MEK-associated tumor, the subject has a MEK-associated glioma and was previously treated with an antibody therapy prior to treatment with a compound of Formula I, or a pharmaceutically acceptable salt thereof, a compound of Formula II, or a pharmaceutically acceptable salt thereof. In one embodiment, the subject previously received treatment with an antibody therapy which is bevacizumab. In one embodiment, the subject became refractory to said prior treatment. In one embodiment, the glioma is a Grade 2, Grade 3 or Grade 4 glioma.

In one embodiment of a method disclosed herein for of treating a subject having a MEK-associated tumor, the subject has a MEK-associated glioma and was previously treated with surgery and radiotherapy prior to treatment with a compound of Formula I, or a pharmaceutically acceptable salt thereof, a compound of Formula II, or a pharmaceutically acceptable salt thereof. In one embodiment, the subject became refractory to said prior treatment. In one embodiment, the glioma is a Grade 2, Grade 3 or Grade 4 glioma.

In one embodiment of a method disclosed herein for of treating a subject having a MEK-associated tumor, the subject has a MEK-associated glioma and was previously treated with surgery, radiotherapy and an alkylating agent prior to treatment with a compound of Formula I, or a pharmaceutically acceptable salt thereof, a compound of Formula II, or a pharmaceutically acceptable salt thereof. In one embodiment, the subject was previously treated with surgery, radiotherapy (e.g., whole brain radiotherapy or stereotactic radiosurgery) and an alkylating agent selected from temozolomide, lomustine, and carmustine. In one embodiment, the subject became refractory to said prior treatment. In one embodiment, the glioma is a Grade 2, Grade 3 or Grade 4 glioma.

In one embodiment of a method disclosed herein for of treating a subject having a MEK-associated tumor, the subject has a MEK-associated glioma and was previously treated with a BRAF inhibitor prior to treatment with compound of Formula II, or a pharmaceutically acceptable salt thereof. In one embodiment, the subject previously received treatment with a BRAF inhibitor selected from N-[3-(5-chloro-1H-pyrrolo[2,3-b]pyridin-3-ylcarbonyl)-2,4-difluorophenyl]propane-1-sulfonamide (PLX4720), vemurafenib, dabrafenib, encorafenib and (3R)—N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394). In one embodiment, the subject became refractory to said prior treatment. In one embodiment, the glioma is a Grade 2, Grade 3 or Grade 4 glioma.

In one embodiment of a method disclosed herein for of treating a subject having a MEK-associated tumor, the subject has a MEK-associated glioma and was previously treated with a BRAF inhibitor and a MEK inhibitor prior to treatment with compound of Formula I, or a pharmaceutically acceptable salt, solvate or polymorph thereof, or Formula II, or a pharmaceutically acceptable salt, solvate or polymorph thereof. In one embodiment, the subject previously received treatment with a BRAF inhibitor selected from N-[3-(5-chloro-1H-pyrrolo[2,3-b]pyridin-3-ylcarbonyl)-2,4-difluorophenyl]propane-1-sulfonamide (PLX4720), vemurafenib, dabrafenib, encorafenib and (3R)—N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394) and a MEK inhibitor selected from binimetinib, trametinib, cobimetinib, selumetinib, pimasertib, refametinib, N-[2(R),3-dihydroxypropoxy]-3,4-difluoro-2-(2-fluoro-4-iodophenylamino)benzamide (PD-325901), 2-(2-chloro-4-iodophenylamino)-N-(cyclopropylmethoxy)-3,4-difluorobenzamide (CI-1040), and 3-[2(R),3-dihydroxypropyl]-6-fluoro-5-(2-fluoro-4-iodophenylamino)-8-methylpyrido[2,3-d]pyrimidine-4,7(3H,8H)-dione (TAK-733). In one embodiment, the subject was previously treated with a BRAF inhibitor selected from encorafenib, dabrafenib and vemurafenib and a MEK inhibitor selected from binimetinib, trametinib, and cobimetinib. In one embodiment, the subject became refractory to said prior treatment. In one embodiment, the glioma is a Grade 2, Grade 3 or Grade 4 glioma.

In one embodiment of a method disclosed herein for of treating a subject having a MEK-associated tumor, the subject has a MEK-associated brainstem ganglioglioma and was previously treated with a BRAF inhibitor prior to treatment with a compound of Formula I, or a pharmaceutically acceptable salt thereof, a compound of Formula II, or a pharmaceutically acceptable salt thereof. In one embodiment, the subject was previously treated with a BRAF inhibitor selected from encorafenib, dabrafenib, vemurafenib, N-[3-(5-chloro-1H-pyrrolo[2,3-b]pyridin-3-ylcarbonyl)-2,4-difluorophenyl]propane-1-sulfonamide (PLX4720), and (3R)—N-(3-[[5-(2-cyclopropylpyrimidin-5-yl)-1H-pyrrolo[2,3-b]pyridin-3-yl]carbonyl]-2,4-difluorophenyl)-3-fluoropyrrolidine-1-sulfonamide (PLX8394). In one embodiment, the subject was previously treated with a BRAF inhibitor selected from encorafenib, dabrafenib and vemurafenib. In one embodiment, the subject became refractory to said prior treatment.

Although the genetic basis of tumorigenesis may vary between different cancer types, the cellular and molecular mechanisms required for metastasis appear to be similar for all solid tumor types. During a metastatic cascade, the cancer cells lose growth inhibitory responses, undergo alterations in adhesiveness and produce enzymes that can degrade extracellular matrix components. This leads to detachment of tumor cells from the original tumor, infiltration into the circulation through newly formed vasculature, migration and extravasation of the tumor cells at favorable distant sites where they may form colonies. A number of genes have been identified as being promoters or suppressors of metastasis.

Accordingly, also provided herein are methods for treating, inhibiting, preventing, aiding in the prevention, or decreasing metastasis of a MEK-associated tumor in a subject in need thereof, the method comprising administering to the subject a therapeutically effective amount of a compound of Formula I or a pharmaceutically acceptable salt thereof or a compound of Formula II or a pharmaceutically acceptable salt thereof. In one embodiment, the compound of Formula I or a pharmaceutically acceptable salt thereof, is used in combination with one or more anticancer therapies independently selected from surgery (e.g., at least partial resection of a tumor), radiotherapy, and an anticancer agent.

As used herein, the term "treating metastasis" means reducing the size, progression, and/or further spread of one or more metastases.

As used herein, the term "inhibiting metastasis" means reducing the occurrence (or reoccurrence) of one or more metastases, preventing the occurrence (or reoccurrence) of one or more metastases, or reducing the spread of one or more metastases.

In one embodiment, a subject treated according to any of the methods disclosed herein may be assessed according to one or more standard response assessment criteria known in the art, including RECIST (Response Evaluation Criteria in Solid Tumors, e.g., RECIST version 1.0, RECIST version 1.1, and modified RECIST 1.1 (mRECIST 1.1)), RANO-BM (Response Assessment in Neuro-Oncology Brain Metastases), Macdonald, RANO-LMD, and NANO (Neurologic Assessment in Neuro-Oncology). In one embodiment of any of said criteria, the tumor is assessed by an imaging study (e.g., MRI, CT, MDCT or PET). In one embodiment the treatment response is assessed in accordance with RECIST version 1.1, wherein: complete response (CR) is defined as the complete disappearance of all tumor lesions; partial response (PR) is defined as a reduction in the sum of tumor measurements by at least 30%; progressive disease (PD) is defined as at least 20% increase in the sum of tumor measurements (wherein the development of new lesions or substantial progression of non-target lesions is also was defined as PD) wherein an increase of at least 5 mm from baseline is evaluated as PD; and stable disease (SD) is defined as neither sufficient shrinkage to qualify for PR nor sufficient increase to qualify for PD, taking as reference the smallest sum diameters while on treatment. In one embodiment, assessments include intracranial response (assessed as per modified RECIST using gadolinium enhanced MRI), extracranial response, global response rate, disease control rate (DCR), duration of response (DOR), progression free survival (PFS), and overall survival (OS).

As used herein, an "effective dosage" or "effective amount" of drug, compound or pharmaceutical composition is an amount sufficient to affect any one or more beneficial or desired, including biochemical, histological and/or behavioral symptoms, of the disease, its complications and intermediate pathological phenotypes presenting during development of the disease. For therapeutic use, a "therapeutically effective amount" refers to that amount of a compound being administered which will relieve to some extent one or more of the symptoms of the disorder being treated. In reference to the treatment of cancer, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth or tumor invasiveness, (4) relieving to some extent (or, preferably, eliminating) one or more signs or symptoms associated with the cancer, (5) decreasing the dose of other medications required to treat the disease, and/or (6) enhancing the effect of another medication, and/or (7) delaying the progression of the disease in a patient.

An effective dosage can be administered in one or more administrations. For the purposes of this invention, an effective dosage of drug, compound, or pharmaceutical composition is an amount sufficient to accomplish prophylactic or therapeutic treatment either directly or indirectly. As is understood in the clinical context, an effective dosage of drug, compound or pharmaceutical composition may or may not be achieved in conjunction with another drug, compound or pharmaceutical composition.

A "pharmaceutical composition" refers to a mixture of one or more of the compounds of the invention, or a pharmaceutically acceptable salt, solvate, hydrate or prodrug thereof as an active ingredient, and at least one pharmaceutically acceptable carrier or excipient. In one embodiment, the pharmaceutical composition comprises two or more pharmaceutically acceptable carriers and/or excipients.

In one embodiment, the invention provides a pharmaceutical composition comprising a compound of the invention, or a pharmaceutically acceptable salt thereof, and at least one pharmaceutically acceptable carrier or excipient. In one embodiment, the pharmaceutical composition comprises two or more pharmaceutically acceptable carriers and/or excipients.

Accordingly, in one embodiment, the invention provides a pharmaceutical composition for use in the treatment of abnormal cell growth in a subject in need thereof, which pharmaceutical composition comprises a compound of the invention, or a pharmaceutically acceptable salt thereof, and at least one pharmaceutically acceptable carrier or excipient.

As used herein, a "pharmaceutically acceptable carrier" refers to a carrier or diluent that does not cause significant irritation to an organism and does not abrogate the biological activity and properties of the administered compound.

The pharmaceutical acceptable carrier may comprise any conventional pharmaceutical carrier or excipient. The choice of carrier and/or excipient will to a large extent depend on factors such as the particular mode of administration, the effect of the carrier or excipient on solubility and stability, and the nature of the dosage form.

Suitable pharmaceutical carriers include inert diluents or fillers, water and various organic solvents (such as hydrates and solvates). The pharmaceutical compositions may, if desired, contain additional ingredients such as flavorings, binders, excipients and the like.

The term 'excipient' is used herein to describe any ingredient other than the compound(s) of the invention. The choice of excipient will to a large extent depend on factors such as the mode of administration, the effect of the excipient on solubility and stability, and the nature of the dosage form.

As used herein, "excipient" includes any and all solvents, dispersion media, coatings, antibacterial and antifungal agents, isotonic and absorption delaying agents, carriers, diluents and the like that are physiologically compatible. Examples of excipients include one or more of water, saline, phosphate buffered saline, dextrose, glycerol, ethanol and the like, as well as combinations thereof, and may include isotonic agents, for example, sugars, sodium chloride, or polyalcohols such as mannitol, or sorbitol in the composition. Examples of excipients also include various organic solvents (such as hydrates and solvates). The pharmaceutical compositions may, if desired, contain additional excipients such as flavorings, binders/binding agents, lubricating agents, disintegrants, sweetening or flavoring agents, coloring matters or dyes, and the like. For example, for oral administration, tablets containing various excipients, such as citric acid may be employed together with various disintegrants such as starch, alginic acid and certain complex silicates and with binding agents such as sucrose, gelatin and acacia. Examples, without limitation, of excipients include calcium carbonate, calcium phosphate, various sugars and types of starch, cellulose derivatives, gelatin, vegetable oils and polyethylene glycols. Thus, for oral administration, tablets containing various excipients, such as citric acid may be employed together with various disintegrants such as starch, alginic acid and certain complex silicates and with binding agents such as sucrose, gelatin and acacia. Examples, without limitation, of excipients include calcium carbonate, calcium phosphate, various sugars and types of starch, cellulose derivatives, gelatin, vegetable oils and polyethylene glycols. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Examples of excipients also include pharmaceutically acceptable substances such as wetting agents or minor amounts of auxiliary substances such as wetting or emulsifying agents, preservatives, or buffers, which enhance the shelf life or effectiveness of the compound.

The pharmaceutical composition may, for example, be in a form suitable for oral administration as a tablet, capsule, pill, powder, sustained release formulations, solution suspension, liquid solutions (e.g., injectable and infusible solutions) for parenteral injection as a sterile solution, suspension or emulsion, for topical administration as an ointment or cream, powders, liposomes and suppositories (e.g., for rectal administration as a suppository). Exemplary parenteral administration forms include solutions or suspensions of active compounds in sterile aqueous solutions, for example, aqueous propylene glycol or dextrose solutions. Such dosage forms may be suitably buffered, if desired. The form depends on the intended mode of administration and therapeutic application.

The pharmaceutical composition may be in unit dosage forms suitable for single administration of precise dosages.

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid filled), chews, multi and nano particulates, gels, solid solution, liposome, films (including muco adhesive), ovules, sprays and liquid formulations. Such capsules or tablets may comprise a controlled release formulation. In the case of capsules, tablets, and pills, the dosage forms also may comprise buffering agents or may be prepared with enteric coatings.

Liquid formulations include suspensions, solutions, syrups and elixirs. Such formulations may be used as fillers in soft or hard capsules and typically include a carrier or adjuvant, for example such as one or more of wetting, emulsifying, suspending, flavoring (e.g., sweetening), or perfuming agents, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast dissolving, fast disintegrating dosage forms such as those described in Expert Opinion in Therapeutic Patents, 11 (6), 981 986 by Liang and Chen (2001), the disclosure of which is incorporated herein by reference in its entirety.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl substituted hydroxypropyl cellulose, starch, pregelatinized starch and sodium alginate. Generally, the disintegrant will comprise from 1 wt % to 25 wt %, preferably from 5 wt % to 20 wt % of the dosage form. Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray dried monohydrate, anhydrous and the like), mannitol, xylitol, dextrose, sucrose, sorbitol, microcrystalline cellulose, starch and dibasic calcium phosphate dihydrate. Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet. Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet. Other conventional ingredients include anti-oxidants, colorants, flavoring agents, preservatives and taste masking agents. Tablet blends may be compressed directly or by roller to form tablets. Tablet blends or portions of blends may alternatively be wet, dry, or melt granulated, melt congealed, or extruded before tableting. The final formulation may include one or more layers and may be coated or uncoated; or encapsulated. Solid formulations for oral administration may be formulated to be immediate and/or modified release. Modified release formulations include delayed, sustained, pulsed, controlled, targeted and programmed release.

For oral administration, the compositions may be provided in the form of tablets or capsules containing 0.01, 0.05, 0.1, 0.25, 0.5, 1.0, 2.5, 5.0, 10.0, 15.0, 25.0, 50.0, 75.0, or 100 milligrams of the active ingredient for the symptomatic adjustment of the dosage to the patient. A medicament typically contains from about 0.01 mg to about 100 mg of the active ingredient. In another embodiment, a medicament contains from about 0.01 to 0.25 mg of the active ingredient. In another embodiment, a medicament contains about 0.25, 0.5, 1.0, 5.0, 15 or 25 mg of the active ingredient.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including micro needle) injectors, needle free injectors and infusion techniques. Injectable preparations (i.e., sterile injectable aqueous or oleaginous suspensions) may be formulated according to the known art using one or more of suitable dispersing, wetting agents, or suspending agents. Parenteral formulations are typically aqueous solutions which may contain excipients such as salts, carbohydrates and buffering agents (preferably to a pH of from 3 to 9), but, for some applications, they may be more suitably formulated as a sterile non aqueous solution or as a dried form to be used in conjunction with a suitable vehicle such as sterile, pyrogen free water. The preparation of parenteral formulations under sterile conditions, for example, by lyophilization, may readily be accomplished using standard pharmaceutical techniques well known to those skilled in the art. The solubility of compounds of the invention used in the preparation of parenteral solutions may be increased by the use of appropriate formulation techniques, such as the incorporation of solubility enhancing agents.

Formulations for parenteral administration may be formulated to be immediate and/or modified release. Modified release formulations include delayed, sustained, pulsed, controlled, targeted and programmed release. Thus, compounds of the invention may be formulated as a solid, semi solid, or thixotropic liquid for administration as an implanted depot providing modified release of the active compound. Examples of such formulations include drug coated stents and PGLA microspheres.

The compounds of the invention may also be administered topically to the skin or mucosa, that is, dermally or transdermally, such as via transdermal patches or iontophoresis devices, intraocular administration, or intranasal or inhalation administration. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated. Other means of topical administration include delivery by electroporation, iontophoresis, phonophoresis, sonophoresis and micro needle or needle free (e.g. Powderject™, Bioject™, etc.) injection.

Formulations suitable for topical administration to the eye include, for example, eye drops wherein the compound of this invention is dissolved or suspended in a suitable excipient. A typical formulation suitable for ocular or aural administration may be in the form of drops of a micronized suspension or solution in isotonic, pH-adjusted, sterile saline. Other formulations suitable for ocular and aural administration include ointments, biodegradable (i.e., absorbable gel sponges, collagen) and non-biodegradable (i.e., silicone) implants, wafers, lenses and particulate or vesicular systems, such as niosomes or liposomes. A polymer such as crossed linked polyacrylic acid, polyvinyl alcohol, hyaluronic acid, a cellulosic polymer, for example, hydroxypropylmethylcellulose, hydroxyethylcellulose, or methylcellulose, or a heteropolysaccharide polymer, for example, gelan gum, may be incorporated together with a preservative, such as benzalkonium chloride. Such formulations may also be delivered by iontophoresis.

Formulations for topical administration may be formulated to be immediate and/or modified release. Modified release formulations include delayed, sustained, pulsed, controlled, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2 tetrafluoroethane or 1,1,1,2,3,3,3 heptafluoropropane. For intranasal use, the powder may include a bioadhesive agent, for example, chitosan or cyclodextrin. The pressurized container, pump, spray, atomizer, or nebulizer contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid. Prior to use in a dry powder or suspension formulation, the drug product may be micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as I leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

Suitable flavors, such as menthol and levomenthol, or sweeteners, such as saccharin or saccharin sodium, may be added to those formulations of the invention intended for inhaled/intranasal administration.

Compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed, sustained, pulsed, controlled, targeted and programmed release.

Compounds of the invention may also be administered directly to the eye or ear, typically in the form of drops of a micronized suspension or solution in isotonic, pH adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed, sustained, pulsed, controlled, targeted, or programmed release.

Other excipients and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pennsylvania, 1975; Liberman et al., Eds., Pharmaceutical Dosage Forms, Marcel Decker, New York, N.Y., 1980; and Kibbe et al., Eds., Handbook of Pharmaceutical Excipients (3rd Ed.), American Pharmaceutical Association, Washington, 1999.

Acceptable excipients are nontoxic to subjects at the dosages and concentrations employed, and may comprise one or more of the following: 1) buffers such as phosphate, citrate, or other organic acids; 2) salts such as sodium chloride; 3) antioxidants such as ascorbic acid or methionine; 4) preservatives such as octadecyldimethylbenzyl ammonium chloride, hexamethonium chloride, benzalkonium chloride, benzethonium chloride, phenol, butyl or benzyl alcohol; 5) alkyl parabens such as methyl or propyl paraben, catechol, resorcinol, cyclohexanol, 3-pentanol, or m-cresol; 6) low molecular weight (less than about 10 residues) polypeptides; 7) proteins such as serum albumin, gelatin, or immunoglobulins; 8) hydrophilic polymers such as polyvinylpyrrolidone; 9) amino acids such as glycine, glutamine, asparagine, histidine, arginine, or lysine; 10) monosaccharides, disaccharides, or other carbohydrates including glucose, mannose, or dextrins; 11) chelating agents such as EDTA; 12) sugars such as sucrose, mannitol, trehalose or sorbitol; 13) salt-forming counter-ions such as sodium, metal complexes (e.g., Zn-protein complexes), or 14) non-ionic surfactants such as polysorbates (e.g., polysorbate 20 or polysorbate 80), poloxamers or polyethylene glycol (PEG).

Liposome containing compounds of the invention may be prepared by methods known in the art (See, for example, Chang, H. I.; Yeh, M. K.; Clinical development of liposome-based drugs: formulation, characterization, and therapeutic efficacy; Int J Nanomedicine 2012; 7: 49-60). Particularly useful liposomes may be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

Compounds of the invention may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy, 20th Ed., Mack Publishing (2000).

Sustained-release preparations may be used. Suitable examples of sustained-release preparations include semipermeable matrices of solid hydrophobic polymers containing a compound of the invention, which matrices are in the form of shaped articles, e.g., films, or microcapsules. Examples of sustained-release matrices include polyesters, hydrogels (for example, poly(2-hydroxyethyl-methacrylate), or 'poly(vinylalcohol)), polylactides, copolymers of L-glutamic acid and 7 ethyl-L-glutamate, non-degradable ethylene-vinyl acetate, degradable lactic acid-glycolic acid copolymers such as those used in leuprolide acetate for depot suspension (injectable microspheres composed of lactic acid-glycolic acid copolymer and leuprolide acetate), sucrose acetate isobutyrate, and poly-D-(−)-3-hydroxybutyric acid.

The formulations to be used for intravenous administration must be sterile. This is readily accomplished by, for example, filtration through sterile filtration membranes. Compounds of the invention are generally placed into a container having a sterile access port, for example, an intravenous solution bag or vial having a stopper pierceable by a hypodermic injection needle.

Suitable emulsions may be prepared using commercially available fat emulsions, such as a lipid emulsions comprising soybean oil, a fat emulsion for intravenous administration (e.g., comprising safflower oil, soybean oil, egg phosphatides and glycerin in water), emulsions containing soya bean oil and medium-chain triglycerides, and lipid emulsions of cottonseed oil. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion may comprise fat droplets between 0.1 and 1.0 µm, particularly 0.1 and 0.5 µm, and have a pH in the range of 5.5 to 8.0.

For example, the emulsion compositions may be those prepared by mixing a compound of the invention with a lipid emulsions comprising soybean oil or the components thereof (soybean oil, egg phospholipids, glycerol and water).

A drug product intermediate (DPI) is a partly processed material that must undergo further processing steps before it becomes bulk drug product. Compounds of the invention may be formulated into drug product intermediate DPI containing the active ingredient in a higher free energy form than the crystalline form. One reason to use a DPI is to improve oral absorption characteristics due to low solubility, slow dissolution, improved mass transport through the mucus layer adjacent to the epithelial cells, and in some cases, limitations due to biological barriers such as metabolism and transporters. Other reasons may include improved solid state stability and downstream manufacturability. In one embodiment, the drug product intermediate contains a compound of the invention isolated and stabilized in the amorphous state (for example, amorphous solid dispersions (ASDs)). There are many techniques known in the art to manufacture ASD's that produce material suitable for integration into a bulk drug product, for example, spray dried dispersions (SDD's), melt extrudates (often referred to as HME's), co-precipitates, amorphous drug nanoparticles, and nano-adsorbates. In one embodiment amorphous solid dispersions comprise a compound of the invention and a polymer excipient. Other excipients as well as concentrations of said excipients and the compound of the invention are well known in the art and are described in standard textbooks. See, for example, "Amorphous Solid Dispersions Theory and Practice" by Navnit Shah et al.

In another aspect, the invention provides a compound of the invention, or a pharmaceutically acceptable salt thereof, for use as a medicament, in particular a medicament for the treatment of abnormal cell growth.

In yet another aspect, the invention provides the use of a compound of the invention, or a pharmaceutically acceptable salt thereof, for manufacture of a medicament for the treatment of abnormal cell growth in a subject, for example a tumor, for example a MEK-associated tumor, in a subject.

In yet another aspect, the invention provides a compound according to any of the formulae described herein, or a pharmaceutically acceptable salt thereof, for use in the treatment of abnormal cell growth, for example a tumor, for example a MEK-associated tumor.

Administration of the compounds of the invention may be affected by any method that enables delivery of the compounds to the site of action. These methods include oral routes, intraduodenal routes, parenteral injection (including intravenous, subcutaneous, intramuscular, intravascular or infusion), topical, and rectal administration.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the compound administered and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intrapatient dose escalation as determined by the skilled artisan. Determining appropriate dosages and regimens for administration of the chemotherapeutic agent are well known in the relevant art and would be understood to be encompassed by the skilled artisan once provided the teachings disclosed herein. In one embodiment, an effective dosage is typically in the range of about 0.001 to about 100 mg per kg body weight per day, and frequently about 0.01 to about 35 mg/kg/day, in single or divided doses. For a 70 kg human, this would amount to about 0.07 mg/day to about 7000 mg/day, more commonly, from about 10 mg/day to about 1000 mg/day. Sometimes, the dosage is about 10, 20, 30, 40, 50, 60, 75, 100, 125, 150, 175, 200, 225, 250, 275, 300, 325, 350, 375, 400, 425, 450, 475, 500, 525, 550, 575, 600, 625, 650, 675, 700, 750, 800, 900 or 1000 mg/day. Sometimes, the dosage is from about 10 mg/day to about 1000 mg/day, from about 10 mg/day to about 750 mg/day, from about 10 mg/day to about 600 mg/day, from about 10 mg/day to about 300 mg/day, from about 10 mg/day to about 150 mg/day, from about 20 mg/day to about 750 mg/day, from about 20 mg/day to about to 600 mg/day, from about 20 mg/day to about to 300 mg/day, from about 20 mg/day to about to 150 mg/day, from about 50 mg/day to about 750 mg/day, from about 50 mg/day to about 600 mg/day, from about 50 mg/day to about 300 mg/day, from about 50 mg/day to about 150 mg/day, from about 75 mg/day to about 750 mg/day, from about 75 mg/day to about 600 mg/day, from about 75 mg/day to about 300 mg/day, or from about 75 mg/day to about 150 mg/day. In some instances, dosage levels below the lower limit of the aforesaid range may be more than adequate, while in other cases still larger doses may be used without causing any harmful side effect, with such larger doses typically divided into several smaller doses for administration throughout the day. In one embodiment, the subject is administered about 50 mg/day.

Inasmuch as it may be desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for co-administration of the compositions. Thus, the kit of the invention includes two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically includes directions for administration and may be provided with a memory aid. In some embodiments, the kit includes the compound or a pharmaceutical composition thereof and a diagnostic agent. In other embodiments, the kit includes the compound or a pharmaceutical composition thereof and one or more therapeutic agents, such as a BRAF inhibitor, for example, a BRAF inhibitor selected from N-(3-((3,5-dimethyl-4-oxo-3,4-dihydroquinazolin-6-yl)amino)-2,4-difluorophenyl)propane-1-sulfonamide; N-(2-chloro-3-((3,5-dimethyl-4-oxo-3,4-dihydroquinazolin-6-yl)amino)phenyl)-3-fluoropropane-1-sulfonamide; N-(2-chloro-3-((3,5-dimethyl-4-oxo-3,4-dihydroquinazolin-6-yl)amino)-4,5-difluorophenyl)propane-1-sulfonamide; N-(2-chloro-3-((3,5-dimethyl-4-oxo-3,4-dihydroquinazolin-6-yl)amino)-4-fluorophenyl)propane-1-sulfonamide; N-(2-chloro-3-((3,5-dimethyl-4-oxo-3,4-dihydroquinazolin-6-yl)amino)-4-fluorophenyl)-3-fluoropropane-1-sulfonamide; N-(2-chloro-4-fluoro-3-((5-methyl-3-(methyl-d3)-4-oxo-3,4-dihydroquinazolin-6-yl)amino)-phenyl)-3-fluoropropane-1-sulfonamide; N-{2-chloro-3-[(3,5-dimethyl-4-oxo-3,4-dihydroquinazolin-6-yl)oxy]-4-fluorophenyl}propane-1-sulfonamide; N-(3-chloro-4-((3,5-dimethyl-4-oxo-3,4-dihydroquinazolin-6-yl)oxy)-5-fluoropyridin-2-yl)propane-1-sulfonamide: N-{2-chloro-3-[(3,5-dimethyl-4-oxo-3,4-dihydroquinazolin-6-yl)oxy]-4-fluorophenyl}-3-fluoropropane-1-sulfonamide; N-(2-chloro-4-fluoro-3-((5-fluoro-3-methyl-4-oxo-3,4-dihydroquinazolin-6-yl)amino)phenyl)-2-azabicyclo[2.1.1]hexane-2-sulfonamide, (R)—N-(2-chloro-4-fluoro-3-((5-fluoro-3-methyl-4-oxo-3,4-dihydroquinazolin-6-yl)amino)phenyl)-3-fluoropyrrolidine-1-sulfonamide, and N-(2-chloro-3-((5-chloro-3-methyl-4-oxo-3,4-dihydroquinazolin-6-yl)amino)-4-fluorophenyl)-3-fluoroazetidine-1-sulfonamide; or a pharmaceutically acceptable salt thereof;

The following schemes and written descriptions provide general details regarding the preparation of the compounds of the invention.

The compounds of the invention may be prepared by any method known in the art for the preparation of compounds of analogous structure. In particular, the compounds of the invention can be prepared by the procedures described by reference to the Schemes that follow, or by the specific methods described in the Examples, or by similar processes to either.

The skilled person will appreciate that the experimental conditions set forth in the schemes that follow are illustrative of suitable conditions for effecting the transformations shown, and that it may be necessary or desirable to vary the precise conditions employed for the preparation of compounds of Formula I, and compounds that fall within Formula I, e.g., compounds of Formula II and the like.

In addition, the skilled person will appreciate that it may be necessary or desirable at any stage in the synthesis of compounds of the invention to protect one or more sensitive groups, to prevent undesirable side reactions. In particular, it may be necessary or desirable to protect amino or alcohol groups. The protecting groups (PGs) used in the preparation of the compounds of the invention may be used in conventional manner. See, for example, those described in 'Greene's Protective Groups in Organic Synthesis' by Theodora W Greene and Peter G M Wuts, third edition, (John Wiley and Sons, 1999), in particular chapters 7 ("Protection for the Amino Group") and 2 ("Protection for the Hydroxyl Group, Including 1,2- and 1,3-Diols"), incorporated herein by reference, which also describes methods for the removal of such groups.

Scheme 1

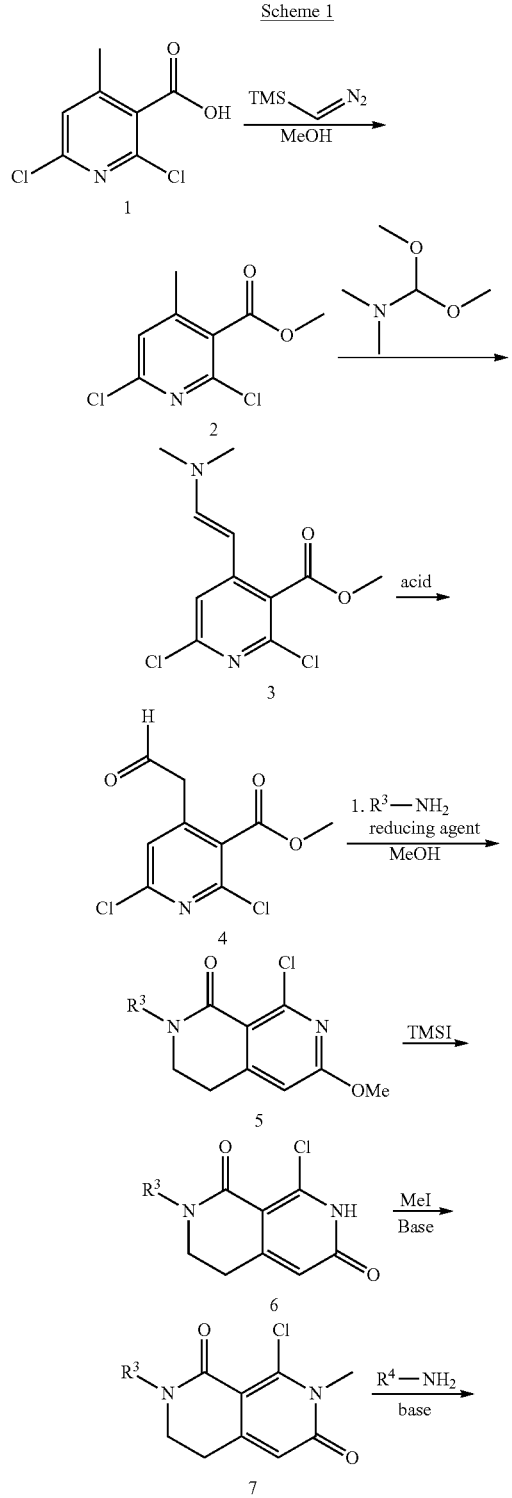

-continued

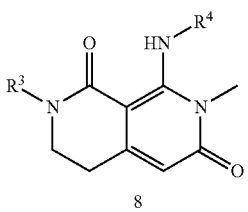

Scheme 1 describes a general method for preparing compound 8, which is a compound of Formula I wherein $R^1$ is H, $R^2$ is H, $R^3$ is C3-C6 cycloalkyl, and $R^4$ is as defined for Formula I. Commercially available 2,6-dichloro-4-methylnicotinic acid (compound 1) may be converted to the ester analog 2 upon treatment with (trimethylsilyl)diazomethane. Compound 2 may be converted to the dimethylaminovinyl intermediate compound 3 upon treatment with N,N-dimethylformamide dimethylacetal. Compound 3 may be converted to the aldehyde intermediate compound 4 upon treatment with a suitable acid such as hydrochloric acid in a suitable solvent such as ether. Cyclization of compound 4 may be achieved by treatment with compound 4 with a reagent having the formula $R^3NH_2$, wherein $R^3$ is C3-C6 cycloalkyl, in the presence of a reducing agent (e.g., sodium cyanoborohydride), in a suitable solvent such as methanol to provide compound 5. Compound 5 may be converted to compound 6 upon treatment with trimethylsilyl iodide in a suitable solvent, such as acetonitrile. Compound 6 may be methylated by treatment with methyl iodide in the presence of a suitable base, such as an alkaline carbonate, such as potassium carbonate, in the presence of a suitable solvent such as THF, to provide compound 7. Compound 7 may undergo aromatic nucleophilic substitution upon treatment with a reagent having the formula $R^4NH_2$ wherein $R^4$ is as defined for Formula I, in the presence of a strong base, such as lithium hexamethyldisilazide in a suitable solvent, such as THF, to provide compound 8.

Scheme 2

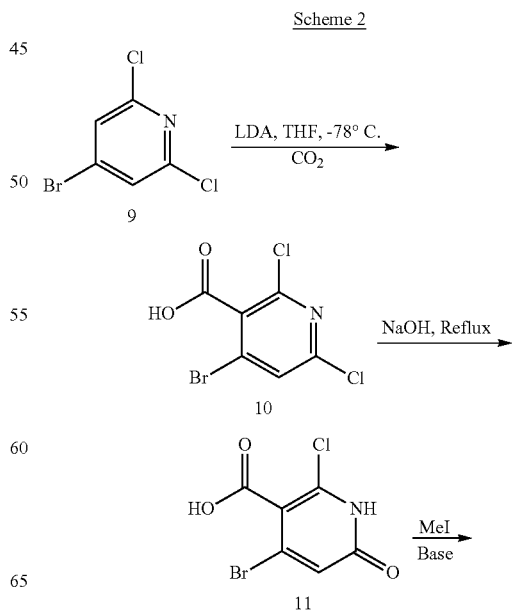

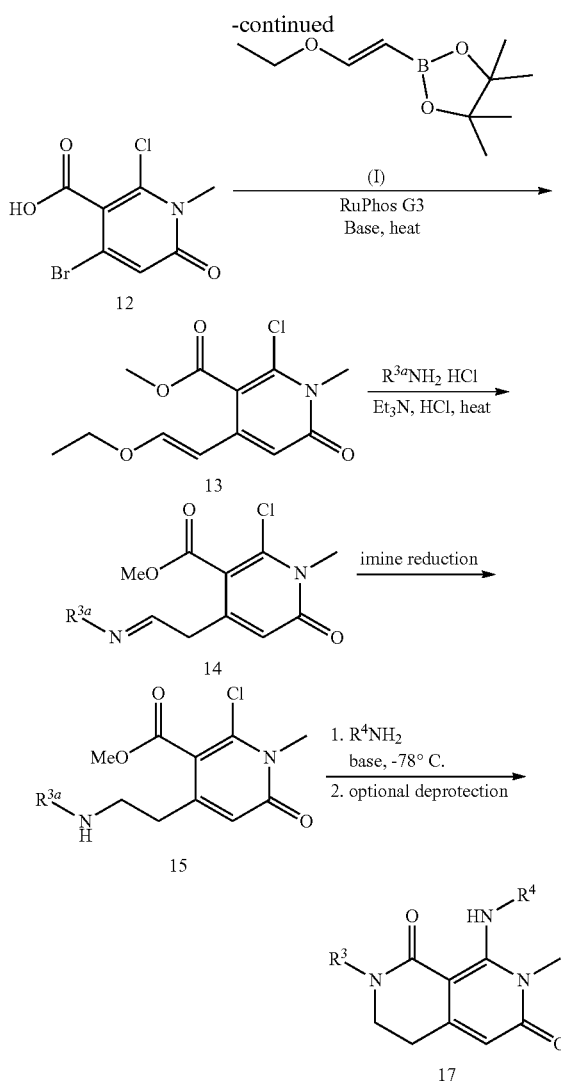

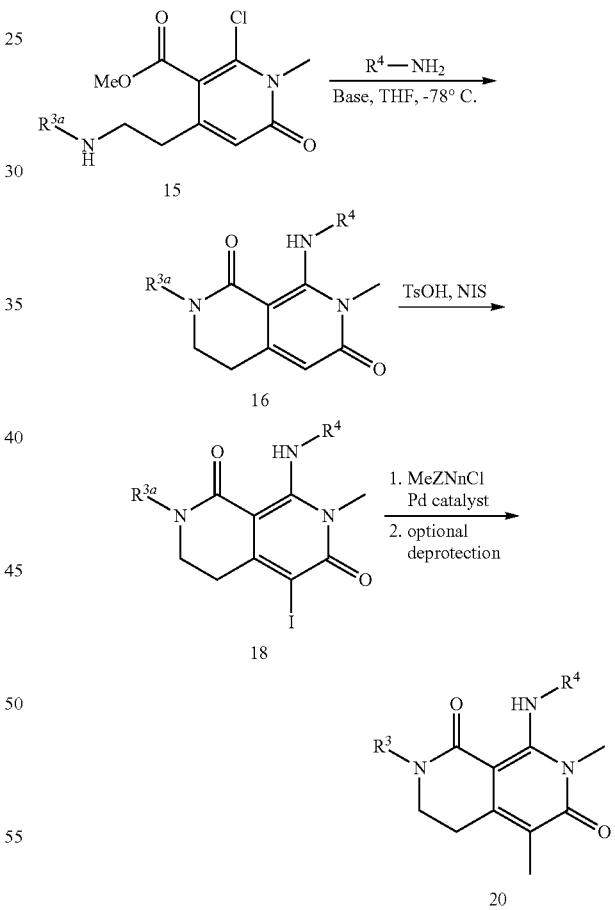

fluoroC1-C6 alkoxy, or (C3-C6 cycloalkyl)C1-C6 alkoxy- and $P^1$ is an alcohol protecting group such as tert-butyl, benzyl or tert-butyldimethylsilyl, using triethylamine and HCl and heating in a suitable solvent such as 1,4-dioxane to provide compound 14. Compound 14 may be reduced to alkoxyamine intermediate 15 using an appropriate reducing agent such as sodium cyanoborohydride in a suitable solvent such as isopropanol. Compound 15 may undergo aromatic nucleophilic substitution upon treatment with a reagent having the formula $R^4NH_2$ wherein $R^4$ is as defined for Formula I in the presence of a strong base, such as lithium hexamethyldisilazide in a suitable solvent, such as THF and concomitantly cyclized, followed by optional deprotection if compound 16 contains a $P^1$ protecting group (using standard alcohol deprotection conditions known to persons skilled in the art, such as phosphoric acid, trifluoroacetic acid or tetrabutylammonium fluoride) to provide compound 17 wherein $R^3$ is hydroxy-C1-C6 alkoxy-, C1-C6 alkoxy, fluoroC1-C6 alkoxy, or (C3-C6 cycloalkyl)C1-C6 alkoxy-.

Scheme 2 describes a general method for preparing compound 17, which is a compound of Formula I wherein $R^1$ is H, $R^2$ is H, $R^3$ is hydroxy-C1-C6 alkoxy-, C1-C6 alkoxy, fluoroC1-C6 alkoxy, or (C3-C6 cycloalkyl)C1-C6 alkoxy-, and $R^4$ is as defined for Formula I. Commercially available 4-bromo-2,6-dichloropyridine may be lithiated with a reagent such as lithium diisopropylamide and trapped with carbon dioxide to afford carboxylic acid 10. Compound 10 may be converted to compound 11 by refluxing in an aqueous base such as 4M sodium hydroxide. Compound 11 may be methylated by treatment with methyl iodide in the presence of a suitable base, such as an alkaline carbonate, such as potassium carbonate, in the presence of a suitable solvent such as DMF, to provide compound 12. Compound 12 may be converted to vinyl ether intermediate 13 via Suzuki reaction with (E)-2-(2-ethoxyvinyl)-4,4,5,5-tetramethyl-1,3,2-dioxaborolane (compound (i)) using a catalyst such as methanesulfonato(2-dicyclohexylphosphino-2',6'-di-i-propoxy-1,1'-biphenyl)(2-amino-1,1'-biphenyl-2-yl)palladium(II) and alkaline base (e.g., an alkaline carbonate, e.g., aqueous potassium carbonate) in a suitable solvent such as 1,4-dioxane. Compound 13 may undergo oximine formation upon treatment with a reagent of formula $R^{3a}$—$NH_2$·HCl, wherein $R^{3a}$ is $P^1O$-C1-C6 alkoxy-, C1-C6 alkoxy, Scheme 3 describes a general method for preparing compound 20, which is a compound of Formula I wherein $R^1$ is H, $R^2$ is $CH_3$—, $R^3$ is hydroxy-C1-C6 alkoxy-, C1-C6 alkoxy, fluoroC1-C6 alkoxy, or (C3-C6 cycloalkyl)C1-C6 alkoxy-, and $R^4$ is as defined for Formula I. Compound 15, prepared as described in Scheme 2, wherein $R^{3a}$ is $P^1O$-C1-C6 alkoxy-, C1-C6 alkoxy, fluoroC1-C6 alkoxy, or (C3-C6 cycloalkyl)C1-C6 alkoxy- and $P^1$ is an alcohol protecting group such as tert-butyl, benzyl or tert-butyldimethylsilyl, and wherein $R^4$ is as defined for Formula I, may be cyclized upon treatment with a reagent having the formula $R^4NH_2$ wherein $R^4$ is as defined for Formula I in the presence of a strong base, such as lithium hexamethyldisilazide, in a suitable solvent, such as THF, to provide compound 16. Compound 16 may be iodinated using n-iodosuccinimide and p-toluenesulfonic acid in a suitable solvent such as 1:1 MeOH:THF, to provide compound 18. Compound 18 may undergo Negishi coupling with methylzinc(II)chloride using a catalyst, e.g., a palladium catalyst such as bis(tri-t-butylphosphine)palladium (0) in a suitable solvent such as THF, followed by optional deprotection if compound 19 contains a protecting group (using standard alcohol deprotection conditions known to persons skilled in the art, such as phosphoric acid, trifluoroacetic acid or tetrabutylammonium fluoride) to provide compound 20 wherein $R^3$ is hydroxy-C1-C6 alkoxy-, C1-C6 alkoxy, fluoroC1-C6 alkoxy, or (C3-C6 cycloalkyl)C1-C6 alkoxy.

undergo aromatic nucleophilic substitution upon treatment with a reagent having the formula $R^4NH_2$ wherein $R^4$ is as defined for Formula I in the presence of a strong base, such as lithium hexamethyldisilazide, in a suitable solvent, such as THF, to provide compound 21. Compound 21 may be hydrolyzed to aldehyde intermediate 22 under acidic conditions using an acid such as trifluoroacetic acid in a suitable solvent such as dichloromethane. Compound 22 may be cyclized upon treatment with a reagent having the formula $P^2$—$NH_2$ where $P^2$ is an amine protecting group such as benzyl, p-methoxybenzyl or 2,4-dimethoxybenzyl, using a reducing agent such as sodium triacetoxyborohydride in a suitable solvent such as dichloroethane to provide compound 23. Deprotection of compound 23 may be achieved using standard deprotection conditions known to persons skilled in the art, such as heating with trifluoroacetic acid or hydrochloric acid to provide compound 24.

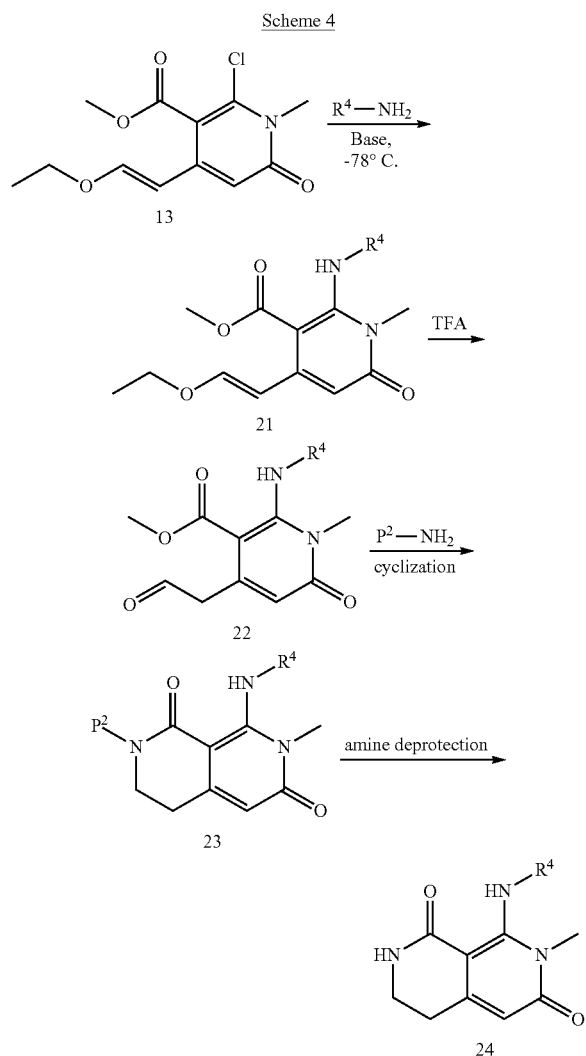

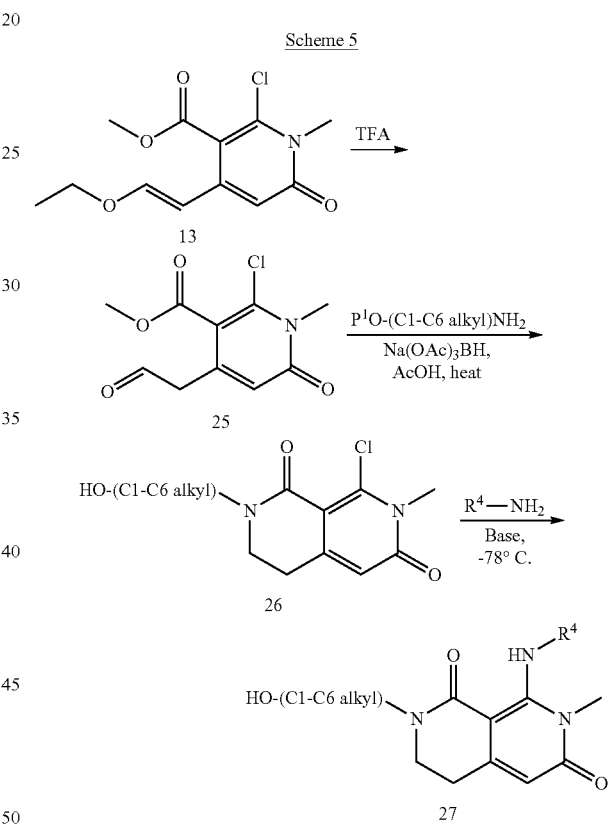

Scheme 4 describes a general method for preparing compound 24, which is a compound of Formula I wherein $R^1$ is H, $R^2$ is H, $R^3$ is H, and $R^4$ is as defined for Formula I. Compound 13, prepared as described in Scheme 2, may Scheme 5 describes a general method for preparing compound 27, which is a compound of Formula I wherein $R^1$ is H, $R^2$ is H, $R^3$ is hydroxyC1-C6 alkyl, and $R^4$ is as defined for Formula I. Compound 13, prepared as described in Scheme 2, may be hydrolyzed to aldehyde intermediate 25 using a suitable acid such as trifluoroacetic acid. Compound 25 may be reacted with a reagent of formula $P^1O$—(C1-C6 alkyl)-$ONH_2HCl$, where $P^1$ is an alcohol protecting group such as tert-butyldimethylsilyl, using a suitable reducing agent such as sodium triacetoxyborohydride and acetic acid in a suitable solvent such as dichloroethane at 60° C. to afford cyclized, deprotected compound 26. Compound 26 may undergo aromatic nucleophilic substitution upon treatment with a reagent having the formula $R^4NH_2$, wherein $R^4$ is as defined for Formula I, in the presence of a strong base, such as lithium hexamethyldisilazide in a suitable solvent, such as THF, to provide compound 27.

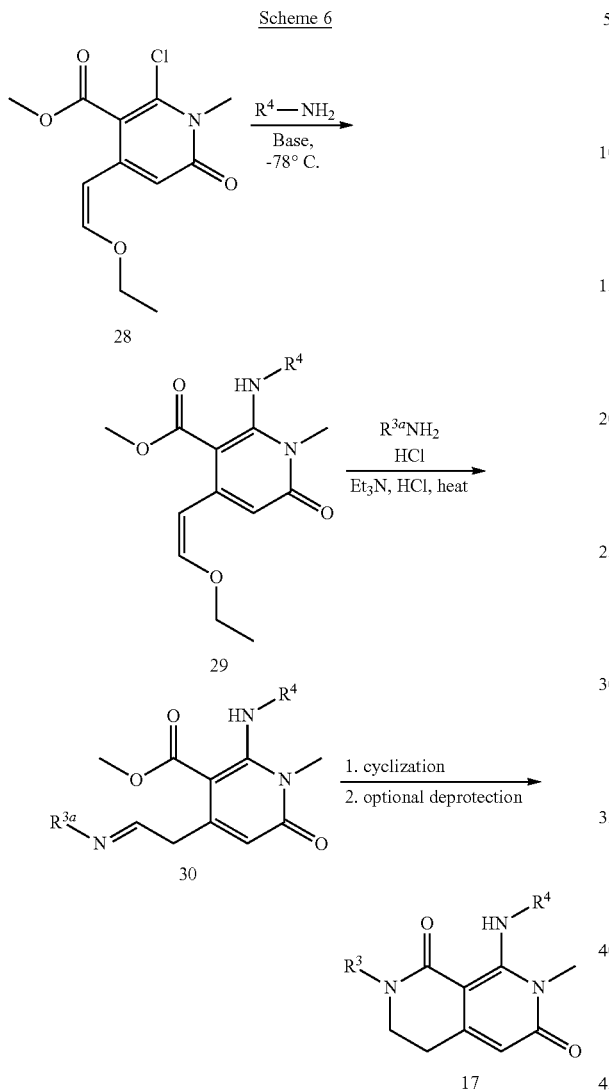

Scheme 6 describes an alternative general method for preparing compound 17, which is a compound of Formula I wherein $R^1$ is H, $R^2$ is H, $R^3$ is hydroxy-C1-C6 alkoxy-, C1-C6 alkoxy, fluoroC1-C6 alkoxy, or (C3-C6 cycloalkyl) C1-C6 alkoxy, and $R^4$ is as defined for Formula I. Compound 28, prepared according to a method similar to that described for compound 13, may undergo aromatic nucleophilic substitution upon treatment with a reagent having the formula $R^4NH_2$ wherein $R^4$ is as defined for Formula I, in the presence of a strong base, such as lithium hexamethyldisilazide, in a suitable solvent, such as THF, to provide compound 29. Compound 29 may undergo oximine formation upon treatment with a reagent of formula $R^3NH_2HCl$, wherein $R^3$ is $P^1O$-C1-C6 alkoxy-, C1-C6 alkoxy, fluoroC1-C6 alkoxy, or (C3-C6 cycloalkyl)C1-C6 alkoxy and $P^1$ is an alcohol protecting group such as tert-butyl, benzyl or tert-butyldimethylsilyl, using triethylamine and HCl and heating in a suitable solvent such as 1,4-dioxane to provide compound 30. Compound may be cyclized with an appropriate reducing agent such as sodium cyanoborohydride and acetic acid in a suitable solvent such as isopropanol, followed by optional deprotection if compound 30 contains a $P^1$ protecting group (using standard alcohol deprotection conditions known to persons skilled in the art, such as phosphoric acid, trifluoroacetic acid or tetrabutylammonium fluoride) to provide compound 17 wherein $R^3$ is hydroxy-C1-C6 alkoxy-, C1-C6 alkoxy, fluoroC1-C6 alkoxy, or (C3-C6 cycloalkyl) C1-C6 alkoxy.

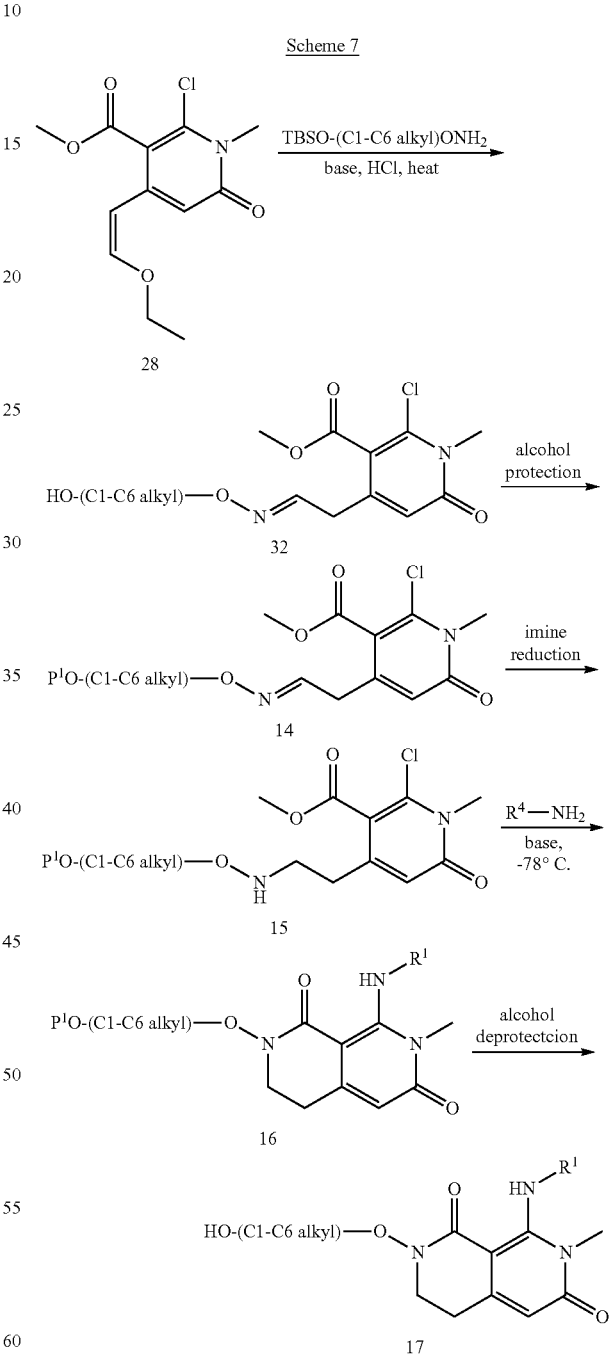

Scheme 7 describes an alternative general method for preparing compound 17, which is a compound of Formula I wherein $R^1$ is H, $R^2$ is H, $R^3$ is hydroxyC1-C6 alkoxy, and $R^4$ is as defined for Formula I. Compound 28 may undergo oximine formation upon treatment with a reagent of formula TBSO-(C1-C6 alkyl)-ONH$_2$ HCl, using triethylamine and HCl and heating in a suitable solvent such as 1,4-dioxane to provide compound 32. Compound 32 may be protected with an appropriate alcohol protecting group P$^1$ such as tert-butyldimethylsilyl, using tert-butylsimethylsilyl chloride and a suitable base such as imidazole, in a suitable solvent such as DMF, to provide compound 14. Compound 14 may be reduced to alkoxyamine intermediate 15 using an appropriate reducing agent such as sodium cyanoborohydride in a suitable solvent such as isopropanol. Compound 15 may undergo aromatic nucleophilic substitution upon treatment with a reagent having the formula R$^4$NH$_2$ wherein R$^4$ is as defined for Formula I in the presence of a strong base, such as lithium hexamethyldisilazide in a suitable solvent, such as THF, to provide compound 16. Compound 16 may be deprotected using standard alcohol deprotection conditions known to persons skilled in the art, such as phosphoric acid, trifluoroacetic acid or tetrabutylammonium fluoride to provide compound 17.

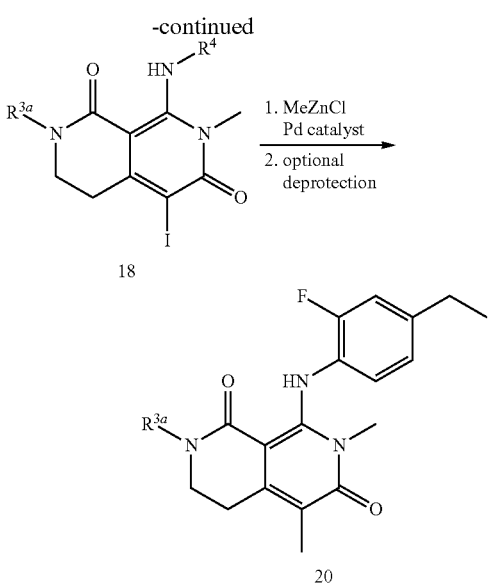

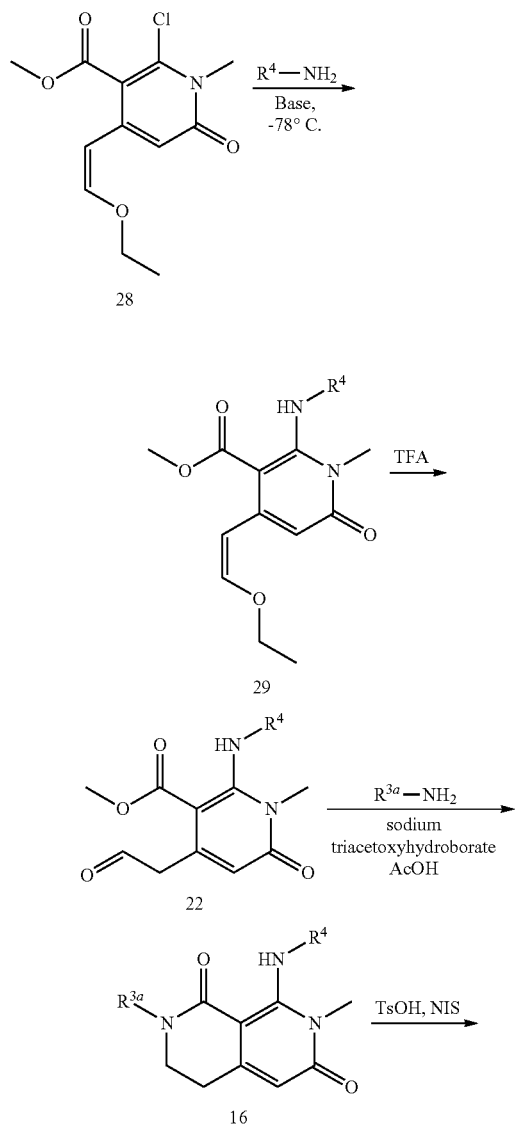

Scheme 8

Scheme 8 describes an alternative general method for preparing compound 20, which is a compound of Formula I wherein R$^1$ is H, R$^2$ is CH$_3$—, R$^3$ is hydroxy-C1-C6 alkoxy-, C1-C6 alkoxy, fluoroC1-C6 alkoxy, or (C3-C6 cycloalkyl) C1-C6 alkoxy, and R$^4$ is as defined for Formula I. Compound 28 may undergo aromatic nucleophilic substitution upon treatment with a reagent having the formula R$^4$NH$_2$ wherein R$^4$ is as defined for Formula I, in the presence of a strong base, such as lithium hexamethyldisilazide, in a suitable solvent, such as THF, to provide compound 29. Compound 29 may be hydrolyzed to aldehyde intermediate 22 using a suitable acid such as trifluoroacetic acid. Compound 22 may be reacted with a reagent of formula R$^3$NH$_2$ HCl, wherein R$^3$ is P$^1$O-C1-C6 alkoxy-, C1-C6 alkoxy, fluoroC1-C6 alkoxy, or (C3-C6 cycloalkyl)C1-C6 alkoxy and P$^1$ is an alcohol protecting group such as tert-butyl, benzyl or tert-butyldimethylsilyl, using a suitable reducing agent such as sodium triacetoxyborohydride and acetic acid in a solvent such as dichloroethane at 60° C. to afford cyclized compound 16. Compound 16 may be iodinated using n-iodosuccinimide and p-toluenesulfonic acid in a suitable solvent such as 1:1 MeOH:THF, to provide compound 18. Compound 18 may undergo Negishi coupling with methylzinc(II)chloride using a catalyst such as bis(tri-t-butylphosphine)palladium (0) in a suitable solvent such as THF, followed by optional deprotection if compound 18 contains a P$^1$ protecting group (using standard alcohol deprotection conditions known to persons skilled in the art, such as phosphoric acid, trifluoroacetic acid or tetrabutylammonium fluoride) to provide compound 20 wherein R$^3$ is hydroxy-C1-C6 alkoxy-C1-C6 alkoxy, fluoroC1-C6 alkoxy, or (C3-C6 cycloalkyl)C1-C6 alkoxy.

Scheme 9

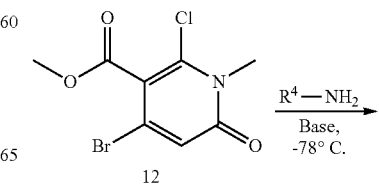

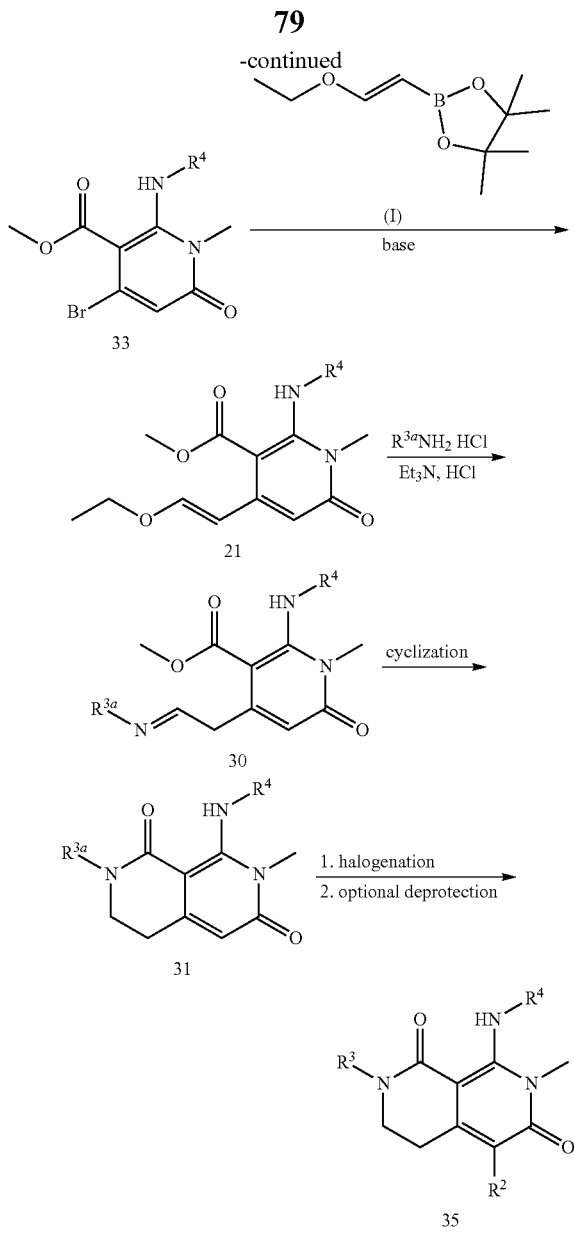

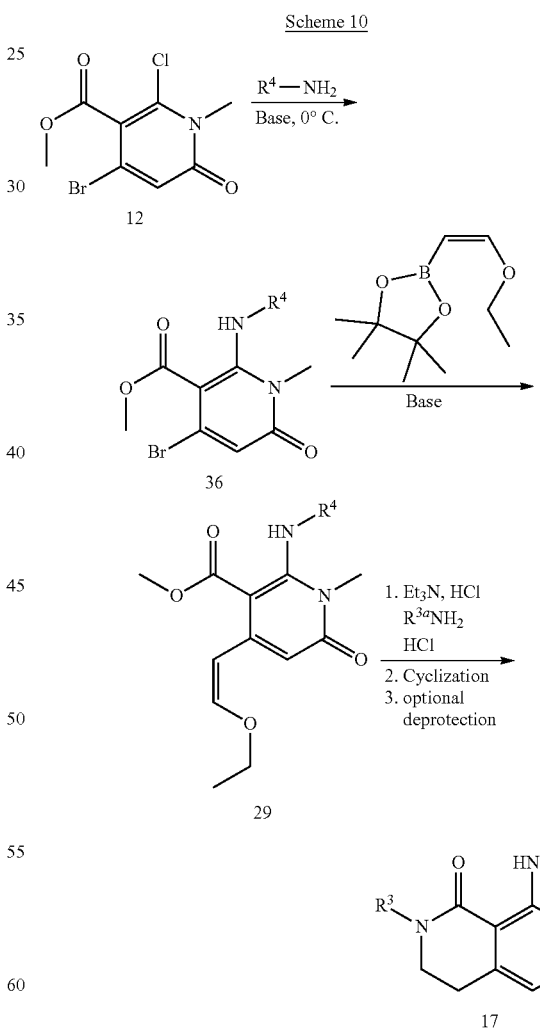

alkoxy, fluoroC1-C6 alkoxy, or (C3-C6 cycloalkyl)C1-C6 alkoxy and $P^1$ is an alcohol protecting group such as tert-butyl, benzyl or tert-butyldimethylsilyl, using triethylamine and HCl and heating in a suitable solvent such as 1,4-dioxane to provide compound 30. Compound 30 may be treated with an appropriate reducing agent such as sodium cyanoborohydride and acetic acid in a suitable solvent such as isopropanol, to generate cyclized compound 31. Compound 31 may be halogenated using conditions such as treatment with N-iodosuccinimide and p-toluenesulfonic acid in 1:1 THF/MeOH, or N-bromosuccinimide in a suitable solvent such as DMF, or N-chlorosuccinimide in a suitable solvent such as DMF, or Selectfluor in a suitable solvent such as acetonitrile, followed by optional deprotection if compound 31 has a $P^1$ protecting group (such as phosphoric acid, trifluoroacetic acid or tetrabutylammonium fluoride) to provide compound 35 wherein $R^2$ is iodo, bromo, chloro or fluoro, respectively, and $R^3$ is hydroxy-C1-C6 alkoxy-, C1-C6 alkoxy, fluoroC1-C6 alkoxy, or (C3-C6 cycloalkyl)C1-C6 alkoxy Scheme 9 describes a general process for the synthesis of compound 35, which is a compound of Formula I wherein $R^1$ is H, $R^2$ is halogen, $R^3$ is hydroxy-C1-C6 alkoxy-, C1-C6 alkoxy, fluoroC1-C6 alkoxy, or (C3-C6 cycloalkyl)C1-C6 alkoxy, and $R^4$ is as defined for Formula I. Compound 12 may undergo aromatic nucleophilic substitution upon treatment with a reagent having the formula $R^4NH_2$ wherein $R^4$ is as defined for Formula I, in the presence of a strong base, such as lithium hexamethyldisilazide, in a suitable solvent, such as THF, to provide compound 33. Compound 33 may be converted to vinyl ether intermediate 21 via Suzuki reaction with (E)-2-(2-ethoxyvinyl)-4,4,5,5-tetramethyl-1,3,2-dioxaborolane using a catalyst, e.g., a palladium catalyst such as methanesulfonato(2-dicyclohexylphosphino-2',6'-di-i-propoxy-1,1'-biphenyl)(2-amino-1,1'-biphenyl-2-yl)palladium(II) and alkaline base, e.g., an alkaline carbonate base such as aqueous potassium carbonate, in a suitable solvent such as 1,4-dioxane. Compound 21 may undergo oximine formation upon treatment with a reagent of formula $R^{3a}NH_2$ HCl, wherein $R^{3a}$ is $P^1O$-C1-C6 alkoxy-, C1-C6

Scheme 10 describes an alternative general method for preparing compound 17, which is a compound of Formula I wherein $R^1$ is H, $R^2$ is H, $R^3$ is hydroxy-C1-C6 alkoxy-, C1-C6 alkoxy, fluoroC1-C6 alkoxy, or (C3-C6 cycloalkyl)

C1-C6 alkoxy, and R⁴ is as defined for Formula I. Compound 12 may undergo aromatic nucleophilic substitution upon treatment with a reagent having the formula R⁴NH₂ wherein R⁴ is as defined for Formula I, in the presence of a suitable base, such as potassium tert-butoxide in a suitable solvent, such as THF, to provide compound 36. Compound 36 may be converted to vinyl ether intermediate 29 via Suzuki reaction with (Z)-2-(2-ethoxyvinyl)-4,4,5,5-tetramethyl-1,3,2-dioxaborolane using a catalyst, e.g., a palladium catalyst such as methanesulfonato(2-dicyclohexylphosphino-2',6'-di-i-propoxy-1,1'-biphenyl)(2-amino-1,1'-biphenyl-2-yl)palladium(II) and suitable base such as an alkaline base, e.g., an alkaline carbonate base, e.g., aqueous potassium carbonate in a solvent such as 2-methyltetrahydrofuran. Compound 29 may be reacted with a reagent of formula R³NH₂·HCl, wherein R³ᵃ is P¹O-C1-C6 alkoxy-, C1-C6 alkoxy, fluoroC1-C6 alkoxy, or (C3-C6 cycloalkyl)C1-C6 alkoxy and P¹ is an alcohol protecting group such as tert-butyl, benzyl or tert-butyldimethylsilyl, using triethylamine and hydrochloric acid in a suitable solvent such as 1,4-dioxane, then treated with a suitable reducing agent such as pyridine borane and hydrochloric acid and heated at 60° C., followed by optional deprotection if compound 29 has a P¹ protecting group (such as phosphoric acid, tifluoroacetic acid or tetrabutylammonium fluoride) to provide compound 17 wherein R³ is hydroxy-C1-C6 alkoxy-, C1-C6 alkoxy, fluoroC1-C6 alkoxy, or (C3-C6 cycloalkyl)C1-C6 alkoxy.

Scheme 11

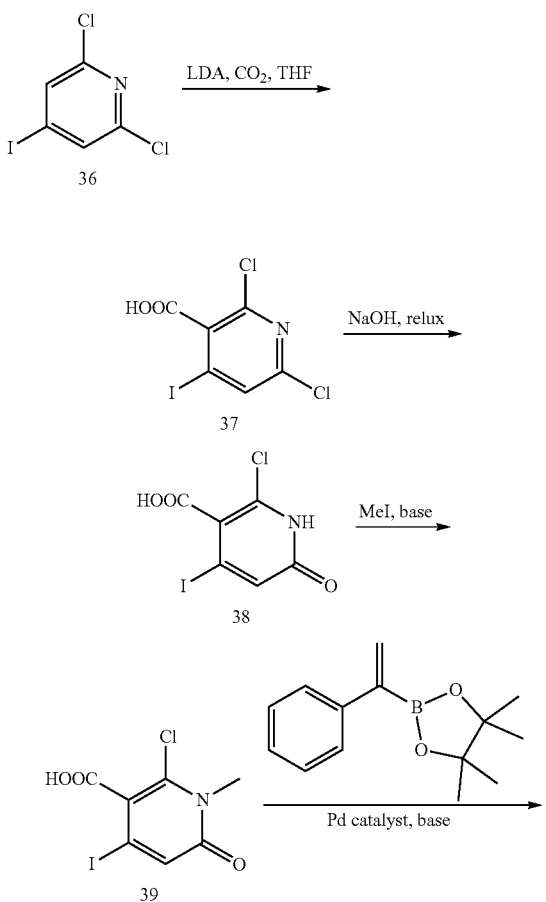

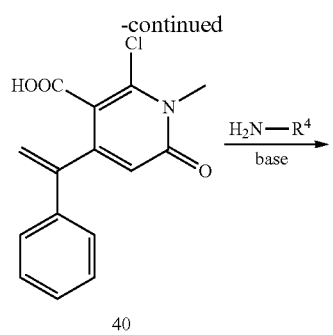

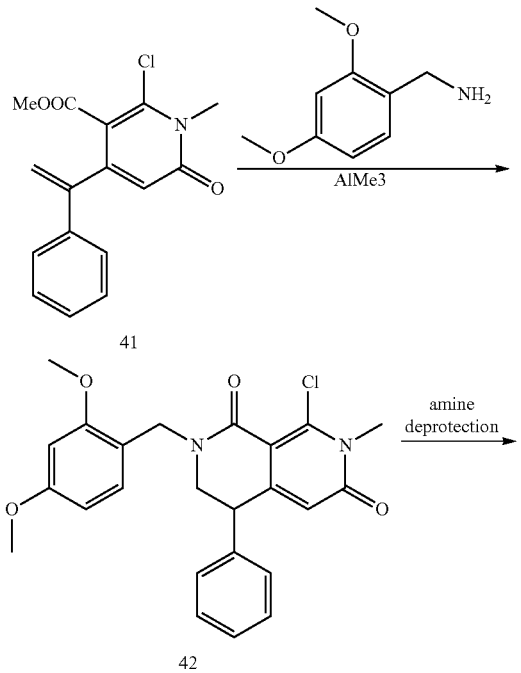

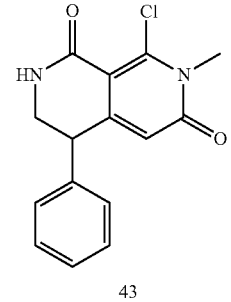

Scheme 11 describes a process for preparing compound 43, which is a compound of Formula I wherein R¹ is phenyl, R² is hydrogen, R³ is hydrogen, and R⁴ is as described for Formula I. Commercially available 2,6-dichloro-4-iodopyridine may be lithiated with a reagent such as lithium diisopropylamide and trapped with carbon dioxide to afford compound 37. Compound 37 may be converted to compound 38 by refluxing in an aqueous base such as 4M sodium hydroxide. Compound 38 may be methylated by treatment with methyl iodide in the presence of a suitable base, such as an alkaline carbonate, such as potassium carbonate, in the presence of a suitable solvent such as DMF, to provide compound 39. Compound 39 may be converted to vinyl ether intermediate 40 via Suzuki reaction with 4,4,5,5-tetramethyl-2-(1-phenylvinyl)-1,3,2-dioxaborolane using a suitable catalyst, for example a palladium catalyst (for example Pd(dppf)Cl₂) and base such as such as an alkaline carbonate (for example aqueous potassium carbonate) in a suitable solvent such as 1,4-dioxane. Compound 40 may undergo aromatic nucleophilic substitution upon treatment with a reagent having the formula R⁴NH₂, wherein R⁴ is as defined for Formula I, in the presence of a strong base, such as lithium hexamethyldisilazide, in a suitable solvent such as THF, to provide compound 41. Compound 41 may be cyclized with (2,4-dimethoxyphenyl)methanamine in the presence of a Lewis acid such as trimethylaluminum by heating in a suitable solvent such as toluene to afford compound 42. Compound 42 may be deprotected by heating with a suitable acid such as TFA to afford compound 43.

Scheme 12

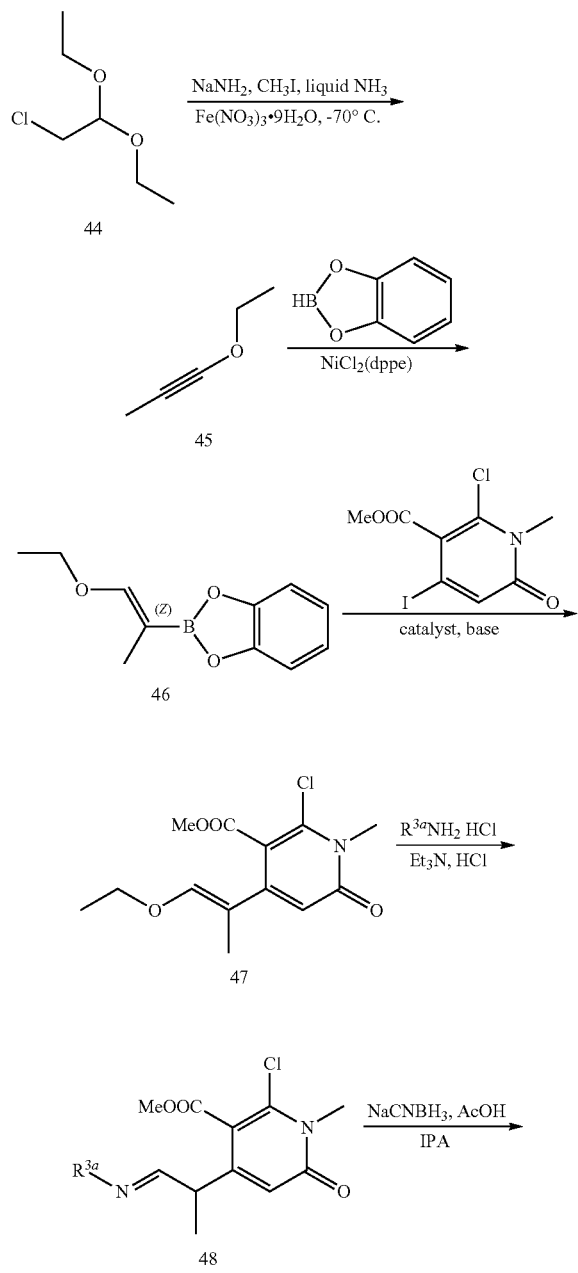

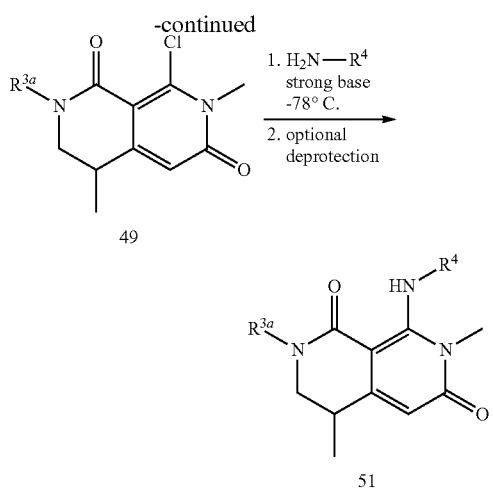

Scheme 12 describes a method of preparing compound 51, which is a compound of Formula I wherein R¹ is methyl, R² is hydrogen, R³ is hydroxy-C1-C6 alkoxy-, C1-C6 alkoxy, fluoroC1-C6 alkoxy, or (C3-C6 cycloalkyl)C1-C6 alkoxy, and R⁴ is as defined for Formula I. Compound 44 may be treated with NH₃, Fe(NO₃)₃·9H₂O and NaNH₂ at low temperature, followed by treatment with methyl iodide to provide compound 45. Compound 45 can be heated with benzo[d][1,3,2]dioxaborole in a suitable solvent such as toluene with a catalyst such as NiCl₂(dppe) to provide compound 46. Compound 46 may be converted to compound 47 by reaction with compound 39 using Suzuki reaction conditions, for example in the presence of a catalyst, for example a palladium catalyst such as Pd(dppf)Cl₂, and base such as K₃PO₄, K₂CO₃, KOtBu, Cs₂CO₃, NaOH, or triethylamine, in a suitable solvent, for example 1 solvent mixture such as toluene/THF. Compound 47 may undergo oximine formation upon treatment with a reagent of formula R³NH₂ HCl, wherein R³ᵃ is P¹O-C1-C6 alkoxy-, C1-C6 alkoxy, fluoroC1-C6 alkoxy, or (C3-C6 cycloalkyl)C1-C6 alkoxy and P¹ is an alcohol protecting group such as tert-butyl, benzyl or tert-butyldimethylsilyl, using triethylamine and HCl and heating in a suitable solvent such as 1,4-dioxane to provide compound 48. Compound 48 may be treated with an appropriate reducing agent such as sodium cyanoborohydride and acetic acid in a suitable solvent such as isopropanol, to generate cyclized product 49. Compound 49 may undergo aromatic nucleophilic substitution upon treatment with a reagent having the formula R⁴NH₂, wherein R⁴ is as defined for Formula I, in the presence of a strong base, such as lithium hexamethyldisilazide in a suitable solvent, such as THF, followed by optional deprotection if compound 49 contains a P¹ protecting group (using standard alcohol deprotection conditions known to persons skilled in the art, such as phosphoric acid, trifluoroacetic acid or tetrabutylammonium fluoride) to provide compound 51 wherein R³ is hydroxy-C1-C6 alkoxy-, C1-C6 alkoxy, fluoroC1-C6 alkoxy, or (C3-C6 cycloalkyl)C1-C6 alkoxy.

The term "amine protecting group" as used herein refers to a derivative of the groups commonly employed to block or protect an amino group while reactions are carried out on other functional groups on the compound. Examples of suitable protecting groups for use in any of the processes described herein include carbamates, amides, alkyl and aryl groups, imines, as well as many N-heteroatom derivatives which can be removed to regenerate the desired amine group. Non-limiting examples of amine protecting groups are t-butyloxycarbonyl ("Boc"), 2-trimethylsilylethoxymethyl (SEM), and p-methoxybenzyl (PMB). Further examples of these groups, and other protecting groups, are found in T. W. Greene, et al., Greene's Protective Groups in Organic Synthesis. New York: Wiley Interscience, 2006.

The term "alcohol protecting group" as used herein refers to a derivative of the groups commonly employed to block a hydroxy group while reactions are carried out on other functional groups on the compound. Examples of suitable protecting groups for use in any of the processes described herein include benzyl, trityl, silyl ethers, and the like.

Intermediate compounds 7, 15, 18, 22, 26, 29, 30, and 31, as illustrated in the above Schemes, are also novel intermediates useful for the preparation of compounds of Formula I and provide further embodiments of the invention.

In one embodiment, provided herein is a process for preparing compounds of Formula I, comprising:

(a) for a compound of Formula I wherein $R^1$ is H, $R^2$ is H, $R^3$ is C3-C6 cycloalkyl, and $R^4$ is as defined for Formula I, reacting a compound of formula 7

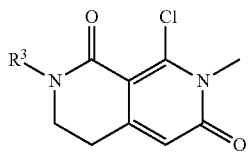

7 with a reagent having the formula $R^4NH_2$ wherein $R^4$ is as defined for Formula I, in the presence of a strong base; or (b) for a compound of Formula I wherein $R^1$ is H, $R^2$ is H, $R^3$ is hydroxy-C1-C6 alkoxy-, C1-C6 alkoxy, fluoroC1-C6 alkoxy, or (C3-C6 cycloalkyl)C1-C6 alkoxy-, and $R^4$ is as defined for Formula I, cyclizing a compound of formula 15

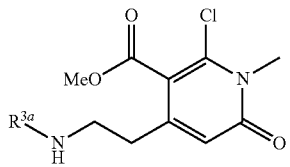

15 wherein $R^{3a}$ is $P^1O$-C1-C6 alkoxy-, C1-C6 alkoxy, fluoroC1-C6 alkoxy, or (C3-C6 cycloalkyl)C1-C6 alkoxy- and $P^1$ is an alcohol protecting group, in the presence of a reagent having the formula $R^4NH_2$ wherein $R^4$ is as defined for Formula I, in the presence of a strong base, optionally followed by removal of the alcohol protecting group if present; or (c) for a compound of Formula I wherein $R^1$ is H, $R^2$ is CH—, $R^3$ is hydroxy-C1-C6 alkoxy-, C1-C6 alkoxy, fluoroC1-C6 alkoxy, or (C3-C6 cycloalkyl)C1-C6 alkoxy-, and $R^4$ is as defined for Formula I, treating a compound of formula 18

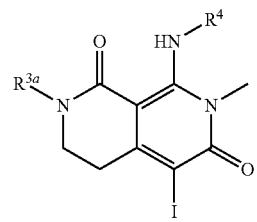

18 wherein $R^3$ is $P^1O$-C1-C6 alkoxy-, C1-C6 alkoxy, fluoroC1-C6 alkoxy, or (C3-C6 cycloalkyl)C1-C6 alkoxy, $P^1$ is an alcohol protecting group, and $R^4$ is as defined for Formula I, with methylzinc(II) chloride in the presence of a palladium catalyst, followed by removal of the alcohol protecting group if present; or (d) for a compound of Formula I wherein $R^1$ is H, $R^2$ is H, $R^3$ is H, and $R^4$ is as defined for Formula I, cyclizing a compound of formula 22

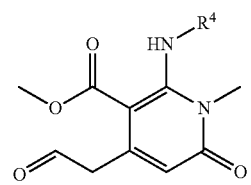

22 wherein $R^4$ is as defined for Formula I, in the presence of a reagent having the formula $P^2$—$NH_2$ where $P^2$ is an amine protecting group, followed by removing the amine protecting group; or (e) for a compound of Formula I wherein $R^1$ is H, $R^2$ is H, $R^3$ is hydroxyC1-C6 alkyl, and $R^4$ is as defined for Formula I, reacting a compound of the formula 26

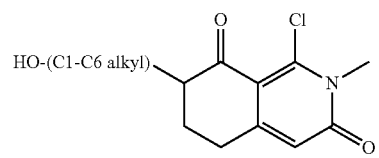

26 in the presence of a reagent having the formula $R^4NH_2$ in the presence of a strong base, wherein $R^4$ is as defined for Formula I; or (f) for a compound of Formula I wherein $R^1$ is H, $R^2$ is H, $R^3$ is hydroxyC1-C6 alkyl, and $R^4$ is as defined for Formula I, cyclizing a compound having formula 30

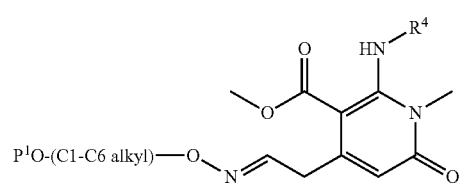

30 wherein $P^1$ is an alcohol protecting group and $R^4$ is as defined for Formula I, in the presence of a reducing agent, followed by removal of the alcohol protecting group; or (g) for a compound of Formula I wherein $R^1$ is H, $R^2$ is halogen, $R^3$ is hydroxy-C1-C6 alkoxy-, C1-C6 alkoxy, fluoroC1-C6 alkoxy, or (C3-C6 cycloalkyl)C1-C6 alkoxy-, and $R^4$ is as defined for Formula I, halogenating a compound of formula 31

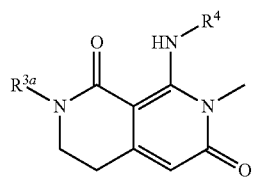

31 wherein $R^4$ is as defined for Formula I, $R^{3a}$ is $P^1$O-C1-C6 alkoxy-, C1-C6 alkoxy, fluoroC1-C6 alkoxy, or (C3-C6 cycloalkyl)C1-C6 alkoxy- and $P^1$ is an alcohol protecting group, followed by removal of the alcohol protecting group if present; or (h) for a compound of Formula I wherein $R^1$ is H, $R^2$ is H, $R^3$ is hydroxy-C1-C6 alkoxy-, C1-C6 alkoxy, fluoroC1-C6 alkoxy, or (C3-C6 cycloalkyl)C1-C6 alkoxy-, and $R^4$ is as defined for Formula I, reacting a compound of formula 29

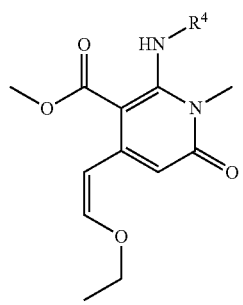

29 wherein $R^4$ is as defined for Formula I, with a reagent of formula $P^1$O—(C1-C6 alkyl)-ONH$_2$HCl, where $P^1$ is an alcohol protecting group, in the presence of triethylamine and hydrochloric acid, followed by removal of the alcohol protecting group; or (i) for a compound of Formula I wherein $R^1$ is phenyl, $R^2$ is hydrogen, $R^3$ is hydrogen, and $R^4$ is as described for Formula I, cyclizing a compound having the formula 41

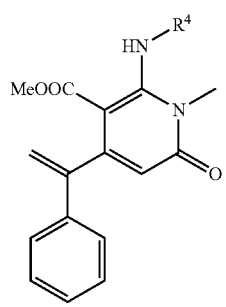

41 wherein $R^4$ is defined as for Formula I, with (2,4-dimethoxyphenyl)methanamine in the presence of a Lewis acid at an elevated temperature to provide a compound having the formula 42:

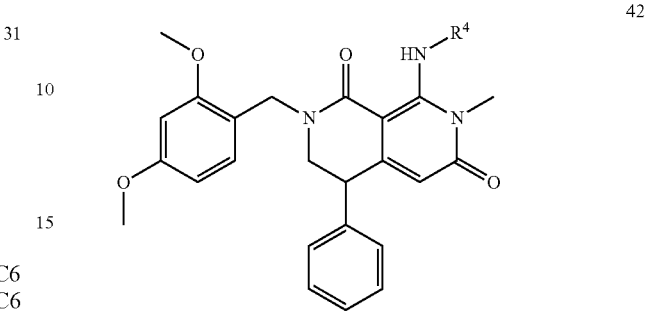

42 followed by treatment of compound 42 with acid; or (j) for a compound of Formula I wherein $R^1$ is methyl, $R^2$ is hydrogen, $R^3$ is hydroxy-C1-C6 alkoxy-, C1-C6 alkoxy, fluoroC1-C6 alkoxy, or (C3-C6 cycloalkyl)C1-C6 alkoxy and $R^4$ is as defined for Formula I, reacting a compound having the formula 49

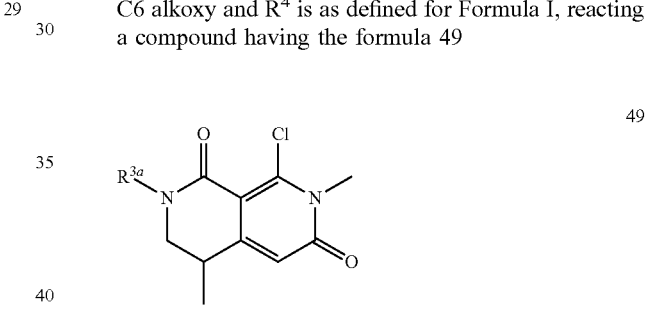

49 wherein $R^{3a}$ is $P^1$O-C1-C6 alkoxy-, C1-C6 alkoxy, fluoroC1-C6 alkoxy, or (C3-C6 cycloalkyl)C1-C6 alkoxy- and $P^1$ is an alcohol protecting group, with a reagent having the formula $R^4$NH$_2$, wherein $R^4$ is as defined for Formula I, in the presence of a strong base, followed by removal of the $P^1$ protecting group if present; and optionally converting the compound of Formula I to a pharmaceutically acceptable salt.

Synthetic intermediates 3, 4, 5, 6, 7, 13, 14, 15, 16, 18, 21, 22, 23, 25, 26, 28, 29, 30, 32, 33, 36, 37, 38, 39, 40, 41, 42, 47, 48, and 49 are also believed to be novel and are further embodiments of this invention.

The present invention may be further understood by reference to the following detailed description of the embodiments of the invention and the Examples included herein. It is to be understood that this invention is not limited to specific synthetic methods of making that may of course vary. It is to be also understood that the terminology used herein is for the purpose of describing specific embodiments only and is not intended to be limiting.

E1. A compound of Formula I:

$$\text{I}$$

or a pharmaceutically acceptable salt thereof, wherein:
$R^1$ is H, Br, C1-C6 alkyl or phenyl;
$R^2$ is H, halogen or $CH_3$—;
$R^3$ is H, hydroxyC1-C6 alkyl-, hydroxyC1-C6 alkoxy-, C1-C6 alkoxy, fluoroC1-C6 alkoxy, C3-C6 cycloalkyl, or (C3-C6 cycloalkyl)C1-C6 alkoxy-; and
$R^4$ is phenyl substituted with 1, 2 or 3 substituents independently selected from halogen, C1-C6 alkyl, C1-C6 alkylthio, fluoroC1-C6 alkylthio, fluoroC1-C6 alkyl, C1-C6 alkoxy, fluoroC1-C6 alkoxy, C3-C6 cycloalkyl, and C1-C6 alkyl-C(=O)—.

E2. A compound according to embodiment E1, or a pharmaceutically acceptable salt thereof, wherein $R^1$ is H.

E3. A compound according to embodiment E1 or E2, or a pharmaceutically acceptable salt thereof, wherein $R^2$ is H.

E4. A compound according to embodiment E1 or E2, or a pharmaceutically acceptable salt thereof, wherein $R^2$ is $CH_3$—.

E5. A compound according to any one of embodiments E1 to E4 or a pharmaceutically acceptable salt thereof, wherein $R^3$ is hydroxyC1-C6 alkyl-.

E6. A compound according to any one of embodiments E1 to E5, or a pharmaceutically acceptable salt thereof, wherein $R^4$ is phenyl substituted with 1 or 2 substituents independently selected from halogen, C1-C6 alkyl, C1-C6 alkylthio, fluoroC1-C6 alkylthio, fluoroC1-C6 alkyl, C1-C6 alkoxy, fluoroC1-C6 alkoxy, C3-C6 cycloalkyl, and C1-C6 alkyl-C(=O)—.

E7. A compound according to any one of embodiments E1 to E6 or a pharmaceutically acceptable salt thereof, wherein $R^4$ is phenyl substituted with 1 or 2 substituents independently selected from halogen and C1-C6 alkylthio.

E8. A compound of Formula II:

$$\text{II}$$

or a pharmaceutically acceptable salt thereof, wherein
$R^1$ is H, Br, C1-C6 alkyl or phenyl;
$R^2$ is H, halogen or $CH_3$—;
$R^3$ is H, hydroxyC1-C6 alkyl-, hydroxyC1-C6 alkoxy-, C1-C6 alkoxy, fluoroC1-C6 alkoxy, C3-C6 cycloalkyl, or (C3-C6 cycloalkyl)C1-C6 alkoxy-; and $R^a$ and $R^b$ are independently selected from halogen, C1-C6 alkyl, C1-C6 alkylthio, fluoroC1-C6 alkylthio, fluoroC1-C6 alkyl, C1-C6 alkoxy, fluoroC1-C6 alkoxy, C3-C6 cycloalkyl, and C1-C6 alkyl-C(=O)—.

E9. A compound according to embodiment E8, or a pharmaceutically acceptable salt thereof, wherein $R^1$ is H.

E10. A compound according to embodiment E8 or E9, or a pharmaceutically acceptable salt thereof, wherein $R^2$ is H.

E11. A compound according to embodiment E8 or E9, or a pharmaceutically acceptable salt thereof, wherein $R^2$ is $CH_3$—.

E12. A compound according to any one of embodiments E8 to E11, or a pharmaceutically acceptable salt thereof, wherein $R^3$ is hydroxyC1-C6 alkyl-.

E13. A compound according to any one of embodiments E8 to E11, or a pharmaceutically acceptable salt thereof, wherein $R^3$ is H.

E14 A compound according to any one of embodiment E8 to E13, or a pharmaceutically acceptable salt thereof, wherein $R^a$ is halogen.

E15. A compound according to any one of embodiments E8 to E14, or a pharmaceutically acceptable salt thereof, wherein $R^b$ is halogen, C1-C6 alkyl, C1-C6 alkylthio, or fluoroC1-C6 alkoxy.

E16. A compound according to embodiment E15, or a pharmaceutically acceptable salt thereof, wherein $R^b$ is C1-C6 alkylthio.

E17. A compound according to embodiment E1, selected from:
8-((4-bromo-2-fluorophenyl)amino)-2-cyclopropyl-7-methyl-3,4-dihydro-2,7-naphthyridine-1,6(2H,7H)-dione;
8-((4-bromo-2-fluorophenyl)amino)-2-(cyclopropylmethoxy)-7-methyl-3,4-dihydro-2,7-naphthyridine-1,6(2H,7H)-dione;
8-((4-bromo-2-fluorophenyl)amino)-2-ethoxy-7-methyl-3,4-dihydro-2,7-naphthyridine-1,6(2H,7H)-dione;
2-cyclopropyl-8-((2-fluoro-4-(methylthio)phenyl)amino)-7-methyl-3,4-dihydro-2,7-naphthyridine-1,6(2H,7H)-dione;
2-cyclopropyl-8-((2-fluoro-4-iodophenyl)amino)-7-methyl-3,4-dihydro-2,7-naphthyridine-1,6(2H,7H)-dione;
8-((2-fluoro-4-(methylthio)phenyl)amino)-2-(2-hydroxyethoxy)-7-methyl-3,4-dihydro-2,7-naphthyridine-1,6(2H,7H)-dione;
8-((4-bromo-2-fluorophenyl)amino)-2-(2-hydroxyethoxy)-7-methyl-3,4-dihydro-2,7-naphthyridine-1,6(2H,7H)-dione;
8-((2-fluoro-4-iodophenyl)amino)-2-(2-hydroxyethoxy)-7-methyl-3,4-dihydro-2,7-naphthyridine-1,6(2H,7H)-dione;
8-((2-chloro-4-iodophenyl)amino)-2-(2-hydroxyethoxy)-7-methyl-3,4-dihydro-2,7-naphthyridine-1,6(2H,7H)-dione;
8-((4-bromo-2-chlorophenyl)amino)-2-(2-hydroxyethoxy)-7-methyl-3,4-dihydro-2,7-naphthyridine-1,6(2H,7H)-dione;
8-((4-bromo-2,3-difluorophenyl)amino)-2-(2-hydroxyethoxy)-7-methyl-3,4-dihydro-2,7-naphthyridine-1,6(2H,7H)-dione;
8-((4-bromo-3-chloro-2-fluorophenyl)amino)-2-(2-hydroxyethoxy)-7-methyl-3,4-dihydro-2,7-naphthyridine-1,6(2H,7H)-dione;
8-((2-fluoro-4-(trifluoromethyl)phenyl)amino)-2-(2-hydroxyethoxy)-7-methyl-3,4-dihydro-2,7-naphthyridine-1,6(2H,7H)-dione;

8-((4-ethyl-2-fluorophenyl)amino)-2-(2-hydroxyethoxy)-7-methyl-3,4-dihydro-2,7-naphthyridine-1,6(2H,7H)-dione;

8-((4-cyclopropyl-2-fluorophenyl)amino)-2-(2-hydroxyethoxy)-7-methyl-3,4-dihydro-2,7-naphthyridine-1,6(2H,7H)-dione;

8-((2-fluoro-4-methoxyphenyl)amino)-2-(2-hydroxyethoxy)-7-methyl-3,4-dihydro-2,7-naphthyridine-1,6(2H,7H)-dione;

8-((2-fluoro-4-((trifluoromethyl)thio)phenyl)amino)-2-(2-hydroxyethoxy)-7-methyl-3,4-dihydro-2,7-naphthyridine-1,6(2H,7H)-dione;

8-((2-fluoro-4-isopropylphenyl)amino)-2-(2-hydroxyethoxy)-7-methyl-3,4-dihydro-2,7-naphthyridine-1,6(2H,7H)-dione;

8-((2-chloro-4-cyclopropylphenyl)amino)-2-(2-hydroxyethoxy)-7-methyl-3,4-dihydro-2,7-naphthyridine-1,6(2H,7H)-dione;

8-((4-acetyl-2-fluorophenyl)amino)-2-(2-hydroxyethoxy)-7-methyl-3,4-dihydro-2,7-naphthyridine-1,6(2H,7H)-dione;

8-((2-chloro-4-(methylthio)phenyl)amino)-2-(2-hydroxyethoxy)-7-methyl-3,4-dihydro-2,7-naphthyridine-1,6(2H,7H)-dione;

8-((4-(difluoromethoxy)-2-fluorophenyl)amino)-2-(2-hydroxyethoxy)-7-methyl-3,4-dihydro-2,7-naphthyridine-1,6(2H,7H)-dione;

8-((2-chloro-4-ethylphenyl)amino)-2-(2-hydroxyethoxy)-7-methyl-3,4-dihydro-2,7-naphthyridine-1,6(2H,7H)-dione;

8-((2-fluoro-4-(trifluoromethoxy)phenyl)amino)-2-(2-hydroxyethoxy)-7-methyl-3,4-dihydro-2,7-naphthyridine-1,6(2H,7H)-dione;

8-((4-((difluoromethyl)thio)-2-fluorophenyl)amino)-2-(2-hydroxyethoxy)-7-methyl-3,4-dihydro-2,7-naphthyridine-1,6(2H,7H)-dione;

8-((4-bromo-2-fluorophenyl)amino)-2-isopropoxy-7-methyl-3,4-dihydro-2,7-naphthyridine-1,6(2H,7H)-dione;

8-((2-fluoro-4-iodophenyl)amino)-2-isopropoxy-7-methyl-3,4-dihydro-2,7-naphthyridine-1,6(2H,7H)-dione;

2-ethoxy-8-((2-fluoro-4-iodophenyl)amino)-7-methyl-3,4-dihydro-2,7-naphthyridine-1,6(2H,7H)-dione;

8-((2-fluoro-4-iodophenyl)amino)-2-methoxy-7-methyl-3,4-dihydro-2,7-naphthyridine-1,6(2H,7H)-dione;

2-(tert-butoxy)-8-((2-fluoro-4-iodophenyl)amino)-7-methyl-3,4-dihydro-2,7-naphthyridine-1,6(2H,7H)-dione;

(S)-8-((2-fluoro-4-iodophenyl)amino)-2-(2-hydroxypropoxy)-7-methyl-3,4-dihydro-2,7-naphthyridine-1,6(2H,7H)-dione;

(R)-8-((2-fluoro-4-iodophenyl)amino)-2-(2-hydroxypropoxy)-7-methyl-3,4-dihydro-2,7-naphthyridine-1,6(2H,7H)-dione;

(S)-8-((4-bromo-2-fluorophenyl)amino)-2-(2-hydroxypropoxy)-7-methyl-3,4-dihydro-2,7-naphthyridine-1,6(2H,7H)-dione;

(R)-8-((4-bromo-2-fluorophenyl)amino)-2-(2-hydroxypropoxy)-7-methyl-3,4-dihydro-2,7-naphthyridine-1,6(2H,7H)-dione;

(R)-8-((4-bromo-2-fluorophenyl)amino)-2-(2-hydroxypropoxy)-5,7-dimethyl-3,4-dihydro-2,7-naphthyridine-1,6(2H,7H)-dione;

8-((4-bromo-2-fluorophenyl)amino)-2-(2-hydroxyethoxy)-5,7-dimethyl-3,4-dihydro-2,7-naphthyridine-1,6(2H,7H)-dione;

8-((4-bromo-2-fluorophenyl)amino)-5-chloro-2-(2-hydroxyethoxy)-7-methyl-3,4-dihydro-2,7-naphthyridine-1,6(2H,7H)-dione;

5-chloro-8-((2-fluoro-4-iodophenyl)amino)-2-(2-hydroxyethoxy)-7-methyl-3,4-dihydro-2,7-naphthyridine-1,6(2H,7H)-dione;

8-((4-bromo-2-fluorophenyl)amino)-5-fluoro-2-(2-hydroxyethoxy)-7-methyl-3,4-dihydro-2,7-naphthyridine-1,6(2H,7H)-dione;

8-((2-fluoro-4-iodophenyl)amino)-2-(2-hydroxyethoxy)-5,7-dimethyl-3,4-dihydro-2,7-naphthyridine-1,6(2H,7H)-dione;

8-((2-fluorophenyl)amino)-2-(2-hydroxyethoxy)-5-iodo-7-methyl-3,4-dihydro-2,7-naphthyridine-1,6(2H,7H)-dione;

5-bromo-8-((4-bromo-2-fluorophenyl)amino)-2-(2-hydroxyethoxy)-7-methyl-3,4-dihydro-2,7-naphthyridine-1,6(2H,7H)-dione;

4-bromo-8-((2-fluorophenyl)amino)-2-(2-hydroxyethoxy)-5,7-dimethyl-3,4-dihydro-2,7-naphthyridine-1,6(2H,7H)-dione:

8-((4-ethyl-2-fluorophenyl)amino)-2-(2-hydroxyethoxy)-5,7-dimethyl-3,4-dihydro-2,7-naphthyridine-1,6(2H,7H)-dione;

8-((4-cyclopropyl-2-fluorophenyl)amino)-2-(2-hydroxyethoxy)-5,7-dimethyl-3,4-dihydro-2,7-naphthyridine-1,6(2H,7H)-dione;

8-((4-bromo-2-fluorophenyl)amino)-7-methyl-3,4-dihydro-2,7-naphthyridine-1,6(2H,7H)-dione;

8-((4-bromo-2-fluorophenyl)amino)-5,7-dimethyl-3,4-dihydro-2,7-naphthyrdine-1,6(2H,7H)-dione;

8-((2-fluoro-4-iodophenyl)amino)-5,7-dimethyl-3,4-dihydro-2,7-naphthyridine-1,6(2H,7H)-dione;

8-((4-iodo-2-fluorophenyl)amino)-7-methyl-3,4-dihydro-2,7-naphthyridine-1,6(2H,7H)-dione;

8-((2-fluoro-4-(methylthio)phenyl)amino)-7-methyl-3,4-dihydro-2,7-naphthyridine-1,6(2H,7H)-dione;

8-((4-ethyl-2-fluorophenyl)amino)-7-methyl-3,4-dihydro-2,7-naphthyridine-1,6(2H,7H)-dione;

8-((4-cyclopropyl-2-fluorophenyl)amino)-7-methyl-3,4-dihydro-2,7-naphthyridine-1,6(2H,7H)-dione;

8-((4-(difluoromethoxy)-2-fluorophenyl)amino)-7-methyl-3,4-dihydro-2,7-naphthyridine-1,6(2H,7H)-dione;

8-((2-fluoro-4-propylphenyl)amino)-7-methyl-3,4-dihydro-2,7-naphthyridine-1,6(2H,7H)-dione;

8-((2-fluoro-4-(methylthio)phenyl)amino)-5,7-dimethyl-3,4-dihydro-2,7-naphthyridine-1,6(2H,7H)-dione;

8-((4-ethyl-2-fluorophenyl)amino)-5,7-dimethyl-3,4-dihydro-2,7-naphthyrdine-1,6(2H,7H)-dione;

8-((4-cyclopropyl-2-fluorophenyl)amino)-5,7-dimethyl-3,4-dihydro-2,7-naphthyridine-1,6(2H,7H)-dione;

8-((4-(difluoromethoxy)-2-fluorophenyl)amino)-5,7-dimethyl-3,4-dihydro-2,7-naphthyridine-1,6(2H,7H)-dione;

8-((4-bromo-2-chlorophenyl)amino)-7-methyl-3,4-dihydro-2,7-naphthyridine-1,6(2H,7H)-dione;

8-((4-bromo-2-fluorophenyl)amino)-2-(2-hydroxyethyl)-7-methyl-3,4-dihydro-2,7-naphthyridine-1,6(2H,7H)-dione;

8-((2-fluoro-4-(methylthio)phenyl)amino)-2-(2-hydroxyethoxy)-5,7-dimethyl-3,4-dihydro-2,7-naphthyridine-1,6(2H,7H)-dione;

8-((4-(difluoromethoxy)-2-fluorophenyl)amino)-2-(2-hydroxyethoxy)-5,7-dimethyl-3,4-dihydro-2,7-naphthyridine-1,6(2H,7H)-dione;

2-(2,2-difluoroethoxy)-8-((2-fluoro-4-(methylthio)phenyl)amino)-7-methyl-3,4-dihydro-2,7-naphthyridine-1,6(2H,7H)-dione;

8-((4-bromo-2-fluorophenyl)amino)-7-methyl-4-phenyl-3,4-dihydro-2,7-naphthyridine-1,6(2H,7H)-dione;

8-((2-fluoro-4-(methylthio)phenyl)amino)-7-methyl-4-phenyl-3,4-dihydro-2,7-naphthyridine-1,6(2H,7H)-dione;

8-((4-bromo-2-fluorophenyl)amino)-4,7-dimethyl-3,4-dihydro-2,7-naphthyridine-1,6(2H,7H)-dione;

8-((2-fluoro-4-(methylthio)phenyl)amino)-4,7-dimethyl-3,4-dihydro-2,7-naphthyridine-1,6(2H,7H)-dione;

8-((4-bromo-2-fluorophenyl)amino)-2-(2-hydroxyethoxy)-4,7-dimethyl-3,4-dihydro-2,7-naphthyridine-1,6(2H,7H)-dione;

8-((2-fluoro-4-(methylthio)phenyl)amino)-2-(2-hydroxyethoxy)-4,7-dimethyl-3,4-dihydro-2,7-naphthyridine-1,6(2H,7H)-dione;

or a pharmaceutically acceptable salt thereof.

E18. A compound which is 8-((2-fluoro-4-(methylthio)phenyl)amino)-2-(2-hydroxyethoxy)-7-methyl-3,4-dihydro-2,7-naphthyridine-1,6(2H,7H)-dione having the structure:

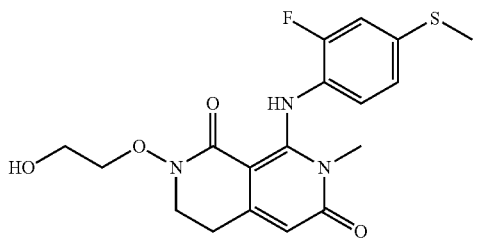 [SMILES: CSc1ccc(Nc2c3c(cc(=O)n2C)CCN(OCCO)C3=O)c(F)c1]

or a pharmaceutically acceptable salt thereof.

E19. A compound which is 8-((2-fluoro-4-(methylthio)phenyl)amino)-2-(2-hydroxyethoxy)-7-methyl-3,4-dihydro-2,7-naphthyridine-1,6(2H,7H)-dione having the structure:

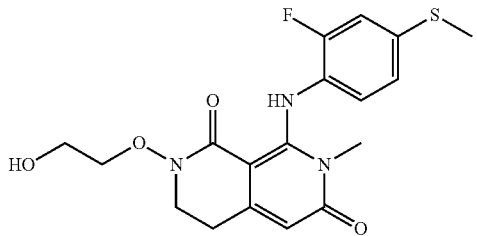

E20. A crystal comprising 8-((2-fluoro-4-(methylthio)phenyl)amino)-2-(2-hydroxyethoxy)-7-methyl-3,4-dihydro-2,7-naphthyridine-1,6(2H,7H)-dione.

E21. Crystalline anhydrous 8-((2-fluoro-4-(methylthio)phenyl)amino)-2-(2-hydroxyethoxy)-7-methyl-3,4-dihydro-2,7-naphthyridine-1,6(2H,7H)-dione, Form 1.

E22. Crystalline anhydrous 8-((2-fluoro-4-(methylthio)phenyl)amino)-2-(2-hydroxyethoxy)-7-methyl-3,4-dihydro-2,7-naphthyridine-1,6(2H,7H)-dione, Form 1 according to embodiment E21, having a PXRD pattern comprising characterizing peaks at 5.0, 8.7, 9.3, 10.8, 14.5, 15.3, 18.8 and 20.5 degrees 2-theta (±0.2 degrees 2-theta).

E23. Crystalline anhydrous 8-((2-fluoro-4-(methylthio)phenyl)amino)-2-(2-hydroxyethoxy)-7-methyl-3,4-dihydro-2,7-naphthyridine-1,6(2H,7H)-dione, Form 1 according to embodiment E21, having a PXRD pattern comprising peaks at 2-theta values essentially the same as shown in FIG. 1.

E24. Crystalline anhydrous 8-((2-fluoro-4-(methylthio)phenyl)amino)-2-(2-hydroxyethoxy)-7-methyl-3,4-dihydro-2,7-naphthyridine-1,6(2H,7H)-dione, Form 2.

E25. Crystalline anhydrous 8-((2-fluoro-4-(methylthio)phenyl)amino)-2-(2-hydroxyethoxy)-7-methyl-3,4-dihydro-2,7-naphthyridine-1,6(2H,7H)-dione, Form 2 according to embodiment E24, having a PXRD pattern comprising characterizing peaks at 7.1, 9.4, 12.4, 12.8, 14.3, 15.6, 16.4, 17.4, 18.5, 18.9, 19.5, 19.9, 21.1, 21.4, 23.2, 23.7, 24.8, 25.6, 27.6, 30.3, 33.2, 33.5, and 37.5 degrees 2-theta (±0.2 degrees 2-theta).

E26. Crystalline anhydrous 8-((2-fluoro-4-(methylthio)phenyl)amino)-2-(2-hydroxyethoxy)-7-methyl-3,4-dihydro-2,7-naphthyridine-1,6(2H,7H)-dione, Form 2 according to embodiment E24, having a PXRD pattern comprising peaks at 2-theta values essentially the same as shown in FIG. 2.

E27. Crystalline anhydrous 8-((2-fluoro-4-(methylthio)phenyl)amino)-2-(2-hydroxyethoxy)-7-methyl-3,4-dihydro-2,7-naphthyridine-1,6(2H,7H)-dione, Form 2 according Embodiment E25 or E26, wherein the PXRD pattern is obtained by PXRD analysis conducted at 25° C. and at a relative humidity below 10%.

E28. Crystalline monohydrate 8-((2-fluoro-4-(methylthio)phenyl)amino)-2-(2-hydroxyethoxy)-7-methyl-3,4-dihydro-2,7-naphthyridine-1,6(2H,7H)-dione, Form 3.

E29. Crystalline monohydrate 8-((2-fluoro-4-(methylthio)phenyl)amino)-2-(2-hydroxyethoxy)-7-methyl-3,4-dihydro-2,7-naphthyridine-1,6(2H,7H)-dione, Form 3 according to embodiment E28, having PXRD peaks at 13.7, 18.0 and 18.3 degrees 2-theta (±0.2 degrees 2-theta).

E30. Crystalline monohydrate 8-((2-fluoro-4-(methylthio)phenyl)amino)-2-(2-hydroxyethoxy)-7-methyl-3,4-dihydro-2,7-naphthyridine-1,6(2H,7H)-dione, Form 3 according to embodiment E28, having PXRD peaks at 6.9, 9.1, 13.7, 18.0 and 18.3 degrees 2-theta (±0.2 degrees 2-theta).

E31. Crystalline monohydrate 8-((2-fluoro-4-(methylthio)phenyl)amino)-2-(2-hydroxyethoxy)-7-methyl-3,4-dihydro-2,7-naphthyridine-1,6(2H,7H)-dione, Form 3 according to embodiment E28, having PXRD peaks, in terms of 2-theta, at 6.9, 9.1, 11.8, 12.0, 13.7, 14.0, 15.2, 15.8, 18.0, 18.3, 19.0, 19.3, 20.2, 20.9, 21.6, 22.6, 23.6, 24.0, 24.9, 25.2, 25.8, 27.5, 28.1, 28.4, 29.8, 30.9, 31.7, 32.3 and 36.5 degrees 2-theta (±0.2 degrees 2-theta.

E32. Crystalline monohydrate 8-((2-fluoro-4-(methylthio)phenyl)amino)-2-(2-hydroxyethoxy)-7-methyl-3,4-dihydro-2,7-naphthyridine-1,6(2H,7H)-dione, Form 3 according to embodiment E28, having a PXRD pattern comprising peaks at 2-theta values essentially the same as shown in FIG. 3.

E33. Crystalline monohydrate 8-((2-fluoro-4-(methylthio)phenyl)amino)-2-(2-hydroxyethoxy)-7-methyl-3,4-dihydro-2,7-naphthyridine-1,6(2H,7H)-dione, Form 3 according to any one of embodiments E29 to E32, wherein the PXRD pattern is obtained by PXRD analysis conducted at 25° C. and at a relative humidity above 35%.

E34. Amorphous 8-((2-fluoro-4-(methylthio)phenyl)amino)-2-(2-hydroxyethoxy)-7-methyl-3,4-dihydro-2,7-naphthyridine-1,6(2H,7H)-dione, Form 4.

E35. Amorphous 8-((2-fluoro-4-(methylthio)phenyl)amino)-2-(2-hydroxyethoxy)-7-methyl-3,4-dihydro-2,7-naphthyridine-1,6(2H,7H)-dione, Form 4 according to embodiment E34, having a PXRD pattern comprising peaks at 2-theta values essentially the same as shown in FIG. 4.

E36. A pharmaceutical composition, comprising a compound according to any one of embodiments E1 to E35, or a pharmaceutically acceptable salt thereof, and at least one pharmaceutically acceptable excipient.

E37. A method of treating a MEK-associated tumor, comprising administering to a subject in need thereof a therapeutically effective amount of a compound according to any one of embodiments E1 to E35, or a pharmaceutically acceptable salt thereof.

E38. The method according to embodiment E37, wherein the tumor has a BRAF V600 mutation selected from V600E, V600K, V600D, V600R and V600S.

E39. The method according to embodiment E37 or E38, wherein the tumor has a BRAF V600E mutation.

E40. The method according to any one of embodiments E37 to E39, wherein the tumor is an extracranial tumor.

E41. The method according to embodiment E40, wherein the extracranial tumor is selected from melanoma, colorectal cancer, thyroid cancer, non-small cell lung cancer, ovarian cancer, and neuroblastoma.

E42. The method according to any one of embodiments E37 to E39, wherein the tumor is a CNS tumor.

E43. The method according to embodiment E42, wherein the CNS tumor is an intracranial tumor.

E44. The method according to embodiment E43, wherein the intracranial tumor is a brain cancer.

E45. The method according to embodiment E44, wherein the brain cancer is a metastatic brain cancer.

E46. The method according to embodiment E45, wherein the metastatic brain cancer is selected from metastatic melanoma, metastatic colorectal cancer, metastatic non-small cell lung cancer, metastatic thyroid cancer, and metastatic ovarian cancer.

E47. The method according to embodiment E42, wherein the CNS tumor is intracranial LMD or extracranial LMD.

E48. The method according to embodiment E47, wherein the LMD is selected from metastatic melanoma, metastatic colorectal cancer, and metastatic non-small cell lung cancer.

E49. The method according to embodiment E43, wherein the intracranial tumor is a primary tumor.

E50. The method of embodiment E49, wherein the primary brain tumor is a malignant tumor.

E51. The method according to embodiment E50, wherein the primary brain tumor is a Grade 2 glioma, a Grade 3 glioma or a Grade 4 glioma.

E52. The method according to embodiment E49, wherein the primary brain tumor is a benign tumor.

E53. The method according to embodiment E37, wherein the tumor has a BRAF fusion.

E54. The method according to embodiment E53, wherein the tumor has a BRAF fusion selected from KIAA11549-BRAF, MKRN1-BRAF, TRIM24-BRAF, AGAP3-BRAF, ZC3HAV1-BRAF, AKAP9-BRAF, CCDC6-BRAF, AGK-BRAF, EPS15-BRAF, NUP214-BRAF, ARMC10-BRAF, BTF3L4-BRAF, GHR-BRAF, ZC3HAV1-BRAF, ZNF767-BRAF, CCDC91-BRAF, DYNC112-BRAF, ZKSCAN1-BRAF, GTF21-BRAF, MZT1-BRAF, RAD18-BRAF, CUX1-BRAF, SLC12A7-BRAF, MYRIP-BRAF, SND1-BRAF, NUB1-BRAF, KLHL7-BRAF, TANK-BRAF, RBMS3-BRAF, STRN3-BRAF, STK35-BRAF, ETFA-BRAF, SVOPL-BRAF, and JHDM1D-BRAF.

E55. The method according to embodiment E54, wherein the tumor is breast carcinoma (e.g., breast invasive ductal carcinoma), colorectal carcinoma (e.g., colon adenocarcinoma), esophageal carcinoma (e.g., esophagus adenocarcinoma), glioma (e.g., brain desmoplastic infantile ganglioglioma, brain pilocytic astrocytoma, brain pleomorphic xanthoastrocytoma, spinal cord low-grade glioma (NOS), anaplastic oligodendroglioma, anaplastic ganglioglioma), head and neck carcinoma (e.g., head and neck neuroendocrine carcinoma), lung carcinoma (e.g., lung adenocarcinoma, lung non-small cell lung cancer (NOS)), melanoma (e.g., cutaneous melanoma Spitzoid, mucosal melanoma non-Spitzoid, cutaneous melanoma Spitzoid, unknown primary melanoma, cutaneous melanoma non-Spitzoid), pancreatic carcinoma (e.g., adenocarcinoma, pancreas acinar cell carcinoma), prostatic carcinoma (e.g., prostate acinar adenocarcinoma), sarcoma (malignant solid fibrous tumor), thyroid carcinoma (thyroid papillary carcinoma), unknown primary carcinoma (e.g., unknown primary, adenocarcinoma), pleura mesothelioma, rectum adenocarcinoma, uterus endometrial carcinoma (e.g., uterus endometrial adenocarcinoma (NOS)), or ovary serous carcinoma.

E56. The method according to embodiment E37, wherein the tumor is a BRAF wild-type tumor.

E57. The method according to any one of embodiments E37 to E56, wherein the method further comprises administering one or more additional anticancer therapies.

E58. The method according to embodiment E57, wherein the one or more additional anticancer therapies is independently selected from surgery, radiotherapy and anticancer agents.

E59. The method according to embodiment E58, wherein the additional anticancer therapy is selected from one or more anticancer agents.

E60. The method according to embodiment E59, wherein the anticancer agent is selected from MEK inhibitors, BRAF inhibitors, EGFR inhibitors, inhibitors of HER2 and/or HER3, SHP2 inhibitors, Axl inhibitors, PI3K inhibitors, SOS1 inhibitors, signal transduction pathway inhibitors, checkpoint inhibitors, modulators of the apoptosis pathway, cytotoxic chemotherapeutics, angiogenesis-targeted therapies, and immune-targeted agents including immunotherapy.

E61. The method of embodiment E60, where in the anticancer agent is a BRAF inhibitor.

E62. The method of embodiment E61, wherein the BRAF inhibitor is encorafenib or a pharmaceutically acceptable salt thereof.

E63. The method of embodiment E61, wherein the BRAF inhibitor is selected from:
N-(3-((3,5-dimethyl-4-oxo-3,4-dihydroquinazolin-6-yl) amino)-2,4-difluorophenyl)propane-1-sulfonamide;
N-(2-chloro-3-((3,5-dimethyl-4-oxo-3,4-dihydroquinazolin-6-yl)amino)phenyl)-3-fluoropropane-1-sulfonamide;
N-(2-chloro-3-((3,5-dimethyl-4-oxo-3,4-dihydroquinazolin-6-yl)amino)-4,5-difluorophenyl)propane-1-sulfonamide;
N-(2-chloro-3-((3,5-dimethyl-4-oxo-3,4-dihydroquinazolin-6-yl)amino)-4-fluorophenyl)propane-1-sulfonamide;
N-(2-chloro-3-((3,5-dimethyl-4-oxo-3,4-dihydroquinazolin-6-yl)amino)-4-fluorophenyl)-3-fluoropropane-1-sulfonamide;
N-(2-chloro-4-fluoro-3-((5-methyl-3-(methyl-d3)-4-oxo-3,4-dihydroquinazolin-6-yl)amino)-phenyl)-3-fluoropropane-1-sulfonamide;
N-{2-chloro-3-[(3,5-dimethyl-4-oxo-3,4-dihydroquinazolin-6-yl)oxy]-4-fluorophenyl}propane-1-sulfonamide;
N-(3-chloro-4-((3,5-dimethyl-4-oxo-3,4-dihydroquinazolin-6-yl)oxy)-5-fluoropyridin-2-yl)propane-1-sulfonamide; and
N-{2-chloro-3-[(3,5-dimethyl-4-oxo-3,4-dihydroquinazolin-6-yl)oxy]-4-fluorophenyl}-3-fluoropropane-1-sulfonamide;
or a pharmaceutically acceptable salt thereof.

E64. The method of embodiment E63, wherein the BRAF inhibitor is N-(2-chloro-3-((3,5-dimethyl-4-oxo-3,4-dihydroquinazolin-6-yl)amino)-4-fluorophenyl)-3-fluoropropane-1-sulfonamide or a pharmaceutically acceptable salt thereof.

E65. The method of embodiment E61, wherein the BRAF inhibitor is selected from:

N-(2-chloro-4-fluoro-3-((5-fluoro-3-methyl-4-oxo-3,4-dihydroquinazolin-6-yl)amino)phenyl)-2-azabicyclo[2.1.1]hexane-2-sulfonamide, (R)—N-(2-chloro-4-fluoro-3-((5-fluoro-3-methyl-4-oxo-3,4-dihydroquinazolin-6-yl)amino)phenyl)-3-fluoropyrrolidine-1-sulfonamide, and N-(2-chloro-3-((5-chloro-3-methyl-4-oxo-3,4-dihydroquinazolin-6-yl)amino)-4-fluorophenyl)-3-fluoroazetidine-1-sulfonamide, or a pharmaceutically acceptable salt thereof.

E66. The method of embodiment E65, wherein the BRAF inhibitor is N-(2-chloro-3-((5-chloro-3-methyl-4-oxo-3,4-dihydroquinazolin-6-yl)amino)-4-fluorophenyl)-3-fluoroazetidine-1-sulfonamide, or a pharmaceutically acceptable salt thereof.

E67. The method of embodiment E60, wherein the anticancer agent is a SHP2 inhibitor.

E68. The method of embodiment E67, wherein the SHP2 inhibitor is (S)-1'-(6-((2-amino-3-chloropyridin-4-yl)thio)-1,2,4-triazin-3-yl)-1,3-dihydrospiro[indene-2,4'-piperidin]-1-amine or a pharmaceutically acceptable salt thereof.

E69. The method according to any one of embodiments E37 to E68, wherein the compound is 8-((2-fluoro-4-(methylthio)phenyl)amino)-2-(2-hydroxyethoxy)-7-methyl-3,4-dihydro-2,7-naphthyridine-1,6(2H,7H)-dione and wherein the subject is administered 50 mg of 8-((2-fluoro-4-(methylthio)phenyl)amino)-2-(2-hydroxyethoxy)-7-methyl-3,4-dihydro-2,7-naphthyridine-1,6(2H,7H)-dione once a day.

E70. A compound according to any one of embodiments E1 to E35, or a pharmaceutically acceptable salt thereof, for use as a medicament.

E71. A compound according to one of embodiments E1 to E35, or a pharmaceutically acceptable salt thereof, for use in the treatment of a MEK-associated tumor.

E72. Use of a compound according to any one of embodiments E1 to E35 or a pharmaceutically acceptable salt thereof, for the manufacture of a medicament for the treatment of a MEK-associated tumor in a subject.

In order that this invention may be better understood, the following examples are set forth. These examples are for purposes of illustration only and are not to be construed as limiting the scope of the invention in any manner.

The compounds and intermediates described below were named using the naming convention provided with ChemDraw, Version 20.1.1.125 (Perkin Elmer Informatics). The naming convention provided with ChemDraw, Version 20.1.1.125 is well known by those skilled in the art and it is believed that the naming convention provided with ChemDraw, Version 20.1.1.125 generally comports with the IUPAC (International Union for Pure and Applied Chemistry) recommendations on Nomenclature of Organic Chemistry and the CAS Index rules. Unless noted otherwise, all reactants were obtained commercially without further purifications or were prepared using methods known in the literature.

EXAMPLES

Biological Examples

Example A

Cellular Phospho-p44/42 MAPK (Erk1/2) (Thr202/Tyr204) Assay

Inhibition of ERK1/2(Thr202/Tyr204) phosphorylation was determined by the following cellular assay, which comprises incubating cells with a compound for 1 hour and quantifying pERK signal by In-Cell Western on fixed cells and normalizing to GAPDH signal. A375 cells were obtained from the ATCC and grown in DMEM supplemented with 10% fetal bovine serum, penicillin/streptomycin, Glutamax®, non-essential amino acids, and sodium pyruvate. Cells were plated in 96-well plates at 30,000 cells/well and allowed to attach overnight at 37° C./5% $CO_2$. Cells were treated with compounds prepared as a 10-point, 1:3 dilution series (range: 20 μM-0.05 nM; maximum concentration varied from 20 μM-1 μM), with a final DMSO concentration of 0.5%. Control wells contained either 0.5% DMSO alone (no inhibition control) or 1 μM of a potent control compound (complete inhibition control). After a 1-hour incubation, cells were fixed in 3.7% formaldehyde in dPBS (Dulbecco's phosphate-buffered saline) at room temperature for 20 minutes. Cells were then washed with dPBS and permeabilized in 100% MeOH at room temperature for 10 minutes. Following permeabilization, cells were washed in dPBS and incubated in LI-COR Blocking Buffer (LI-COR Biosciences, Cat #927-40000) for 1 hour or longer. Plates were then incubated with an antibody specific for the MEK-dependent ERK1/2 phosphorylation sites, threonine 202 and tyrosine 204 (Cell Signaling Technologies; Cat #9101), downstream of MEK in the MAP kinase signal transduction pathway, as well as GAPDH (Millipore; Cat #MAB374). pErk1/2 (Thr202/Tyr204) antibody was diluted in LI-COR blocking buffer containing 0.05% Tween-20 at 1:250; GAPDH was diluted at 1:2,500. The plates were incubated overnight at 4° C. After washing with PBS/0.05% Tween-20, the cells were incubated with fluorescently-labeled secondary antibodies (Anti-rabbit-Alexa Flour680, Invitrogen Cat #A21109; Anti-mouse-IRDye800CW, LI-COR Biosciences Cat #926-32210, both at 1:1000 dilution) for 1 hour. Cells were then washed, as above, and analyzed for fluorescence at both 680 and 800 nm wavelengths using the Odyssey CLx Infrared Imaging System (LI-COR Biosciences). Phosphorylated Erk1/2 (Thr202/Tyr204) signal was normalized to GAPDH signal for each well. $IC_{50}$ values were calculated from the normalized values using a 4-parameter fit in BioAssay software and are provided in Table A.

TABLE A

| Ex. No. | A375 cell $IC_{50}$(nM) |
| --- | --- |
| 1 | 562 |
| 2 | 1034 |
| 3 | 456 |
| 4 | 74 |
| 5 | 20 |
| 6 | 8 |
| 7 | 23 |
| 8 | 1 |
| 9 | 3 |
| 10 | 58 |
| 11 | 199 |
| 12 | 1060 |
| 13 | 178 |
| 14 | 15 |
| 15 | 17 |
| 16 | 274 |
| 17 | 256 |
| 18 | 39 |
| 19 | 29 |
| 20 | 632 |
| 21 | 10 |
| 22 | 21 |
| 23 | 26 |

TABLE A-continued

| Ex. No. | A375 cell IC$_{50}$(nM) |
|---|---|
| 24 | 466 |
| 25 | 3 |
| 27 | 142 |
| 28 | 26 |
| 29 | 17 |
| 30 | 421 |
| 31 | 1 |
| 32 | 10 |
| 33 | 19 |
| 34 | 207 |
| 35 | 229 |
| 36 | 30 |
| 37 | 116 |
| 38 | 7 |
| 39 | 62 |
| 40 | 4 |
| 41 | 74 |
| 42 | 143 |
| 43 | 155 |
| 44 | 13 |
| 45 | 20 |
| 46 | 30 |
| 47 | 97 |
| 48 | 6 |
| 49 | 2 |
| 50 | 12 |
| 51 | 26 |
| 52 | 30 |
| 53 | 30 |
| 54 | 167 |
| 55 | 28 |
| 56 | 56 |
| 57 | 94 |
| 58 | 45 |
| 59 | 72 |
| 60 | 508 |
| 61 | 11 |
| 62 | 17 |
| 63 | 114 |
| 64 | 2 |
| 65 | 2 |
| 66 | 27 |
| 67 | 8 |
| 68 | 3 |
| 69 | 2 |

Example B

MDR1 LLC-PK1 and BCRP MDCKII Permeability Assay

Both LLC-PK1 and MDR1 transfected LLC-PK1 cells were cultured and plated according to manufacturer's recommendations with the exception that the passage media contained only 2% fetal bovine serum to extend passage time out to seven days.

BCRP transfected MDCKII canine P-gp knockout cell line was cultured and plated according to manufacturer's recommendations.

Both positive and negative controls were used to assess functionality of P-gp or BCRP efflux in the assays. Stock solutions for assay controls and the test article were prepared in DMSO for final test concentrations of 10 and 1 µM, respectively. Final organic concentration in the assay was 1%. All dosing solutions contained 10 µM lucifer yellow to monitor LLC-PK1 or MDCKII cell monolayer integrity.

For the apical to basolateral determination (A to B), 75 µL of the test article in transport buffer were added to the apical side of the individual transwells and 250 µL of basolateral media, without compound or lucifer yellow, were added to each well. For the basolateral to apical determination (B to A), 250 µL of test article in transport buffer were added to each well and 75 µL transport buffer, without compound or lucifer yellow, were added to each transwell. All tests were performed in triplicate, and each compound was tested for both apical to basolateral and basolateral to apical transport. The plates were incubated for 2 hours on a Lab-Line Instruments Titer Orbital Shaker (VWR, West Chester, PA) at 50 rpm and 37° C. with 5% $CO_2$. All culture plates were removed from the incubator and 50 µL of media were removed from the apical and basolateral portion of each well and added to 150 µL of 1 µM labetalol in 2:1 acetonitrile (acetonitrile): $H_2O$, v/v.

The plates were read using a Molecular Devices (Sunnyvale, CA) Gemini Fluorometer to evaluate the lucifer yellow concentrations at excitation/emission wavelengths of 425/535 nm. These values were accepted when found to be below 2% for apical to basolateral and 5% basolateral to apical flux across the MDR1-transfected LLC-PK1 or BCRP-transfected MDCKII cell monolayers. The plates were sealed and the contents of each well analyzed by LC-MS/MS. The compound concentrations were determined from the ratio of the peak areas of the compound to the internal standard (labetalol) in comparison to the dosing solution.

LC-MS Analysis

The LC-MS/MS system was comprised of an HTS-PAL autosampler (Leap Technologies, Carrboro, NC), an HP1200 HPLC (Agilent, Palo Alto, CA), and a MDS Sciex 4000 Q Trap system (Applied Biosystems, Foster City, CA). Chromatographic separation of the analyte and internal standard was achieved at room temperature using a C18 column (Kinetics, 50×300 mm, 2.6 µm particle size, Phenomenex, Torrance, CA) in conjunction with gradient conditions using mobile phases A (water containing 1% isopropyl alcohol and 0.1% formic acid) and B (0.1% formic acid in acetonitrile). The total run time, including re-equilibration, for a single injection was 1.2 minutes. Mass spectrometric detection of the analytes was accomplished using the ion spray positive mode. Analyte responses were measured by multiple reaction monitoring (MRM) of transitions unique to each compound (the protonated precursor ion and selected product ions for each test article and m/z 329 to m/z 162 for labetalol, the internal standard).

The permeability coefficient ($P_{app}$) is calculated from the following equation:

$$P_{app}=[((C_d*V*(1\times10^6))/(t*0.12\ cm^2*C)]$$

where $C_d$, V, t and $C_0$ are the detected concentration (µM), the volume on the dosing side (mL), the incubation time (s) and the initial dosing concentration (µM), respectively. The calculations for $P_{app}$ were made for each replicate and then averaged. Permeability coefficients for compounds of Formula I are provided in Table B1. In this assay, a compound is defined has having high permeability if the permeability is greater than $8\times10^{-6}$ cm/sec, a compound is defined has having medium permeability if the permeability is from $2\times10^{-6}$ cm/sec to $8\times10^{-6}$ cm/sec, and a compound is defined has having low permeability if the permeability is less than $2\times10^{-6}$ cm/sec.

An efflux ratio is calculated from the mean apical to basolateral (A–B) $P_{app}$ data and basolateral to apical (B–A) $P_{app}$ data:

$$\text{Efflux ratio}=P_{app}(B-A)/P_{app}(A-B)$$

TABLE B1

| Ex. No. | Permeability (*10$^{-6}$ cm/s) |
|---|---|
| 1 | 27.2 |
| 3 | 46.2 |
| 4 | 26.1 |
| 5 | 27.8 |
| 6 | 32.1 |
| 7 | 34.5 |
| 8 | 34.2 |
| 9 | 27.1 |
| 10 | 26.5 |
| 14 | 31.1 |
| 15 | 27.5 |
| 19 | 25.9 |
| 21 | 28.8 |
| 22 | 24.6 |
| 23 | 30.4 |
| 25 | 26.4 |
| 27 | 25.1 |
| 28 | 26.1 |
| 29 | 32.8 |
| 31 | 24.8 |
| 32 | 24.8 |
| 33 | 24.7 |
| 36 | 31.1 |
| 37 | 28.6 |
| 38 | 24.6 |
| 39 | 32.3 |
| 40 | 28.4 |
| 42 | 29.4 |
| 44 | 33.0 |
| 45 | 31.8 |
| 46 | 37.0 |
| 47 | 31.5 |
| 48 | 16.2 |
| 49 | 39.3 |
| 50 | 36.7 |
| 51 | 41.2 |
| 52 | 36.8 |
| 53 | 36.9 |
| 55 | 37.4 |
| 56 | 32.1 |
| 57 | 31.8 |
| 58 | N/A |
| 59 | N/A |
| 60 | N/A |
| 61 | 26.9 |
| 62 | 26.1 |
| 63 | N/A |
| 64 | N/A |
| 65 | 12.5 |
| 66 | 24.9 |
| 67 | 28.3 |
| 68 | 18.7 |
| 69 | 19.6 |

N/A: Not available

An efflux ratio is calculated from the mean apical to basolateral (A–B) $P_{app}$ data and basolateral to apical (B–A) $P_{app}$ data:

Efflux ratio = $P_{app}(B-A)/P_{app}(A-B)$

Table B2 provides efflux ratios for compounds of Formula I when tested in this assay.

TABLE B2

| Ex. No. | LLC-PK1 MDR1 | MDCKII-hBCRP knock-in, canine pg-P KO |
|---|---|---|
| 1 | 1.4 | 1.1 |
| 3 | 1.0 | 0.9 |
| 4 | 1.3 | 1.1 |
| 5 | 1.6 | 1.0 |
| 6 | 3.4 | 5.5 |
| 7 | 5.4 | 9.6 |
| 8 | 7.1 | 3.4 |
| 9 | 7.7 | 3.2 |
| 10 | 6.7 | 6.3 |
| 14 | 2.7 | 3.4 |
| 15 | 3.7 | 2.2 |
| 18 | 2.3 | 2.0 |
| 19 | 3.3 | 1.5 |
| 21 | 4.2 | 3.0 |
| 22 | 6.2 | 9.0 |
| 23 | 3.2 | 2.0 |
| 25 | 5.7 | 14.1 |
| 27 | 0.9 | 1.4 |
| 28 | 1.1 | 1.1 |
| 29 | 1.5 | 1.1 |
| 31 | 5.3 | 4.4 |
| 32 | 6.5 | 5.2 |
| 33 | 4.0 | 8.3 |
| 36 | 2.9 | 3.5 |
| 37 | 2.7 | 3.3 |
| 38 | 4.5 | 2.9 |
| 39 | 3.9 | 3.2 |
| 40 | 3.6 | 1.9 |
| 42 | 2.8 | 3.3 |
| 44 | 1.1 | 2.7 |
| 45 | 2.2 | 1.3 |
| 46 | 1.1 | 1.2 |
| 47 | 1.3 | N/A |
| 48 | 1.4 | 1.0 |
| 49 | 1.4 | 1.0 |
| 50 | 1.2 | 1.3 |
| 51 | 1.2 | 1.2 |
| 52 | 1.3 | 1.2 |
| 53 | 1.1 | 1.8 |
| 55 | 1.4 | 1.4 |
| 56 | 0.8 | 1.1 |
| 57 | 0.9 | 1.2 |
| 58 | N/A | N/A |
| 59 | N/A | N/A |
| 60 | N/A | N/A |
| 61 | 3 | N/A |
| 62 | 5 | N/A |
| 63 | N/A | N/A |
| 64 | N/A | 1.5 |
| 65 | N/A | 0.8 |
| 66 | N/A | 1 |
| 67 | N/A | 1.1 |
| 68 | N/A | 2.5 |
| 69 | N/A | 2.3 |

N/A: Not available

Example C

PK (Free Brain-to-Free Plasma Ratio) (Mouse)

The ability of representative compounds to penetrate the BBB in mice was determined by evaluating the unbound brain-to-unbound plasma (also referred to as free brain-to-free plasma) concentration ratio in male CD-1 mice.

Brain compound levels were generated from oral mouse PK dosing with typical sampling times of 2, 4, 8, 12 and 24 hours post oral gavage dosing at 10 mg/kg. Brain samples were stored at −20±5° C. prior to analysis. Concentrations of test compound in mouse brain homogenate were determined by liquid chromatography tandem mass spectrometry (LC-MS/MS) following protein precipitation with acetonitrile. A 12-point calibration curve, ranging from 0.5 to 10,000 ng/mL, was prepared in duplicate. A solution of 400 µg/mL of test compound in dimethyl sulfoxide (DMSO) was serially diluted (3-fold) in 100% DMSO, and then 2.5 µL of each standard solution was added to 100 µL of naïve male CD-1 mice brain homogenate. To mimic the extraction in the standard curve, 2.5 μL of DMSO was added to all test samples. Both calibration and test brain homogenate samples were spiked with 10 μL of an IS (1 μg/mL of a structural analog). Brain homogenate was generated by adding 0.75 mL of 4:1 water:MeOH to each brain sample followed by homogenization for 1 minute with bead beater tubes a 6 m/s using an MP Fast Prep-24®. Proteins were precipitated from 100 μL of brain homogenate sample by the addition of 300 μL of acetonitrile. Samples were vortex-mixed for 5 minutes and spun in an Allegra X-12R centrifuge (Beckman Coulter, Fullerton, CA; SX4750A rotor) for 15 min at about 1,500×g at 4° C. A 100 μL aliquot of each supernatant was transferred via a 550 μL Personal Pipettor (Apricot Designs, Monrovia, CA) to 96-well plates and diluted 1:1 with HPLC grade water. The resulting plates were sealed with aluminum for LC-MS/MS analysis.

Brain-to-plasma ratios were calculated using the concentration of compound measured in the brain divided by the concentration of compound measured in the plasma. Brain-to-plasma ratios were always generated from a single animal and time point. Free brain-to-free plasma ratios were calculated by multiplying the brain-to-plasma ratio by the in vitro brain homogenate free fraction divided by the in vitro plasma free fraction using the following equation: (B/P)* $(B_{fu}/P_{fu})$.

Table C provides free brain-to-free plasma ratios of the representative compounds of Examples 6, 7, 8, 14, 22, 36 and 46 disclosed herein.

TABLE C

| Ex, # | B/P ratio (free) |
|---|---|
| 6 | 0.88-1.26 |
| 7 | 0.62-1.06 |
| 8 | 1.01-16.1 |
| 14 | 0.57-1.58 |
| 22 | 0.33-2.92 |
| 36 | 0.83-2.09 |
| 46 | 3.29-6.75 |

SYNTHETIC EXAMPLES

Intermediate 1

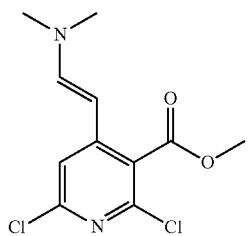 [SMILES: COC(=O)c1c(/C=C/N(C)C)cc(Cl)nc1Cl]

Methyl (E)-2,6-dichloro-4-(2-(dimethylamino)vinyl) nicotinate

Step 1. Preparation of methyl 2,6-dichloro-4-methylnicotinate. To a solution of 2,6-dichloro-4-methylnicotinic acid (1.0 g, 4.9 mmol) in 1:1 MeOH:dioxane (10 mL) at 0° C. was added (trimethylsilyl)diazomethane (3.3 mL, 2M in hexanes, 6.6 mmol). The mixture was removed from the ice bath and stirred for 10 minutes, then concentrated to half volume and partitioned between water (20 mL) and EtOAc (20 mL). The aqueous layer was extracted with EtOAc (2×20 mL) and the combined organic phases were washed with brine (10 mL), dried over $Na_2SO_4$, filtered and carefully concentrated. The residue was purified by column chromatography eluting with 0-15% EtOAc/petroleum ether to afford methyl 2,6-dichloro-4-methylnicotinate (0.81 g, 76%). $^1$H NMR (400 MHz, $CDCl_3$) δ 7.2 (s, 1H), 4.0 (s, 3H), 2.3 (s, 3H) ppm.

Step 2. Preparation of methyl (E)-2,6-dichloro-4-(2-(dimethylamino)vinyl)nicotinate. To a solution of methyl 2,6-dichloro-4-methylnicotinate (810 mg, 3.68 mmol) in DMF (5 mL) was added N,N-dimethylformamide dimethylacetal (978 mL, 7.36 mmol) and the mixture was stirred at 100° C. for 16 hours. The cooled mixture was treated with water (40 mL), stirred for 10 minutes and then the solids were collected by filtration, washed with water and dried in vacuo to afford methyl (E)-2,6-dichloro-4-(2-(dimethylamino)vinyl) nicotinate (764 mg, 75%). $^1$H NMR (400 MHz, $CDCl_3$) δ 7.3 (s, 1H), 7.1 (d, 1H), 4.8 (d, 1H), 3.1 (s, 3H), 2.9 (s, 6H) ppm.

Intermediate 2

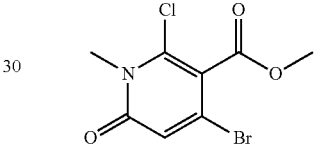

Methyl 4-bromo-2-chloro-1-methyl-6-oxo-1,6-dihydropyridine-3-carboxylate

Step 1. Preparation of 4-bromo-2,6-dichloronicotinic acid. A solution of 4-bromo-2,6-dichloropyridine (100 g, 440.7 mmol) in THF (1000 mL) was cooled to −78° C. LDA (2 M in THF, 242.4 mL, 484.8 mmol) was added dropwise at −78° C. and stirring continued for 1 hour at −78° C. Solid $CO_2$ (155.1 g, 3.53 mol) was added portion-wise to the reaction and stirring continued for 2 hours at −78° C. The reaction was quenched by adding 1M $Na_2CO_3$ (1600 mL) followed by water (500 mL) and stirred for 10 minutes. The aqueous layer was extracted with EtOAc (300 mL). The pH value of the aqueous was adjusted with 2N HCl to afford a solution with pH 2. The aqueous was then extracted with EtOAc (3×300 mL). The combined organic layers were dried over $Na_2SO_4$, filtered and concentrated to afford 4-bromo-2,6-dichloronicotinic acid (540 g, 75%). $^1$H NMR (400 MHz, DMSO-$d_6$) δ 15.51-12.87 (m, 1H), 8.13 (s, 1H) ppm.

Step 2. Preparation of 4-bromo-2-chloro-6-oxo-1,6-dihydropyridine-3-carboxylic acid. A solution of NaOH (4 M, 1.62 L, 6.46 mol) was heated to 110° C., and 4-bromo-2,6-dichloronicotinic acid (70 g, 258.4 mmol) was added in one portion. The mixture was stirred for 8 hours then cooled to 0° C. The reaction was adjusted pH to 1 with HCl (6 M) and stirred for 30 minutes. Solids were collected by filtration and dried in vacuo to afford 4-bromo-2-chloro-6-oxo-1,6-dihydropyridine-3-carboxylic acid (assumed 100%).

Step 3. Preparation of methyl 4-bromo-2-chloro-1-methyl-6-oxo-1,6-dihydropyridine-3-carboxylate. To a mixture of 4-bromo-2-chloro-6-oxo-1,6-dihydropyridine-3-carboxylic acid (100 g, 396 mmol) in DMF (800 mL) was added methyl iodide (168.6 g, 1.19 mol, 73.98 mL) and K₂CO₃ (164.2 g, 1.19 mol) in one portion. The mixture was stirred at 25° C. for 3 hours then poured into saturated NH₄Cl (1800 mL), and the aqueous phase was extracted with EtOAc (2×500 mL). The combined organic phases were washed with brine (400 mL), dried over Na₂SO₄, filtered and concentrated. The combined residues (5 batches) were purified by column chromatography eluting with 2-100% EtOAc/petroleum ether to afford methyl 4-bromo-2-chloro-1-methyl-6-oxo-1,6-dihydropyridine-3-carboxylate (from 5 batches, 141.83 g, 24.7%). ¹H NMR (400 MHz, CDCl₃) δ 6.86 (s, 1H), 3.94 (s, 3H), 3.69-3.66 (m, 3H); MS (apci, m/z)=280.0, 282.0 (M+H).

Intermediate 3

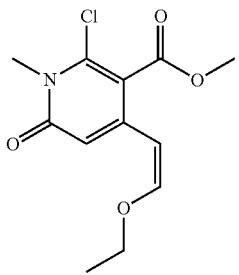 [SMILES: CCO/C=C\c1cc(=O)n(C)c(Cl)c1C(=O)OC]

Methyl (Z)-2-chloro-4-(2-ethoxyvinyl)-1-methyl-6-oxo-1,6-dihydropyridine-3-carboxylate Methyl 4-bromo-2-chloro-1-methyl-6-oxo-1,6-dihydropyridine-3-carboxylate (20.0 g, 71.3 mmol, methanesulfonato(2-dicyclohexylphosphino-2',6'-di-i-propoxy-1,1'-biphenyl)(2-amino-1,1'-biphenyl-2-yl)palladium(II) (5.96 g, 7.13 mmol) and (Z)-2-(2-ethoxyvinyl)-4,4,5,5-tetramethyl-1,3,2-dioxaborolane (14.8 g, 74.9 mmol) were suspended in 1,4-dioxane (700 mL) and K₂CO₃ (53.5 mL, 107 mmol) (2 N aqueous) was added. The mixture was stirred at 60° C. for 6 hours then at ambient temperature for 12 hours under argon atmosphere. The reaction was partitioned between water (1500 mL) and EtOAc (500 mL). The aqueous layer was extracted with EtOAc (2×400 mL) and the combined organic layers were washed with brine (500 mL), dried over Na₂SO₄, filtered and concentrated. The residue was purified by column chromatography eluting with 0-40-60% EtOAc/heptanes to afford methyl (Z)-2-chloro-4-(2-ethoxyvinyl)-1-methyl-6-oxo-1,6-dihydropyridine-3-carboxylate (13.3 g, 68%). ¹H NMR (400 MHz, CDCl₃) δ 7.23 (s, 1H), 6.45 (d, 1H), 4.86 (d, 1H), 4.40 (q, 2H), 3.89 (s, 3H), 3.67 (s, 3H), 1.35 (t, 3H); MS (apci, m/z)=272.0 (M+H).

Intermediate 4

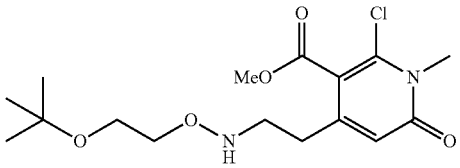 [SMILES: COC(=O)c1c(CCNOCCOC(C)(C)C)cc(=O)n(C)c1Cl]

Methyl 4-(2-((2-(tert-butoxy)ethoxy)amino)ethyl)-2-chloro-1-methyl-6 oxo-1,6-dihydropyridine-3-carboxylate Step 1. Preparation of methyl (E/Z)-4-(2-((2-(tert-butoxy)ethoxy)imino)ethyl)-2-chloro-1-methyl-6-oxo-1,6-dihydropyridine-3-carboxylate. Methyl (Z)-2-chloro-4-(2-ethoxyvinyl)-1-methyl-6-oxo-1,6-dihydropyridine-3-carboxylate (0.95 g, 3.50 mmol) and O-(2-(tert-butoxy)ethyl)hydroxylamine hydrochloride (593 mg, 3.50 mmol) were combined in 1,4-dioxane (10 mL). Et₃N (487 mL, 3.50 mmol) and HCl (1.75 mL, 6.99 mmol) (4N/dioxane) were added. The suspension was heated to 60° C. for 1 hour then cooled and filtered. The filtrate was concentrated to afford methyl (E/Z)-4-(2-((2-(tert-butoxy)ethoxy)imino)ethyl)-2-chloro-1-methyl-6-oxo-1,6-dihydropyridine-3-carboxylate (assumed 100%) as a 1:1 mixture of isomers. MS (apci, m/z)=359.1 (M+H).

Step 2. Preparation of Methyl 4-(2-((2-(tert-butoxy)ethoxy)amino)ethyl)-2-chloro-1-methyl-6-oxo-1,6-dihydropyridine-3-carboxylate. To a solution of methyl (E/Z)-4-(2-((2-(tert-butoxy)ethoxy)imino)ethyl)-2-chloro-1-methyl-6-oxo-1,6-dihydropyridine-3-carboxylate (1.25 g, 3.48 mmol) in IPA (20 mL) was added sodium cyanoborohydride (1.09 g, 17.4 mmol) followed by acetic acid (1.0 mL, 17.4 mmol). The mixture was stirred at ambient temperature for 16 hours then partitioned between saturated NaHCO₃ (50 mL) and EtOAc (50 mL). The aqueous layer was extracted with EtOAc (2×30 mL) and the combined organic phases were washed with brine (30 mL) then dried over Na₂SO₄, filtered and concentrated. The residue was purified by column chromatography eluting with 0-80% EtOAc/DCM to afford methyl 4-(2-((2-(tert-butoxy)ethoxy)amino)ethyl)-2-chloro-1-methyl-6-oxo-1,6-dihydropyridine-3-carboxylate (0.66 g, 53%). ¹H NMR (400 MHz, CDCl₃) δ 6.43 (s, 1H), 3.90 (s, 3H), 3.78 (t, 2H), 3.68 (s, 3H), 3.50 (t, 2H), 3.10 (t, 2H), 2.71 (t, 2H), 1.20 (s, 9H) ppm; MS (apci, m/z)=361.1, 363.1 (M+H).

Intermediate 5

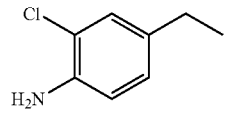

2-Chloro-4-ethylaniline

Step 1. Preparation of N-(4-ethylphenyl)acetamide. 4-Ethylaniline (513 μL, 4.13 mmol) was dissolved in DCM (10.3 mL). After adding triethylamine (690 μL, 4.95 mmol) and cooling to 0° C., acetic anhydride (467 μL, 4.95 mmol) was added dropwise. After 30 minutes, the reaction was quenched by addition of saturated NaHCO₃ (50 mL). The organic layers were separated and the aqueous layer was extracted with DCM (2×25 mL). The combined organic layers were dried over Na₂SO₄, filtered, and concentrated. The residue was triturated with hexanes and solids collected by filtration to afford N-(4-ethylphenyl)acetamide (600 mg, 89%). ¹H NMR (400 MHz, CDCl₃) δ 7.40-7.38 (d, 2H), 7.16-7.14 (d, 2H), 7.07 (br s, 1H), 2.64-2.58 (q, 2H), 2.16 (s, 3H), 1.23-1.20 (t, 3H) ppm.

Step 2. Preparation of N-(2-chloro-4-ethylphenyl)acetamide. N-(4-ethylphenyl)acetamide (50 mg, 0.31 mmol) was dissolved in DMF (613 μL). After adding N-chlorosuccinimide (65 mg, 0.49 mmol), the solution was heated to 70° C. for 6 hours, then allowed to cool to ambient temperature over 16 hours. The reaction mixture was poured into 2N HCl (4 mL) and stirred for 15 minutes. The mixture was extracted with EtOAc (10 mL). The organic layers were washed with water (3×10 mL), dried over Na$_2$SO$_4$, filtered, and concentrated. The residue was purified by column chromatography, eluting with 0-25% EtOAc/hexanes, to afford N-(2-chloro-4-ethylphenyl)acetamide (36 mg, 59%). $^1$H NMR (400 MHz, CDCl$_3$) δ 8.23-8.21 (d, 1H), 7.51 (br s, 1H), 7.20-7.19 (d, 1H), 7.11-7.08 (dd, 1H), 2.63-2.57 (q, 2H), 2.23 (s, 3H), 1.23-1.20 (t, 3H) ppm.

Step 3. Preparation of 2-chloro-4-ethylaniline. N-(2-chloro-4-ethylphenyl)acetamide (36 mg, 0.18 mmol) was dissolved in EtOH (0.5 mL) and 12N HCl (0.5 mL, 6.0 mmol) was added. The mixture was stirred for 2 hours at 120° C. The reaction mixture was cooled to ambient temperature, brought to pH 10 by addition of 6N NaOH, then extracted with MTBE (3×25 mL). The combined organic layers were dried over Na$_2$SO$_4$, filtered, and concentrated to afford 2-chloro-4-ethylaniline (26 mg, 92%). $^1$H NMR (400 MHz, CDCl$_3$) δ 7.09-7.08 (d, 1H), 6.91-6.88 (dd, 1H), 6.71-6.69 (d, 1H), 2.55-2.49 (q, 2H), 1.20-1.16 (t, 3H) ppm. MS (apci, m/z)=156.1 (M+H).

Intermediate 6

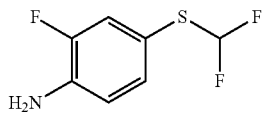

4-((Difluoromethyl)thio)-2-fluoroaniline

LiBF$_4$ (196 mg, 2.10 mmol) and UH (17.5 mg, 2.10 mmol) were combined in DMF (8.8 mL, 1.75 mmol). 4-Amino-3-fluorobenzenethiol (250 mg, 1.75 mmol) was added, and the mixture was stirred for 5 minutes at ambient temperature. (Trifluoromethyl)trimethylsilane (0.644 mL, 4.37 mmol) was added quickly, then the solution stirred for 10 minutes at the same temperature. TBAF (6 mL, 1N/THF, 6.00 mmol) was added quickly, then the solution was stirred for 10 minutes at the same temperature. The reaction mixture was quenched with water (50 mL). The mixture was extracted with EtOAc (2×25 mL) and the combined organic layers were washed with water (3×50 mL) and brine (50 mL), then dried over Na$_2$SO$_4$, filtered and concentrated. The residue was purified by column chromatography, eluting with 0-15% EtOAc/hexanes, to afford 4-((difluoromethyl)thio)-2-fluoroaniline (56 mg, 17%). $^1$H NMR (400 MHz, CDCl$_3$) δ 7.25-7.22 (dd, 1H), 7.19-7.16 (ddd, 1H), 6.86-6.58 (t, 1H), 6.77-6.73 (dd, 1H), 3.95 (br s, 1H) ppm.

Intermediate 7

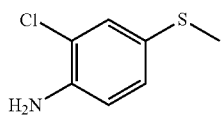

2-Chloro-4-(methylthio)aniline

2-Chloro-4-iodoaniline (250 mg, 0.986 mmol), NiBr$_2$ (22 mg, 0.099 mmol), Zn powder (129 mg, 1.97 mmol) and 2,2'-bipyridine (15 mg, 0.099 mmol) were dissolved in THF (1.6 mL) under Ar atmosphere. 1,2-Dimethyldisulfane (44 μL, 0.493 mmol) was added and the mixture was sealed and heated to 65° C. for 16 hours. The reaction mixture was diluted with EtOAc (50 mL) and washed with concentrated NH$_4$OH (50 mL) followed by 10% citric acid solution (50 mL). The combined organic layers were dried over Na$_2$SO$_4$, filtered, and concentrated. The residue was purified by column chromatography, eluting with 0-15% EtOAc/hexanes, to afford 2-chloro-4-(methylthio)aniline (116 mg, 68%). $^1$H NMR (400 MHz, CDCl$_3$) δ 7.27-7.26 (m, 1H), 7.09-7.06 (dd, 1H), 6.71-6.69 (d, 1H), 4.02 (br s, 2H), 2.41 (s, 3H) ppm. MS (apci, m/z)=174.0 (M+H).

Intermediate 8

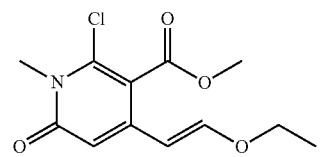 [SMILES: CCO/C=C/c1cc(=O)n(C)c(Cl)c1C(=O)OC]

Methyl (E)-2-chloro-4-(2-ethoxyvinyl)-1-methyl-6-oxo-1,6-dihydropyridine-3-carboxylate Methyl 4-bromo-2-chloro-1-methyl-6-oxo-1,6-dihydropyridine-3-carboxylate (1.0 g, 3.565 mmol), Methanesulfonato(2-dicyclohexylphosphino-2',6'-di-i-propoxy-1,1'-biphenyl)(2-amino-1,1'-biphenyl-2-yl)palladium(II) (0.2982 g, 0.3565 mmol), and (E)-2-(2-ethoxyvinyl)-4,4,5,5-tetramethyl-1,3,2-dioxaborolane (0.7414 g, 3.743 mmol) were suspended in 1,4-dioxane (35.65 mL) and potassium carbonate (2.674 mL, 2N aqueous, 5.35 mmol) was added. After degassing with argon, the mixture was stirred at 60° C. for 4 hours. The cooled reaction was partitioned between water (150 mL) and EtOAc (50 mL). The aqueous layer was washed with EtOAc (2×40 mL). The combined organic layers were washed with brine (150 mL), dried over sodium sulfate, filtered and concentrated. The residue was purified by column chromatography eluting with 0-40% EtOAc/heptane to afford methyl (E)-2-chloro-4-(2-ethoxyvinyl)-1-methyl-6-oxo-1,6-dihydropyridine-3-carboxylate (379 mg, 39%). $^1$H NMR (400 MHz, CDCl$_3$) δ 7.27 (s, 1H), 7.03 (d, 1H), 6.43 (s, 1H), 5.53 (d, 1H), 3.95-3.83 (m, 5H), 3.67 (s, 3H), 1.34 (t, 2H) ppm. MS (apci, m/z)=272.1 (M+H).

Example 1

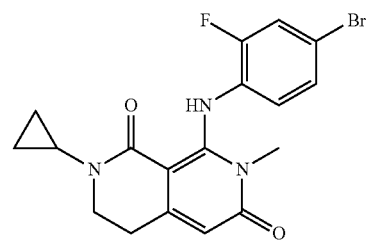 [SMILES: Cn1c(Nc2ccc(Br)cc2F)c2c(cc1=O)CCN(C1CC1)C2=O]

8-(4-bromo-2-fluorophenyl)amino)-2-cyclopropyl-7-methyl-3,4-dihydro-2,7-naphthyridine-1,6(2H,7H)-dione Step 1. Preparation of methyl 2,6-dichloro-4-(2-oxoethyl) nicotinate. A suspension of methyl (E)-2,6-dichloro-4-(2-(dimethylamino)vinyl)nicotinate (0.797 g, 2.90 mmol) in Et$_2$O (30 mL) and 1N HCl (30 mL) was stirred vigorously at ambient temperature for 1 hour. The resulting solution was treated with brine (20 mL) and extracted with Et$_2$O (3×10 mL). The combined organic phases were washed with brine (10 mL), dried over MgSO$_4$, filtered and carefully concentrated to afford methyl 2,6-dichloro-4-(2-oxoethyl) nicotinate (assumed 100%) which was used immediately.

Step 2. Preparation of 8-chloro-2-cyclopropyl-6-methoxy-3,4-dihydro-2,7-naphthyridin-1(2H)-one. To a solution of methyl 2,6-dichloro-4-(2-oxoethyl)nicotinate (0.719 g, 2.90 mmol) in 1:1 IPA:MeOH (20 mL) at 0° C. was added cyclopropylamine (201 mL, 2.90 mmol). The mixture was stirred at ambient temperature for 10 minutes then sodium cyanoborohydride (546 mg, 8.70 mmol) and acetic acid (498 mL, 8.70 mmol) were added. After stirring at ambient temperature for 16 hours, the mixture was partitioned between saturated NaHCO$_3$ (50 mL) and EtOAc (20 mL) and the aqueous layer was extracted with EtOAc (2×20 mL). The combined organic phases were washed with brine (10 mL), dried over Na$_2$SO$_4$, filtered and concentrated. The residue was dissolved in methanol (10 mL), treated with 1N NaOH (3.33 mL, 3.33 mmol) and stirred at ambient temperature for 1 hour. The mixture was concentrated to half volume then partitioned between water (20 mL) and DCM (20 mL). The aqueous layer was extracted with DCM (2×10 mL) and the combined organic phases were washed with brine (10 mL), dried over Na$_2$SO$_4$, filtered and concentrated. The residue was purified by column chromatography eluting with 0-10% (20% MeOH/DCM)/DCM to afford 8-chloro-2-cyclopropyl-6-methoxy-3,4-dihydro-2,7-naphthyridin-1 (2H)-one (310 mg, 42%). $^1$H NMR (400 MHz, CDCl$_3$) δ 6.5 (s, 1H), 4.0 (s, 3H), 3.5 (t, 2H), 2.9 (m, 3H), 0.9 (m, 2H), 0.7 (m, 2H) ppm; MS (apci, m/z)=253.1, 255.1 (M+H).

Step 3. Preparation of 8-chloro-2-cyclopropyl-3,4-dihydro-2,7-naphthyridine-1,6(2H,7H)-dione. To a solution of 8-chloro-2-cyclopropyl-6-methoxy-3,4-dihydro-2,7-naphthyridin-1(2H)-one (99 mg, 0.39 mmol) in acetonitrile (2 mL) was added trimethylsilyl iodide (2.94 mL, 1.96 mmol). The mixture was stirred at ambient temperature for 48 hours then concentrated. The residue was purified by column chromatography eluting with 0-15-20% (20% MeOH/DCM)/DCM to afford 8-chloro-2-cyclopropyl-3,4-dihydro-2,7-naphthyridine-1,6(2H,7H)-dione (assume 100%) which was used immediately. MS (apci, m/z)=239.0 (M+H).

Step 4. Preparation of 8-chloro-2-cyclopropyl-7-methyl-3,4-dihydro-2,7-naphthyridine-1,6(2H,7H)-dione. To a solution of 8-chloro-2-cyclopropyl-3,4-dihydro-2,7-naphthyridine-1,6(2H,7H)-dione (93 mg, 0.39 mmol) in THF (2 mL) was added K$_2$CO$_3$ (110 mg, 0.78 mmol) followed by methyl iodide (29 mL, 0.47 mmol). The mixture was stirred at ambient temperature for 2 hours then treated with additional methyl iodide (50 mL, 0.84 mmol) and stirred for a further 16 hours. The mixture was filtered, washed with (4:1) DCM/MeOH (10 mL) and the filtrate concentrated. The residue was purified by column chromatography eluting with 0-15% (20% MeOH/DCM)/DCM to afford 8-chloro-2-cyclopropyl-7-methyl-3,4-dihydro-2,7-naphthyridine-1,6 (2H,7H)-dione (31 mg, 31%). $^1$H NMR (400 MHz, CDCl$_3$) δ 6.29 (s, 1H), 3.73 (s, 3H), 3.45 (t, 2H), 2.87-2.81 (m, 1H), 2.77 (t, 2H), 0.94-0.89 (m, 2H), 0.72-0.68 (m, 2H) ppm; MS (apci, m/z)=253.1 (M+H).

Step 5. Preparation of 8-((4-bromo-2-fluorophenyl) amino)-2-cyclopropyl-7-methyl-3,4-dihydro-2,7-naphthyridine-1,6(2H,7H)-dione. To a solution of 4-bromo-2-fluoroaniline (24 mg, 0.12 mmol) in THF (1 mL) at −78° C. under N$_2$ was added LiHMDS (1.84 mL, 1.0 M/THF, 0.184 mmol). The mixture was stirred for 45 minutes then a suspension of 8-chloro-2-cyclopropyl-7-methyl-3,4-dihydro-2,7-naphthyridine-1,6(2H,7H)-dione (31 mg, 0.13 mmol) in THF (2 mL) was added. The mixture was stirred at −78° C. for 20 minutes then quenched with saturated NH$_4$Cl (10 mL), stirred at ambient temperature for 10 minutes then extracted with EtOAc (3×10 mL). The combined organic phases were washed with brine (10 mL), dried over Na$_2$SO$_4$, filtered and concentrated. The residue was purified by column chromatography eluting with 0-80% EtOAc/hexanes to afford 8-((4-bromo-2-fluorophenyl)amino)-2-cyclopropyl-7-methyl-3,4-dihydro-2,7-naphthyridine-1,6(2H,7H)-dione (24.9 mg, 50%). $^1$H NMR (400 MHz, CDCl$_3$) δ 11.6 (s, 1H), 7.29 (dd, 1H), 7.19 (ddd, 1H), 6.71 (t, 1H), 5.99 (s, 1H), 3.50 (t, 2H), 3.20 (s, 3H), 2.77 (t, 2H), 2.74-2.70 (m, 1H), 0.93-0.87 (m, 2H), 0.72-0.67 (m, 2H) ppm; MS (apci, m/z)=406.0, 408.0 (M+H).

Example 2

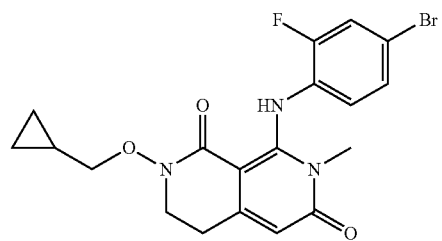 [SMILES: Cn1c(Nc2ccc(Br)cc2F)c2c(cc1=O)CCN(OCC1CC1)C2=O]

8-((4-bromo-2-fluorophenyl)amino)-2-(cyclopropylmethoxy)-7-methyl-3,4-dihydro-2,7-naphthyridine-1,6(2H,7H)-dione Prepared according to Example 1, substituting O-(cyclopropylmethyl)hydroxylamine hydrochloride in place of cyclopropylamine in step 2 to afford 8-((4-bromo-2-fluorophenyl)amino)-2-(cyclopropylmethoxy)-7-methyl-3,4-dihydro-2,7-naphthyridine-1,6(2H,7H)-dione (20 mg, 57%). $^1$H NMR (400 MHz, CDCl$_3$) δ 11.32 (s, 1H), 7.30 (dd, 1H), 7.21 (m, 1H), 6.72 (t, 1H), 6.00 (s, 1H), 3.85 (d, 2H), 3.77 (t, 2H), 3.18 (s, 3H), 2.98 (t, 2H), 1.22-1.14 (m, 1H), 0.64-0.59 (m, 2H), 0.36-0.31 (m, 2H) ppm; MS (apci, m/z)=436.0, 438.0 (M+H).

Example 3

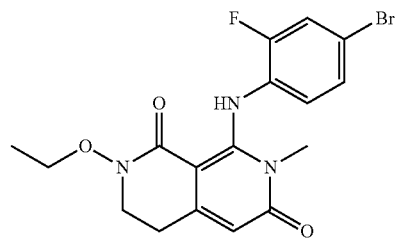 [SMILES: CCON1CCc2cc(=O)n(C)c(Nc3ccc(Br)cc3F)c2C1=O]

8-((4-bromo-2-fluorophenyl)amino)-2-ethoxy-7-methyl-3,4-dihydro-2,7-naphthyridine-1,6(2H,7H)-dione Prepared according to Example 1, substituting O-ethylhydroxylamine hydrochloride in place of cyclopropylamine in step 2 to afford 8-((4-bromo-2-fluorophenyl)amino)-2-ethoxy-7-methyl-3,4-dihydro-2,7-naphthyridine-1,6(2H,7H)-dione (22 mg, 55%). ¹H NMR (400 MHz, CDCl₃) δ 11.34 (s, 1H), 7.30 (dd, 1H), 7.21 (m, 1H), 6.72 (t, 1H), 5.99 (s, 1H), 4.08 (q, 2H), 3.73 (t, 2H), 3.19 (s, 3H), 2.99 (t, 2H), 1.32 (t, 3H) ppm; MS (apci, m/z)=410.0, 412.0 (M+H).

Example 4

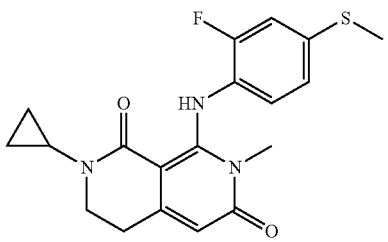 [SMILES: CSc1ccc(Nc2c3c(cc(=O)n2C)CCN(C2CC2)C3=O)c(F)c1]

2-cyclopropyl-8-((2-fluoro-4-(methylthio)phenyl)amino)-7-methyl-3,4-dihydro-2,7-naphthyridine-1,6(2H,7H)-dione Prepared according to Example 1, substituting 2-fluoro-4-(methylthio)aniline in place of 4-bromo-2-fluoroaniline in step 5 to afford 2-cyclopropyl-8-((2-fluoro-4-(methylthio)phenyl)amino)-7-methyl-3,4-dihydro-2,7-naphthyridine-1,6(2H,7H)-dione (50.4 mg, 66%). ¹H NMR (400 MHz, CDCl₃) δ 11.62 (s, 1H), 7.01 (dd, 1H), 6.95 (dd, 1H), 6.79 (t, 1H), 5.95 (s, 1H), 3.49 (t, 2H), 3.18 (s, 3H), 2.80-2.68 (m, 3H), 2.47 (s, 3H), 0.93-0.87 (m, 2H), 0.72-0.67 (m, 2H) ppm; MS (apci, m/z)=374.1 (M+H).

Example 5

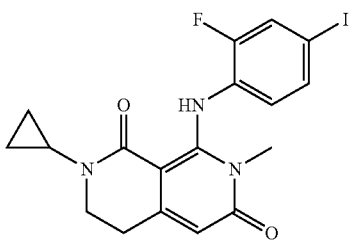 [SMILES: Cn1c(Nc2ccc(I)cc2F)c2c(cc1=O)CCN(C1CC1)C2=O]

2-cyclopropyl-8-((2-fluoro-4-iodophenyl)amino)-7-methyl-3,4-dihydro-2,7-naphthyridine-1,6(2H,7H)-dione Prepared according to Example 1 substituting 2-fluoro-4-iodoaniline in place of 4-bromo-2-fluoroaniline in step 5 to afford 2-cyclopropyl-8-((2-fluoro-4-iodophenyl)amino)-7-methyl-3,4-dihydro-2,7-naphthyridine-1,6(2H,7H)-dione (46.7 mg, 52%). ¹H NMR (400 MHz, CDCl₃) δ 11.60 (s, 1H), 7.46 (dd, 1H), 7.37 (dt, 1H), 6.55 (t, 1H), 6.00 (s, 1H), 3.50 (t, 2H), 3.21 (s, 3H), 2.81-2.69 (m, 3H), 0.93-0.87 (m, 2H), 0.72-0.67 (m, 2H) ppm; MS (apci, m/z)=454.0 (M+H).

Example 6

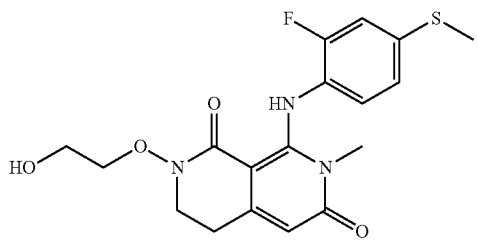 [SMILES: CSc1ccc(Nc2c3c(cc(=O)n2C)CCN(OCCO)C3=O)c(F)c1]

8-((2-fluoro-4-(methylthio)phenyl)amino)-2-(2-hydroxyethoxy)-7-methyl-3,4-dihydro-2,7-naphthyridine-1,6(2H,7H)-dione 8-((2-Fluoro-4-(methylthio)phenyl)amino)-2-(2-hydroxyethoxy)-7-methyl-3,4-dihydro-2,7-naphthyridine-1,6(2H,7H)-dione was prepared either by Method A or Method B.

Method A.

Step 1. Preparation of 4-bromo-2,6-dichloronicotinic acid. A solution of 4-bromo-2,6-dichloropyridine (100 g, 440.7 mmol) in THF (1000 mL) was cooled to −78° C. LDA (242.4 mL, 2M/THF, 484.8 mmol) was added dropwise at −78° C. and stirring continued for 1 hour at −78° C. Solid CO₂ (155.1 g, 3.53 mol) was added portion-wise to the reaction and stirring continued for 2 hours at −78° C. The reaction was quenched by adding 1M Na₂CO₃ (1600 mL) followed by water (500 mL) and stirred for 10 minutes. The aqueous layer was extracted with EtOAc (300 mL). The pH value of the aqueous was adjusted with 2N HCl to afford a solution with pH 2. The aqueous was then extracted with EtOAc (3×300 mL). The combined organic layers were dried over Na₂SO₄, filtered and concentrated to afford 4-bromo-2,6-dichloronicotinic acid (540 g, 75%). ¹H NMR (400 MHz, DMSO-d₆) δ 15.51-12.87 (m, 1H), 8.13 (s, 1H) ppm.

Step 2. Preparation of 4-bromo-2-chloro-6-oxo-1,6-dihydropyridine-3-carboxylic acid. A solution of NaOH (1.62 L, 4M, 6.46 mol) was heated to 110° C., and 4-bromo-2,6-dichloronicotinic acid (70 g, 258.4 mmol) obtained in step 1 was added in one portion. The mixture was stirred for 8 hours then cooled to 0° C. The reaction was adjusted pH to 1 with HCl (6 M) and stirred for 30 minutes. Solids were collected by filtration and dried in vacuo to afford 4-bromo-2-chloro-6-oxo-1,6-dihydropyridine-3-carboxylic acid (assumed 100%).

Step 3. Preparation of methyl 4-bromo-2-chloro-1-methyl-6-oxo-1,6-dihydropyridine-3-carboxylate. To a mixture of 4-bromo-2-chloro-6-oxo-1,6-dihydropyridine-3-carboxylic acid (100 g, 396 mmol) in DMF (800 mL) was added methyl iodide (168.6 g, 1.19 mol, 73.98 mL) and K₂CO₃ (164.2 g, 1.19 mol) in one portion. The mixture was stirred at 25° C. for 3 hours then poured into saturated NH₄Cl (1800 mL), and the aqueous phase was extracted with EtOAc (2×500 mL). The combined organic phases were washed with brine (400 mL), dried over Na₂SO₄, filtered and concentrated. The combined residues (5 batches) were purified by column chromatography eluting with 2-100% EtOAc/petroleum ether to afford methyl 4-bromo- 2-chloro-1-methyl-6-oxo-1,6-dihydropyridine-3-carboxylate (from 5 batches, 141.83 g, 24.7%). ¹H NMR (400 MHz, CDCl₃) δ 6.86 (s, 1H), 3.94 (s, 3H), 3.69-3.66 (m, 3H); MS (apci, m/z)=280.0, 282.0 (M+H).

Step 4. Preparation of methyl (Z)-2-chloro-4-(2-ethoxyvinyl)-1-methyl-6-oxo-1,6-dihydropyridine-3-carboxylate. Methyl 4-bromo-2-chloro-1-methyl-6-oxo-1,6-dihydropyridine-3-carboxylate (20.0 g, 71.3 mmol) obtained in step 3, methanesulfonato(2-dicyclohexylphosphino-2',6'-di-i-propoxy-1,1'-biphenyl)(2-amino-1,1'-biphenyl-2-yl)palladium(II) (5.96 g, 7.13 mmol) and (Z)-2-(2-ethoxyvinyl)-4,4,5,5-tetramethyl-1,3,2-dioxaborolane (14.8 g, 74.9 mmol) were suspended in 1,4-dioxane (700 mL) and K₂CO₃ (53.5 mL, 2N aq, 107 mmol) was added. The mixture was stirred at 60° C. for 6 hours then at ambient temperature for 12 hours under argon atmosphere. The reaction was partitioned between water (1500 mL) and EtOAc (500 mL). The aqueous layer was extracted with EtOAc (2×400 mL) and the combined organic layers were washed with brine (500 mL), dried over Na₂SO₄, filtered and concentrated. The residue was purified by column chromatography eluting with 0-40-60% EtOAc/heptanes to afford methyl (Z)-2-chloro-4-(2-ethoxyvinyl)-1-methyl-6-oxo-1,6-dihydropyridine-3-carboxylate (13.3 g, 68%). ¹H NMR (400 MHz, CDCl₃) δ 7.23 (s, 1H), 6.45 (d, 1H), 4.86 (d, 1H), 4.40 (q, 2H), 3.89 (s, 3H), 3.67 (s, 3H), 1.35 (t, 3H) ppm; MS (apci, m/z)=272.0 (M+H).

Step 5. Preparation of methyl (E/Z)-4-(2-((2-(tert-butoxy)ethoxy)imino)ethyl)-2-chloro-1-methyl-6-oxo-1,6-dihydropyridine-3-carboxylate. Methyl (Z)-2-chloro-4-(2-ethoxyvinyl)-1-methyl-6-oxo-1,6-dihydropyridine-3-carboxylate (0.95 g, 3.50 mmol) obtained in step 4 and O-(2-(tert-butoxy)ethyl)hydroxylamine hydrochloride (593 mg, 3.50 mmol) were combined in 1,4-dioxane (10 mL). Et₃N (487 mL, 3.50 mmol) and HCl (1.75 mL, 4N/dioxane, 6.99 mmol) were added. The suspension was heated to 60° C. for 1 hour then cooled and filtered. The filtrate was concentrated to afford methyl (E/Z)-4-(2-((2-(tert-butoxy)ethoxy)imino)ethyl)-2-chloro-1-methyl-6-oxo-1,6-dihydropyridine-3-carboxylate (assumed 100%) as a 1:1 mixture of isomers. MS (apci, m/z)=359.1 (M+H).

Step 6. Preparation of Methyl 4-(2-((2-(tert-butoxy)ethoxy)amino)ethyl)-2-chloro-1-methyl-6-oxo-1,6-dihydropyridine-3-carboxylate. To a solution of methyl (E/Z)-4-(2-((2-(tert-butoxy)ethoxy)imino)ethyl)-2-chloro-1-methyl-6-oxo-1,6-dihydropyridine-3-carboxylate (1.25 g, 3.48 mmol) in IPA (20 mL) obtained in step 5 was added sodium cyanoborohydride (1.09 g, 17.4 mmol) followed by acetic acid (1.0 mL, 17.4 mmol). The mixture was stirred at ambient temperature for 16 hours then partitioned between saturated NaHCO₃ (50 mL) and EtOAc (50 mL). The aqueous layer was extracted with EtOAc (2×30 mL) and the combined organic phases were washed with brine (30 mL) then dried over Na₂SO₄, filtered and concentrated. The residue was purified by column chromatography eluting with 0-80% EtOAc/DCM to afford methyl 4-(2-((2-(tert-butoxy)ethoxy)amino)ethyl)-2-chloro-1-methyl-6-oxo-1,6-dihydropyridine-3-carboxylate (0.66 g, 53%). ¹H NMR (400 MHz, CDCl₃) δ 6.43 (s, 1H), 3.90 (s, 3H), 3.78 (t, 2H), 3.68 (s, 3H), 3.50 (t, 2H), 3.10 (t, 2H), 2.71 (t, 2H), 1.20 (s, 9H) ppm; MS (apci, m/z)=361.1, 363.1 (M+H).

Step 7. Preparation of 2-(2-(tert-butoxy)ethoxy)-8-((2-fluoro-4-(methylthio)phenyl)amino)-7-methyl-3,4-dihydro-2,7-naphthyridine-1,6(2H,7H)-dione. 2-Fluoro-4-(methylthio)aniline (114 mg, 0.73 mmol) was dissolved in THF (5.0 mL, 0.69 mmol) and cooled to −78° C. under N₂ atmosphere. LiHMDS (1.39 mL, 1.0 m/THF, 1.39 mmol) was added dropwise, then the mixture stirred for 45 minutes. A solution of methyl 4-(2-((2-(tert-butoxy)ethoxy)amino)ethyl)-2-chloro-1-methyl-6-oxo-1,6-dihydropyridine-3-carboxylate (250 mg, 0.69 mmol) obtained in step 6 in THF (5.0 mL) was then added dropwise. After stirring for 10 minutes, additional LiHMDS (1.0 mL, 1.0 mmol) was added and stirring continued at −78° C. for 1 hour. The reaction mixture was quenched with saturated NH₄Cl (20 mL), then extracted with EtOAc (3×10 mL). The combined organic phases were dried over Na₂SO₄, filtered and concentrated. The residue was purified by column chromatography eluting with 0-15% (20% MeOH/DCM)/DCM) to afford 2-(2-(tert-butoxy)ethoxy)-8-((2-fluoro-4-(methylthio)phenyl)amino)-7-methyl-3,4-dihydro-2,7-naphthyridine-1,6(2H,7H)-dione (111 mg, 36%). ¹H NMR (400 MHz, CDCl3) δ 11.35 (s, 1H), 7.02-6.99 (dd, 1H), 6.97-6.94 (m, 1H), 6.82-6.77 (t, 1H), 5.95 (s, 1H), 4.16-4.14 (m, 2H), 3.80-3.77 (t, 2H), 3.62-3.60 (m, 2H), 3.17 (s, 3H), 2.99-2.95 (t, 2H), 2.47 (s, 3H), 1.21 (s, 9H) ppm; MS (apci, m/z)=450.2 (M+H).

Step 8. Preparation of 8-((2-fluoro-4-(methylthio)phenyl)amino)-2-(2-hydroxyethoxy)-7-methyl-3,4-dihydro-2,7-naphthyridine-1,6(2H,7H)-dione. To a solution of 2-(2-(tert-butoxy)ethoxy)-8-((2-fluoro-4-(methylthio)phenyl)amino)-7-methyl-3,4-dihydro-2,7-naphthyridine-1,6(2H,7H)-dione (111 mg, 0.247 mmol) obtained in step 7 in acetonitrile (2.0 mL) was added H₃PO₄ (2.0 mL, 38.5 mmol). The solution was heated to 60° C. for 15 minutes then cooled and quenched with saturated NaHCO₃ (20 mL). The mixture was extracted with EtOAc (3×10 mL) and the combined organic phases were dried over Na₂SO₄, filtered and concentrated. The residue was purified by column chromatography eluting with 0-20% (20% MeOH/DCM)/DCM, then by reverse phase HPLC (5-95% acetonitrile/water/0.1% TFA over 30 min). Fractions containing the clean desired product were combined and the product was converted to the free base with DCM/NaHCO₃ to afford 8-((2-fluoro-4-(methylthio)phenyl)amino)-2-(2-hydroxyethoxy)-7-methyl-3,4-dihydro-2,7-naphthyridine-1,6(2H,7H)-dione (62 mg, 64%). ¹H NMR (400 MHz, CDCl₃) δ 11.17 (s, 1H), 7.03-6.97 (m, 2H), 6.85 (t, 1H), 5.95 (s, 1H), 4.03 (t, 2H), 3.74-3.70 (m, 4H), 3.16 (s, 3H), 2.98 (t, 2H), 2.48 (s, 3H) ppm; MS (apci, m/z)=394.1 (M+H). PXRD analysis was performed as described in Example 77. The PXRD pattern, which is shown in FIG. 4, confirmed that the material obtained was amorphous. On this basis, the material was designated as amorphous 8-((2-fluoro-4-(methylthio)phenyl)amino)-2-(2-hydroxyethoxy)-7-methyl-3,4-dihydro-2,7-naphthyridine-1,6(2H,7H)-dione, Form 4.

Method B.

Step 1. Preparation of methyl 4-bromo-2-((2-fluoro-4-(methylthio)phenyl)amino)-1-methyl-6-oxo-1,6-dihydropyridine-3-carboxylate. To a solution of methyl 4-bromo-2-chloro-1-methyl-6-oxo-1,6-dihydropyridine-3-carboxylate (prepared according to any of the methods described herein; 50.0 g, 87.2%, 155 mmol) and 2-fluoro-4-(methylthio)aniline (24.4 g, 55 mmol) in THF (50 mL) at 0° C. was added potassium tert-butoxide (34.9 g, 311 mL, 1.0 molar, 311 mmol) over 40 minutes. The reaction was held at 0° C. for 50 minutes then diluted with saturated NH₄Cl (600 mL) and EtOAc (500 mL). Water was added to dissolve solids and the layers were separated. The aqueous layer was extracted with EtOAc (2×300 mL) and the combined organic phases were washed with water (500 mL) and brine (500 mL), then dried over Na₂SO₄, filtered and concentrated. The residue was suspended in MeOH (57 mL) and briefly sonicated then heated to 60° C. for 10 minutes. The mixture was allowed to cool slowly to ambient temperature, then cooled to 0° C. for 30 minutes. Solids were filtered and collected to afford methyl 4-bromo-2-((2-fluoro-4-(methylthio)phenyl)amino)-1-methyl-6-oxo-1,6-dihydropyridine-3-carboxylate (40.14 g, 64.4%). ¹H NMR CDCl₃ δ 9.03 (s, 1H), 7.04 (dd, 1H), 6.96 (m, 1H), 6.71-6.65 (m, 2H), 3.85 (s, 3H), 3.24 (s, 3H), 2.47 (s, 3H) ppm. MS (apci, m/z)=401.0, 403.0 (M+H).

Step 2. Preparation of methyl (Z)-4-(2-ethoxyvinyl)-2-((2-fluoro-4-(methylthio)phenyl)amino)-1-methyl-6-oxo-1,6-dihydropyridine-3-carboxylate. (Z)-2-(2-Ethoxyvinyl)-4,4,5,5-tetramethyl-1,3,2-dioxaborolane (80.25 g, 82.3 mL, 405.17 mmol) was added to a stirred solution of methyl 4-bromo-2-((2-fluoro-4-(methylthio)phenyl)amino)-1-methyl-6-oxo-1,6-dihydropyridine-3-carboxylate (130.06 g, 324.14 mmol) obtained according to the procedure of step 1, K₂CO₃ (67.2 g, 243.10 mL, 2M, 486.21 mmol) and methanesulfonato(2-dicyclohexylphosphino-2',6'-di-i-'propoxy-1,1'-biphenyl)'2-amino-1,1-biphenyl-2-yl)palladium(II) (6.78 g, 8.10 mmol) in 2-methyltetrahydrofuran (860 mL) at ambient temperature under argon. The reaction mixture was sparged with argon for 30 minutes. The reaction was heated to 60° C. and stirred for 13 hours, then stirred at ambient temperature for 6 hours. The reaction was diluted with water (1800 mL) and EtOAc (1100 mL), then filtered through GF/F paper. Filtrate layers were separated, and the aqueous layer was extracted with EtOAc (2×650 mL). The combined organic layers were washed with brine (1500 mL), dried over Na₂SO₄, filtered and concentrated. The residue was treated with MTBE (30 mL), concentrated and dried in vacuo. The residue was suspended in MTBE (330 mL) and stirred at 60° C. for 1 hour. The mixture was allowed to cool slowly to ambient temperature then stirred at 0° C. for 40 minutes. Solids were filtered, washed with cold MTBE (110 mL), then cold MTBE:heptane (1:1 mixture, 150 mL) and dried in vacuo to afford methyl (Z)-4-(2-ethoxyvinyl)-2-((2-fluoro-4-(methylthio)phenyl)amino)-1-methyl-6-oxo-1,6-dihydropyridine-3-carboxylate (98.54 g, 77.46%). 1H NMR CDCl₃ δ 8.65 (s, 1H), 7.04 (dd, 1H), 6.97 (s, 1H), 6.92 (m, 1H), 6.56 (t, 1H), 6.37 (d, 1H), 5.36 (d, 1H), 4.01 (q, 2H), 3.79 (s, 3H), 3.31 (s, 3H), 2.46 (s, 3H), 1.35 (t, 3H) ppm. MS (apci, m/z)=393.1 (M+H).

Step 3. Preparation of 2-(2-(tert-butoxy)ethoxy)-8-((2-fluoro-4-(methylthio)phenyl)amino)-7-methyl-3,4-dihydro-2,7-naphthyridine-1,6(2H,7H)-dione. Triethylamine (2.84 g, 3.91 mL, 28.0 mmol) was added to a stirred solution of methyl (Z)-4-(2-ethoxyvinyl)-2-((2-fluoro-4-(methylthio)phenyl)amino)-1-methyl-6-oxo-1,6-dihydropyridine-3-carboxylate (10.0 g, 25.5 mmol) obtained according to the procedure of step 2 and O-(2-(tert-butoxy)ethyl)hydroxylamine hydrochloride (4.95 g, 96%, 28.0 mmol) in 1,4-dioxane (255 mL). The reaction was placed in a bath of cold water, purged with Ar, and HCl (2.04 g, 14.0 mL, 4M/dioxanes, 56.1 mmol) was added dropwise via addition funnel. The mixture was heated at 60° C. for 1 hour, then cooled to ambient temperature using a cold water bath. Pyridine borane (4.74 g, 5.42 mL, 51.0 mmol) was slowly added and the mixture stirred for 10 minutes at ambient temperature. HCl (1.11 g, 7.64 mL, 4M/dioxane, 30.6 mmol) was added over 5 minutes, and stirring continued for 20 minutes. The reaction was heated at 60° C. for 21 hours, then cooled to ambient temperature. The cooled mixture was neutralized to about pH 7 by slow addition of saturated NaHCO₃ (140 mL), then diluted with EtOAc (400 mL) and H₂O (300 mL). The layers were separated, and the aqueous layer was extracted with EtOAc (2×150 mL). The combined organic phases were washed with brine (600 mL), dried over Na₂SO₄, filtered and concentrated. The residue was dissolved in minimal DCM and filtered through a 5 inch silica plug, eluting with 3% MeOH:DCM (1 L). The filtrate was concentrated to afford 2-(2-(tert-butoxy)ethoxy)-8-((2-fluoro-4-(methylthio)phenyl)amino)-7-methyl-3,4-dihydro-2,7-naphthyridine-1,6(2H,7H)-dione (assumed 100%) which was used without further purification. MS (apci, m/z)=450.2 (M+H).

Step 4. Preparation of 8-((2-fluoro-4-(methylthio)phenyl)amino)-2-(2-hydroxyethoxy)-7-methyl-3,4-dihydro-2,7-naphthyridine-1,6(2H,7H)-dione. To a solution of 2-(2-(tert-butoxy)ethoxy)-8-((2-fluoro-4-(methylthio)phenyl)amino)-7-methyl-3,4-dihydro-2,7-naphthyridine-1,6(2H,7H)-dione (14.18 g, 31.54 mmol) obtained according to the procedure of step 3 in acetonitrile (63.09 mL, 31.54 mmol) at ambient temperature was added phosphoric acid (36.36 g, 21.60 mL, 85%, 315.4 mmol) dropwise, over 20 minutes. The reaction was heated to 60° C. for 4 hours, then cooled slowly to ambient temperature. The reaction was poured slowly into a cold solution of potassium phosphate (66.95 g, 157.7 mL, 2M, 315.4 mmol) in an ice bath, with vigorous stirring. After stirring for 10 minutes, EtOAc (300 mL) was added and the layers were separated. The organic layer was washed with brine (300 mL), then the aqueous layer extracted with EtOAc (100 mL). The combined organic phases were dried over Na₂SO₄, filtered and concentrated. The residue was purified by column chromatography, eluting with 0-40% (20% MeOH/DCM)/MTBE to afford 8-((2-fluoro-4-(methylthio)phenyl)amino)-2-(2-hydroxyethoxy)-7-methyl-3,4-dihydro-2,7-naphthyridine-1,6(2H,7H)-dione (9.48 g, 76.4%). PXRD analysis confirmed that the material obtained is amorphous ¹H NMR CDCl₃ δ 11.19 (s, 1H), 7.06-6.93 (m, 2H), 6.91-6.76 (m, 1H), 5.95 (t, 1H), 4.44 (s, 1H), 4.21-3.87 (m, 2H), 3.84-3.54 (m, 4H), 3.16 (s, 3H), 2.98 (td, 2H), 2.48 (s, 3H). MS (apci, m/z)=394.1 (M+H).

Example 7

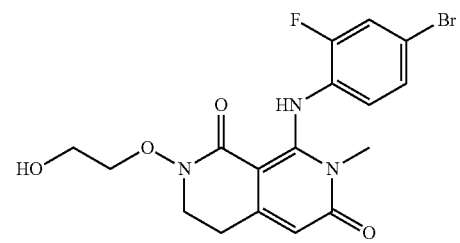 [SMILES: Cn1c(Nc2ccc(Br)cc2F)c2c(cc1=O)CCN(OCCO)C2=O]

8-((4-bromo-2-fluorophenyl)amino)-2-(2-hydroxyethoxy)-7-methyl-3,4-dihydro-2,7-naphthyridine-1,6(2H,7H)-dione Prepared according to Example 6, Method A, substituting 4-bromo-2-fluoroaniline in place of 2-fluoro-4-(methylthio)aniline in step 7 to afford 8-((4-bromo-2-fluorophenyl)amino)-2-(2-hydroxyethoxy)-7-methyl-3,4-dihydro-2,7-naphthyridine-1,6(2H,7H)-dione (15 mg, 63%). ¹H NMR (400 MHz, CDCl₃) δ 11.14 (s, 1H), 7.33 (dd, 1H), 7.24 (m, 1H), 6.78 (t, 1H), 5.99 (s, 1H), 4.38 (t, 1H), 4.05-4.01 (m, 2H), 3.75-3.70 (m, 4H), 3.17 (s, 3H), 3.00 (t, 2H) ppm; MS (apci, m/z)=426.0, 428.0 (M+H).

Example 8

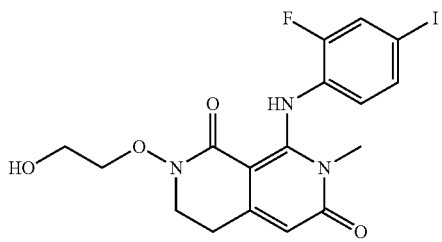 [SMILES: Cn1c(Nc2ccc(I)cc2F)c2c(cc1=O)CCN(OCCO)C2=O]

8-((2-fluoro-4-iodophenol)amino)-2-(2-hydroxy-ethoxy)-7-methyl-3,4-dihydro-2,7-naphthyridine-1,6(2H,7H)-dione Prepared according to Example 6, Method A, substituting 4-iodo-2-fluoroaniline in place of 2-fluoro-4-(methylthio)aniline in step 7 to afford 8-((2-fluoro-4-iodophenyl)amino)-2-(2-hydroxyethoxy)-7-methyl-3,4-dihydro-2,7-naphthyridine-1,6(2H,7H)-dione (12 mg, 74%). $^1$H NMR (400 MHz, CDCl$_3$) δ 11.11 (s, 1H), 7.49 (dd, 1H), 7.42 (m, 1H), 6.63 (t, 1H), 6.00 (s, 1H), 4.42-4.33 (m, 1H), 4.05-4.00 (m, 2H), 3.76-3.69 (m, 4H), 3.18 (s, 3H), 2.99 (t, 2H) ppm; MS (apci, m/z)=474.0 (M+H).

Example 9

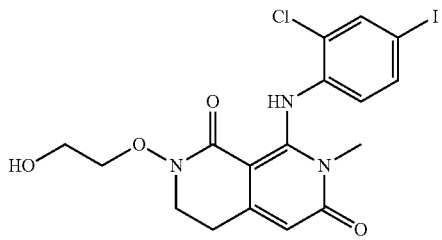

8-((2-chloro-4-iodophenyl)amino)-2-(2-hydroxy-ethoxy)-7-methyl-3,4-dihydro-2,7-naphthyridine-1,6(2H,7H)-dione Prepared according to Example 6, Method A, substituting 2-chloro-4-iodoaniline in place of 2-fluoro-4-(methylthio)aniline in step 7 to afford 8-((2-chloro-4-iodophenyl)amino)-2-(2-hydroxyethoxy)-7-methyl-3,4-dihydro-2,7-naphthyridine-1,6(2H,7H)-dione (6.4 mg, 50%). $^1$H NMR (400 MHz, CDCl$_3$) δ 11.09 (s, 1H), 7.79 (s, 1H), 7.48 (d, 1H), 6.46 (d, 1H), 6.02 (s, 1H), 4.03 (t, 2H), 3.78-3.70 (m, 4H), 3.14 (s, 3H), 3.00 (t, 2H) ppm; MS (apci, m/z)=490.0 (M+H).

Example 10

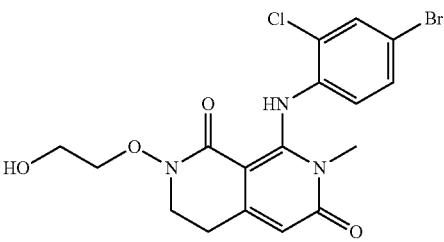

8-((4-bromo-2-chlorophenyl)amino)-2-(2-hydroxy-ethoxy)-7-methyl-3,4-dihydro-2,7-naphthyridine-1,6(2H,7H)-dione Prepared according to Example 6, Method A, substituting 4-bromo-2-chloroaniline in place of 2-fluoro-4-(methylthio)aniline in step 7 to afford 8-((4-bromo-2-chlorophenyl)amino)-2-(2-hydroxyethoxy)-7-methyl-3,4-dihydro-2,7-naphthyridine-1,6(2H,7H)-dione (7.9 mg, 52%). $^1$H NMR 11.10 (s, 1H), 7.62 (d, 1H), 7.31 (dd, 1H), 6.61 (d, 1H), 6.02 (s, 1H), 4.03 (t, 2H), 3.77-3.68 (m, 4H), 3.14 (s, 3H), 3.00 (t, 2H) ppm; MS (apci, m/z)=442.0, 444.0 (M+H).

Example 11

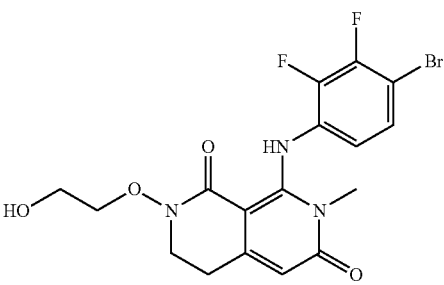 [SMILES: Cn1c(Nc2ccc(Br)c(F)c2F)c2c(cc1=O)CCN(OCCO)C2=O]

8-((4-bromo-2,3-difluorophenyl)amino)-2-(2-hydroxyethoxy)-7-methyl-3,4-dihydro-2,7-naphthyridine-1,6(2H,7H)-dione Prepared according to Example 6, Method A, substituting 4-bromo-2,3-difluoroaniline in place of 2-fluoro-4-(methylthio)aniline in step 7 to afford 8-((4-bromo-2,3-difluorophenyl)amino)-2-(2-hydroxyethoxy)-7-methyl-3,4-dihydro-2,7-naphthyridine-1,6(2H,7H)-dione (12.2 mg, 75%). $^1$H NMR 11.17 (s, 1H), 7.30-7.22 (m, 1H), 6.65 (dt, 1H), 6.04 (s, 1H), 4.32 (bs, 1H), 4.04 (t, 2H), 3.78-3.69 (m, 4H), 3.21 (s, 3H), 3.01 (t, 2H) ppm; MS (apci, m/z)=444.0 (M+H).

Example 12

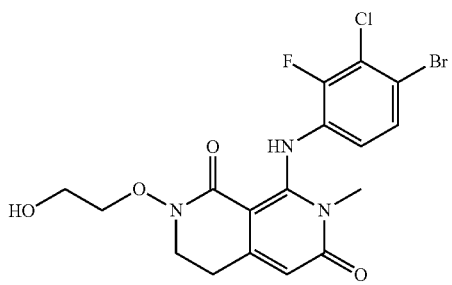 [SMILES: Cn1c(Nc2ccc(Br)c(Cl)c2F)c2c(cc1=O)CCN(OCCO)C2=O]

8-((4-bromo-3-chloro-2-fluorophenyl)amino)-2-(2-hydroxyethoxy)-7-methyl-3,4-dihydro-2,7-naphthyridine-1,6(2H,7H)-dione Prepared according to Example 6, Method A, substituting 4-bromo-3-chloro-2-fluoroaniline in place of 2-fluoro-4-(methylthio)aniline in step 7 to afford 8-((4-bromo-3-chloro-2-fluorophenyl)amino)-2-(2-hydroxyethoxy)-7-methyl-3,4-dihydro-2,7-naphthyridine-1,6(2H,7H)-dione (10.6 mg, 68%). $^1$H NMR 11.17 (s, 1H), 7.37 (d, 1H), 6.68 (t, 1H), 6.04 (s, 1H), 4.06-4.00 (m, 2H), 3.77-3.69 (m, 4H), 3.20 (s, 3H), 3.01 (t, 2H) ppm; MS (apci, m/z)=460.0, 462.0 (M+H).

Example 13

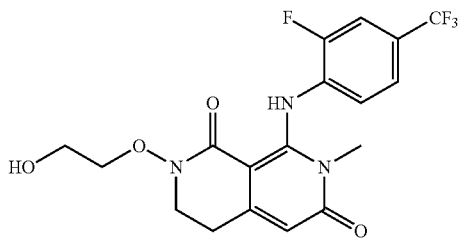 [SMILES: Cn1c(Nc2ccc(C(F)(F)F)cc2F)c2c(cc1=O)CCN(OCCO)C2=O]

8-((2-fluoro-4-(trifluoromethyl)phenyl)amino)-2-(2-hydroxyethoxy)-7-methyl-3,4-dihydro-2,7-naphthyridine-1,6(2H,7H)-dione Step 1. Preparation of 2-(2-(tert-butoxy)ethoxy)-8-((2-fluoro-4-(trifluoromethyl)phenyl)amino)-7-methyl-3,4-dihydro-2,7-naphthyridine-1,6(2H,7H)-dione. Prepared according to Example 6, Step 7 of Method A, substituting 2-fluoro-4-(trifluoromethyl)aniline in place of 2-fluoro-4-(methylthio)aniline to afford 2-(2-(tert-butoxy)ethoxy)-8-((2-fluoro-4-(trifluoromethyl)phenyl)amino)-7-methyl-3,4-dihydro-2,7-naphthyridine-1,6(2H,7H)-dione (11 mg, 22%). MS (apci, m/z)=472.2 (M+H).

Step 2. Preparation of 8-((2-fluoro-4-(trifluoromethyl)phenyl)amino)-2-(2-hydroxyethoxy)-7-methyl-3,4-dihydro-2,7-naphthyridine-1,6(2H,7H)-dione. Prepared according to Example 6, Step 8 of Method A, substituting 2-(2-(tert-butoxy)ethoxy)-8-((2-fluoro-4-(trifluoromethyl)phenyl)amino)-7-methyl-3,4-dihydro-2,7-naphthyridine-1,6(2H,7H)-dione in place of 2-(2-(tert-butoxy)ethoxy)-8-((2-fluoro-4-(methylthio)phenyl)amino)-7-methyl-3,4-dihydro-2,7-naphthyridine-1,6(2H,7H)-dione to afford 8-((2-fluoro-4-(trifluoromethyl)phenyl)amino)-2-(2-hydroxyethoxy)-7-methyl-3,4-dihydro-2,7-naphthyridine-1,6(2H,7H)-dione (6 mg, 62%) $^1$H NMR (400 MHz, CDCl$_3$) δ 11.18 (s, 1H), 7.44-7.41 (dd, 1H), 7.38-7.36 (d, 1H), 6.92-6.88 (t, 1H), 6.08 (s, 1H), 4.05-4.03 (m, 2H), 3.76-3.72 (m, 4H), 3.23 (s, 3H), 3.03-3.00 (t, 2H) ppm; MS (apci, m/z)=416.1 (M+H).

Example 14

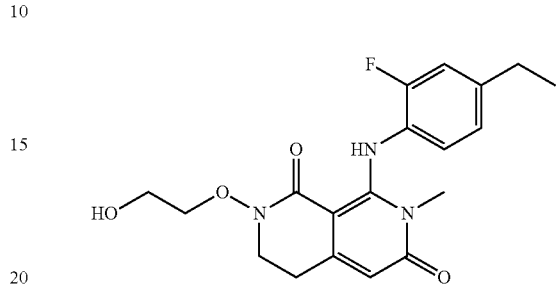

8-((4-ethyl-2-fluorophenyl)amino)-2-(2-hydroxyethoxy)-7-methyl-3,4-dihydro-2,7-naphthyridine-1,6(2H,7H)-dione Step 1. Preparation of 2-(2-(tert-butoxy)ethoxy)-8-((4-ethyl-2-fluorophenyl)amino)-7-methyl-3,4-dihydro-2,7-naphthyridine-1,6(2H,7H)-dione. Prepared according to Example 6, Step 7 of Method A, substituting 4-ethyl-2-fluoroaniline in place of 2-fluoro-4-(methylthio)aniline to afford 2-(2-(tert-butoxy)ethoxy)-8-((4-ethyl-2-fluorophenyl)amino)-7-methyl-3,4-dihydro-2,7-naphthyridine-1,6(2H,7H)-dione (19 mg, 42%). MS (apci, m/z)=432.2 (M+H).

Step 2. Preparation of 8-((4-ethyl-2-fluorophenyl)amino)-2-(2-hydroxyethoxy)-7-methyl-3,4-dihydro-2,7-naphthyridine-1,6(2H,7H)-dione. Prepared according to Example 6, Step 8 of Method A, substituting 2-(2-(tert-butoxy)ethoxy)-8-((4-ethyl-2-fluorophenyl)amino)-7-methyl-3,4-dihydro-2,7-naphthyridine-1,6(2H,7H)-dione in place of 2-(2-(tert-butoxy)ethoxy)-8-((2-fluoro-4-(methylthio)phenyl)amino)-7-methyl-3,4-dihydro-2,7-naphthyridine-1,6(2H,7H)-dione to afford 8-((4-ethyl-2-fluorophenyl)amino)-2-(2-hydroxyethoxy)-7-methyl-3,4-dihydro-2,7-naphthyrdine-1,6(2H,7H)-dione (10 mg, 61%). $^1$H NMR (400 MHz, CDCl$_3$) δ 11.17 (s, 1H), 7.00-6.91 (m, 2H), 6.87-6.83 (t, 1H), 5.93 (s, 1H), 4.03-4.01 (m, 2H), 3.74-3.70 (m, 4H), 3.15 (s, 3H), 3.00-2.97 (t, 2H), 2.66-2.61 (q, 2H), 1.25-1.21 (t, 3H) ppm; MS (apci, m/z)=376.2 (M+H).

Example 15

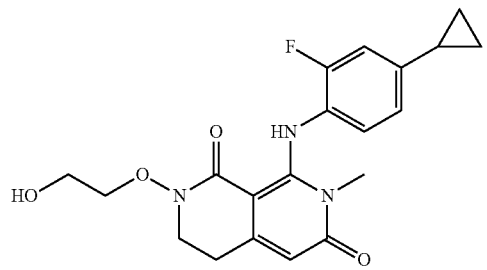 [SMILES: Cn1c(Nc2ccc(C3CC3)cc2F)c2c(cc1=O)CCN(OCCO)C2=O]

8-((4-cyclopropyl-2-fluorophenyl)amino)-2-(2-hydroxyethoxy)-7-methyl-3,4-dihydro-2,7-naphthyridine-1,6(2H,7H)-dione Step 1. Preparation of 2-(2-(tert-butoxy)ethoxy)-8-((4-cyclopropyl-2-fluorophenyl)amino)-7-methyl-3,4-dihydro-2,7-naphthyrdine-1,6(2H,7H)-dione. Prepared according to Example 6, Step 7 of Method A, substituting 4-cyclopropyl-2-fluoroaniline in place of 2-fluoro-4-(methylthio)aniline to afford 2-(2-(tert-butoxy)ethoxy)-8-((4-cyclopropyl-2-fluorophenyl)amino)-7-methyl-3,4-dihydro-2,7-naphthyridine-1,6(2H,7H)-dione (32 mg, 52%). MS (apci, m/z)=444.2 (M+H).

Step 2. Preparation of 8-((4-cyclopropyl-2-fluorophenyl)amino)-2-(2-hydroxyethoxy)-7-methyl-3,4-dihydro-2,7-naphthyridine-1,6(2H,7H)-dione. Prepared according to Example 6, Step 8 of Method A, substituting 2-(2-(tert-butoxy)ethoxy)-8-((4-cyclopropyl-2-fluorophenyl)amino)-7-methyl-3,4-dihydro-2,7-naphthyridine-1,6(2H,7H)-dione in place of 2-(2-(tert-butoxy)ethoxy)-8-((2-fluoro-4-(methylthio)phenyl)amino)-7-methyl-3,4-dihydro-2,7-naphthyridine-1,6(2H,7H)-dione to afford 8-((4-cyclopropyl-2-fluorophenyl)amino)-2-(2-hydroxyethoxy)-7-methyl-3,4-dihydro-2,7-naphthyridine-1,6(2H,7H)-dione (19 mg, 68%). $^1$H NMR (400 MHz, CDCl$_3$) δ 11.18 (s, 1H), 6.83-6.78 (m, 3H), 5.92 (s, 1H), 4.49 (br s, 1H), 4.03-4.01 (m, 2H), 3.74-3.69 (m, 4H), 3.13 (s, 3H), 3.0-2.96 (t, 2H), 1.90-1.84 (m, 1H), 1.03-0.98 (m, 2H), 0.69-0.65 (m, 2H) ppm; MS (apci, m/z)=388.1 (M+H).

Example 16

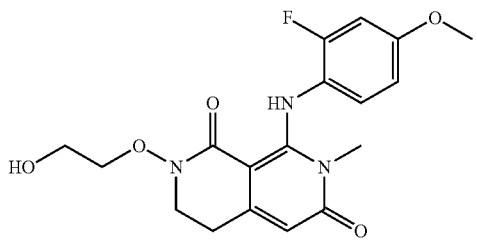 [SMILES: COc1ccc(Nc2c3c(cc(=O)n2C)CCN(OCCO)C3=O)c(F)c1]

8-((2-fluoro-4-methoxyphenyl)amino)-2-(2-hydroxyethoxy)-7-methyl-3,4-dihydro-2,7-naphthyridine-1,6(2H,7H)-dione Step 1. Preparation of 2-(2-(tert-butoxy)ethoxy)-8-((2-fluoro-4-methoxyphenyl)amino)-7-methyl-3,4-dihydro-2,7-naphthyridine-1,6(2H,7H)-dione. Prepared according to Example 6, Step 7 of Method A, substituting 2-fluoro-4-methoxyaniline in place of 2-fluoro-4-(methylthio)aniline to afford 2-(2-(tert-butoxy)ethoxy)-8-((2-fluoro-4-methoxyphenyl)amino)-7-methyl-3,4-dihydro-2,7-naphthyridine-1,6(2H,7H)-dione (8 mg, 17%). MS (apci, m/z)=434.2 (M+H).

Step 2. Preparation of 8-((2-fluoro-4-methoxyphenyl)amino)-2-(2-hydroxyethoxy)-7-methyl-3,4-dihydro-2,7-naphthyridine-1,6(2H,7H)-dione. Prepared according to Example 6, Step 8 of Method A, substituting 2-(2-(tert-butoxy)ethoxy)-8-((2-fluoro-4-methoxyphenyl)amino)-7-methyl-3,4-dihydro-2,7-naphthyridine-1,6(2H,7H)-dione in place of 2-(2-(tert-butoxy)ethoxy)-8-((2-fluoro-4-(methylthio)phenyl)amino)-7-methyl-3,4-dihydro-2,7-naphthyridine-1,6(2H,7H)-dione to afford 8-((2-fluoro-4-methoxyphenyl)amino)-2-(2-hydroxyethoxy)-7-methyl-3,4-dihydro-2,7-naphthyridine-1,6(2H,7H)-dione (3 mg, 43%). $^1$H NMR (400 MHz, CDCl$_3$) δ 11.18 (s, 1H), 6.94-6.90 (t, 1H), 6.07-6.64 (m, 2H), 5.91 (s, 1H), 4.04-4.01 (m, 2H), 3.80 (s, 3H), 3.75-3.69 (m, 4H), 3.12 (s, 3H), 3.00-2.96 (t, 2H) ppm; MS (apci, m/z)=378.1 (M+H).

Example 17

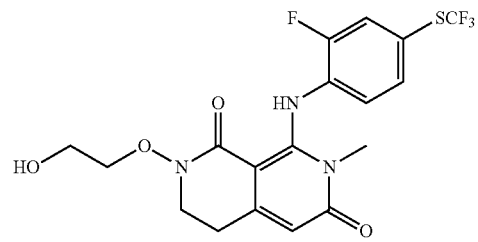

8-((2-fluoro-4-((trifluoromethyl)thio)phenyl)amino)-2-(2-hydroxyethoxy)-7-methyl-3,4-dihydro-2,7-naphthyridine-1,6(2H,7H)-dione Step 1. Preparation of 2-(2-(tert-butoxy)ethoxy)-8-((2-fluoro-4-((trifluoromethyl)thio)phenyl)amino)-7-methyl-3,4-dihydro-2,7-naphthyridine-1,6(2H,7H)-dione.

Prepared according to Example 6, Step 7 of Method A, substituting 2-fluoro-4-((trifluoromethyl)thio)aniline in place of 2-fluoro-4-(methylthio)aniline to afford 2-(2-(tert-butoxy)ethoxy)-8-((2-fluoro-4-((trifluoromethyl)thio)phenyl)amino)-7-methyl-3,4-dihydro-2,7-naphthyridine-1,6(2H,7H)-dione (17 mg, 31%). MS (apci, m/z)=504.1 (M+H).

Step 2. Preparation of 8-((2-fluoro-4-((trifluoromethyl)thio)phenyl)amino)-2-(2-hydroxyethoxy)-7-methyl-3,4-dihydro-2,7-naphthyridine-1,6(2H,7H)-dione. Prepared according to Example 6, Step 8 of Method A, substituting 2-(2-(tert-butoxy)ethoxy)-8-((2-fluoro-4-((trifluoromethyl)thio)phenyl)amino)-7-methyl-3,4-dihydro-2,7-naphthyridine-1,6(2H,7H)-dione in place of 2-(2-(tert-butoxy)ethoxy)-8-((2-fluoro-4-(methylthio)phenyl)amino)-7-methyl-3,4-dihydro-2,7-naphthyridine-1,6(2H,7H)-dione to afford 8-((2-fluoro-4-((trifluoromethyl)thio)phenyl)amino)-2-(2-hydroxyethoxy)-7-methyl-3,4-dihydro-2,7-naphthyridine-1,6(2H,7H)-dione (10 mg, 66%). $^1$H NMR (400 MHz, CDCl$_3$) δ 11.16 (s, 1H), 7.49-7.46 (dd, 1H), 7.40-7.38 (d, 1H), 6.86-6.82 (t, 1H), 6.06 (s, 1H), 4.31 (br s, 1H), 4.05-4.02 (t, 2H), 3.76-3.72 (m, 4H), 3.23 (s, 3H), 3.03-3.00 (t, 2H); MS (apci, m/z)=448.1 (M+H).

Example 18

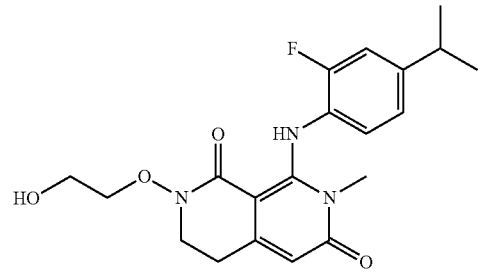 [SMILES: CC(C)c1ccc(Nc2c3c(cc(=O)n2C)CCN(OCCO)C3=O)c(F)c1]

8-((2-fluoro-4-isopropylphenyl)amino)-2-(2-hydroxyethoxy)-7-methyl-3,4-dihydro-2,7-naphthyridine-1,6(2H,7H)-dione Step 1. Preparation of 2-(2-(tert-butoxy)ethoxy)-8-((2-fluoro-4-isopropylphenyl)amino)-7-methyl-3,4-dihydro-2,7-naphthyridine-1,6(2H,7H)-dione. Prepared according to Example 6, Step 7 of Method A, substituting 2-fluoro-4-isopropylaniline in place of 2-fluoro-4-(methylthio)aniline to afford 2-(2-(tert-butoxy)ethoxy)-8-((2-fluoro-4-isopropylphenyl)amino)-7-methyl-3,4-dihydro-2,7-naphthyridine-1,6(2H,7H)-dione (17 mg, 34%). MS (apci, m/z)=446.2 (M+H).

Step 2. Preparation of 8-((2-fluoro-4-isopropylphenyl)amino)-2-(2-hydroxyethoxy)-7-methyl-3,4-dihydro-2,7-naphthyridine-1,6(2H,7H)-dione. Prepared according to Example 6, Step 8 of Method A, substituting 2-(2-(tert-butoxy)ethoxy)-8-((2-fluoro-4-isopropylphenyl)amino)-7-methyl-3,4-dihydro-2,7-naphthyridine-1,6(2H,7H)-dione in place of 2-(2-(tert-butoxy)ethoxy)-8-((2-fluoro-4-(methylthio)phenyl)amino)-7-methyl-3,4-dihydro-2,7-naphthyridine-1,6(2H,7H)-dione to afford 8-((2-fluoro-4-isopropylphenyl)amino)-2-(2-hydroxyethoxy)-7-methyl-3,4-dihydro-2,7-naphthyridine-1,6(2H,7H)-dione (10 mg, 67%). $^1$H NMR (400 MHz, CDCl$_3$) δ 11.16 (s, 1H), 7.00-6.93 (m, 2H), 6.97-6.83 (t, 1H), 5.93 (s, 1H), 4.51-4.48 (t, 1H), 4.03-4.01 (t, 2H), 3.75-3.69 (m, 4H), 3.14 (s, 3H), 3.00-2.96 (t, 2H), 2.92-2.85 (m, 1H), 1.24-1.22 (d, 6H) ppm; MS (apci, m/z)=390.2 (M+H).

Example 19

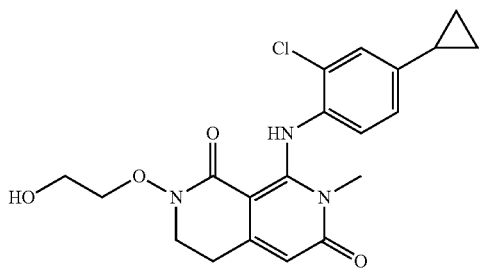

8-((2-chloro-4-cyclopropylphenyl)amino)-2-(2-hydroxyethoxy)-7-methyl-3,4-dihydro-2,7-naphthyridine-1,6(2H,7H)-dione Step 1. Preparation of 2-(2-(tert-butoxy)ethoxy)-8-((2-chloro-4-cyclopropylphenyl)amino)-7-methyl-3,4-dihydro-2,7-naphthyridine-1,6(2H,7H)-dione. Prepared according to Example 6, Step 7 of Method A, substituting 2-chloro-4-cyclopropylaniline in place of 2-fluoro-4-(methylthio)aniline to afford 2-(2-(tert-butoxy)ethoxy)-8-((2-chloro-4-cyclopropylphenyl)amino)-7-methyl-3,4-dihydro-2,7-naphthyridine-1,6(2H,7H)-dione (21 mg, 41%). MS (apci, m/z)=460.2 (M+H).

Step 2. Preparation of 8-((2-chloro-4-cyclopropylphenyl)amino)-2-(2-hydroxyethoxy)-7-methyl-3,4-dihydro-2,7-naphthyridine-1,6(2H,7H)-dione. Prepared according to Example 6, Step 8 of Method A, substituting 2-(2-(tert-butoxy)ethoxy)-8-((2-chloro-4-cyclopropylphenyl)amino)-7-methyl-3,4-dihydro-2,7-naphthyridine-1,6(2H,7H)-dione in place of 2-(2-(tert-butoxy)ethoxy)-8-((2-fluoro-4-(methylthio)phenyl)amino)-7-methyl-3,4-dihydro-2,7-naphthyridine-1,6(2H,7H)-dione to afford 8-((2-chloro-4-cyclopropylphenyl)amino)-2-(2-hydroxyethoxy)-7-methyl-3,4-dihydro-2,7-naphthyridine-1,6(2H,7H)-dione (12 mg, 65%). $^1$H NMR (400 MHz, CDCl$_3$) δ 11.13 (s, 1H), 7.14 (d, 1H), 6.91-6.88 (dd, 1H), 6.69-6.67 (d, 1H), 5.95 (s, 1H), 4.47-4.44 (t, 1H), 4.04-4.01 (t, 2H), 3.75-3.69 (m, 4H), 3.09 (s, 3H), 3.01-2.98 (t, 2H), 1.89-1.82 (m, 1H), 1.02-0.97 (m, 2H), 0.69-0.65 (m, 2H) ppm; MS (apci, m/z)=404.1 (M+H).

Example 20

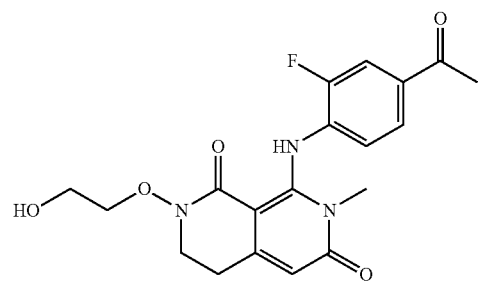 [SMILES: CC(=O)c1ccc(Nc2c3c(cc(=O)n2C)CCN(OCCO)C3=O)c(F)c1]

8-((4-acetyl-2-fluorophenyl)amino)-2-(2-hydroxyethoxy)-7-methyl-3,4-dihydro-2,7-naphthyridine-1,6(2H,7H)-dione Step 1. Preparation of 2-(2-(tert-butoxy)ethoxy)-8-((4-ethynyl-2-fluorophenyl)amino)-7-methyl-3,4-dihydro-2,7-naphthyrdine-1,6(2H,7H)-dione. 2-Fluoro-4-((trimethylsilyl)ethynyl)aniline (30.2 mg, 0.145 mmol) was dissolved in THF (1.0 mL, 0.139 mmol) and cooled to −78° C. under N$_2$ atmosphere. LiHMDS (0.277 mL, 1N/THF, 0.277 mmol) was added dropwise, and the mixture was stirred for 45 minutes at the same temperature. Methyl 4-(2-((2-(tert-butoxy)ethoxy)amino)ethyl)-2-chloro-1-methyl-6-oxo-1,6-dihydropyridine-3-carboxylate (50 mg, 0.139 mmol) was dissolved in THF (1.0 mL, 0.139 mmol) and added dropwise to the reaction mixture. After stirring for 10 minutes, LiHMDS (0.160 mL, 1N/THF, 0.160 mmol) was added and the reaction was stirred for 1 hour at the same temperature. The reaction mixture was quenched with saturated NH$_4$Cl (25 mL), then extracted with EtOAc (3×25 mL). The combined organic layers were dried over Na$_2$SO$_4$, filtered, and concentrated. The material was dissolved in THF (1.0 mL, 0.139 mmol) and treated with TBAF (0.1 mL, 1N/THF, 0.100 mmol) at ambient temperature for 30 minutes. The mixture was partitioned between EtOAc (25 mL) and saturated NH$_4$Cl (25 mL). The organic layer was removed and the aqueous layer was washed with EtOAc (2×25 mL). The combined organic layers were dried over Na$_2$SO$_4$, filtered, and concentrated. The residue was purified by column chromatography, eluting with 0-15% (20% MeOH/DCM)/DCM to afford 2-(2-(tert-butoxy)ethoxy)-8-((4-ethynyl-2-fluorophenyl)amino)-7-methyl-3,4-dihydro-2,7-naphthyridine-1,6(2H,7H)-dione (19 mg, 32%). MS (apci, m/z)=428.2 (M+H).

Step 2. Preparation of 8-((4-acetyl-2-fluorophenyl)amino)-2-(2-hydroxyethoxy)-7-methyl-3,4-dihydro-2,7-naphthyridine-1,6(2H,7H)-dione. Prepared according to Example 6, Step 8 of Method A, substituting 2-(2-(tert-butoxy)ethoxy)-8-((4-ethynyl-2-fluorophenyl)amino)-7-methyl-3,4-dihydro-2,7-naphthyridine-1,6(2H,7H)-dione in place of 2-(2-(tert-butoxy)ethoxy)-8-((2-fluoro-4-(methylthio)phenyl)amino)-7-methyl-3,4-dihydro-2,7-naphthyridine-1,6(2H,7H)-dione to afford 8-((4-acetyl-2-fluorophenyl)amino)-2-(2-hydroxyethoxy)-7-methyl-3,4-dihydro-2,7-naphthyridine-1,6(2H,7H)-dione (11 mg, 64%). $^1$H NMR (400 MHz, CDCl$_3$) δ 11.19 (s, 1H), 7.76-7.73 (dd, 1H), 7.71-7.69 (dd, 1H), 6.87-6.83 (t, 1H), 6.07 (s, 1H), 4.31 (br s, 1H), 4.05-4.03 (m, 2H), 3.76-3.73 (m, 4H), 3.24 (s, 3H), 3.03-3.00 (t, 2H), 2.58 (s, 3H) ppm; MS (apci, m/z)=390.1 (M+H).

Example 21

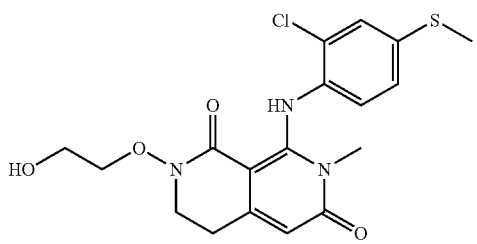 [SMILES: CSc1ccc(Nc2c3c(cc(=O)n2C)CCN(OCCO)C3=O)c(Cl)c1]

8-((2-chloro-4-(methylthio)phenyl)amino)-2-(2-hydroxyethoxy)-7-methyl-3,4-dihydro-2,7-naphthyridine-1,6(2H,7H)-dione Step 1. Preparation of 2-(2-(tert-butoxy)ethoxy)-8-((2-chloro-4-(methylthio)phenyl)amino)-7-methyl-3,4-dihydro-2,7-naphthyridine-1,6(2H,7H)-dione. Prepared according to Example 6, Step 7 of Method A, substituting 2-chloro-4-(methylthio)aniline in place of 2-fluoro-4-(methylthio)aniline to afford 2-(2-(tert-butoxy)ethoxy)-8-((2-chloro-4-(methylthio)phenyl)amino)-7-methyl-3,4-dihydro-2,7-naphthyridine-1,6(2H,7H)-dione (15 mg, 29%). MS (apci, m/z)=466.1 (M+H).

Step 2. Preparation of 8-((2-chloro-4-(methylthio)phenyl)amino)-2-(2-hydroxyethoxy)-7-methyl-3,4-dihydro-2,7-naphthyrdine-1,6(2H,7H)-dione. Prepared according to Example 6, Step 8 of Method A, substituting 2-(2-(tert-butoxy)ethoxy)-8-((2-chloro-4-(methylthio)phenyl)amino)-7-methyl-3,4-dihydro-2,7-naphthyridine-1,6(2H,7H)-dione in place of 2-(2-(tert-butoxy)ethoxy)-8-((2-fluoro-4-(methylthio)phenyl)amino)-7-methyl-3,4-dihydro-2,7-naphthyridine-1,6(2H,7H)-dione to afford 8-((2-chloro-4-(methylthio)phenyl)amino)-2-(2-hydroxyethoxy)-7-methyl-3,4-dihydro-2,7-naphthyridine-1,6(2H,7H)-dione (9 mg, 68%). $^1$H NMR (400 MHz, CDCl$_3$) δ 11.15 (s, 1H), 7.33 (d, 1H), 7.09-7.06 (dd, 1H), 6.71-6.69 (d, 1H), 5.97 (s, 1H), 4.42 (br s, 1H), 4.04-4.02 (t, 2H), 3.75-3.71 (m, 4H), 3.12 (s, 3H), 3.01-2.98 (t, 2H), 2.48 (s, 3H) ppm; MS (apci, m/z)=410.1 (M+H).

Example 22

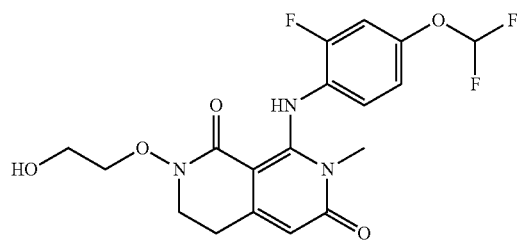 [SMILES: Cn1c(Nc2ccc(OC(F)F)cc2F)c2c(cc1=O)CCN(OCCO)C2=O]

8-((4-(difluoromethoxy)-2-fluorophenyl)amino)-2-(2-hydroxyethoxy)-7-methyl-3,4-dihydro-2,7-naphthyridine-1,6(2H,7H)-dione Step 1. Preparation of 2-(2-(tert-butoxy)ethoxy)-8-((4-(difluoromethoxy)-2-fluorophenyl)amino)-7-methyl-3,4-dihydro-2,7-naphthyridine-1,6(2H,7H)-dione. Prepared according to Example 6, Step 7 of Method A, substituting 4-(difluoromethoxy)-2-fluoroaniline in place of 2-fluoro-4-(methylthio)aniline to afford 2-(2-(tert-butoxy)ethoxy)-8-((4-(difluoromethoxy)-2-fluorophenyl)amino)-7-methyl-3,4-dihydro-2,7-naphthyridine-1,6(2H,7H)-dione (17 mg, 33%). MS (apci, m/z)=470.2 (M+H).

Step 2. 8-(4-(difluoromethoxy)-2-fluorophenyl)amino)-2-(2-hydroxyethoxy)-7-methyl-3,4-dihydro-2,7-naphthyridine-1,6(2H,7H)-dione. Prepared according to Example 6, Step 8 of Method A, substituting 2-(2-(tert-butoxy)ethoxy)-8-((4-(difluoromethoxy)-2-fluorophenyl)amino)-7-methyl-3,4-dihydro-2,7-naphthyridine-1,6(2H,7H)-dione in place of 2-(2-(tert-butoxy)ethoxy)-8-((2-fluoro-4-(methylthio)phenyl)amino)-7-methyl-3,4-dihydro-2,7-naphthyridine-1,6(2H,7H)-dione to afford 8-((4-(difluoromethoxy)-2-fluorophenyl)amino)-2-(2-hydroxyethoxy)-7-methyl-3,4-dihydro-2,7-naphthyridine-1,6(2H,7H)-dione (10 mg, 67%). $^1$H NMR (400 MHz, CDCl$_3$) δ 11.18 (s, 1H), 7.00-6.91 (m, 3H), 6.68-6.31 (t, 1H), 5.98 (s, 1H), 4.43-4.40 (t, 1H), 4.04-4.02 (t, 2H), 3.75-3.71 (m, 4H), 3.16 (s, 3H), 3.01-2.98 (t, 2H) ppm; MS (apci, m/z)=414.1 (M+H).

Example 23

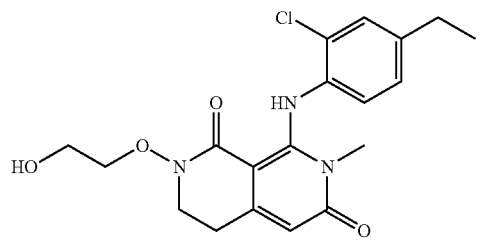 [SMILES: CCc1ccc(Nc2c3c(cc(=O)n2C)CCN(OCCO)C3=O)c(Cl)c1]

8-((2-chloro-4-ethylphenyl)amino)-2-(2-hydroxyethoxy)-7-methyl-3,4-dihydro-2,7-naphthyridine-1,6(2H,7H)-dione Step 1. Preparation of 2-(2-(tert-butoxy)ethoxy)-8-((2-chloro-4-ethylphenyl)amino)-7-methyl-3,4-dihydro-2,7-naphthyridine-1,6(2H,7H)-dione. Prepared according to Example 6, Step 7 of Method A, substituting 2-chloro-4-ethylaniline in place of 2-fluoro-4-(methylthio)aniline to afford 2-(2-(tert-butoxy)ethoxy)-8-((2-chloro-4-ethylphenyl)amino)-7-methyl-3,4-dihydro-2,7-naphthyrdine-1,6(2H,7H)-dione (9 mg, 14%). MS (apci, m/z)=448.2 (M+H).

Step 2. 8-((2-chloro-4-ethylphenyl)amino)-2-(2-hydroxyethoxy)-7-methyl-3,4-dihydro-2,7-naphthyridine-1,6(2H,7H)-dione. Prepared according to Example 6, Step 8 of Method A, substituting 2-(2-(tert-butoxy)ethoxy)-8-((2-chloro-4-ethylphenyl)amino)-7-methyl-3,4-dihydro-2,7-naphthyridine-1,6(2H,7H)-dione in place of 2-(2-(tert-butoxy)ethoxy)-8-((2-fluoro-4-(methylthio)phenyl)amino)-7-methyl-3,4-dihydro-2,7-naphthyridine-1,6(2H,7H)-dione to afford 8-((2-chloro-4-ethylphenyl)amino)-2-(2-hydroxyethoxy)-7-methyl-3,4-dihydro-2,7-naphthyridine-1,6(2H,7H)-dione (6 mg, 80%). $^1$H NMR (400 MHz, CDCl$_3$) δ 11.13 (s, 1H), 7.29 (d, 1H), 7.02-7.00 (dd, 1H), 6.72-6.70 (d, 1H), 5.95 (s, 1H), 4.46 (br s, 1H), 4.04-4.01 (m, 2H), 3.75-3.70 (m, 4H), 3.10 (s, 3H), 3.01-2.97 (t, 2H), 2.65-2.59 (q, 2H), 1.24-1.21 (t, 3H) ppm; MS (apci, m/z)=392.1 (M+H).

Example 24

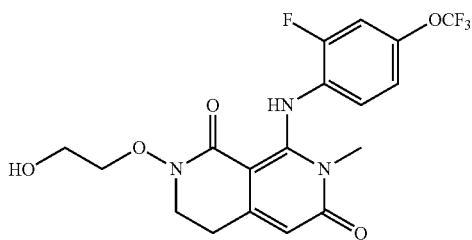 [SMILES: Cn1c(Nc2ccc(OC(F)(F)F)cc2F)c2c(cc1=O)CCN(OCCO)C2=O]

8-((2-fluoro-4-(trifluoromethoxy)phenyl)amino)-2-(2-hydroxyethoxy)-7-methyl-3,4-dihydro-2,7-naphthyridine-1,6(2H,7H)-dione Step 1. Preparation of 2-(2-(tert-butoxy)ethoxy)-8-((2-fluoro-4-(trifluoromethoxy)phenyl)amino)-7-methyl-3,4-dihydro-2,7-naphthyridine-1,6(2H,7H)-dione. Prepared according to Example 6, Step 7 of Method A, substituting 2-fluoro-4-(trifluoromethoxy)aniline in place of 2-fluoro-4-(methylthio)aniline to afford 2-(2-(tert-butoxy)ethoxy)-8-((2-fluoro-4-(trifluoromethoxy)phenyl)amino)-7-methyl-3,4-dihydro-2,7-naphthyridine-1,6(2H,7H)-dione (22 mg, 41%). MS (apci, m/z)=488.2 (M+H).

Step 2. 8-((2-fluoro-4-(trifluoromethoxy)phenyl)amino)-2-(2-hydroxyethoxy)-7-methyl-3,4-dihydro-2,7-naphthyridine-1,6(2H,7H)-dione. Prepared according to Example 6, Step 8 of Method A, substituting 2-(2-(tert-butoxy)ethoxy)-8-((2-fluoro-4-(trifluoromethoxy)phenyl)amino)-7-methyl-3,4-dihydro-2,7-naphthyridine-1,6(2H,7H)-dione in place of 2-(2-(tert-butoxy)ethoxy)-8-((2-fluoro-4-(methylthio)phenyl)amino)-7-methyl-3,4-dihydro-2,7-naphthyridine-1,6(2H,7H)-dione to afford 8-((2-fluoro-4-(trifluoromethoxy)phenyl)amino)-2-(2-hydroxyethoxy)-7-methyl-3,4-dihydro-2,7-naphthyridine-1,6(2H,7H)-dione (13 mg, 67%). $^1$H NMR (400 MHz, CDCl$_3$) δ 11.17 (s, 1H), 7.08-7.06 (d, 1H), 7.02-6.99 (d, 1H), 6.94-6.90 (t, 1H), 6.01 (s, 1H), 4.40-4.36 (t, 1H), 4.05-4.02 (t, 2H), 3.75-3.72 (t, 4H), 3.18 (s, 3H), 3.02-2.99 (t, 2H) ppm; MS (apci, m/z)=432.1 (M+H).

Example 25

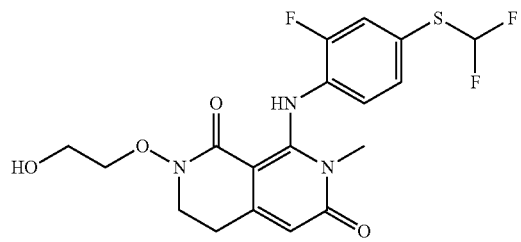

8-((4-(((difluoromethyl)thio)-2-fluorophenyl)amino)-2-(2-hydroxyethoxy)-7-methyl-3,4-dihydro-2,7-naphthyridine-1,6(2H,7H)-dione Step 1. Preparation of 2-(2-(tert-butoxy)ethoxy)-8-((4-((difluoromethyl)thio)-2-fluorophenyl)amino)-7-methyl-3,4-dihydro-2,7-naphthyridine-1,6(2H,7H)-dione. Prepared according to Example 6, Step 7 of Method A, substituting 4-((difluoromethyl)thio)-2-fluoroaniline in place of 2-fluoro-4-(methylthio)aniline to afford 2-(2-(tert-butoxy)ethoxy)-8-((4-((difluoromethyl)thio)-2-fluorophenyl)amino)-7-methyl-3,4-dihydro-2,7-naphthyridine-1,6(2H,7H)-dione (19 mg, 35%). δ 11.31 (s, 1H), 7.40-7.37 (dd, 1H), 7.30-7.28 (m, 1H), 6.94-6.66 (t, 1H), 6.80-6.76 (t, 1H), 6.04 (s, 1H), 4.17-4.14 (m, 2H), 3.82-3.79 (t, 2H), 3.62-3.59 (m, 2H), 3.24 (s, 3H), 3.01-2.97 (t, 2H), 1.21 (s, 9H) ppm. MS (apci, m/z)=486.2 (M+H).

Step 2. 8-((4-((difluoromethyl)thio)-2-fluorophenyl)amino)-2-(2-hydroxyethoxy)-7-methyl-3,4-dihydro-2,7-naphthyridine-1,6(2H,7H)-dione. Prepared according to Example 6, Step 8 of Method A, substituting 2-(2-(tert-butoxy)ethoxy)-8-((4-((difluoromethyl)thio)-2-fluorophenyl)amino)-7-methyl-3,4-dihydro-2,7-naphthyridine-1,6(2H,7H)-dione in place of 2-(2-(tert-butoxy)ethoxy)-8-((2-fluoro-4-(methylthio)phenyl)amino)-7-methyl-3,4-dihydro-2,7-naphthyridine-1,6(2H,7H)-dione to afford 8-((4-((difluoromethyl)thio)-2-fluorophenyl)amino)-2-(2-hydroxyethoxy)-7-methyl-3,4-dihydro-2,7-naphthyridine-1,6(2H,7H)-dione (11 mg, 57%). $^1$H NMR (400 MHz, CDCl$_3$) δ 11.16 (s, 1H), 7.42-7.39 (dd, 1H), 7.33-7.32 (d, 1H), 6.96-6.68 (t, 1H), 6.87-6.82 (t, 1H), 6.04 (s, 1H), 4.37-4.33 (t, 1H), 4.05-4.02 (t, 2H), 3.75-3.72 (t, 4H), 3.22 (s, 3H), 3.03-2.99 (t, 2H) ppm; MS (apci, m/z)=430.1 (M+H).

Example 26

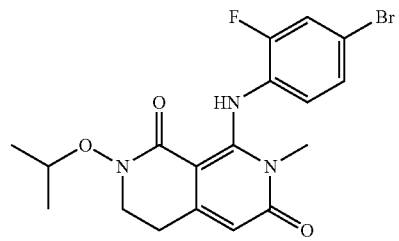 [SMILES: CC(C)ON1CCc2cc(=O)n(C)c(Nc3ccc(Br)cc3F)c2C1=O]

8-((4-bromo-2-fluorophenyl)amino)-2-isopropoxy-7-methyl-3,4-dihydro-2,7-naphthyridine-1,6(2H,7H)-dione Prepared according to Example 6, steps 1-7 of Method A, substituting O-isopropylhydroxylamine hydrochloride in place of 0-(2-(tert-butoxy)ethyl)hydroxylamine hydrochloride in step 5 and 4-bromo-2-fluoroaniline in place of 2-fluoro-4-(methylthio)aniline in step 7 to afford 8-((4-bromo-2-fluorophenyl)amino)-2-isopropoxy-7-methyl-3,4-dihydro-2,7-naphthyridine-1,6(2H,7H)-dione (10.3 mg, 14%). $^1$H NMR (400 MHz, CDCl$_3$) δ 11.37 (s, 1H), 7.30 (dd, 1H), 7.21 (dq, 1H), 6.73 (t, 1H), 6.00 (s, 1H), 4.33 (m, 1H), 3.68 (t, 2H), 3.18 (s, 3H), 2.99 (t, 2H), 1.30 (d, 6H) ppm; MS (apci, m/z)=424.1, 426.1 (M+H).

Example 27

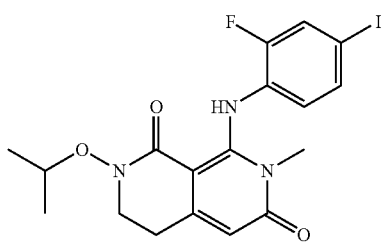 [SMILES: CC(C)ON1CCc2cc(=O)n(C)c(Nc3ccc(I)cc3F)c2C1=O]

8-((2-fluoro-4-iodophenyl)amino)-2-isopropoxy-7-methyl-3,4-dihydro-2,7-naphthyridine-1,6(2H,7H)-dione Prepared according to Example 6, steps 1-7 of Method A, substituting O-isopropylhydroxylamine hydrochloride in place of 0-(2-(tert-butoxy)ethyl)hydroxylamine hydrochloride in step 5 and 2-fluoro-4-iodoaniline in place of 2-fluoro-4-(methylthio)aniline in step 7 to afford 8-((2-fluoro-4-iodophenyl)amino)-2-isopropoxy-7-methyl-3,4-dihydro-2,7-naphthyridine-1,6(2H,7H)-dione (15.2 mg, 23%). $^1$H NMR (400 MHz, CDCl$_3$) δ 11.36 (s, 1H), 7.46 (dd, 1H), 7.38 (dt, 1H), 6.58 (t, 1H), 6.00 (s, 1H), 4.33 (m, 1H), 3.68 (t, 2H), 3.19 (s, 3H), 2.99 (t, 2H), 1.30 (d, 6H) ppm; MS (apci, m/z)=472.1 (M+H).

Example 28

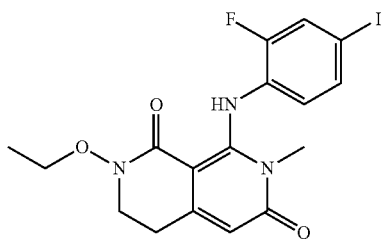 [SMILES: CCON1CCc2cc(=O)n(C)c(Nc3ccc(I)cc3F)c2C1=O]

2-ethoxy-8-((2-fluoro-4-iodophenyl)amino)-7-methyl-3,4-dihydro-2,7-naphthyrdine-1,6(2H,7H)-dione Prepared according to Example 6, steps 1-7 of Method A, substituting O-ethylhydroxylamine hydrochloride in place of O-(2-(tert-butoxy)ethyl)hydroxylamine hydrochloride in step 5 and 2-fluoro-4-iodoaniline in place of 2-fluoro-4-(methylthio)aniline in step 7 to afford 2-ethoxy-8-((2-fluoro-4-iodophenyl)amino)-7-methyl-3,4-dihydro-2,7-naphthyridine-1,6(2H,7H)-dione (24.3 mg, 25%). $^1$H NMR 11.33 (s, 1H), 7.46 (d, 1H), 7.38 (d, 1H), 6.57 (t, 1H), 6.00 (s, 1H), 4.07 (q, 2H), 3.72 (t, 2H), 3.19 (s, 3H), 2.99 (t, 2H), 1.31 (t, 3H) ppm; MS (apci, m/z)=458.0 (M+H).

Example 29

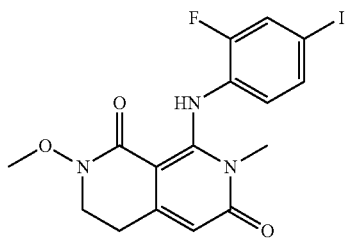 [SMILES: CON1CCc2cc(=O)n(C)c(Nc3ccc(I)cc3F)c2C1=O]

8-((2-fluoro-4-iodophenyl)amino)-2-methoxy-7-methyl-3,4-dihydro-2,7-naphthyridine-1,6(2H,7H)-dione Prepared according to Example 6, steps 1-7 of Method A, substituting O-methylhydroxylamine hydrochloride in place of 0-(2-(tert-butoxy)ethyl)hydroxylamine hydrochloride in step 5 and 2-fluoro-4-iodoaniline in place of 2-fluoro-4-(methylthio)aniline in step 7 to afford 8-((2-fluoro-4-iodophenyl)amino)-2-methoxy-7-methyl-3,4-dihydro-2,7-naphthyridine-1,6(2H,7H)-dione (16.7 mg, 33%). $^1$H NMR (400 MHz, CDCl$_3$) δ 11.32 (s, 1H), 7.47 (d, 1H), 7.39 (d, 1H), 6.58 (t, 1H), 6.00 (s, 1H), 3.84 (s, 3H), 3.73 (t, 2H), 3.19 (s, 3H), 3.00 (t, 2H) ppm; MS (apci, m/z)=444.0 (M+H).

Example 30

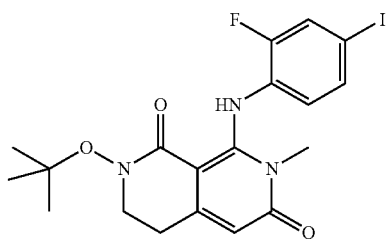 [SMILES: Cn1c(Nc2ccc(I)cc2F)c2c(cc1=O)CCN(OC(C)(C)C)C2=O]

2-(tert-butoxy)-8-((2-fluoro-4-iodophenyl)amino)-7-methyl-3,4-dihydro-2,7-naphthyridine-1,6(2H,7H)-dione Steps 1-7. Preparation of methyl 4-(2-(tert-butoxyamino)ethyl)-2-((2-fluoro-4-iodophenyl)amino)-1-methyl-6-oxo-1,6-dihydropyridine-3-carboxylate. Prepared according to Example 6, steps 1-7, substituting O-(tert-butyl)hydroxylamine hydrochloride in place of O-(2-(tert-butoxy)ethyl) hydroxylamine hydrochloride in step 5 and 2-fluoro-4-iodoaniline in place of 2-fluoro-4-(methylthio)aniline in step 7 to afford methyl 4-(2-(tert-butoxyamino)ethyl)-2-((2- fluoro-4-iodophenyl)amino)-1-of Method A methyl-6-oxo-1,6-dihydropyridine-3-carboxylate (40.3 mg, 62%). MS (apci, m/z)=518.1 (M+H).

Step 8. Preparation of 2-(tert-butoxy)-8-((2-fluoro-4-iodophenyl)amino)-7-methyl-3,4-dihydro-2,7-naphthyridine-1,6(2H,7H)-dione. A solution of methyl 4-(2-(tert-butoxyamino)ethyl)-2-((2-fluoro-4-iodophenyl)amino)-1-methyl-6-oxo-1,6-dihydropyridine-3-carboxylate (40.3 mg, 0.078 mmol) in THF (1 mL) was treated with Et₃N (10.9 µL, 0.078 mmol). The reaction mixture was heated to 50° C. for 1 hour. More Et₃N (10.9 µL, 0.078 mmol) was added to the reaction and left to stir at 50° C. for another hour. An additional aliquot of Et₃N (10.9 µL, 0.078 mmol) was added and the reaction was stirred at 50° C. for 5 days. The reaction mixture was partitioned between water (40 mL) and EtOAc (20 mL). The aqueous layer was washed with EtOAc (2×15 mL). The combined organic layers were washed with brine (25 mL), dried over sodium sulfate, filtered, and concentrated. The residue was purified by reverse phase HPLC (5-95% acetonitrile/water/0.1% TFA over 20 minutes) and the clean fractions were combined, washed with saturated bicarbonate, and extracted with EtOAc (3×15 mL). The combined organic layers were washed with saturated bicarbonate (20 mL) and brine (25 mL), dried over sodium sulfate, filtered, and concentrated in vacuo to afford 2-(tert-butoxy)-8-((2-fluoro-4-iodophenyl)amino)-7-methyl-3,4-dihydro-2,7-naphthyridine-1,6(2H,7H)-dione (16.5 mg, 43%). ¹H NMR (400 MHz, CDCl₃) δ 11.49 (s, 1H), 7.46 (dd, 1H), 7.39 (td, 1H), 6.59 (t, 1H), 5.99 (s, 1H), 3.70-3.60 (m, 2H), 3.18 (s, 3H), 3.10-2.87 (m, 2H), 1.34 (s, 9H) ppm; MS (apci, m/z)=486.1 (M+H).

Example 31

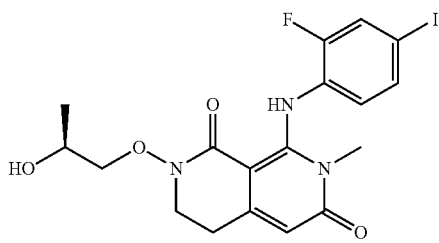 [SMILES: C[C@H](O)CON1CCc2cc(=O)n(C)c(Nc3ccc(I)cc3F)c2C1=O]

(S)-8-((2-fluoro-4-iodophenyl)amino)-2-(2-hydroxypropoxy)-7-methyl-3,4-dihydro-2,7-naphthyridine-1,6(2H,7H)-dione Step 1. Preparation of methyl (S,E)-2-chloro-4-(2-((2-hydroxypropoxy)imino)ethyl)-1-methyl-6-oxo-1,6-dihydropyridine-3-carboxylate. Methyl (Z)-2-chloro-4-(2-ethoxyvinyl)-1-methyl-6-oxo-1,6-dihydropyridine-3-carboxylate (200 mg, 0.736 mmol) and (S)—O-(2-((tert-butyldimethylsilyl)oxy)propyl)hydroxylamine (151 mg, 0.736) were taken up in 1,4-dioxane (5 mL). TEA (103 µL, 0.736 mmol) and HCl (368 µL, 4N/dioxane, 1.47 mmol) were added. The suspension was heated to 60° C. for 3 hours. The reaction mixture was filtered and concentrated. The residue was purified by column chromatography eluting with 0-80% EtOAc/hexanes to afford methyl (S,E)-2-chloro-4-(2-((2-hydroxypropoxy)imino)ethyl)-1-methyl-6-oxo-1,6-dihydropyridine-3-carboxylate (66.6 mg, 29%). MS (apci, m/z)=317.1 (M+H).

Step 2. Preparation of methyl (S,E)-2-chloro-1-methyl-6-oxo-4-(6,8,8,9,9-pentamethyl-4,7-dioxa-3-aza-8-siladec-2-en-1-yl)-1,6-dihydropyridine-3-carboxylate. Methyl (S,E)-2-chloro-4-(2-((2-hydroxypropoxy)imino)ethyl)-1-methyl-6-oxo-1,6-dihydropyridine-3-carboxylate (66.6 mg, 0.210 mmol) and imidazole (0.043 g, 0.631 mmol) were dissolved in DMF (2 mL) and cooled to 0° C. TBS-Cl (63.4 mg, 0.421 mmol) was subsequently added and the reaction was allowed to warm to room temperature over 2 hours. The reaction was diluted with water (40 mL) and EtOAc (20 mL). The aqueous layer was washed with EtOAc (2×15 mL). The combined organic layers were washed with water (5×20 mL) and brine (25 mL), dried over sodium sulfate, filtered and concentrated. The residue was purified by column chromatography eluting with 0-40% EtOAc/hexanes to afford methyl (S,E)-2-chloro-1-methyl-6-oxo-4-(6,8,8,9,9-pentamethyl-4,7-dioxa-3-aza-8-siladec-2-en-1-yl)-1,6-dihydropyridine-3-carboxylate (63.4 mg, 70%). MS (apci, m/z)=431.2 (M+H).

Step 3. Preparation of methyl (S)-2-chloro-1-methyl-6-oxo-4-(6,8,8,9,9-pentamethyl-4,7-dioxa-3-aza-8-siladecyl)-1,6-dihydropyridine-3-carboxylate. Methyl (S,E)-2-chloro-1-methyl-6-oxo-4-(6,8,8,9,9-pentamethyl-4,7-dioxa-3-aza-8-siladec-2-en-1-yl)-1,6-dihydropyridine-3-carboxylate (63.4 mg, 0.147 mmol) was dissolved in 2-propanol (1 mL). Sodium cyanoborohydride (46.2 mg, 0.735 mmol) and acetic acid (42.1 µL, 0.735 mmol) were added. The mixture was stirred at room temperature for 16 hours. The reaction mixture was partitioned between saturated bicarbonate (30 mL) and EtOAc (20 mL). The aqueous layer was washed with EtOAc (2×15 mL). The combined organic layers were washed with brine (20 mL), dried over sodium sulfate, filtered, and concentrated. The residue was purified by column chromatography eluting with 0-40% EtOAc/hexanes to afford methyl (S)-2-chloro-1-methyl-6-oxo-4-(6,8,8,9,9-pentamethyl-4,7-dioxa-3-aza-8-siladecyl)-1,6-dihydropyridine-3-carboxylate (30.6 mg, 48%). MS (apci, m/z)=433.2 (M+H).

Step 4. Preparation of (S)-2-(2-((tert-butyldimethylsilyl)oxy)propoxy)-8-((2-fluoro-4-iodophenyl)amino)-7-methyl-3,4-dihydro-2,7-naphthyridine-1,6(2H,7H)-dione. To a solution of 2-fluoro-4-iodoaniline (16.9 mg, 0.071 mmol) in anhydrous THF (1 mL) at −78° C. under N₂ was added LiHMDS (0.141 ml, 1M/THF, 0.141 mmol). The mixture was stirred for 45 minutes then a solution of methyl (S)-2-chloro-1-methyl-6-oxo-4-(6,8,8,9,9-pentamethyl-4,7-dioxa-3-aza-8-siladecyl)-1,6-dihydropyridine-3-carboxylate (30.6 mg, 0.071 mmol) in THF (0.5 mL) was added. The mixture was stirred at −78° C. for 10 minutes. The mixture was quenched with saturated NH₄Cl (30 mL), stirred at ambient temperature for 10 minutes, then extracted with EtOAc (3×10 mL). The combined organic phases were washed with brine (20 mL), dried over sodium sulfate, filtered and concentrated. The residue was purified by column chromatography eluting with 0-50% EtOAc/hexanes to afford (S)-2-(2-((tert-butyldimethylsilyl)oxy)propoxy)-8-((2-fluoro-4-iodophenyl)amino)-7-methyl-3,4-dihydro-2,7-naphthyridine-1,6(2H,7H)-dione (15.2 mg, 36%). MS (apci, m/z)=602.2 (M+H).

Step 5. Preparation of (S)-8-((2-fluoro-4-iodophenyl)amino)-2-(2-hydroxypropoxy)-7-methyl-3,4-dihydro-2,7-naphthyridine-1,6(2H,7H)-dione. (S)-2-(2-((tert-butyldimethylsilyl)oxy)propoxy)-8-((2-fluoro-4-iodophenyl)amino)-7-methyl-3,4-dihydro-2,7-naphthyridine-1,6(2H,7H)-dione (15.2 mg, 0.025 mmol) was dissolved in MeOH (0.5 mL). The reaction mixture was treated with HCl (12.6 µL, 4N/dioxane, 0.051 mmol) and stirred for 1 hour. The reaction mixture was concentrated and the residue was purified by reverse phase HPLC (5-95% acetonitrile/water/0.1% TFA over 20 minutes) and the clean fractions were combined, washed with saturated bicarbonate, and extracted with EtOAc (3×20 mL). The combined organic layers were washed with saturated bicarbonate (15 mL) and brine (15 mL), dried over sodium sulfate, filtered, and concentrated to afford (S)-8-((2-fluoro-4-iodophenyl)amino)-2-(2-hydroxypropoxy)-7-methyl-3,4-dihydro-2,7-naphthyridine-1,6(2H,7H)-dione (6.8 mg, 55%). ¹H NMR (400 MHz, CDCl₃) δ 11.16 (s, 1H), 7.48 (dd, 1H), 7.42 (dt, 1H), 6.62 (t, 1H), 6.00 (s, 1H), 4.05-3.91 (m, 2H), 3.78-3.60 (m, 3H), 3.17 (s, 3H), 3.10-2.90 (m, 2H), 1.15 (d, 3H) ppm; MS (apci, m/z)=488.0 (M+H).

Example 32

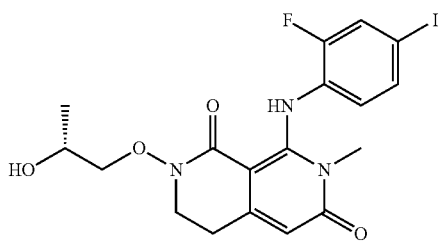 [SMILES: C[C@@H](O)CON1CCc2cc(=O)n(C)c(Nc3ccc(I)cc3F)c2C1=O]

(R)-8-((2-fluoro-4-iodophenyl)amino)-2-(2-hydroxypropoxy)-7-methyl-3,4-dihydro-2,7-naphthyridine-1,6(2H,7H)-dione Prepared according to Example 31, substituting (R)—O-(2-((tert-butyldimethylsilyl)oxy)propyl)hydroxylamine in place of (S)—O-(2-((tert-butyldimethylsilyl)oxy)propyl)hydroxylamine in step 1 to afford (R)-8-((2-fluoro-4-iodophenyl)amino)-2-(2-hydroxypropoxy)-7-methyl-3,4-dihydro-2,7-naphthyridine-1,6(2H,7H)-dione (8.6 mg, 49%). ¹H NMR (400 MHz, CDCl₃) δ 11.16 (s, 1H), 7.48 (dd, 1H), 7.42 (dt, 1H), 6.62 (t, 1H), 5.99 (s, 1H), 4.05-3.91 (m, 2H), 3.78-3.60 (m, 3H), 3.17 (s, 3H), 3.09-2.90 (m, 2H), 1.15 (d, 3H) ppm; MS (apci, m/z)=488.0 (M+H).

Example 33

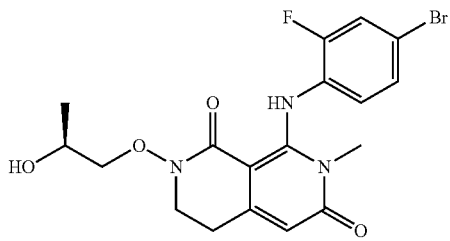 [SMILES: C[C@H](O)CON1CCc2cc(=O)n(C)c(Nc3ccc(Br)cc3F)c2C1=O]

(S)-8-((4-bromo-2-fluorophenyl)amino)-2-(2-hydroxypropoxy)-7-methyl-3,4-dihydro-2,7-naphthyridine-1,6(2H,7H)-dione Prepared according to Example 31, substituting 4-bromo-2-fluoroaniline in place of 2-fluoro-4-iodoaniline in step 4 to afford (S)-8-((4-bromo-2-fluorophenyl)amino)-2-(2-hydroxypropoxy)-7-methyl-3,4-dihydro-2,7-naphthyridine-1,6(2H,7H)-dione (9.2 mg, 55%). ¹H NMR (400 MHz, CDCl₃) δ 11.16 (s, 1H), 7.32 (dd, 1H), 7.26-7.22 (m, 1H), 6.78 (t, 1H), 5.99 (s, 1H), 4.05-3.92 (m, 2H), 3.78-3.60 (m, 3H), 3.17 (s, 3H), 3.10-2.90 (m, 2H), 1.15 (d, 3H) ppm; MS (apci, m/z)=440.1, 442.1 (M+H).

Example 34

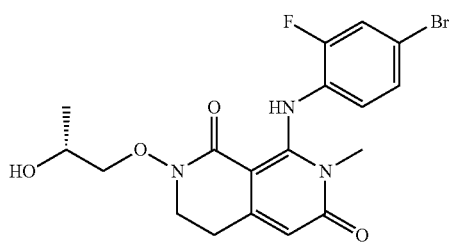 [SMILES: C[C@@H](O)CON1CCc2cc(=O)n(C)c(Nc3ccc(Br)cc3F)c2C1=O]

(R)-8-((4-bromo-2-fluorophenyl)amino)-2-(2-hydroxypropoxy)-7-methyl-3,4-dihydro-2,7-naphthyridine-1,6(2H,7H)-dione Prepared according to Example 31, substituting (R)—O-(2-((tert-butyldimethylsilyl)oxy)propyl)hydroxylamine in place of (S)—O-(2-((tert-butyldimethylsilyl)oxy)propyl)hydroxylamine in step 1 and 4-bromo-2-fluoroaniline in place of 2-fluoro-4-iodoaniline in step 4 to afford (R)-8-((4-bromo-2-fluorophenyl)amino)-2-(2-hydroxypropoxy)-7-methyl-3,4-dihydro-2,7-naphthyridine-1,6(2H,7H)-dione (9.2 mg, 55%). ¹H NMR (400 MHz, CDCl₃) δ 11.17 (s, 1H), 7.32 (dd, 1H), 7.24 (dt, 1H), 6.78 (t, 1H), 5.99 (s, 1H), 4.06-3.91 (m, 2H), 3.78-3.60 (m, 3H), 3.17 (s, 3H), 3.10-2.90 (m, 2H), 1.15 (d, 3H) ppm; MS (apci, m/z)=440.0 (M+H).

Example 35

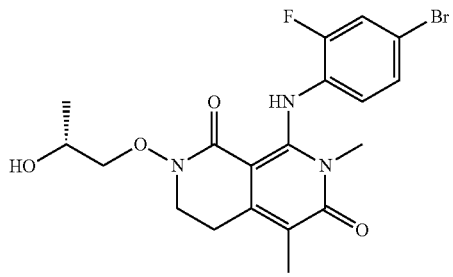 [SMILES: Cc1c2c(c(Nc3ccc(Br)cc3F)n(C)c1=O)C(=O)N(OC[C@@H](C)O)CC2]

(R)-8-((4-bromo-2-fluorophenyl)amino)-2-(2-hydroxypropoxy)-5,7-dimethyl-3,4-dihydro-2,7-naphthyridine-1,6(2H,7H)-dione Steps 1-4: Preparation of (R)-8-((4-bromo-2-fluorophenyl)amino)-2-(2-((tert-butyldimethylsilyl)oxy)propoxy)-7-methyl-3,4-dihydro-2,7-naphthyridine-1,6(2H,7H)-dione. Prepared according to Example 31, steps 1-4 substituting (R)—O-(2-((tert-butyldimethylsilyl)oxy)propyl)hydroxylamine in place of (S)—O-(2-((tert-butyldimethylsilyl)oxy)propyl)hydroxylamine in step 1 to afford (R)-8-((4- bromo-2-fluorophenyl)amino)-2-(2-((tert-butyldimethylsilyl)oxy)propoxy)-7-methyl-3,4-dihydro-2,7-naphthyridine-1,6(2H,7H)-dione (63.5 mg, 62%). MS (apci, m/z)=554.1 (M+H).

Step 5. Preparation of (R)-8-((4-bromo-2-fluorophenyl)amino)-2-(2-hydroxypropoxy)-5-iodo-7-methyl-3,4-dihydro-2,7-naphthyridine-1,6(2H,7H)-dione. (R)-8-((4-bromo-2-fluorophenyl)amino)-2-(2-((tert-butyldimethylsilyl)oxy)propoxy)-7-methyl-3,4-dihydro-2,7-naphthyridine-1,6(2H,7H)-dione (42.3 mg, 0.076 mmol) was dissolved in THF (1 mL) and MeOH (1 mL). p-Toluenesulfonic acid monohydrate (21.8 mg, 0.114 mmol) was added. After 5 minutes, N-iodosuccinimide (17.2 mg, 0.076 mmol) was added and left to stir for 30 minutes. The reaction mixture was partitioned between EtOAc (15 mL) and saturated bicarbonate (30 mL) and the aqueous layer was extracted with EtOAc (2×10 mL). The combined organic phases were washed with brine (25 mL), dried over sodium sulfate, filtered, and concentrated. The residue was purified by column chromatography eluting with 0-50% EtOAc/heptane to afford (R)-8-((4-bromo-2-fluorophenyl)amino)-2-(2-hydroxypropoxy)-5-iodo-7-methyl-3,4-dihydro-2,7-naphthyridine-1,6(2H,7H)-dione (23.8 mg, 54%). MS (apci, m/z)=566.0 (M+H).

Step 6. Preparation of (R)-8-((4-bromo-2-fluorophenyl)amino)-2-(2-hydroxypropoxy)-5,7-dimethyl-3,4-dihydro-2,7-naphthyridine-1,6(2H,7H)-dione. To a solution of (R)-8-((4-bromo-2-fluorophenyl)amino)-2-(2-hydroxypropoxy)-5-iodo-7-methyl-3,4-dihydro-2,7-naphthyridine-1,6(2H,7H)-dione (21.7 mg, 0.038 mmol) in THF (400 µL) at 0° C. was added Pd(Pt-Bu$_3$)$_2$ (1.96 mg, 0.004 mmol) followed by methylzinc(II) chloride (19.4 µL, 0.039 mmol). The mixture was removed from the ice bath and stirred for 5 minutes. The mixture was partitioned between saturated NH$_4$Cl (20 mL) and EtOAc (15 mL). The aqueous layer was extracted with EtOAc (2×10 mL). The combined organic phases were washed with brine (20 mL), dried over sodium sulfate, filtered, and concentrated. The residue was purified by reverse phase HPLC (5-95% acetonitrile/water/0.1% TFA over 20 minutes) and the clean fractions were combined, washed with saturated bicarbonate, and extracted with EtOAc (3×10 mL). The combined organic layers were washed with saturated bicarbonate (25 mL) and brine (30 mL), dried over sodium sulfate, filtered, and concentrated to afford (R)-8-((4-bromo-2-fluorophenyl)amino)-2-(2-hydroxypropoxy)-5,7-dimethyl-3,4-dihydro-2,7-naphthyridine-1,6(2H,7H)-dione (7.5 mg, 43%). $^1$H NMR (400 MHz, CDCl$_3$) δ 10.97 (s, 1H), 7.30 (dd, 1H), 7.19 (dt, 1H), 6.68 (t, 1H), 4.05-3.91 (m, 2H), 3.71 (m, 2H), 3.64 (m, 1H), 3.22 (s, 3H), 3.13-3.04 (m, 1H), 3.03-2.92 (m, 1H), 2.08 (s, 3H), 1.14 (d, 3H) ppm; MS (apci, m/z)=454.1 (M+H).

Example 36

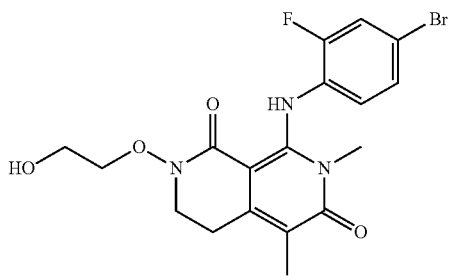

8-((4-bromo-2-fluorophenyl)amino)-2-(2-hydroxyethoxy)-5,7-dimethyl-3,4-dihydro-2,7-naphthyridine-1,6(2H,7H)-dione Step 1. Preparation of 8-((4-bromo-2-fluorophenyl)amino)-2-(2-(tert-butoxy)ethoxy)-7-methyl-3,4-dihydro-2,7-naphthyridine-1,6(2H,7H)-dione. To a solution of 4-bromo-2-fluoroaniline (88 mg, 0.47 mmol) in anhydrous THF (5 mL) at −78° C. under N$_2$ was added LiHMDS (694 mL, 1.0 M/THF, 0.694 mmol). The mixture was stirred for 45 min, then a solution of methyl 4-(2-((2-(tert-butoxy)ethoxy)amino)ethyl)-2-chloro-1-methyl-6-oxo-1,6-dihydropyridine-3-carboxylate (167 mg, 0.46 mmol) in THF (2 mL) was added. Stirring was continued at −78° C. for 10 minutes, then LiHMDS (300 mL, 1.0 M/THF, 0.300 mmol) was added. After stirring for another 10 minutes at −78° C., LiHMDS (100 mL, 1.0 M/THF, 0.100 mmol) was added, and stirring continued for 10 minutes. The mixture was quenched with saturated NH$_4$Cl (10 mL), stirred at ambient temperature for 10 minutes, then extracted with EtOAc (3×10 mL). The combined organic phases were washed with brine (10 mL), dried over Na$_2$SO$_4$, filtered and concentrated. The residue was purified by column chromatography, eluting with 0-15% (20% MeOH/DCM)/DCM, to afford 8-((4-bromo-2-fluorophenyl)amino)-2-(2-(tert-butoxy)ethoxy)-7-methyl-3,4-dihydro-2,7-naphthyridine-1,6(2H,7H)-dione (78 mg, 35%). MS (apci, m/z)=482.1 (M+H).

Step 2. Preparation of 8-((4-bromo-2-fluorophenyl)amino)-2-(2-(tert-butoxy)ethoxy)-5-iodo-7-methyl-3,4-dihydro-2,7-naphthyridine-1,6(2H,7H)-dione. To a solution of 8-((4-bromo-2-fluorophenyl)amino)-2-(2-(tert-butoxy)ethoxy)-7-methyl-3,4-dihydro-2,7-naphthyridine-1,6(2H,7H)-dione (78 mg, 0.16 mmol) in THF (2 mL) and MeOH (2 mL) was added p-toluenesulfonic acid monohydrate (46 mg, 0.24 mmol). After 5 minutes, N-iodosuccinimide (36 mg, 0.16 mmol) was added. After stirring at ambient temperature for 30 minutes, the reaction mixture was partitioned between EtOAc (10 mL) and saturated NaHCO$_3$ (10 mL). The aqueous was extracted with EtOAc (2×10 mL) and the combined organic phases were washed with brine (10 mL), dried over Na$_2$SO$_4$, filtered, and concentrated. The residue was purified by column chromatography eluting with 0-30% EtOAc/hexanes to afford 8-((4-bromo-2-fluorophenyl)amino)-2-(2-(tert-butoxy)ethoxy)-5-iodo-7-methyl-3,4-dihydro-2,7-naphthyridine-1,6(2H,7H)-dione (62 mg, 63%). $^1$H NMR (400 MHz, CDCl$_3$) δ 11.54 (s, 1H), 7.31 (dd. 1H), 7.22 (m, 1H), 6.73 (t, 1H), 4.17-4.13 (m, 2H), 3.80 (t, 2H), 3.63-3.59 (m, 2H), 3.27 (s, 3H), 3.17 (t, 2H), 1.22 (s, 9H) ppm; MS (apci, m/z)=608.0 (M+H).

Step 3. Preparation of 8-((4-bromo-2-fluorophenyl)amino)-2-(2-(tert-butoxy)ethoxy)-5,7-dimethyl-3,4-dihydro-2,7-naphthyridine-1,6(2H,7H)-dione. To a solution of 8-((4-bromo-2-fluorophenyl)amino)-2-(2-(tert-butoxy)ethoxy)-5-iodo-7-methyl-3,4-dihydro-2,7-naphthyridine-1,6(2H,7H)-dione (62 mg, 0.10 mmol) in anhydrous THF (2 mL) at 0° C. was added Pd(Pt-Bu$_3$)$_2$ (5 mg, 0.01 mmol) followed by methylzinc(II)chloride (61 mL, 2M/THF, 0.12 mmol). The mixture was removed from the ice bath and stirred for 5 minutes, then partitioned between saturated NH$_4$Cl (10 mL) and EtOAc (10 mL). The aqueous layer was extracted with EtOAc (2×10 mL) and the combined organic phases were washed with brine (10 mL), dried over Na$_2$SO$_4$, filtered and concentrated. The residue was purified by column chromatography eluting with 0-60% EtOAc/hexanes to afford 8-((4-bromo-2-fluorophenyl)amino)-2-(2-(tert-butoxy)ethoxy)-5,7-dimethyl-3,4-dihydro-2,7-naphthyridine-1,6(2H,7H)-dione (39 mg, 77%). $^1$H NMR (400 MHz, CDCl$_3$) δ 11.11 (s, 1H), 7.28 (dd, 1H), 7.16 (dt, 1H), 6.61 (t, 1H), 4.17-4.13 (m, 2H), 3.78 (t, 2H), 3.64-3.59 (m, 2H), 3.25 (s, 3H), 3.02 (t, 2H), 2.09 (s, 3H), 1.22 (s, 9H) ppm; MS (apci, m/z)=496.1 (M+H).

Step 4. Preparation of 8-((4-bromo-2-fluorophenyl)amino)-2-(2-hydroxyethoxy)-5,7-dimethyl-3,4-dihydro-2,7-naphthyridine-1,6(2H,7H)-dione. To a solution of 8-((4-bromo-2-fluorophenyl)amino)-2-(2-(tert-butoxy)ethoxy)-5,7-dimethyl-3,4-dihydro-2,7-naphthyridine-1,6(2H,7H)-dione (39 mg, 0.079 mmol) in acetonitrile (0.5 mL) was added phosphoric acid (0.5 mL). The mixture was warmed to 60° C. for 1 hour then cooled to ambient temperature. The mixture was stirred with saturated NaHCO$_3$ (10 mL) and EtOAc (10 mL) for 10 minutes and the layers separated. The aqueous layer was extracted with EtOAc (2×10 mL) and the combined organic phases were washed with brine (10 mL), dried over Na$_2$SO$_4$, filtered and concentrated. The residue was purified by reverse phase HPLC (0-95% acetonitrile/water/0.1% TFA over 20 min) and clean fractions were worked up with saturated NaHCO$_3$/EtOAc to afford 8-((4-bromo-2-fluorophenyl)amino)-2-(2-hydroxyethoxy)-5,7-dimethyl-3,4-dihydro-2,7-naphthyridine-1,6(2H,7H)-dione (18 mg, 52%). $^1$H NMR (400 MHz, CDCl$_3$) δ 10.96 (s, 1H), 7.31 (dd, 1H), 7.20 (dt, 1H), 6.68 (t, 1H), 4.05-4.01 (m, 2H), 3.75-3.69 (m, 4H), 3.23 (s, 3H), 3.03 (t, 2H), 2.08 (s, 3H) ppm; MS (apci, m/z)=440.0 (M+H).

Example 37

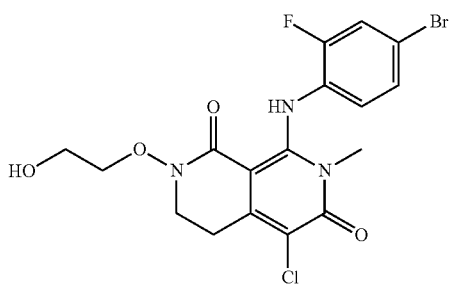 [SMILES: Cn1c(Nc2ccc(Br)cc2F)c2c(c(F)c1=O)CCN(OCCO)C2=O]

8-((4-bromo-2-fluorophenyl)amino)-5-chloro-2-(2-hydroxyethoxy)-7-methyl-3,4-dihydro-2,7-naphthyridine-1,6(2H,7H)-dione Step 1. Preparation of 8-((4-bromo-2-fluorophenyl)amino)-2-(2-(tert-butoxy)ethoxy)-7-methyl-3,4-dihydro-2,7-naphthyridine-1,6(2H,7H)-dione. Prepared according to Example 6, steps 1-7 of Method A, substituting 4-bromo-2-fluoroaniline in place of 2-fluoro-4-(methylthio)aniline in step 7 to afford 8-((4-bromo-2-fluorophenyl)amino)-2-(2-(tert-butoxy)ethoxy)-7-methyl-3,4-dihydro-2,7-naphthyridine-1,6(2H,7H)-dione (28 mg, 35%). MS (apci, m/z)=482.1 (M+H).

Step 2. Preparation of 8-((4-bromo-2-fluorophenyl)amino)-2-(2-(tert-butoxy)ethoxy)-5-chloro-7-methyl-3,4-dihydro-2,7-naphthyridine-1,6(2H,7H)-dione. To a solution of 8-((4-bromo-2-fluorophenyl)amino)-2-(2-(tert-butoxy)ethoxy)-7-methyl-3,4-dihydro-2,7-naphthyridine-1,6(2H,7H)-dione (28 mg, 0.058 mmol) in DMF (0.5 mL) was added NCS (8 mg, 0.058 mmol). The mixture was stirred at ambient temperature for 1 hour, then at 50° C. for 2 hours. The cooled mixture was partitioned between saturated NaHCO$_3$ (10 mL) and EtOAc (10 mL) and the aqueous layer was extracted with EtOAc (2×10 mL). The combined organic phases were washed with water (5×10 mL) and brine (10 mL) then dried over Na$_2$SO$_4$, filtered and concentrated. The residue was purified by column chromatography eluting with 0-50% EtOAc/hexanes to afford 8-((4-bromo-2-fluorophenyl)amino)-2-(2-(tert-butoxy)ethoxy)-5-chloro-7-methyl-3,4-dihydro-2,7-naphthyridine-1,6(2H,7H)-dione (14 mg, 47%). MS (apci, m/z)=516.0 (M+H).

Step 3. Preparation of 8-((4-bromo-2-fluorophenyl)amino)-5-chloro-2-(2-hydroxyethoxy)-7-methyl-3,4-dihydro-2,7-naphthyridine-1,6(2H,7H)-dione. To a solution of 8-((4-bromo-2-fluorophenyl)amino)-2-(2-(tert-butoxy)ethoxy)-5-chloro-7-methyl-3,4-dihydro-2,7-naphthyridine-1,6(2H,7H)-dione (14 mg, 0.027 mmol) in acetonitrile (0.5 mL) was added phosphoric acid (0.5 mL). The mixture was warmed to 60° C. for 30 minutes then cooled to ambient temperature. The mixture was stirred with saturated NaHCO$_3$ (10 mL) and EtOAc (10 mL) for 10 minutes and the layers separated. The aqueous layer was extracted with EtOAc (2×10 mL) and the combined organic phases were washed with brine (10 mL), dried over Na$_2$SO$_4$, filtered and concentrated. The residue was purified by column chromatography eluting with 0-15% (20% MeOH/DCM)/DCM to afford 8-((4-bromo-2-fluorophenyl)amino)-5-chloro-2-(2-hydroxyethoxy)-7-methyl-3,4-dihydro-2,7-naphthyridine-1,6(2H,7H)-dione (11 mg, 88%). $^1$H NMR (400 MHz, CDCl$_3$) δ 11.22 (s, 1H), 7.33 (dd, 1H), 7.26 (dt, 1H), 6.78 (t, 1H), 4.07-4.02 (m, 2H), 3.78-3.70 (m, 4H), 3.25 (s, 3H), 3.22 (t, 2H) ppm; MS (apci, m/z)=460.0 (M+H).

Example 38

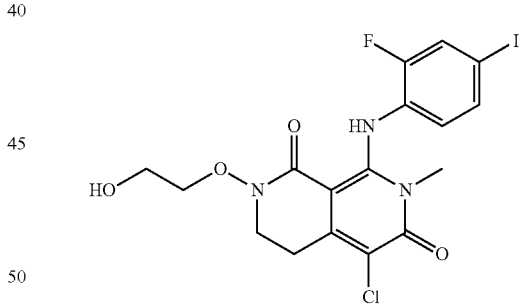

5-chloro-8-((2-fluoro-4-iodophenyl)amino)-2-(2-hydroxyethoxy)-7-methyl-3,4-dihydro-2,7-naphthyridine-1,6(2H,7H)-dione Prepared according to Example 37, substituting 4-iodo-2-fluoroaniline in place of 4-bromo-2-fluoroaniline in Step 1 to afford 5-chloro-8-((2-fluoro-4-iodophenyl)amino)-2-(2-hydroxyethoxy)-7-methyl-3,4-dihydro-2,7-naphthyridine-1,6(2H,7H)-dione (10 mg, 93%). $^1$H NMR (400 MHz, CDCl$_3$) δ 11.21 (s, 1H), 7.49 (dd, 1H), 7.43 (dt, 1H), 6.63 (t, 1H), 4.25-4.17 (m, 1H), 4.07-4.02 (m, 2H), 3.79-3.70 (m, 4H), 3.25 (s, 3H), 3.22 (t, 2H) ppm; MS (apci, m/z)=508.0 (M+H).

Example 39

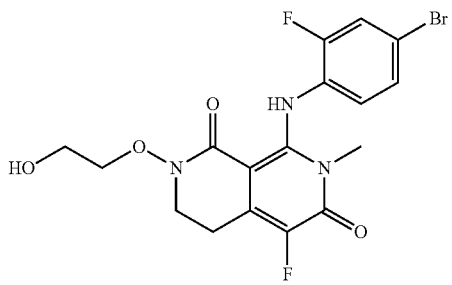

8-((4-bromo-2-fluorophenyl)amino)-5-fluoro-2-(2-hydroxyethoxy)-7-methyl-3,4-dihydro-2,7-naphthyridine-1,6(2H,7H)-dione Step 1. Preparation of 8-((4-bromo-2-fluorophenyl)amino)-2-(2-(tert-butoxy)ethoxy)-5-fluoro-7-methyl-3,4-dihydro-2,7-naphthyridine-1,6(2H,7H)-dione. A solution of 8-((4-bromo-2-fluorophenyl)amino)-2-(2-(tert-butoxy)ethoxy)-7-methyl-3,4-dihydro-2,7-naphthyridine-1,6(2H, 7H)-dione (77 mg, 0.16 mmol) and 1-(chloromethyl)-4-fluoro-1,4-diazabicyclo[2.2.2]octane-1,4-diium tetrafluoroborate (57 mg, 0.16 mmol) in acetonitrile (9.0 mL) was stirred at 0° C. for 1 hour. The reaction mixture was diluted with EtOAc (50 mL) and washed with water (25 mL) followed by brine (25 mL). The organic phase was dried over Na$_2$SO$_4$, filtered and concentrated. The residue was purified by reverse phase HPLC (5-95% acetonitrile/water/ 0.1% TFA over 20 minutes). The fractions containing the desired product were combined and diluted with saturated NaHCO$_3$ (15 mL) then extracted with EtOAc (2×25 mL). The organic phases were combined and dried over Na$_2$SO$_4$, filtered and concentrated to afford 8-((4-bromo-2-fluorophenyl)amino)-2-(2-(tert-butoxy)ethoxy)-5-fluoro-7-methyl-3,4-dihydro-2,7-naphthyridine-1,6(2H,7H)-dione (10 mg, 13%). MS (apci, m/z)=500.1 (M+H).

Step 2. Preparation of 8-((4-bromo-2-fluorophenyl)amino)-5-fluoro-2-(2-hydroxyethoxy)-7-methyl-3,4-dihydro-2,7-naphthyridine-1,6(2H,7H)-dione. A solution of 8-((4-bromo-2-fluorophenyl)amino)-2-(2-(tert-butoxy)ethoxy)-5-fluoro-7-methyl-3,4-dihydro-2,7-naphthyridine-1,6(2H,7H)-dione (13 mg, 0.026 mmol) and conc. H$_3$PO$_4$ (0.20 mL, 3.0 mmol) in acetonitrile (1.0 mL) was stirred at 60° C. for 1 hour. The reaction mixture was concentrated then diluted with K$_3$PO$_4$ (1M in water, 3.0 mL, 3.0 mmol). The aqueous phase was extracted with EtOAc (2×15 mL) and the organic phases were combined, dried over Na$_2$SO$_4$, filtered and concentrated. The residue was purified by HPLC (10-95% acetonitrile/water/0.1% TFA). The fractions containing the desired product were combined and diluted with saturated NaHCO$_3$ (15 mL). The aqueous was extracted with EtOAc (2×15 mL) and the organic phases were combined, dried over Na$_2$SO$_4$, filtered and concentrated to afford 8-((4-bromo-2-fluorophenyl)amino)-5-fluoro-2-(2-hydroxyethoxy)-7-methyl-3,4-dihydro-2,7-naphthyridine-1,6 (2H,7H)-dione (5.0 mg, 43%). 1H NMR (400 MHz, CDCl3) δ 10.79 (s, 1H), 7.34-7.30 (m, 1H), 7.25-7.21 (m, 1H), 6.72 (t, 1H), 4.23 (t, 1H), 4.06-4.02 (m, 2H), 3.80-3.70 (m, 4H), 3.25 (s, 3H), 3.17-3.12 (m, 2H) ppm; MS (apci, m/z)=444.0 (M+H).

Example 40

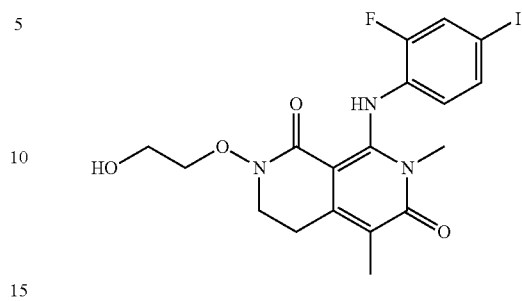

8-((2-fluoro-4-iodophenyl)amino)-2-(2-hydroxyethoxy)-5,7-dimethyl-3,4-dihydro-2,7-naphthyridine-1,6(2H,7H)-dione Step 1. Preparation of 2-(2-(tert-butoxy)ethoxy)-8-((2-fluoro-4-iodophenyl)amino)-5,7-dimethyl-3,4-dihydro-2,7-naphthyridine-1,6(2H,7H)-dione. 8-((4-Bromo-2-fluorophenyl)amino)-2-(2-(tert-butoxy)ethoxy)-5,7-dimethyl-3,4-dihydro-2,7-naphthyridine-1,6(2H,7H)-dione (Prepared according to Example 36, Steps 1-3; 65 mg, 0.13 mmol), copper(I) iodide (6.2 mg, 0.033 mmol), sodium iodide (39 mg, 0.26 mmol), and (1S,2S)—N1,N2-dimethylcyclohexane-1,2-diamine (9.3 mg, 0.065 mmol) were combined in 1,4-dioxane (1 mL) and sparged with argon. The mixture was heated at 110° C. for 18 hours then at ambient temperature for 48 hours. The mixture was partitioned between EtOAc (20 mL) and ammonium hydroxide (10 mL/water 10 mL). The organic phase was separated and the aqueous extracted with EtOAc (2×10 mL). Combined organic phases were washed with brine (10 mL), dried over Na$_2$SO$_4$, filtered and concentrated. The residue was purified by column chromatography eluting with 0-80% EtOAc/heptane to afford 2-(2-(tert-butoxy)ethoxy)-8-((2-fluoro-4-iodophenyl) amino)-5,7-dimethyl-3,4-dihydro-2,7-naphthyridine-1,6 (2H,7H)-dione (49 mg, 69%). MS (apci, m/z)=544.1 (M+H).

Step 2. Preparation of 8-((2-fluoro-4-iodophenyl)amino)-2-(2-hydroxyethoxy)-5,7-dimethyl-3,4-dihydro-2,7-naphthyridine-1,6(2H,7H)-dione. To a solution of 2-(2-(tert-butoxy)ethoxy)-8-((2-fluoro-4-iodophenyl)amino)-5,7-dimethyl-3,4-dihydro-2,7-naphthyridine-1,6(2H,7H)-dione (49 mg, 0.09 mmol) in acetonitrile (1 mL) was added phosphoric acid (0.5 mL). The mixture was warmed to 60° C. for 1 hour then cooled to ambient temperature. The mixture was stirred with saturated NaHCO$_3$ (10 mL) and EtOAc (10 mL) for 10 minutes and the layers separated. The aqueous layer was extracted with EtOAc (2×10 mL) and the combined organic phases were washed with brine (10 mL), dried over Na$_2$SO$_4$, filtered and concentrated. The residue was purified by reverse phase HPLC (5-95% acetonitrile/ H$_2$O/0.1% TFA over 20 min) and clean fractions were worked up with EtOAc/saturated NaHCO$_3$ to afford 8-((2-fluoro-4-iodophenyl)amino)-2-(2-hydroxyethoxy)-5,7-dimethyl-3,4-dihydro-2,7-naphthyridine-1,6(2H,7H)-dione (23 mg, 52%). $^1$H NMR (400 MHz, CDCl$_3$) δ 10.95 (s, 1H), 7.47 (dd, 1H), 7.37 (dt, 1H), 6.52 (t, 1H), 4.05-4.02 (m, 2H), 3.75-3.65 (m, 4H), 3.24 (s, 3H), 3.03 (t, 2H), 3.02 (s, 3H) ppm; MS (apci, m/z)=488.0 (M+H).

Example 41

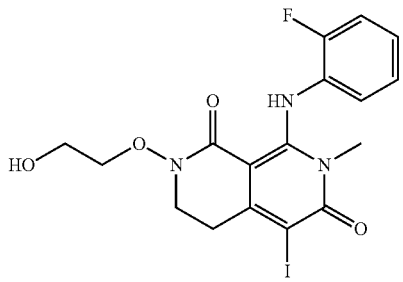 [SMILES: Cn1c(Nc2ccccc2F)c2c(c(I)c1=O)CCN(OCCO)C2=O]

8-((2-fluorophenyl)amino)-2-(2-hydroxyethoxy)-5-iodo-7-methyl-3,4-dihydro-2,7-naphthyridine-1,6(2H,7H)-dione Step 1. Preparation of methyl 4-bromo-2-((2-fluorophenyl)amino)-1-methyl-6-oxo-1,6-dihydropyridine-3-carboxylate. To a solution of 2-fluoroaniline (100 mg, 0.90 mmol) in anhydrous THF (5 mL) at −78° C. under N₂ was added LiHMDS (1.34 mL, 1.0 M/THF, 1.34 mmol). The mixture was stirred for 45 minutes, then a solution of methyl 4-bromo-2-chloro-1-methyl-6-oxo-1,6-dihydropyridine-3-carboxylate (250 mg, 0.89 mmol) in THF (5 mL) was added. The mixture was stirred at −78° C. for 50 minutes. Additional LiHMDS (0.5 mL, 1.0 M/THF, 0.5 mmol) was added and stirring continued for another 10 minutes. The mixture was quenched with saturated NH₄Cl (20 mL), stirred at ambient temperature for 10 minutes, then extracted with EtOAc (3×20 mL). The combined organic phases were washed with brine (10 mL), dried over sodium sulfate, filtered, and concentrated to afford methyl 4-bromo-2-((2-fluorophenyl)amino)-1-methyl-6-oxo-1,6-dihydropyridine-3-carboxylate (291 mg, 92%). MS (apci, m/z)=355.0 (M+H).

Step 2. Preparation of methyl (E)-4-(2-ethoxyvinyl)-2-((2-fluorophenyl)amino)-1-methyl-6-oxo-1,6-dihydropyridine-3-carboxylate. Methyl 4-bromo-2-((2-fluorophenyl)amino)-1-methyl-6-oxo-1,6-dihydropyridine-3-carboxylate (188 mg, 0.529 mmol), methanesulfonato(2-dicyclohexylphosphino-2',6'-di-i-'propoxy-1,1'-biphenyl)'2-amino-1,1'-biphenyl-2-yl)palladium(II) (44.3 g, 0.053 mmol), and (E)-2-(2-ethoxyvinyl)-4,4,5,5-tetramethyl-1,3,2-dioxaborolane (123 µL, 0.582 mmol) were suspended in 1,4-dioxane (5 mL) and potassium carbonate (0.397 mL, 2N aq, 0.794 mmol) was added. After degassing with argon, the mixture was stirred at ambient temperature for 23 hours. The reaction was partitioned between water (40 mL) and EtOAc (30 mL). The aqueous layer was washed with EtOAc (2×15 mL). The combined organic layers were washed with brine (40 mL), dried over sodium sulfate, and concentrated. The residue was purified by column chromatography eluting with 0-50% EtOAc/hexanes to methyl (E)-4-(2-ethoxyvinyl)-2-((2-fluorophenyl)amino)-1-methyl-6-oxo-1,6-dihydropyridine-3-carboxylate (91.5 mg, 50%). MS (apci, m/z)=347.1 (M+H).

Step 3. Preparation of methyl (E)-4-(2-((2-(tert-butoxy)ethoxy)imino)ethyl)-2-((2-fluorophenyl)amino)-1-methyl-6-oxo-1,6-dihydropyridine-3-carboxylate. Methyl (E)-4-(2-ethoxyvinyl)-2-((2-fluorophenyl)amino)-1-methyl-6-oxo-1,6-dihydropyridine-3-carboxylate (91.5 mg, 0.264 mmol) and O-(2-(tert-butoxy)ethyl)hydroxylamine hydrochloride (44.8 mg, 0.264 mmol) were taken up in 1,4-dioxane (2 mL). TEA (36.8 µL, 0.264 mmol) and HCl (66 µL, 4N/dioxane, 0.264 mmol) were added. The suspension was heated to 60° C. After 2 hours, additional HCl (66 µL, 4N/dioxane, 0.264 mmol) was added and stirring continued at 60° C. for another 2 hours. The reaction mixture was filtered and concentrated. The residue was purified by column chromatography eluting with 0-40% EtOAc/hexanes to afford methyl (E)-4-(2-((2-(tert-butoxy)ethoxy)imino)ethyl)-2-((2-fluorophenyl)amino)-1-methyl-6-oxo-1,6-dihydropyridine-3-carboxylate (67.6 mg, 59%). MS (apci, m/z)=434.2 (M+H).

Step 4. Preparation of 2-(2-(tert-butoxy)ethoxy)-8-((2-fluorophenyl)amino)-7-methyl-3,4-dihydro-2,7-naphthyridine-1,6(2H,7H)-dione. Methyl (E)-4-(2-((2-(tert-butoxy)ethoxy)imino)ethyl)-2-((2-fluorophenyl)amino)-1-methyl-6-oxo-1,6-dihydropyridine-3-carboxylate (67.6 mg, 0.156 mmol) was dissolved in MeOH (1.0 mL) and 2-propanol (1.0 mL). Sodium cyanoborohydride (49 mg, 0.780 mmol) and acetic acid (44.6 µL, 0.780 mmol) were added, and the mixture was stirred at ambient temperature for 16 hours. The reaction was heated at 40° C. for 16 hours. The reaction was partitioned between saturated bicarbonate (20 mL) and EtOAc (10 mL). The aqueous layer was washed EtOAc (2×10 mL). The combined organic layers were dried over sodium sulfate, filtered, and concentrated. The residue was purified by column chromatography eluting with 0-80% EtOAc/hexanes to afford 2-(2-(tert-butoxy)ethoxy)-8-((2-fluorophenyl)amino)-7-methyl-3,4-dihydro-2,7-naphthyridine-1,6(2H,7H)-dione (37.8 mg, 60%). MS (apci, m/z)=404.2 (M+H).

Step 5. Preparation of 2-(2-(tert-butoxy)ethoxy)-8-((2-fluorophenyl)amino)-5-iodo-7-methyl-3,4-dihydro-2,7-naphthyridine-1,6(2H,7H)-dione. 2-(2-(tert-butoxy)ethoxy)-8-((2-fluorophenyl)amino)-7-methyl-3,4-dihydro-2,7-naphthyridine-1,6(2H,7H)-dione (19 mg, 0.047 mmol) was dissolved in THF (0.5 mL) and MeOH (0.5 mL). p-Toluenesulfonic acid monohydrate (13 mg, 0.071 mmol) was added. After 5 minutes, N-Iodosuccinimide (11 mg, 0.047 mmol) was added and left to stir for 1 hour. The reaction mixture was partitioned between EtOAc (20 mL) and saturated bicarbonate (40 mL). The aqueous layer was washed with EtOAc (2×15 mL). The combined organic layers were washed with brine (20 mL), dried over sodium sulfate, filtered, and concentrated. The residue was purified by column chromatography eluting with 0-30% EtOAc/hexanes to afford 2-(2-(tert-butoxy)ethoxy)-8-((2-fluorophenyl)amino)-5-iodo-7-methyl-3,4-dihydro-2,7-naphthyridine-1,6(2H,7H)-dione (9.9 mg, 40%). MS (apci, m/z)=530.1 (M+H).

Step 6. Preparation of 8-((2-fluorophenyl)amino)-2-(2-hydroxyethoxy)-5-iodo-7-methyl-3,4-dihydro-2,7-naphthyridine-1,6(2H,7H)-dione. 2-(2-(tert-butoxy)ethoxy)-8-((2-fluorophenyl)amino)-5-iodo-7-methyl-3,4-dihydro-2,7-naphthyridine-1,6(2H,7H)-dione (9.9 mg, 0.019 mmol) was dissolved in acetonitrile (0.5 mL) and phosphoric acid (0.5 mL) was added. The solution was heated to 60° C. for 1 hour. The reaction mixture was partitioned between saturated bicarbonate (15 mL) and EtOAc (10 mL). The aqueous layer was washed with EtOAc (2×8 mL). The combined organic layers were washed with brine (15 mL), dried over sodium sulfate, filtered, and concentrated. The residue was purified by reverse phase HPLC (5-95% acetonitrile/water/0.1% TFA over 20 minutes) and the clean fractions were combined, washed with saturated bicarbonate, and extracted with EtOAc (3×10 mL). The combined organic layers were washed with saturated bicarbonate (20 mL) and brine (20 mL), dried over sodium sulfate, filtered, and concentrated to afford (8-((2-fluorophenyl)amino)-2-(2-hydroxyethoxy)-5-iodo-7-methyl-3,4-dihydro-2,7-naphthyridine-1,6(2H,7H)-dione (4.5 mg, 51%). ¹H NMR (400 MHz, CDCl₃) δ 11.41 (s, 1H), 7.21-7.08 (m, 3H), 6.94 (t, 1H), 4.04 (t, 2H), 3.76-3.69 (m, 4H), 3.25 (s, 3H), 3.19 (t, 2H) ppm; MS (apci, m/z)=474.0 (M+H).

Example 42

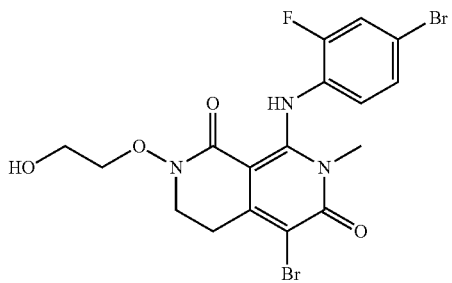

5-bromo-8-((4-bromo-2-fluorophenyl)amino)-2-(2-hydroxyethoxy)-7-methyl-3,4-dihydro-2,7-naphthyridine-1,6(2H,7H)-dione Prepared according to Example 41, substituting 4-bromo-2-fluoro aniline in place of 2-fluoroaniline in step 1 and N-bromosuccinimide in step 5 to afford 5-bromo-8-((4-bromo-2-fluorophenyl)amino)-2-(2-hydroxyethoxy)-7-methyl-3,4-dihydro-2,7-naphthyridine-1,6(2H,7H)-dione (6.5 mg, 29%). ¹H NMR (400 MHz, CDCl₃) δ 11.28 (s, 1H), 7.33 (dd, 1H), 7.25 (m, 1H), 6.80 (t, 1H), 4.05 (t, 2H), 3.78-3.70 (m, 4H), 3.25 (s, 3H), 3.22 (t, 2H) ppm; MS (apci, m/z)=504.0 (M+H).

Example 43

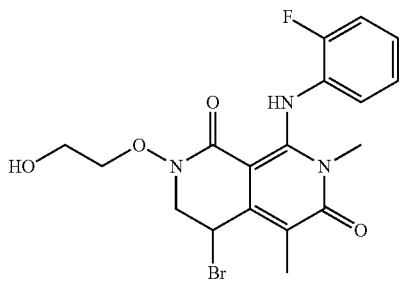 [SMILES: Cc1c2c(c(Nc3ccccc3F)n(C)c1=O)C(=O)N(OCCO)CC2Br]

4-bromo-8-((2-fluorophenyl)amino)-2-(2-hydroxyethoxy)-5,7-dimethyl-3,4-dihydro-2,7-naphthyridine-1,6(2H,7H)-dione Step 1. Preparation of 2-(2-(tert-butoxy)ethoxy)-8-((2-fluorophenyl)amino)-5,7-dimethyl-3,4-dihydro-2,7-naphthyridine-1,6(2H,7H)-dione. To a solution of 2-(2-(tert-butoxy)ethoxy)-8-((2-fluorophenyl)amino)-5-iodo-7-methyl-3,4-dihydro-2,7-naphthyridine-1,6(2H,7H)-dione (75 mg, 0.14 mmol) in anhydrous THF (5 mL) at ambient temperature was added methylzinc(II)chloride (140 mL, 2M, 0.14 mmol). After stirring for 5 minutes, the mixture was concentrated. The residue was purified by column chromatography eluting with 0-80% EtOAc/hexanes to afford 2-(2-(tert-butoxy)ethoxy)-8-((2-fluorophenyl)amino)-5,7-dimethyl-3,4-dihydro-2,7-naphthyridine-1,6(2H,7H)-dione (38 mg, 64%). MS (apci, m/z)=418.2 (M+H).

Step 2. Preparation of 4-bromo-2-(2-(tert-butoxy)ethoxy)-8-((2-fluorophenyl)amino)-5,7-dimethyl-3,4-dihydro-2,7-naphthyridine-1,6(2H,7H)-dione. To a solution of 2-(2-(tert-butoxy)ethoxy)-8-((2-fluorophenyl)amino)-5,7-dimethyl-3,4-dihydro-2,7-naphthyridine-1,6(2H,7H)-dione (38 mg, 0.09 mmol) in anhydrous DMF (1 mL) was added NBS (17 mg, 0.09 mmol). The mixture was stirred at ambient temperature for 2 hours then partitioned between saturated NaHCO₃ (10 mL) and EtOAc (10 mL). The aqueous layer was extracted with EtOAc (2×10 mL) and the combined organic phases were washed with water (5×10 mL) and brine (10 mL) then dried over Na₂SO₄, filtered and concentrated. The residue was purified by column chromatography eluting with 0-60% EtOAc/hexanes to afford 4-bromo-2-(2-(tert-butoxy)ethoxy)-8-((2-fluorophenyl)amino)-5,7-dimethyl-3,4-dihydro-2,7-naphthyridine-1,6(2H,7H)-dione (30 mg, 66%). MS (apci, m/z)=496.2 (M+H).

Step 3. Preparation of 4-bromo-8-((2-fluorophenyl)amino)-2-(2-hydroxyethoxy)-5,7-dimethyl-3,4-dihydro-2,7-naphthyridine-1,6(2H,7H)-dione. To a solution of 4-bromo-2-(2-(tert-butoxy)ethoxy)-8-((2-fluorophenyl)amino)-5,7-dimethyl-3,4-dihydro-2,7-naphthyridine-1,6(2H,7H)-dione (30 mg, 0.060 mmol) in acetonitrile (0.5 mL) was added phosphoric acid (0.5 mL). The mixture was warmed to 60° C. for 1 hour then cooled and stirred with saturated NaHCO₃ (10 mL) and EtOAc (10 mL) for 10 minutes. Layers were separated and the aqueous layer was extracted with EtOAc (2×10 mL). The combined organic phases were washed with brine (10 mL), dried over Na₂SO₄, filtered and concentrated. The residue was purified by column chromatography eluting with 0-15% (20% MeOH/DCM)/DCM to afford 4-bromo-8-((2-fluorophenyl)amino)-2-(2-hydroxyethoxy)-5,7-dimethyl-3,4-dihydro-2,7-naphthyridine-1,6(2H,7H)-dione (10 mg, 38%). ¹H NMR (400 MHz, CDCl₃) δ 11.08 (s, 1H), 7.15-7.05 (m, 2H), 6.86 (t, 1H), 5.36 (t, 1H), 4.17-4.04 (m, 3H), 3.99-3.92 (m, 1H), 3.88 (dd, 1H), 3.68 (dt, 1H), 3.21 (s, 3H), 2.17 (s, 3H), 1.26 (t, 1H) ppm; MS (apci, m/z)=440.1 (M+H).

Example 44

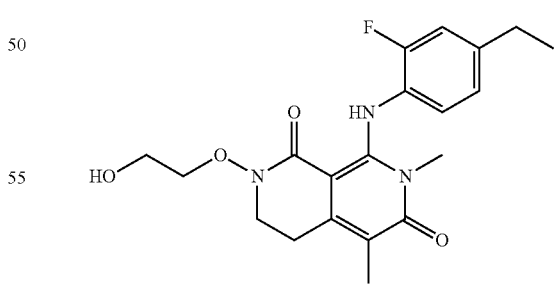

8-((4-ethyl-2-fluorophenyl)amino)-2-(2-hydroxyethoxy)-5,7-dimethyl-3,4-dihydro-2,7-naphthyridine-1,6(2H,7H)-dione Step 1. Preparation of methyl (Z)-4-(2-ethoxyvinyl)-2-((4-ethyl-2-fluorophenyl)amino)-1-methyl-6-oxo-1,6-dihydropyridine-3-carboxylate. To a solution of 4-ethyl-2-fluoroaniline (155 mg, 1.12 mmol) in anhydrous THF (2 mL) at −78° C. under $N_2$ was added LiHMDS (2.21 mL, 1M/THF, 2.21 mmol). The mixture was stirred for 40 minutes, then a solution of methyl (Z)-2-chloro-4-(2-ethoxyvinyl)-1-methyl-6-oxo-1,6-dihydropyridine-3-carboxylate (300 mg, 1.10 mmol) in THF (1 mL) was added via syringe. The mixture was stirred at −78° C. for 45 minutes. The mixture was quenched with saturated $NH_4Cl$ (35 mL), stirred at ambient temperature for 5 minutes, then extracted with EtOAc (3×15 mL). The combined organic phases were washed with brine (30 mL), dried over sodium sulfate, filtered, and concentrated. The residue was purified by column chromatography eluting with 0-50% EtOAc/heptane to afford methyl (Z)-4-(2-ethoxyvinyl)-2-((4-ethyl-2-fluorophenyl)amino)-1-methyl-6-oxo-1,6-dihydropyridine-3-carboxylate (298 mg, 72%). MS (apci, m/z)=375.2 (M+H).

Step 2. Preparation of methyl 2-((4-ethyl-2-fluorophenyl)amino)-1-methyl-6-oxo-4-(2-oxoethyl)-1,6-dihydropyridine-3-carboxylate. Methyl (Z)-4-(2-ethoxyvinyl)-2-((4-ethyl-2-fluorophenyl)amino)-1-methyl-6-oxo-1,6-dihydropyridine-3-carboxylate (298 mg, 0.797 mmol) was dissolved in DCM (800 μL) and TFA (921 μL, 11.9 mmol) was added. The reaction was stirred at ambient temperature for 16 hours. The mixture was partitioned between DCM (20 mL) and saturated sodium bicarbonate (35 mL). The aqueous layer was washed with DCM (2×15 mL). The combined organic layers were washed with saturated sodium bicarbonate (30 mL), dried over sodium sulfate, filtered and concentrated to afford methyl 2-((4-ethyl-2-fluorophenyl)amino)-1-methyl-6-oxo-4-(2-oxoethyl)-1,6-dihydropyridine-3-carboxylate (276 mg, 100%). MS (apci, m/z)=347.1 (M+H).

Step 3. Preparation of 2-(2-(tert-butoxy)ethoxy)-8-((4-ethyl-2-fluorophenyl)amino)-7-methyl-3,4-dihydro-2,7-naphthyridine-1,6(2H,7H)-dione. Methyl 2-((4-ethyl-2-fluorophenyl)amino)-1-methyl-6-oxo-4-(2-oxoethyl)-1,6-dihydropyridine-3-carboxylate (276 mg, 0.797 mmol), O-(2-(tert-butoxy)ethyl)hydroxylamine hydrochloride (117 mg, 0.876 mmol), sodium triacetoxyhydroborate (203 mg, 0.956 mmol), and acetic acid (45.6 μL, 0.797 mmol) were taken up in DCE (8 mL). The reaction was stirred at ambient temperature for 1 hour. The reaction was heated to 55° C. for 20 minutes. More sodium triacetoxyhydroborate (400 mg) and acetic acid (90 μL) were added to the reaction and stirred at ambient temperature for 16 hours. Sodium cyanoborohydride (250 mg, 3.98 mmol) and acetic acid (250 μL) were added to the reaction and allowed to stir at ambient temperature for 3 hours. The solution was partitioned between DCM (40 mL) and saturated sodium bicarbonate (70 mL). The aqueous layer was washed with DCM (2×20 mL). The combined organic layers were washed with brine (50 mL), dried over sodium sulfate, filtered and concentrated. The residue was purified by column chromatography eluting with 0-100% EtOAc/heptane to afford 2-(2-(tert-butoxy)ethoxy)-8-((4-ethyl-2-fluorophenyl)amino)-7-methyl-3,4-dihydro-2,7-naphthyridine-1,6(2H,7H)-dione (137 mg, 40%). MS (apci, m/z)=432.2 (M+H).

Step 4. Preparation of 2-(2-(tert-butoxy)ethoxy)-8-((4-ethyl-2-fluorophenyl)amino)-5-iodo-7-methyl-3,4-dihydro-2,7-naphthyridine-1,6(2H,7H)-dione. 2-(2-(tert-Butoxy)ethoxy)-8-((4-ethyl-2-fluorophenyl)amino)-7-methyl-3,4-dihydro-2,7-naphthyridine-1,6(2H,7H)-dione (137 mg, 0.317 mmol) was dissolved in THF (1 mL)/MeOH (1 mL). p-Toluenesulfonic acid monohydrate (90.4 mg, 0.475 mmol) was added. After 5 minutes, N-iodosuccinimide (71.3 mg, 0.317 mmol) was added and left to stir for 30 minutes. The reaction mixture was partitioned between EtOAc (20 mL) and saturated sodium bicarbonate (30 mL) and the aqueous layer was extracted with EtOAc (2×10 mL). The combined organic phases were washed with brine (25 mL), dried over sodium sulfate, filtered, and concentrated to afford 2-(2-(tert-butoxy)ethoxy)-8-((4-ethyl-2-fluorophenyl)amino)-5-iodo-7-methyl-3,4-dihydro-2,7-naphthyridine-1,6(2H,7H)-dione (143 mg, 81%). MS (apci, m/z)=558.1 (M+H).

Step 5. Preparation of 2-(2-(tert-butoxy)ethoxy)-8-((4-ethyl-2-fluorophenyl)amino)-5,7-dimethyl-3,4-dihydro-2,7-naphthyridine-1,6(2H,7H)-dione. To a solution of 2-(2-(tert-butoxy)ethoxy)-8-((4-ethyl-2-fluorophenyl)amino)-5-iodo-7-methyl-3,4-dihydro-2,7-naphthyridine-1,6(2H,7H)-dione (143 mg, 0.256 mmol) in THF (2.5 mL, 0.256 mmol) at 0° C. was added $Pd(Pt-Bua)_2$ (13.1 mg, 0.026 mmol) followed by methylzinc(II) chloride (130 μL, 0.259 mmol). The mixture was removed from the ice bath and stirred for 45 minutes. The mixture was partitioned between saturated $NH_4Cl$ (50 mL) and EtOAc (20 mL) and the aqueous layer was extracted with EtOAc (2×15 mL). The combined organic phases were washed with brine (40 mL), dried over sodium sulfate, filtered, and concentrated. The residue was purified by column chromatography eluting with 0-50% EtOAc/heptane to afford 2-(2-(tert-butoxy)ethoxy)-8-((4-ethyl-2-fluorophenyl)amino)-5,7-dimethyl-3,4-dihydro-2,7-naphthyridine-1,6(2H,7H)-dione (53.7 mg, 47%). MS (apci, m/z)=446.2 (M+H).

Step 6. Preparation of 8-((4-ethyl-2-fluorophenyl)amino)-2-(2-hydroxyethoxy)-5,7-dimethyl-3,4-dihydro-2,7-naphthyridine-1,6(2H,7H)-dione. 2-(2-(tert-Butoxy)ethoxy)-8-((4-ethyl-2-fluorophenyl)amino)-5,7-dimethyl-3,4-dihydro-2,7-naphthyridine-1,6(2H,7H)-dione (53.7 mg, 0.121 mmol) was dissolved in acetonitrile (0.75 mL) and phosphoric acid (0.75 mL) was added. The reaction was heated to 60° C. for 60 minutes. The reaction mixture was partitioned between saturated sodium bicarbonate (40 mL) and EtOAc (20 mL). The aqueous layer was washed with EtOAc (2×10 mL). The combined organic layers were washed with saturated sodium bicarbonate (30 mL) and brine (25 mL), dried over sodium sulfate, filtered, and concentrated. The residue was purified by column chromatography eluting with 0-100% EtOAc/heptane to afford 8-((4-ethyl-2-fluorophenyl)amino)-2-(2-hydroxyethoxy)-5,7-dimethyl-3,4-dihydro-2,7-naphthyridine-1,6(2H,7H)-dione (40.6 mg, 87%). $^1$H NMR (400 MHz, $CDCl_3$) δ 11.01 (s, 1H), 6.95 (dd, 1H), 6.89 (dd, 1H), 6.77 (t, 1H), 4.53 (t, 1H), 4.02 (t, 2H), 3.75-3.67 (m, 4H), 3.20 (s, 3H), 3.02 (t, 2H), 2.62 (q, 2H), 2.08 (s, 3H), 1.22 (t, 3H) ppm; MS (apci, m/z)=390.2 (M+H).

Example 45

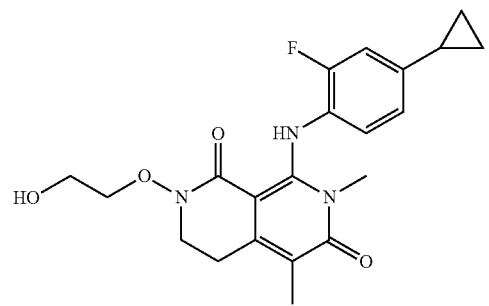 [SMILES: Cc1c2c(c(Nc3ccc(C4CC4)cc3F)n(C)c1=O)C(=O)N(OCCO)CC2]

8-((4-cyclopropyl-2-fluorophenyl)amino)-2-(2-hydroxyethoxy)-5,7-dimethyl-3,4-dihydro-2,7-naphthyridine-1,6(2H,7H)-dione Prepared according to Example 44 substituting 4-cyclopropyl-2-fluoroaniline in place of 4-ethyl-2-fluoroaniline in step 1 to afford 8-((4-cyclopropyl-2-fluorophenyl)amino)-2-(2-hydroxyethoxy)-5,7-dimethyl-3,4-dihydro-2,7-naphthyridine-1,6(2H,7H)-dione (30.7 mg, 75%). $^1$H NMR (400 MHz, CDCl$_3$) δ 11.00 (s, 1H), 6.81-6.71 (m, 3H), 4.52 (t, 1H), 4.02 (m, 2H), 3.75-3.66 (m, 4H), 3.19 (s, 3H), 3.02 (t, 2H), 2.07 (s, 3H), 1.86 (m, 1H), 1.02-0.95 (m, 2H), 0.69-0.63 (m, 2H) ppm; MS (apci, m/z)=402.2 (M+H).

Example 46

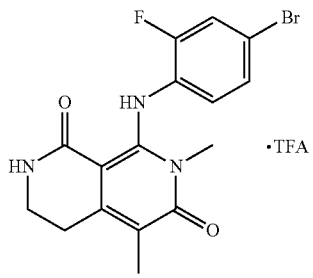 [SMILES: Cc1c2c(c(Nc3ccc(Br)cc3F)n(C)c1=O)C(=O)NCC2]

8-((4-bromo-2-fluorophenyl)amino)-7-methyl-3,4-dihydro-2,7-naphthyridine-1,6(2H,7H)-dione trifluoroacetate Step 1. Preparation of methyl (E)-2-((4-bromo-2-fluorophenyl)amino)-4-(2-ethoxyvinyl)-1-methyl-6-oxo-1,6-dihydropyridine-3-carboxylate. 4-Bromo-2-fluoroaniline (492 mg, 2.59 mmol) and methyl (E)-2-chloro-4-(2-ethoxyvinyl)-1-methyl-6-oxo-1,6-dihydropyridine-3-carboxylate (670 mg, 2.47 mmol) was dissolved in THF (12.3 mL, 0.2 M) and cooled to −78° C. under a nitrogen atmosphere. LiHMDS (4.9 mL, 1.0 M/THF, 4.9 mmol) was added dropwise, then the mixture allowed to warm from −78° C. to ambient temperature over 1 hour. The reaction mixture was quenched with saturated aq. NH$_4$Cl (15 mL), then extracted with EtOAc (2×10 mL). The combined organic phases were dried over MgSO$_4$, filtered, and concentrated. The residue was purified by column chromatography eluting with 0-100% EtOAc/Heptane to afford methyl (E)-2-((4-bromo-2-fluorophenyl)amino)-4-(2-ethoxyvinyl)-1-methyl-6-oxo-1,6-dihydropyridine-3-carboxylate (810 mg, 77%). MS (apci, m/z)=425.0 (M+H).

Step 2. Preparation of methyl 2-((4-bromo-2-fluorophenyl)amino)-1-methyl-6-oxo-4-(2-oxoethyl)-1,6-dihydropyridine-3-carboxylate. To a solution of methyl (E)-2-((4-bromo-2-fluorophenyl)amino)-4-(2-ethoxyvinyl)-1-methyl-6-oxo-1,6-dihydropyridine-3-carboxylate (810 mg, 1.90 mmol) in DCM (5.0 mL) was added TFA (5.0 mL). The solution was allowed to stir at ambient temperature for 16 hours, then concentrated. The crude mixture was then diluted with DCM (10 mL) and washed with saturated aq. NaHCO$_3$ (10 mL). The organic phase was dried over MgSO$_4$, filtered, and concentrated to afford methyl 2-((4-bromo-2-fluorophenyl)amino)-1-methyl-6-oxo-4-(2-oxoethyl)-1,6-dihydropyridine-3-carboxylate which was used without further purification (751 mg, 99%). MS (apci, m/z)=397.0, 399.0 (M+H).

Step 3. Preparation of 8-((4-bromo-2-fluorophenyl)amino)-2-(4-methoxybenzyl)-7-methyl-3,4-dihydro-2,7-naphthyridine-1,6(2H,7H)-dione. Methyl 2-((4-bromo-2-fluorophenyl)amino)-1-methyl-6-oxo-4-(2-oxoethyl)-1,6-dihydropyridine-3-carboxylate (751 mg, 1.89 mmol), (4-methoxyphenyl)methanamine (272 mg, 1.99 mmol), sodium triacetoxyborohydride (441 mg, 2.08 mmol), and acetic acid (11.4 mg, 0.189 mmol) were dissolved in DCE (19 mL) and allowed to stir at ambient temperature for 1 hour. The reaction was warmed to 60° C. and allowed to stir for 1 hour. The reaction was then cooled to ambient temperature, diluted with DCM (10 mL) and washed with saturated aq. NaHCO$_3$ (15 mL). The organic phase was dried over MgSO$_4$, filtered, and concentrated. The residue was purified by column chromatography eluting with 0-100% EtOAc/Heptane to afford 8-((4-bromo-2-fluorophenyl)amino)-2-(4-methoxybenzyl)-7-methyl-3,4-dihydro-2,7-naphthyridine-1,6(2H,7H)-dione (630 mg, 69%). MS (apci, m/z)=486.0 (M+H).

Step 4. Preparation of 8-((4-bromo-2-fluorophenyl)amino)-7-methyl-3,4-dihydro-2,7-naphthyridine-1,6(2H, 7H)-dione trifluoroacetate. 8-((4-bromo-2-fluorophenyl)amino)-2-(4-methoxybenzyl)-7-methyl-3,4-dihydro-2,7-naphthyridine-1,6(2H,7H)-dione (630 mg, 1.30 mmol) was dissolved in TFA (8.0 mL) and heated to 80° C. for 16 hours. The reaction was allowed to cool to ambient temperature and concentrated. The residue was purified by reverse phase HPLC (5-95% acetonitrile/H$_2$O/0.1% TFA). The fractions containing the clean desired product were lyophilized to afford 8-((4-bromo-2-fluorophenyl)amino)-7-methyl-3,4-dihydro-2,7-naphthyridine-1,6(2H,7H)-dione trifluoroacetate (226 mg, 48%). $^1$H NMR (400 MHz, CDCl$_3$) δ 11.28 (s, 1H), 7.32-7.29 (m, 1H), 7.23-7.20 (m, 1H), 6.74 (t, 1H), 6.05 (s, 1H), 5.62 (s, 1H), 3.51-3.47 (m, 2H), 3.20 (s, 3H), 2.84 (t, 2H) ppm. MS (apci, m/z)=366.0, 368.0 (M+H).

Example 47

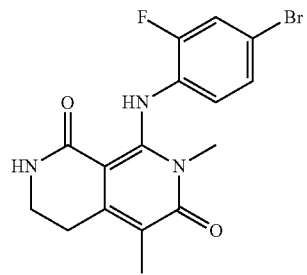 [SMILES: Cc1c2c(c(Nc3ccc(Br)cc3F)n(C)c1=O)C(=O)NCC2]

8-((4-bromo-2-fluorophenyl)amino)-5,7-dimethyl-3,4-dihydro-2,7-naphthyridine-1,6(2H,7H)-dione Step 1. Preparation of 8-((4-bromo-2-fluorophenyl)amino)-5-iodo-7-methyl-3,4-dihydro-2,7-naphthyridine-1,6 (2H,7H)-dione. 8-((4-bromo-2-fluorophenyl)amino)-7-methyl-3,4-dihydro-2,7-naphthyridine-1,6(2H,7H)-dione (Prepared according to Example 46; 41 mg, 0.11 mmol) and p-toluenesulfonic acid (29 mg, 0.17 mmol) were dissolved in 1 mL of a 1:1 THF/MeOH solution. After 5 minutes, NIS (25 mg, 0.11 mmol) was added. The reaction was allowed to stir at ambient temperature for 30 minutes. The crude reaction mixture was then partitioned between EtOAc (10 mL) and saturated aq. NaHCO$_3$ (15 mL) and extracted with EtOAc (2×5 mL). The combined organic phases were dried over MgSO$_4$, filtered, and concentrated to afford 8-((4-bromo-2-fluorophenyl)amino)-5-iodo-7-methyl-3,4-dihydro-2,7-naphthyridine-1,6(2H,7H)-dione which was used without further purification (55 mg, 100%). MS (apci, m/z)=493.9 (M+H).

Step 2. Preparation of 8-((4-bromo-2-fluorophenyl)amino)-5,7-dimethyl-3,4-dihydro-2,7-naphthyridine-1,6(2H,7H)-dione. 8-((4-bromo-2-fluorophenyl)amino)-5-iodo-7-methyl-3,4-dihydro-2,7-naphthyridine-1,6(2H,7H)-dione (55 mg, 0.112 mmol) and bis(tri-t-butylphosphine)palladium(0) (5.71 mg, 0.0112 mmol) were dissolved in THF (1.1 mL) and methylzinc(II) chloride (55.9 µL, 2M/THF, 0.112 mmol) was added dropwise. The reaction was allowed to stir at ambient temperature for 1 hour. The reaction mixture was quenched with saturated aq. NaHCO$_3$ (2 mL), then extracted with EtOAc (2×5 mL). The combined organic phases were dried over MgSO$_4$, filtered, and concentrated. The residue was purified by reverse phase chromatography eluting with 5-95% acetonitrile/H$_2$O to afford 8-((4-bromo-2-fluorophenyl)amino)-5,7-dimethyl-3,4-dihydro-2,7-naphthyridine-1,6(2H,7H)-dione (24 mg, 56%). $^1$H NMR (400 MHz, CDCl$_3$) δ 11.08 (s, 1H), 7.30-7.27 (m, 1H), 7.18-7.15 (m, 1H), 6.63 (t, 1H), 5.72 (s, 1H), 3.50-3.46 (m, 2H), 3.26 (s, 3H), 2.88 (t, 2H), 2.11 (s, 3H) ppm. MS (apci, m/z)=380.0 (M+H).

Example 48

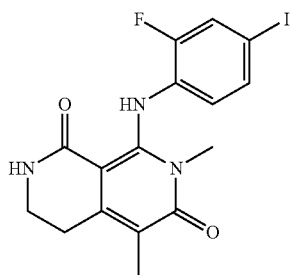 [SMILES: Cc1c2c(c(Nc3ccc(I)cc3F)n(C)c1=O)C(=O)NCC2]

8-((2-fluoro-4-iodophenyl)amino)-5,7-dimethyl-3,4-dihydro-2,7-naphthyridine-1,6(2H,7H)-dione 8-((4-bromo-2-fluorophenyl)amino)-5,7-dimethyl-3,4-dihydro-2,7-naphthyridine-1,6(2H,7H)-dione (Prepared according to Example 46; 20 mg, 0.053 mmol), copper(I) iodide (2.5 mg, 0.013 mmol), sodium iodide (16 mg, 0.11 mmol), and (1S,2S)—N1,N2-dimethylcyclohexane-1,2-diamine (3.7 mg, 0.026 mmol) were combined in 1,4-dioxane (0.5 mL). The reaction was heated to 120° C. for 16 hours. The reaction was then cooled to ambient temperature, quenched with saturated aq. NH$_4$Cl (2 mL), then extracted with EtOAc (2×5 mL). The combined organic phases were dried over MgSO$_4$, filtered, and concentrated. The residue was purified by reverse phase HPLC (5-95% acetonitrile/H$_2$O/0.1% TFA). Fractions containing the clean desired product were combined and the product was converted to the free base with DCM/NaHCO$_3$ to afford 8-((2-fluoro-4-iodophenyl)amino)-5,7-dimethyl-3,4-dihydro-2,7-naphthyridine-1,6(2H,7H)-dione (5.0 mg, 22%). $^1$H NMR (400 MHz, CDCl$_3$) δ 11.07 (s, 1H), 7.46-7.43 (m, 1H), 7.36-7.33 (m, 1H), 6.48 (t, 1H), 5.82 (s, 1H), 3.50-3.46 (m, 2H), 3.27 (s, 3H), 2.88 (t, 2H), 2.11 (s, 3H) ppm. MS (apci, m/z)=428.10 (M+H).

Example 49

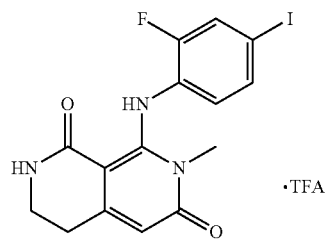

8-((4-iodo-2-fluorophenyl)amino)-7-methyl-3,4-dihydro-2,7-naphthyridine-1,6(2H,7H)-dione trifluoroacetate Step 1. Preparation of methyl (E)-4-(2-ethoxyvinyl)-2-((2-fluoro-4-iodophenyl)amino)-1-methyl-6-oxo-1,6-dihydropyridine-3-carboxylate. 4-iodo-2-fluoroaniline (266 mg, 1.12 mmol) and methyl (E)-2-chloro-4-(2-ethoxyvinyl)-1-methyl-6-oxo-1,6-dihydropyridine-3-carboxylate (290 mg, 0.920 mmol) were dissolved in THF (9.2 mL) and cooled to −78° C. under N$_2$ atmosphere. LiHMDS (2.1 mL, 1.0 M/THF, 2.1 mmol) was added dropwise, then the mixture allowed to warm from −78° C. to ambient temperature over 1 hour. The reaction mixture was quenched with saturated aq. NH$_4$Cl (10 mL), then extracted with EtOAc (2×10 mL). The combined organic phases were dried over MgSO$_4$, filtered, and concentrated. The residue was purified by column chromatography eluting with 0-100% EtOAc/Heptane to afford methyl (E)-4-(2-ethoxyvinyl)-2-((2-fluoro-4-iodophenyl)amino)-1-methyl-6-oxo-1,6-dihydropyridine-3-carboxylate (389 mg, 77%). MS (apci, m/z)=473.1 (M+H).

Step 2. Preparation of methyl 2-((4-iodo-2-fluorophenyl)amino)-1-methyl-6-oxo-4-(2-oxoethyl)-1,6-dihydropyridine-3-carboxylate. To a solution of methyl (E)-2-((4-iodo-2-fluorophenyl)amino)-4-(2-ethoxyvinyl)-1-methyl-6-oxo-1,6-dihydropyridine-3-carboxylate (389 mg, 0.824 mmol) in DCM (4.0 mL) was added TFA (4.0 mL). The solution was allowed to stir at ambient temperature for 16 hours then concentrated. The crude mixture was then diluted with DCM (10 mL) and washed with saturated aq. NaHCO$_3$ (10 mL). The organic phase was dried over MgSO$_4$, filtered, and concentrated to afford methyl 2-((4-iodo-2-fluorophenyl)amino)-1-methyl-6-oxo-4-(2-oxoethyl)-1,6-dihydropyridine-3-carboxylate which was used directly in the next step without further purification (351 mg, 96%). MS (apci, m/z)=445.0 (M+H).

Step 3. Preparation of 8-((4-iodo-2-fluorophenyl)amino)-2-(4-methoxybenzyl)-7-methyl-3,4-dihydro-2,7-naphthyridine-1,6(2H,7H)-dione. Methyl 2-((4-iodo-2-fluorophenyl)amino)-1-methyl-6-oxo-4-(2-oxoethyl)-1,6-dihydropyridine-3-carboxylate (351 mg, 0.790 mmol), (4-methoxyphenyl)methanamine (114 mg, 0.830 mmol), sodium triacetoxyborohydride (184 mg, 0.869 mmol), and acetic acid (4.8 mg, 0.079 mmol) were dissolved in DCE (10 mL) and allowed to stir at ambient temperature for 1 hour. At that time the reaction was warmed to 60° C. and allowed to stir for 1 hour. The reaction was then allowed to cool to ambient temperature, diluted with DCM (5 mL) and washed with saturated aq. NaHCO$_3$ (10 mL). The organic phase was dried over MgSO$_4$, filtered, and concentrated. The residue was purified by column chromatography eluting with 0-100% EtOAc/Heptane to afford 8-((4-iodo-2-fluorophenyl)amino)-2-(4-methoxybenzyl)-7-methyl-3,4-dihydro-2,7-naphthyridine-1,6(2H,7H)-dione (321 mg, 76%). MS (apci, m/z)=534.1 (M+H).

Step 4. Preparation of 8-((4-iodo-2-fluorophenyl)amino)-7-methyl-3,4-dihydro-2,7-naphthyridine-1,6(2H,7H)-dione trifluoroacetate. 8-((4-iodo-2-fluorophenyl)amino)-2-(4-methoxybenzyl)-7-methyl-3,4-dihydro-2,7-naphthyrdine-1,6(2H,7H)-dione (321 mg, 0.602 mmol) was dissolved in TFA (6.0 mL) and heated to 60° C. for 16 hours. The reaction was then allowed to cool to ambient temperature and concentrated. The residue was purified by reverse phase HPLC (5-95% acetonitrile/H$_2$O/0.1% TFA). The fractions containing the clean desired product were lyophilized to afford 8-((4-iodo-2-fluorophenyl)amino)-7-methyl-3,4-dihydro-2,7-naphthyridine-1,6(2H,7H)-dione trifluoroacetate (102 mg, 41%). $^1$H NMR (400 MHz, CDCl$_3$) δ 11.27 (s, 1H), 7.48-7.45 (m, 1H), 7.40-7.38 (m, 1H), 6.58 (t, 1H), 6.05 (s, 1H), 5.84 (s, 1H), 3.51-3.47 (m, 2H), 3.20 (s, 3H), 2.84 (t, 2H) ppm. MS (apci, m/z)=414.0 (M+H).

Example 50

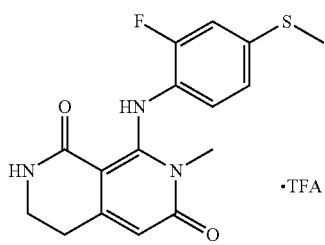 [SMILES: CSc1ccc(Nc2c3c(cc(=O)n2C)CCNC3=O)c(F)c1]

8-((2-fluoro-4-(methylthio)phenyl)amino)-7-methyl-3,4-dihydro-2,7-naphthyridine-1,6(2H,7H)-dione trifluoroacetate Step 1. Preparation of methyl (E)-4-(2-ethoxyvinyl)-2-((2-fluoro-4-(methylthio)phenyl)amino)-1-methyl-6-oxo-1,6-dihydropyridine-3-carboxylate. Methyl (E)-2-chloro-4-(2-ethoxyvinyl)-1-methyl-6-oxo-1,6-dihydropyridine-3-carboxylate (400 mg, 1.47 mmol) and 2-fluoro-4-(methylthio)aniline (243 mg, 1.55 mmol) were dissolved in THF (9.8 mL) and cooled to −78° C. under N$_2$ atmosphere. LiHMDS (2.9 mL, 1.0 M/THF, 2.9 mmol) was added dropwise, then the mixture allowed to warm from −78° C. to ambient temperature over 1 hour. The reaction mixture was quenched with saturated aq. NH$_4$Cl (10 mL), then extracted with EtOAc (2×10 mL). The combined organic phases were dried over MgSO$_4$, filtered, and concentrated. The residue was purified by column chromatography eluting with 0-100% EtOAc/heptane to afford methyl (E)-4-(2-ethoxyvinyl)-2-((2-fluoro-4-(methylthio)phenyl)amino)-1-methyl-6-oxo-1,6-dihydropyridine-3-carboxylate (495 mg, 86%). MS (apci, m/z)=393.1 (M+H).

Step 2. Preparation of methyl 2-((2-fluoro-4-(methylthio)phenyl)amino)-1-methyl-6-oxo-4-(2-oxoethyl)-1,6-dihydropyridine-3-carboxylate. To a solution of methyl (E)-4-(2-ethoxyvinyl)-2-((2-fluoro-4-(methylthio)phenyl)amino)-1-methyl-6-oxo-1,6-dihydropyridine-3-carboxylate (495 mg, 1.26 mmol) in DCM (4.0 mL) was added TFA (4.0 mL). The solution was allowed to stir at ambient temperature overnight then concentrated. The crude mixture was then diluted with DCM (10 mL) and washed with saturated aq. NaHCO$_3$ (10 mL). The organic phase was dried over MgSO$_4$, filtered, and concentrated to afford methyl 2-((2-fluoro-4-(methylthio)phenyl)amino)-1-methyl-6-oxo-4-(2-oxoethyl)-1,6-dihydropyridine-3-carboxylate which was used without further purification (391 mg, 85%). MS (apci, m/z)=365.1 (M+H).

Step 3. Preparation of 8-((2-fluoro-4-(methylthio)phenyl)amino)-2-(4-methoxybenzyl)-7-methyl-3,4-dihydro-2,7-naphthyridine-1,6(2H,7H)-dione. Methyl 2-((2-fluoro-4-(methylthio)phenyl)amino)-1-methyl-6-oxo-4-(2-oxoethyl)-1,6-dihydropyridine-3-carboxylate (391 mg, 1.07 mmol), (4-methoxyphenyl)methanamine (155 mg, 1.13 mmol), sodium triacetoxyborohydride (250 mg, 1.18 mmol), and acetic acid (6.4 mg, 0.079 mmol) were dissolved in DCE (11 mL) and allowed to stir at ambient temperature for 1 hour. At that time the reaction was warmed to 60° C. and allowed to stir for 1 hour. The reaction was then allowed to cool to ambient temperature, diluted with DCM (5 mL) and washed with saturated aq. NaHCO$_3$ (10 mL). The organic phase was dried over MgSO$_4$, filtered, and concentrated. The residue was purified by column chromatography eluting with 0-100% EtOAc/heptane to afford 8-((2-fluoro-4-(methylthio)phenyl)amino)-2-(4-methoxybenzyl)-7-methyl-3,4-dihydro-2,7-naphthyridine-1,6(2H,7H)-dione (401 mg, 82%). MS (apci, m/z)=454.1 (M+H).

Step 4. Preparation of 8-((2-fluoro-4-(methylthio)phenyl)amino)-7-methyl-3,4-dihydro-2,7-naphthyridine-1,6(2H,7H)-dione trifluoroacetate. 8-((2-Fluoro-4-(methylthio)phenyl)amino)-2-(4-methoxybenzyl)-7-methyl-3,4-dihydro-2,7-naphthyridine-1,6(2H,7H)-dione (401 mg, 0.884 mmol) was dissolved in TFA (8.0 mL) and heated to 60° C. for 16 hours. The reaction was then allowed to cool to ambient temperature and concentrated. The residue was purified by reverse phase HPLC (5-95% acetonitrile/H$_2$O/0.1% TFA). Fractions containing the clean desired product were combined and lyophilized to afford 8-((2-fluoro-4-(methylthio)phenyl)amino)-7-methyl-3,4-dihydro-2,7-naphthyridine-1,6(2H,7H)-dione trifluoroacetate (131 mg, 44%). $^1$H NMR (400 MHz, CDCl$_3$) δ 11.10 (s, 1H), 7.04-6.96 (m, 2H), 6.84 (t, 1H), 6.49 (s, 1H), 6.11 (s, 1H), 3.53-3.49 (m, 2H), 3.20 (s, 3H), 2.85 (t, 2H), 2.48 (s, 3H) ppm. MS (apci, m/z)=334.1 (M+H).

Example 51

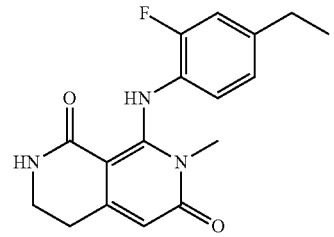 [SMILES: CCc1ccc(Nc2c3c(cc(=O)n2C)CCNC3=O)c(F)c1]

8-((4-ethyl-2-fluorophenyl)amino)-7-methyl-3,4-dihydro-2,7-naphthyridine-1,6(2H,7H)-dione Prepared according to Example 50, substituting 4-ethyl-2-fluoroaniline in place of 2-fluoro-4-(methylthio)aniline in step 1 to afford 8-((4-ethyl-2-fluorophenyl)amino)-7-methyl-3,4-dihydro-2,7-naphthyridine-1,6(2H,7H)-dione (14.9 mg, 47%). $^1$H NMR (400 MHz, CDCl$_3$) δ 11.25 (s, 1H), 6.95 (m, 1H), 6.90 (m, 1H), 6.81 (t, 1H), 6.06 (s, 1H), 5.99 (s, 1H), 3.48 (m, 2H), 3.17 (s, 3H), 2.82 (t, 2H), 2.62 (q, 2H), 1.22 (t, 3H) ppm; MS (apci, m/z)=316.1 (M+H).

Example 52

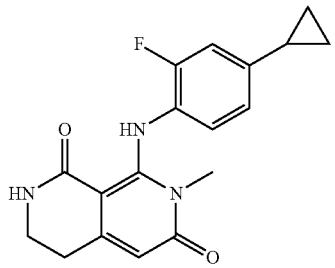 [SMILES: Cn1c(Nc2ccc(C3CC3)cc2F)c2c(cc1=O)CCNC2=O]

8-((4-cyclopropyl-2-fluorophenyl)amino)-7-methyl-3,4-dihydro-2,7-naphthyridine-1,6(2H,7H)-dione Prepared according to Example 50, substituting 4-cyclopropyl-2-fluoroaniline in place of 2-fluoro-4-(methylthio)aniline in step 1 to afford 8-((4-cyclopropyl-2-fluorophenyl)amino)-7-methyl-3,4-dihydro-2,7-naphthyridine-1,6(2H,7H)-dione (5.8 mg, 17%). $^1$H NMR (400 MHz, CDCl$_3$) δ 11.24 (s, 1H), 6.83-6.75 (m, 3H), 5.99 (s, 1H), 5.94 (s, 1H), 3.48 (dt, 2H), 3.16 (s, 3H), 2.82 (t, 2H), 1.86 (m, 1H), 1.02-0.95 (m, 2H), 0.69-0.62 (m, 2H) ppm; MS (apci, m/z)=328.1 (M+H).

Example 53

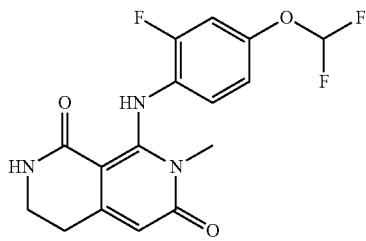 [SMILES: Cn1c(Nc2ccc(OC(F)F)cc2F)c2c(cc1=O)CCNC2=O]

8-((4-(difluoromethoxy)-2-fluorophenyl)amino)-7-methyl-3,4-dihydro-2,7-naphthyridine-1,6(2H,7H)-dione Prepared according to Example 50, substituting 4-(difluoromethoxy)-2-fluoroaniline in place of 2-fluoro-4-(methylthio)aniline in step 1 to afford 8-((4-(difluoromethoxy)-2-fluorophenyl)amino)-7-methyl-3,4-dihydro-2,7-naphthyridine-1,6(2H,7H)-dione (30.6 mg, 47%). $^1$H NMR (400 MHz, CDCl$_3$) δ 11.29 (s, 1H), 6.97 (m, 1H), 6.91-6.84 (m, 2H), 6.49 (t, 1H), 6.03 (s, 1H), 5.79 (s, 1H), 3.49 (dt, 2H), 3.19 (s, 3H), 2.84 (t, 2H) ppm; MS (apci, m/z)=354.1 (M+H).

Example 54

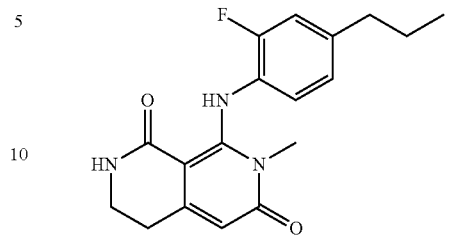

8-((2-fluoro-4-propylphenyl)amino)-7-methyl-3,4-dihydro-2,7-naphthyridine-1,6(2H,7H)-dione Steps 1-4: Preparation of 8-((4-allyl-2-fluorophenyl)amino)-7-methyl-3,4-dihydro-2,7-naphthyridine-1,6(2H,7H)-dione. Prepared according to Example 50, substituting 4-allyl-2-fluoroaniline in place of 2-fluoro-4-(methylthio)aniline in step 1 to afford 8-((4-allyl-2-fluorophenyl)amino)-7-methyl-3,4-dihydro-2,7-naphthyridine-1,6(2H,7H)-dione (3.8 mg, 10%). $^1$H NMR (400 MHz, CDCl$_3$) δ 11.27 (s, 1H), 7.09 (dd, 1H), 7.01 (dd, 1H), 6.80 (t, 1H), 6.35-6.28 (m, 1H), 6.25-6.15 (m, 1H), 6.01 (s, 1H), 5.85 (s, 1H), 3.49 (dt, 2H), 3.19 (s, 3H), 2.83 (t, 2H), 1.88 (dd, 2H) ppm; MS (apci, m/z)=328.1 (M+H).

Step 5. Preparation of 8-((2-fluoro-4-propylphenyl)amino)-7-methyl-3,4-dihydro-2,7-naphthyridine-1,6(2H,7H)-dione. A stirred mixture of 8-((4-allyl-2-fluorophenyl)amino)-7-methyl-3,4-dihydro-2,7-naphthyridine-1,6(2H,7H)-dione (3.8 mg, 0.012 mmol) and Pd/C (5% Degussa type, 1 mg, 0.009 mmol) in MeOH (0.5 mL) was degassed and stirred under H$_2$ atmosphere for 24 hours. The reaction was diluted with DCM, filtered and the filtrate concentrated. The residue was purified by reverse phase HPLC (5-95% acetonitrile/water/0.1% TFA over 20 minutes) and the clean fractions were combined, washed with saturated bicarbonate, and extracted with EtOAc (3×10 mL). The combined organic layers were washed with saturated bicarbonate (30 mL) and brine (30 mL), dried over sodium sulfate, filtered, and concentrated to afford 8-((2-fluoro-4-propylphenyl)amino)-7-methyl-3,4-dihydro-2,7-naphthyridine-1,6(2H,7H)-dione (2.5 mg, 65%). $^1$H NMR (400 MHz, CDCl$_3$) δ 11.22 (s, 1H), 6.93 (dd, 1H), 6.88 (m, 1H), 6.81 (t, 1H), 5.99 (s, 1H), 5.81 (s, 1H), 3.48 (dt, 2H), 3.17 (s, 3H), 2.83 (t, 2H), 2.55 (t, 2H), 1.62 (m, 2H), 0.92 (t, 3H) ppm; MS (apci, m/z)=330.1 (M+H).

Example 55

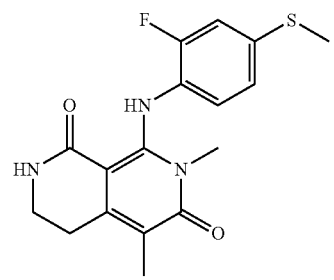 [SMILES: CSc1ccc(Nc2c3c(c(C)c(=O)n2C)CCNC3=O)c(F)c1]

8-((2-fluoro-4-(methylthio)phenyl)amino)-5,7-dimethyl-3,4-dihydro-2,7-naphthyrdine-1,6(2H,7H)-dione Step 1. 8-((2-fluoro-4-(methylthio)phenyl)amino)-5-iodo-7-methyl-3,4-dihydro-2,7-naphthyridine-1,6(2H,7H)-dione. 8-((2-Fluoro-4-(methylthio)phenyl)amino)-7-methyl-3,4-dihydro-2,7-naphthyridine-1,6(2H,7H)-dione (41.2 mg, 0.124 mmol) and p-toluenesulfonic acid (31.9 mg, 0.185 mmol) were dissolved in 1 mL of a 1:1 THF/MeOH solution. After 5 minutes, NIS (27.8 mg, 0.124 mmol) was added. The reaction was allowed to stir at ambient temperature for 30 minutes. The crude reaction mixture was then partitioned between EtOAc (10 mL) and saturated aq. NaHCO$_3$ (15 mL) and extracted with EtOAc (2×5 mL). The combined organic phases were dried over MgSO$_4$, filtered, and concentrated. The residue was purified by column chromatography, eluting with 10-80% EtOAc/heptane to afford 8-((4-bromo-2-fluorophenyl)amino)-5-iodo-7-methyl-3,4-dihydro-2,7-naphthyridine-1,6(2H,7H)-dione (37 mg, 65%). MS (apci, m/z)=460.0 (M+H).

Step 2. Preparation of 8-((2-fluoro-4-(methylthio)phenyl)amino)-5,7-dimethyl-3,4-dihydro-2,7-naphthyridine-1,6(2H,7H)-dione. 8-((2-fluoro-4-(methylthio)phenyl)amino)-5-iodo-7-methyl-3,4-dihydro-2,7-naphthyridine-1,6(2H,7H)-dione (37.0 mg, 0.0806 mmol) and bis(tri-t-butylphosphine)palladium(0) (4.12 mg, 0.00806 mmol) were dissolved in THF (0.8 mL) and methylzinc(II) chloride (80.6 μL, 2M/THF, 0.161 mmol) was added dropwise. The reaction was allowed to stir at ambient temperature for 1 hour. The reaction mixture was quenched with saturated aq. NH$_4$Cl (2 mL), then extracted with EtOAc (2×5 mL). The combined organic phases were dried over MgSO$_4$, filtered, and concentrated. The residue was purified by reverse phase HPLC (5-95% acetonitrile/H$_2$O/0.1% TFA). Fractions containing the clean desired product were combined and the product was converted to the free base with DCM/NaHCO$_3$ to afford 8-((2-fluoro-4-(methylthio)phenyl)amino)-5,7-dimethyl-3,4-dihydro-2,7-naphthyridine-1,6(2H,7H)-dione (15.5 mg, 55%). $^1$H NMR (400 MHz, CDCl$_3$) δ 11.10 (s, 1H), 7.04-7.01 (m, 1H), 6.95-6.93 (m, 1H), 6.71 (t, 1H), 5.96 (s, 1H), 3.49-3.46 (m, 2H), 3.25 (s, 3H), 2.87 (t, 2H), 2.46 (s, 3H), 2.11 (s, 3H) ppm. MS (apci, m/z)=348.1 (M+H).

Example 56

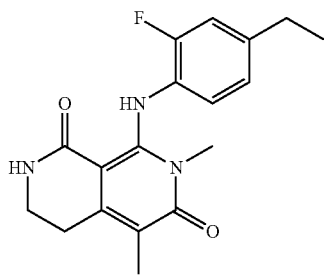 [SMILES: CCc1ccc(Nc2c3c(c(C)c(=O)n2C)CCNC3=O)c(F)c1]

8-((4-ethyl-2-fluorophenyl)amino)-5,7-dimethyl-3,4-dihydro-2,7-naphthyridine-1,6(2H,7H)-dione Prepared according to Example 55, substituting 8-((4-ethyl-2-fluorophenyl)amino)-7-methyl-3,4-dihydro-2,7-naphthyridine-1,6(2H,7H)-dione (prepared according to Example 51) in place of 8-((2-fluoro-4-(methylthio)phenyl)amino)-7-methyl-3,4-dihydro-2,7-naphthyridine-1,6(2H,7H)-dione in step 1 to afford 8-((4-ethyl-2-fluorophenyl)amino)-5,7-dimethyl-3,4-dihydro-2,7-naphthyridine-1,6(2H,7H)-dione (6.7 mg, 62%). $^1$H NMR (400 MHz, CDCl$_3$) δ 11.06 (s, 1H), 6.94 (dd, 1H), 6.86 (dd, 1H), 6.72 (t, 1H), 5.87 (s, 1H), 3.47 (dt, 2H), 3.23 (s, 3H), 2.87 (t, 2H), 2.61 (q, 2H), 2.11 (s, 3H), 1.21 (t, 3H) ppm; MS (apci, m/z)=330.2 (M+H).

Example 57

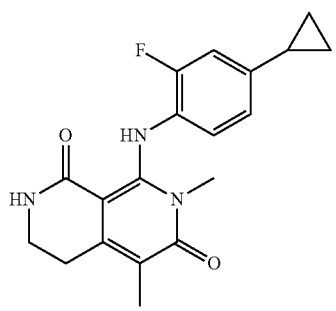 [SMILES: Cc1c2c(c(Nc3ccc(C4CC4)cc3F)n(C)c1=O)C(=O)NCC2]

8-((4-cyclopropyl-2-fluorophenyl)amino)-5,7-dimethyl-3,4-dihydro-2,7-naphthyridine-1,6(2H,7H)-dione Prepared according to Example 55, substituting 8-((4-cyclopropyl-2-fluorophenyl)amino)-7-methyl-3,4-dihydro-2,7-naphthyridine-1,6(2H,7H)-dione (prepared according to Example 52) in place of 8-((2-fluoro-4-(methylthio)phenyl)amino)-7-methyl-3,4-dihydro-2,7-naphthyridine-1,6(2H,7H)-dione in step 1 to afford 8-((4-cyclopropyl-2-fluorophenyl)amino)-5,7-dimethyl-3,4-dihydro-2,7-naphthyridine-1,6(2H,7H)-dione (2.3 mg, 47%). $^1$H NMR (400 MHz, CDCl$_3$) δ 11.05 (s, 1H), 6.80-6.75 (m, 2H), 6.69 (t, 1H), 5.80 (s, 1H), 3.47 (dt, 2H), 3.22 (s, 3H), 2.87 (t, 2H), 2.10 (s, 3H), 1.85 (m, 1H), 1.00-0.94 (m, 2H), 0.67-0.61 (m, 2H) ppm; MS (apci, m/z)=342.2 (M+H).

Example 58

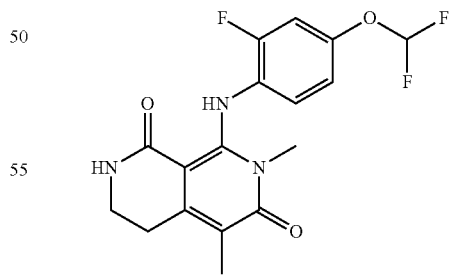

8-((4-(difluoromethoxy)-2-fluorophenyl)amino)-5,7-dimethyl-3,4-dihydro-2,7-naphthyrdine-1,6(2H,7H)-dione Prepared according to Example 55, substituting 8-((4-(difluoromethoxy)-2-fluorophenyl)amino)-7-methyl-3,4-dihydro-2,7-naphthyrdine-1,6(2H,7H)-dione (prepared according to Example 53) in place of 8-((2-fluoro-4-(methylthio)phenyl)amino)-7-methyl-3,4-dihydro-2,7-naphthyridine-1,6(2H,7H)-dione in step 1 to afford 8-((4-(difluoromethoxy)-2-fluorophenyl)amino)-5,7-dimethyl-3,4-dihydro-2,7-naphthyridine-1,6(2H,7H)-dione (9.5 mg, 41%). $^1$H NMR (400 MHz, CDCl$_3$) δ 11.09 (s, 1H), 6.96 (dd, 1H), 6.87-6.82 (m, 1H), 6.76 (t, 1H), 6.47 (t, 1H), 6.01 (s, 1H), 3.48 (dt, 2H), 3.25 (s, 3H), 2.88 (t, 2H), 2.11 (s, 3H) ppm; MS (apci, m/z)=368.1 (M+H).

Example 59

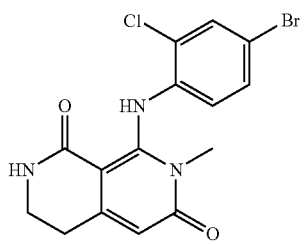 [SMILES: Cn1c(Nc2ccc(Br)cc2Cl)c2c(cc1=O)CCNC2=O]

8-((4-bromo-2-chlorophenyl)amino)-7-methyl-3,4-dihydro-2,7-naphthyridine-1,6(2H,7H)-dione Step 1. Preparation of methyl (E)-2-((4-bromo-2-chlorophenyl)amino)-4-(2-ethoxyvinyl)-1-methyl-6-oxo-1,6-dihydropyridine-3-carboxylate. Methyl (E)-2-chloro-4-(2-ethoxyvinyl)-1-methyl-6-oxo-1,6-dihydropyridine-3-carboxylate (140 mg, 0.515 mmol) and 4-bromo-2-chloroaniline (108 mg, 0.520 mmol) were dissolved in THF (5.2 mL) and cooled to −78° C. under N$_2$ atmosphere. LiHMDS (1.0 mL, 1.0 M/THF, 1.0 mmol) was added dropwise, then the mixture allowed to warm from −78° C. to ambient temperature over 1 hour. The reaction mixture was quenched with saturated aq. NH$_4$Cl (5 mL), then extracted with EtOAc (2×5 mL). The combined organic phases were dried over MgSO$_4$, filtered, and concentrated. The residue was purified by column chromatography eluting with 0-100% EtOAc/Heptane to afford methyl (E)-2-((4-bromo-2-chlorophenyl)amino)-4-(2-ethoxyvinyl)-1-methyl-6-oxo-1,6-dihydropyridine-3-carboxylate (145 mg, 64%). MS (apci, m/z)=441.0, 443.0 (M+H).

Step 2. Preparation of methyl 2-((4-bromo-2-chlorophenyl)amino)-1-methyl-6-oxo-4-(2-oxoethyl)-1,6-dihydropyridine-3-carboxylate. To a solution of methyl (E)-2-((4-bromo-2-chlorophenyl)amino)-4-(2-ethoxyvinyl)-1-methyl-6-oxo-1,6-dihydropyridine-3-carboxylate (145 mg, 0.328 mmol) in DCM (2.0 mL) was added TFA (2.0 mL). The solution was allowed to stir at ambient temperature overnight, then concentrated. The crude mixture was then diluted with DCM (5 mL) and washed with saturated aq. NaHCO$_3$ (5 mL). The organic phase was dried over MgSO$_4$, filtered, and concentrated to afford methyl 2-((4-bromo-2-chlorophenyl)amino)-1-methyl-6-oxo-4-(2-oxoethyl)-1,6-dihydropyridine-3-carboxylate which was used without further purification (136 mg, 100%). MS (apci, m/z)=415.2 (M+H).

Step 3. Preparation of 8-((4-bromo-2-chlorophenyl)amino)-2-(4-methoxybenzyl)-7-methyl-3,4-dihydro-2,7-naphthyridine-1,6(2H,7H)-dione. Methyl 2-((4-bromo-2-chlorophenyl)amino)-1-methyl-6-oxo-4-(2-oxoethyl)-1,6-dihydropyridine-3-carboxylate (136 mg, 0.329 mmol), (4-methoxyphenyl)methanamine (47.4 mg, 0.345 mmol), sodium triacetoxyborohydride (76.6 mg, 0.362 mmol), and acetic acid (2.0 mg, 0.033 mmol) were dissolved in DCE (3.3 mL) and allowed to stir at ambient temperature for 1 hour. At that time the reaction was warmed to 60° C. and allowed to stir for 1 hour. The reaction was then allowed to cool to ambient temperature, diluted with DCM (5 mL) and washed with saturated aq. NaHCO$_3$ (10 mL). The organic phase was dried over MgSO$_4$, filtered, and concentrated. The residue was purified by column chromatography eluting with 0-100% EtOAc/Heptane to afford 8-((4-bromo-2-chlorophenyl)amino)-2-(4-methoxybenzyl)-7-methyl-3,4-dihydro-2,7-naphthyridine-1,6(2H,7H)-dione (104 mg, 63%). MS (apci, m/z)=502.1, 504.1 (M+H).

Step 4. Preparation of 8-((4-bromo-2-chlorophenyl)amino)-7-methyl-3,4-dihydro-2,7-naphthyridine-1,6(2H,7H)-dione. 8-((4-bromo-2-chlorophenyl)amino)-2-(4-methoxybenzyl)-7-methyl-3,4-dihydro-2,7-naphthyridine-1,6(2H,7H)-dione (79.1 mg, 0.207 mmol) was dissolved in TFA (3.0 mL) and heated to 60° C. for 16 hours. The reaction was then allowed to cool to ambient temperature and concentrated. The residue was purified by reverse phase HPLC (5-95% acetonitrile/H$_2$O/0.1% TFA). Fractions containing the clean desired product were combined and the product was converted to the free base with DCM/NaHCO$_3$ to afford 8-((4-bromo-2-chlorophenyl)amino)-7-methyl-3,4-dihydro-2,7-naphthyridine-1,6(2H,7H)-dione (28 mg, 35%). $^1$H NMR (400 MHz, CDCl$_3$) δ 11.27 (s, 1H), 7.61 (d, 1H), 7.31-7.28 (m, 1H), 6.60-6.57 (m, 1H), 6.07 (t, 1H), 5.63 (s, 1H), 3.52-3.48 (m, 2H), 3.17 (s, 3H), 2.85 (t, 2H) ppm. MS (apci, m/z)=382.0, 384.0 (M+H).

Example 60

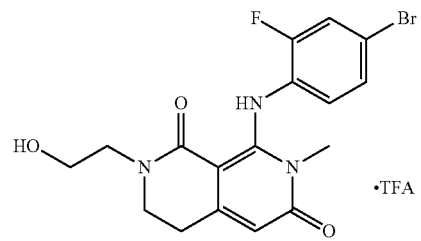 [SMILES: Cn1c(Nc2ccc(Br)cc2F)c2c(cc1=O)CCN(CCO)C2=O]

8-((4-bromo-2-fluorophenyl)amino)-2-(2-hydroxyethyl)-7-methyl-3,4-dihydro-2,7-naphthyridine-1,6(2H,7H)-dione trifluoroacetate Step 1. Preparation of methyl 2-chloro-1-methyl-6-oxo-4-(2-oxoethyl)-1,6-dihydropyridine-3-carboxylate. To a solution of methyl (E)-2-chloro-4-(2-ethoxyvinyl)-1-methyl-6-oxo-1,6-dihydropyridine-3-carboxylate (331 mg, 1.22 mmol) in DCM (5.0 mL) was added TFA (5.0 mL). The solution was allowed to stir at ambient temperature for 16 hours, then concentrated. The crude mixture was then diluted with DCM (10 mL) and washed with saturated aq. NaHCO$_3$ (10 mL). The organic phase was dried over MgSO$_4$, filtered, and concentrated to afford methyl 2-chloro-1-methyl-6-oxo-4-(2-oxoethyl)-1,6-dihydropyridine-3-carboxylate which was used without further purification (236 mg, 80%). MS (apci, m/z)=244.1 (M+H).

Step 2. Preparation of 8-chloro-2-(2-hydroxyethyl)-7-methyl-3,4-dihydro-2,7-naphthyridine-1,6(2H,7H)-dione. Methyl 2-chloro-1-methyl-6-oxo-4-(2-oxoethyl)-1,6-dihydropyridine-3-carboxylate (122 mg, 0.501 mmol), 2-((tert-butyldimethylsilyl)oxy)ethan-1-amine (105 mg, 0.601 mmol), sodium triacetoxyborohydride (127 mg, 0.601 mmol), and acetic acid (6.0 mg, 0.10 mmol) were dissolved in DCE (5 mL) and allowed to stir at ambient temperature for 2 hours. The reaction was warmed to 60° C. and stirred for 16 hours. The reaction was then allowed to cool to ambient temperature, diluted with DCM (10 mL) and washed with saturated aq. NaHCO$_3$ (15 mL). The organic phase was dried over MgSO$_4$, filtered, and concentrated. The residue was purified by reverse phase HPLC (5-95% acetonitrile/H$_2$O/0.1% TFA). Fractions containing the clean desired product were combined and the product was converted to the free base with DCM/NaHCO$_3$ to afford 8-chloro-2-(2-hydroxyethyl)-7-methyl-3,4-dihydro-2,7-naphthyridine-1,6(2H,7H)-dione (20 mg, 16%). MS (apci, m/z)=257.0 (M+H).

Step 3. Preparation of 8-((4-bromo-2-fluorophenyl)amino)-2-(2-hydroxyethyl)-7-methyl-3,4-dihydro-2,7-naphthyridine-1,6(2H,7H)-dione trifluoroacetate. 4-Bromo-2-fluoroaniline (17.7 mg, 0.093 mmol) and 8-chloro-2-(2-hydroxyethyl)-7-methyl-3,4-dihydro-2,7-naphthyridine-1,6(2H,7H)-dione (20 mg, 0.077 mmol) were dissolved in THF (0.7 mL) and cooled to −78° C. under N$_2$ atmosphere. LiHMDS (233 µL, 1.0 M/THF, 0.233 mmol) was added dropwise, then the mixture allowed to warm from −78° C. to ambient temperature over 1 hour. The reaction mixture was quenched with saturated NH$_4$Cl (5 mL), then extracted with EtOAc (3×5 mL). The combined organic phases were dried over MgSO$_4$, filtered, and concentrated. The residue was purified by reverse phase HPLC (5-95% acetonitrile/H$_2$O/0.1% TFA). Clean fractions were lyophilized to afford 8-((4-bromo-2-fluorophenyl)amino)-2-(2-hydroxyethyl)-7-methyl-3,4-dihydro-2,7-naphthyridine-1,6(2H,7H)-dione trifluoroacetate (10.1 mg, 32%). $^1$H NMR (400 MHz, CDCl$_3$) δ 11.36 (s, 1H), 7.32-7.29 (m, 1H), 7.22-7.19 (m, 1H), 6.70 (t, 1H), 6.06 (s, 1H), 3.85 (t, 2H), 3.67 (t, 2H), 3.61 (t, 2H), 3.22 (s, 3H), 2.86 (t, 2H) ppm. MS (apci, m/z)=410.1, 412.1 (M+H).

Example 61

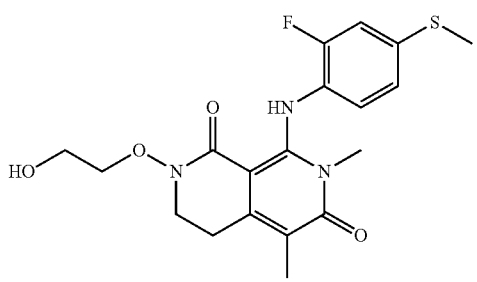 [SMILES: CSc1ccc(Nc2c3c(c(C)c(=O)n2C)CCN(OCCO)C3=O)c(F)c1]

8-((2-fluoro-4-(methylthio)phenyl)amino)-2-(2-hydroxyethoxy)-5,7-dimethyl-3,4-dihydro-2,7-naphthyridine-1,6(2H,7H)-dione Prepared according to Example 44 substituting 2-fluoro-4-(methylthio)aniline in place of 4-ethyl-2-fluoroaniline in step 1 to afford 8-((2-fluoro-4-(methylthio)phenyl)amino)-2-(2-hydroxyethoxy)-5,7-dimethyl-3,4-dihydro-2,7-naphthyridine-1,6(2H,7H)-dione (2.1 mg, 21%). $^1$H NMR (400 MHz, CDCl$_3$) δ 11.01 (s, 1H), 7.02 (dd, 1H), 6.95 (m, 1H), 6.77 (m, 1), 4.48 (t, 1H), 4.03 (t, 2H), 3.76-3.67 (m, 4H), 3.21 (s, 3H), 3.02 (t, 2H), 2.47 (s, 3H), 2.08 (s, 3H) ppm. MS (apci, m/z)=408.1 (M+H).

Example 62

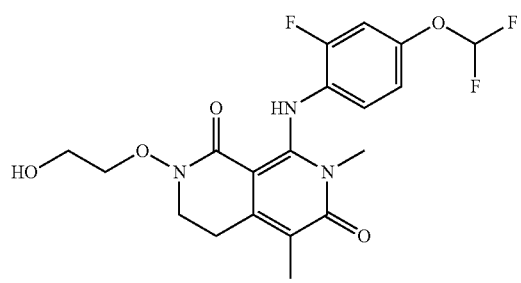 [SMILES: Cc1c2c(c(Nc3ccc(OC(F)F)cc3F)n(C)c1=O)C(=O)N(OCCO)CC2]

8-((4-(difluoromethoxy)-2-fluorophenyl)amino)-2-(2-hydroxyethoxy)-5,7-dimethyl-3,4-dihydro-2,7-naphthyridine-1,6(2H,7H)-dione Steps 1-5. Preparation of 2-(2-(tert-butoxy)ethoxy)-8-((4-(difluoromethoxy)-2-fluorophenyl)amino)-5-iodo-7-methyl-3,4-dihydro-2,7-naphthyridine-1,6(2H,7H)-dione. Prepared according to Example 41, Steps 1-5 substituting 4-(difluoromethoxy)-2-fluoroaniline in place of 2-fluoroaniline in step 1 to afford 2-(2-(tert-butoxy)ethoxy)-8-((4-(difluoromethoxy)-2-fluorophenyl)amino)-5-iodo-7-methyl-3,4-dihydro-2,7-naphthyridine-1,6(2H,7H)-dione (156 mg, 94%). MS (apci, m/z)=596.1 (M+H).

Step 6. Preparation of 2-(2-(tert-butoxy)ethoxy)-8-((4-(difluoromethoxy)-2-fluorophenyl)amino)-5,7-dimethyl-3,4-dihydro-2,7-naphthyridine-1,6(2H,7H)-dione. To a solution of 2-(2-(tert-butoxy)ethoxy)-8-((4-(difluoromethoxy)-2-fluorophenyl)amino)-5-iodo-7-methyl-3,4-dihydro-2,7-naphthyridine-1,6(2H,7H)-dione (156 mg, 0.262 mmol) in THF (2.5 mL) at 0° C. was added Pd(Pt-Bu$_3$)$_2$ (13.4 mg, 0.026 mmol) followed by methylzinc(II) chloride (132 µL, 0.265 mmol). The mixture was removed from the ice bath and stirred for 10 minutes. The reaction was partitioned between saturated NH$_4$Cl (40 mL) and EtOAc (20 mL) and the aqueous layer was extracted with EtOAc (2×10 mL). The combined organic phases were washed with brine (30 mL), dried over sodium sulfate, filtered, and concentrated. The residue was purified by column chromatography eluting with 0-50% EtOAc/heptane to afford 2-(2-(tert-butoxy)ethoxy)-8-((4-(difluoromethoxy)-2-fluorophenyl)amino)-5,7-dimethyl-3,4-dihydro-2,7-naphthyridine-1,6(2H,7H)-dione (89.9 mg, 71%). MS (apci, m/z)=484.2 (M+H).

Step 7. Preparation of 8-((4-(difluoromethoxy)-2-fluorophenyl)amino)-2-(2-hydroxyethoxy)-5,7-dimethyl-3,4-dihydro-2,7-naphthyridine-1,6(2H,7H)-dione. 2-(2-(tert-butoxy)ethoxy)-8-((4-(difluoromethoxy)-2-fluorophenyl)amino)-5,7-dimethyl-3,4-dihydro-2,7-naphthyridine-1,6(2H,7H)-dione (89.9 mg, 0.186 mmol) was dissolved in ACN (750 µL) and phosphoric acid (750 µL) was added. The reaction was heated to 60° C. for 30 minutes. The reaction mixture was partitioned between saturated sodium bicarbonate (50 mL) and EtOAc (20 mL). The aqueous layer was washed with EtOAc (2×15 mL). The combined organic layers were washed with saturated sodium bicarbonate (25 mL), brine (25 mL), dried over sodium sulfate, filtered, and concentrated. The residue was purified by column chromatography eluting with 0-100% EtOAc/heptane to afford 8-((4-(difluoromethoxy)-2-fluorophenyl)amino)-2-(2-hydroxyethoxy)-5,7-dimethyl-3,4-dihydro-2,7-naphthyridine-1,6(2H,7H)-dione (65.9 mg, 83%). ¹H NMR (400 MHz, CDCl₃) δ 11.00 (s, 1H), 6.97 (dd, 1H), 6.90-6.79 (m, 2H), 6.48 (t, 1H), 4.44 (t, 1H), 4.03 (m, 2H), 3.76-3.68 (m, 4H), 3.22 (s, 3H), 3.03 (t, 2H), 2.09 (s, 3H) ppm. MS (apci, m/z)=428.1 (M+H).

Example 63

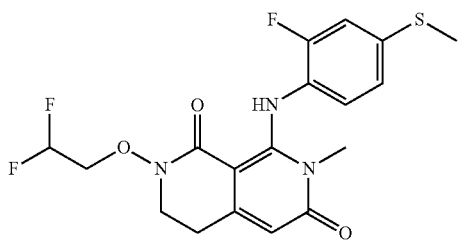 [SMILES: CSc1ccc(Nc2c3c(cc(=O)n2C)CCN(OCC(F)F)C3=O)c(F)c1]

2-(2,2-difluoroethoxy)-8-((2-fluoro-4-(methylthio) phenyl)amino)-7-methyl-3,4-dihydro-2,7-naphthyridine-1,6(2H,7H)-dione Step 1. Preparation of methyl (Z)-4-(2-ethoxyvinyl)-2-((2-fluoro-4-(methylthio)phenyl)amino)-1-methyl-6-oxo-1,6-dihydropyridine-3-carboxylate. Prepared according to Example 44, Step 1 substituting 2-fluoro-4-(methylthio) aniline in place of 4-ethyl-2-fluoroaniline to afford methyl (Z)-4-(2-ethoxyvinyl)-2-((2-fluoro-4-(methylthio)phenyl) amino)-1-methyl-6-oxo-1,6-dihydropyridine-3-carboxylate (0.373 g, 69%). MS (apci, m/z)=393.1 (M+H).

Step 2. Preparation of methyl (E)-4-(2-((2,2-difluoroethoxy)imino)ethyl)-2-((2-fluoro-4-(methylthio)phenyl) amino)-1-methyl-6-oxo-1,6-dihydropyridine-3-carboxylate. Prepared according to Example 6, Step 5 substituting methyl (Z)-4-(2-ethoxyvinyl)-2-((2-fluoro-4-(methylthio)phenyl) amino)-1-methyl-6-oxo-1,6-dihydropyridine-3-carboxylate in place of methyl (Z)-2-chloro-4-(2-ethoxyvinyl)-1-methyl-6-oxo-1,6-dihydropyridine-3-carboxylate and O-(2,2-difluoroethyl)hydroxylamine hydrochloride in place of O-(2-(tert-butoxy)ethyl)hydroxylamine hydrochloride to afford methyl (E)-4-(2-((2,2-difluoroethoxy)imino)ethyl)-2-((2-fluoro-4-(methylthio)phenyl)amino)-1-methyl-6-oxo-1,6-dihydropyridine-3-carboxylate (assumed 100%). MS (apci, m/z)=444.1 (M+H).

Step 3. Preparation of 2-(2,2-difluoroethoxy)-8-((2-fluoro-4-(methylthio)phenyl)amino)-7-methyl-3,4-dihydro-2,7-naphthyridine-1,6(2H,7H)-dione. To a solution of methyl (E)-4-(2-((2,2-difluoroethoxy)imino)ethyl)-2-((2-fluoro-4-(methylthio)phenyl)amino)-1-methyl-6-oxo-1,6-dihydropyridine-3-carboxylate (36 mg, 0.081 mmol) in MeOH (0.8 mL) was added sodium cyanoborohydride (26 mg, 0.406 mmol) and acetic acid (23 µL, 0.406 mmol). The mixture was stirred at 45° C. for 2 hours, then at ambient temperature for 72 hours. The mixture was diluted with sat. aqueous NaHCO₃ (25 mL) and EtOAc (25 mL). The organic phase was separated, dried over Na₂SO₄, filtered, and concentrated. The residue was purified by column chromatography, eluting with 5-100% EtOAc/heptane, to afford 2-(2,2-difluoroethoxy)-8-((2-fluoro-4-(methylthio)phenyl) amino)-7-methyl-3,4-dihydro-2,7-naphthyridine-1,6(2H,7H)-dione (11.8 mg, 35.2%). ¹H NMR (400 MHz, CDCl₃) δ 11.26 (s, 1H), 7.08-6.94 (m, 2H), 6.91-6.76 (m, 1H), 6.51-5.64 (m, 2H), 4.22 (td, 2H), 3.73 (t, 2H), 3.16 (s, 3H), 3.04-2.97 (m, 2H), 2.48 (s, 3H) ppm. MS (apci, m/z)=414.1 (M+H).

Example 64

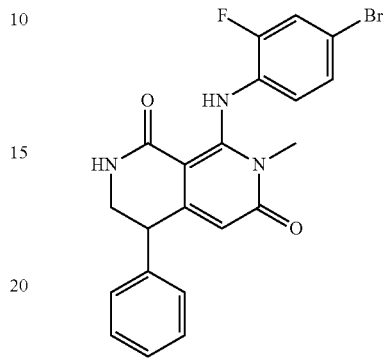

8-((4-bromo-2-fluorophenyl)amino)-7-methyl-4-phenyl-3,4-dihydro-2,7-naphthyridine-1,6(2H,7H)-dione Step 1. Preparation of 2,6-dichloro-4-iodonicotinic acid. A solution of 2,6-dichloro-4-iodopyridine (4.0 g, 14.6 mmol) in THF (30 mL) was cooled to −78° C. LDA (10.95 mL, 2M, 21.9 mmol) was added dropwise to the solution at −78° C. and stirred 2 hours at −78° C. Excess CO₂ gas was bubbled into the reaction solution for 20 minutes at −78° C. The reaction mixture was then poured into dry ice (10 g) and quenched with water (30 mL). The reaction was adjusted to pH 3-4 with 2N HCl and extracted with EtOAc (3×100 mL). The organic layers were combined and dried over sodium sulfate, filtered, and concentrated to afford 2,6-dichloro-4-iodonicotinic acid (3.0 g, 64.6%). MS (apci, m/z)=317.9, 319.8 (M+H).

Step 2. Preparation of 2-chloro-4-iodo-6-oxo-1,6-dihydropyridine-3-carboxylic acid. A solution of NaOH (100 mL, 4M, 236 mmol) was heated to 110° C. and then 2,6-dichloro-4-iodonicotinic acid (3.0 g, 9.44 mmol) was added in one portion and stirred for 8 hours. The reaction was adjusted pH to 1 with HCl (6 M) at 0° C. and stirred for 30 minutes. The resulting solids were collected by filtration and dried in vacuo to afford 2-chloro-4-iodo-6-oxo-1,6-dihydropyridine-3-carboxylic acid (3.0 g, assumed 100%) which was used without further purification. MS (apci, m/z)=299.9, 301.9 (M+H).

Step 3. Preparation of methyl 2-chloro-4-iodo-1-methyl-6-oxo-1,6-dihydropyridine-3-carboxylate. To a mixture of 2-chloro-4-iodo-6-oxo-1,6-dihydropyridine-3-carboxylic acid (3.0 g, 10.02 mmol) in DMF (30 mL) was added MeI (4.27 g, 30.06 mmol) and K₂CO₃ (4.15 g, 30.06 mmol) in one portion at 25° C. After stirring for 3 hours, the reaction was poured into sat. NH₄Cl (10 mL) and the aqueous phase was extracted with ethyl acetate (3×50 mL). The combined organic phases were washed with brine (100 mL), dried over Na₂SO₄, filtered and concentrated. The residue was purified by column chromatography eluting with 2-100% EtOAc/ petroleum ether to afford methyl 2-chloro-4-iodo-1-methyl-6-oxo-1,6-dihydropyridine-3-carboxylate (850 mg, 25.9%).

¹H NMR (400 MHz, CDCl₃) δ 7.16 (s, 1H), 3.93 (s, 3H), 3.65 (s, 3H) ppm. MS (apci, m/z)=327.9 (M+H).

Step 4. Preparation of methyl 2-chloro-1-methyl-6-oxo-4-(1-phenylvinyl)-1,6-dihydropyridine-3-carboxylate. To a solution of methyl 2-chloro-4-iodo-1-methyl-6-oxo-1,6-dihydropyridine-3-carboxylate (0.2 g, 0.611 mmol) in 1,4-dioxane (10 mL) and water (1 mL) was added 4,4,5,5-tetramethyl-2-(1-phenylvinyl)-1,3,2-dioxaborolane (0.148 g, 0.641 mmol), Pd(dppf)Cl₂ (50 mg, 0.061 mmol), Na₂CO₃ (0.194 g, 1.83 mmol) and H₂O (1 mL). Then the mixture was degassed 3 times and stirred at 80° C. for 3 hours. 4,4,5,5-Tetramethyl-2-(1-phenylvinyl)-1,3,2-dioxaborolane (37 mg, 0.153 mmol) and Pd(dppf)Cl₂ (50 mg, 0.061 mmol) were added. The mixture was degassed 3 times and stirred at 80° C. for another 1.5 hours. The cooled mixture was filtered and the filtrate concentrated. The residue was purified by column chromatography eluting with 0-20% EtOAc/petroleum ether to afford methyl 2-chloro-1-methyl-6-oxo-4-(1-phenylvinyl)-1,6-dihydropyridine-3-carboxylate (95 mg, 51%). ¹H NMR (400 MHz, CDCl₃) δ 7.33-7.32 (m, 3H), 7.32-7.25 (m, 2H), 6.58 (s, 1H), 5.62 (s, 1H), 5.42 (s, 1H), 3.75 (s, 3H), 3.36 (s, 3H) ppm. MS (apci, m/z)=303.7 (M+H).

Step 5. Preparation of methyl 2-((4-bromo-2-fluorophenyl)amino)-1-methyl-6-oxo-4-(1-phenylvinyl)-1,6-dihydropyridine-3-carboxylate. To a solution of 4-bromo-2-fluoroaniline (56 mg, 0.29 mmol) in THF (5 mL) was added LiHMDS (0.74 mL, 1.0 M, 0.74 mmol) at −78° C. and stirred for 0.5 hours at −78° C. Then a solution of methyl 2-chloro-1-methyl-6-oxo-4-(1-phenylvinyl)-1,6-dihydropyridine-3-carboxylate (90 mg, 0.296 mmol) in THF (0.5 mL) was added and the mixture was stirred at −78° C. for 30 minutes. The mixture was quenched with saturated NH₄Cl solution (5 mL) and extracted with EtOAc (3×50 mL). The combined organic phases were washed with brine (5 mL), dried over Na₂SO₄, filtered and concentrated. The residue was purified by column chromatography eluting with 0-20% EtOAc/petroleum ether to afford methyl 2-((4-bromo-2-fluorophenyl)amino)-1-methyl-6-oxo-4-(1-phenylvinyl)-1,6-dihydropyridine-3-carboxylate (120 mg, 89%). MS (apci, m/z)=459.2 (M+H).

Step 6. Preparation of 8-((4-bromo-2-fluorophenyl)amino)-2-(2,4-dimethoxybenzyl)-7-methyl-4-phenyl-3,4-dihydro-2,7-naphthyridine-1,6(2H,7H)-dione. To a solution of methyl 2-((4-bromo-2-fluorophenyl)amino)-1-methyl-6-oxo-4-(1-phenylvinyl)-1,6-dihydropyridine-3-carboxylate (120 mg, 0.29 mmol) in toluene (10 mL) was added DMB-NH₂ (43.8 mg, 0.26 mmol) and AlMe₃ (0.4 mL, 2.0 M, 0.79 mmol) at 25° C. under N₂ and the mixture was stirred at 80° C. for 48 hours. The mixture was quenched with saturated NH₄Cl solution (5 mL) and filtered. The filtrate was extracted with EtOAc (3×10 mL) and the organic layer was washed with brine (10 mL), dried over Na₂SO₄, filtered and concentrated. The residue was purified by column chromatography eluting with 0-50% EtOAc/petroleum ether to afford 8-((4-bromo-2-fluorophenyl)amino)-2-(2,4-dimethoxybenzyl)-7-methyl-4-phenyl-3,4-dihydro-2,7-naphthyridine-1,6(2H,7H)-dione (80.0 mg, 52%). MS (apci, m/z)=594.2 (M+H).

Step 7. 8-((4-bromo-2-fluorophenyl)amino)-7-methyl-4-phenyl-3,4-dihydro-2,7-naphthyridine-1,6(2H,7H)-dione. A mixture of 8-((4-bromo-2-fluorophenyl)amino)-2-(2,4-dimethoxybenzyl)-7-methyl-4-phenyl-3,4-dihydro-2,7-naphthyridine-1,6(2H,7H)-dione (80 mg, 0.14 mmol) in TFA (5 mL) was stirred for 1 hour at 80° C. The cooled mixture was concentrated and the residue was dissolved in MeOH (5 mL). NaHCO₃ solid (~1 g) was added and the mixture stirred for 15 minutes then treated with DCM (20 mL) and filtered. The filtrate was concentrated and purified by prep HPLC (Prep HPLC condition: column: Boston Prime C18 150*25 mm*5 um; mobile phase: water (0.225% ammonia hydroxide v/v)-ACN; B %: 40%-70%, FlowRate (ml/min): 25). Fractions were lyophilized to afford 8-((4-bromo-2-fluorophenyl)amino)-7-methyl-4-phenyl-3,4-dihydro-2,7-naphthyridine-1,6(2H,7H)-dione (5.49 mg, 9%). ¹H NMR (400 MHz, MeOD) δ 7.49 (d, 1H), 7.40-7.32 (m, 6H), 6.93 (t, 1H), 5.76 (s, 1H), 4.19 (t, 1H), 3.66 (d, 2H), 3.24 (s, 3H) ppm. MS (apci, m/z)=442.2, 444.1 (M+H).

Example 65

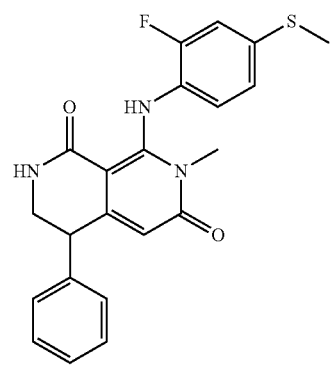 [SMILES: CSc1ccc(Nc2c3c(cc(=O)n2C)C(c2ccccc2)CNC3=O)c(F)c1]

8-((2-fluoro-4-(methylthio)phenyl)amino)-7-methyl-4-phenyl-3,4-dihydro-2,7-naphthyridine-1,6(2H,7H)-dione Prepared according to Example 64, substituting 2-fluoro-4-(methylthio)aniline in place of 4-bromo-2-fluoroaniline in step 5 to afford 8-((2-fluoro-4-(methylthio)phenyl)amino)-7-methyl-4-phenyl-3,4-dihydro-2,7-naphthyridine-1,6(2H,7H)-dione (21 mg, 29%). ¹H NMR (400 MHz, d6-DMSO) δ 11.71 (s, 1H), 8.15 (s, 1H), 7.40-7.25 (m, 6H), 7.08 (d, 1H), 6.97 (t, 1H), 5.59 (s, 1H), 4.13 (t, 1H), 3.54 (bs, 2H), 3.30 (s, 3H), 3.05 (s, 3H) ppm. MS (apci, m/z)=410.1 (M+H).

Example 66

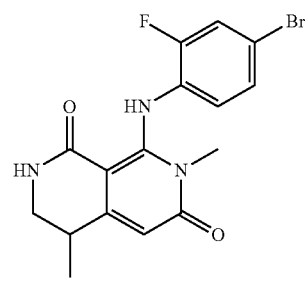 [SMILES: CC1CNC(=O)c2c1cc(=O)n(C)c2Nc1ccc(Br)cc1F]

8-((4-bromo-2-fluorophenyl)amino)-4,7-dimethyl-3,4-dihydro-2,7-naphthyrdine-1,6(2H,7H)-dione Prepared according to Example 64, substituting 4,4,5,5-tetramethyl-2-(prop-1-en-2-yl)-1,3,2-dioxaborolane in place of 4,4,5,5-tetramethyl-2-(1-phenylvinyl)-1,3,2-dioxaborolane in Step 4 to afford 8-((4-bromo-2-fluorophenyl)amino)-4,7-dimethyl-3,4-dihydro-2,7-naphthyrdine-1,6(2H,7H)-dione (3 mg, 13%). $^1$H NMR (400 MHz, MeOD) δ7.48 (d, 1H), 7.35 (d, 1H), 6.88 (t, 1H), 6.15 (s, 1H), 3.51 (dd, 1H), 3.21 (s, 3H), 3.20-3.15 (m, 1H), 2.99-2.86 (m, 1H), 1.33 (d, 3H) ppm. MS (apci, m/z)=380.0, 382.2 (M+H).

Example 67

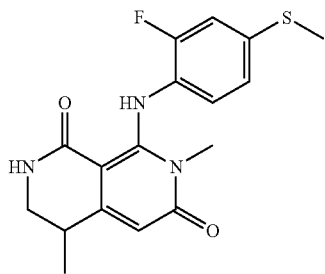 [SMILES: CSc1ccc(Nc2c3c(cc(=O)n2C)C(C)CNC3=O)c(F)c1]

8-((2-fluoro-4-(methylthio)phenyl)amino)-4,7-dimethyl-3,4-dihydro-2,7-naphthyrdine-1,6(2H,7H)-dione Prepared according to Example 64, substituting 4,4,5,5-tetramethyl-2-(prop-1-en-2-yl)-1,3,2-dioxaborolane in place of 4,4,5,5-tetramethyl-2-(1-phenylvinyl)-1,3,2-dioxaborolane in Step 4 and 2-fluoro-4-(methylthio)aniline in place of 4-bromo-2-fluoroaniline in step 5 to afford 8-((2-fluoro-4-(methylthio)phenyl)amino)-4,7-dimethyl-3,4-dihydro-2,7-naphthyrdine-1,6(2H,7H)-dione (3.8 mg, 22%). $^1$H NMR (400 MHz, MeOD) δ 7.16 (d, 1H), 7.09 (d, 1H), 6.92 (t, 1H), 6.09 (s, 1H), 3.51 (dd, 1H), 3.19 (s, 3H), 3.17-3.15 (m, 1H), 2.99-2.94 (m, 1H), 2.51 (s, 3H), 1.33 (d, 3H) ppm. MS (apci, m/z)=348.1 (M+H).

Example 68

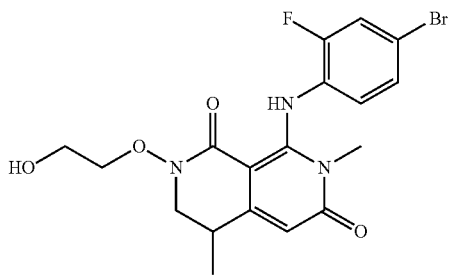 [SMILES: CC1CN(OCCO)C(=O)c2c1cc(=O)n(C)c2Nc1ccc(Br)cc1F]

8-((4-bromo-2-fluorophenyl)amino)-2-(2-hydroxyethoxy)-4,7-dimethyl-3,4-dihydro-2,7-naphthyridine-1,6(2H,7H)-dione Step 1. Preparation of 1-ethoxyprop-1-yne. Anhydrous $NH_3$ (300 mL) was condensed at −70° C. in a reaction flask, and crushed $Fe(NO_3)_3 \cdot 9H_2O$ (252 mg, 0.625 mmol) was added with slow stirring. Solid $NaNH_2$ (34.14 g, 0.875 mol) was added at −60 to −40° C. over 10 minutes, then 2-chloro-1,1-diethoxyethane (38.15 g, 0.25 mol) was added dropwise at this temperature over a period of 30 minutes. The reaction was refluxed at −30° C. for 1 hour, prior to dropwise addition of MeI (177.42 g, 1.25 mol) over 30 minutes. The reaction mixture was stirred vigorously for 90 minutes at this temperature, then cautiously quenched by dropwise addition of a cooled sat. $NH_4Cl$ solution (40 mL), followed by $Et_2O$ (100 mL) and additional sat. $NH_4Cl$ (50 mL). The cooling bath was removed, and the reaction mixture was allowed to warm to 15° C. Water (50 mL) was added, and the organic layer was separated and washed with water (50 mL) and brine (50 mL). The combined aqueous solutions were extracted with $Et_2O$ (50 mL), and the combined organic layers were dried over $Na_2SO_4$ and filtered to afford ~1.3 M ethereal solution of 1-ethoxyprop-1-yne (100 mL, 52%). $^1$H NMR (400 MHz, $CDCl_3$) δ 3.99 (q, 2H), 1.73 (s, 3H), 1.32 (t, 3H) ppm.

Step 2. Preparation of (Z)-2-(1-ethoxyprop-1-en-2-yl)benzo[d][1,3,2]dioxaborole. To a solution of benzo[d][1,3,2]dioxaborole (1.43 g, 11.89 mmol) in toluene (50 mL) was added 1-ethoxyprop-1-yne (7.7 mL, 1.3M/$Et_2O$, 11.89 mmol) and $NiCl_2$(dppe) (314 mg, 0.59 mmol) under $N_2$. The reaction mixture was degassed three times and stirred at 50° C. for 3 hours. The mixture was filtered to afford a toluene solution of (Z)-2-(1-ethoxyprop-1-en-2-yl)benzo[d][1,3,2]dioxaborole (1.5 g, 62%) which was used without further purification.

Step 3. Preparation of methyl (E)-2-chloro-4-(1-ethoxyprop-1-en-2-yl)-1-methyl-6-oxo-1,6-dihydropyridine-3-carboxylate. To a solution of (Z)-2-(1-ethoxyprop-1-en-2-yl)benzo[d][1,3,2]dioxaborole (1.5 g, 7.33 mmol) in toluene (50 mL) and THF (30 mL) was added methyl 2-chloro-4-iodo-1-methyl-6-oxo-1,6-dihydropyridine-3-carboxylate (1.2 g, 3.66 mmol), Pd(dppf)$Cl_2$ (299 mg, 0.37 mmol), $K_3PO_4$ (2.33 g, 10.99 mmol) and $H_2O$ (3 mL). The mixture was degassed 3 times and stirred at 75° C. for 3 hours. The cooled mixture was filtered. The filtrate was diluted with EtOAc (50 mL) then washed with water (3×10 mL) and brine (10 mL), dried over $Na_2SO_4$, filtered and concentrated. The residue was purified by column chromatography eluting with 0-40% EtOAc/petroleum ether to afford methyl (E)-2-chloro-4-(1-ethoxyprop-1-en-2-yl)-1-methyl-6-oxo-1,6-dihydropyridine-3-carboxylate (650 mg, 62%). MS (apci, m/z)=286.0 (M+H).

Step 4. Preparation of methyl (E/Z)-4-(1-((2-(tert-butoxy)ethoxy)imino)propan-2-yl)-2-chloro-1-methyl-6-oxo-1,6-dihydropyridine-3-carboxylate. To a solution of methyl (E)-2-chloro-4-(1-ethoxyprop-1-en-2-yl)-1-methyl-6-oxo-1,6-dihydropyridine-3-carboxylate (600 mg, 2.1 mmol) and O-(2-(tert-butoxy)ethyl)hydroxylamine hydrochloride (356 mg, 2.1 mmol) in dioxane (10 mL) were added TEA (212 mg, 2.1 mmol) and HCl (1 mL, 4M/dioxane, 4.2 mmol) The mixture was heated to 60° C. and stirred for 2 hours. 1,4-Dioxane (20 mL) was added and the mixture was filtered and concentrated to afford methyl (E/Z)-4-(1-((2-(tert-butoxy)ethoxy)imino)propan-2-yl)-2-chloro-1-methyl-6-oxo-1,6-dihydropyridine-3-carboxylate (780 mg, 99.6%) which was used without further purification. MS (apci, m/z)=317.1 (M+H−t-Bu).

Step 5. Preparation of 2-(2-(tert-butoxy)ethoxy)-8-chloro-4,7-dimethyl-3,4-dihydro-2,7-naphthyridine-1,6(2H,7H)-dione. To a solution of methyl (E/Z)-4-(1-((2-(tert-butoxy)ethoxy)imino)propan-2-yl)-2-chloro-1-methyl-6-oxo-1,6-dihydropyridine-3-carboxylate (780 mg, 2.09 mmol) in IPA (10 mL) were added $NaCNBH_3$ (657 mg, 10.46 mmol) and AcOH (628 mg, 10.46 mmol). The mixture was stirred at 20° C. for 48 hours. EtOAc (100 mL) was added and the mixture was washed with saturated $NaHCO_3$ (10 mL) and brine (10 mL), dried over $MgSO_4$, filtered and concentrated.

The residue was purified by column chromatography eluting with 0-40% EtOAc/petroleum ether to afford 2-(2-(tert-butoxy)ethoxy)-8-chloro-4,7-dimethyl-3,4-dihydro-2,7-naphthyridine-1,6(2H,7H)-dione (200 mg, 28%). $^1$H NMR (400 MHz, CDCl$_3$) δ 6.31 (s, 1H), 4.10-4.06 (m, 2H), 3.84 (dd, 1H), 3.70 (s, 3H), 3.59-3.53 (m, 3H), 3.06-3.05 (m, 1H), 1.31 (d, 3H), 1.15 (s, 9H) ppm. MS (apci, m/z)=343.1 (M+H).

Step 6. Preparation of 8-((4-bromo-2-fluorophenyl)amino)-2-(2-(tert-butoxy)ethoxy)-4,7-dimethyl-3,4-dihydro-2,7-naphthyridine-1,6(2H,7H)-dione. To a solution of 4-bromo-2-fluoroaniline (55 mg, 0.29 mmol) in THF (8 mL) was added LiHMDS (0.73 mL, 1M, 0.73 mmol) dropwise at −78° C. under N$_2$. The mixture was stirred at −78° C. for 30 minutes then a solution of 2-(2-(tert-butoxy)ethoxy)-8-chloro-4,7-dimethyl-3,4-dihydro-2,7-naphthyridine-1,6(2H,7H)-dione (100 mg, 0.29 mmol) in THF (2 mL) was added dropwise and stirring continued at −78° C. for 30 minutes. The mixture was treated with sat. NH$_4$Cl (5 mL) and extracted with EtOAc (2×30 mL). The combined organic layers were washed with brine (5 mL), dried over MgSO$_4$, filtered and concentrated to afford 8-((4-bromo-2-fluorophenyl)amino)-2-(2-(tert-butoxy)ethoxy)-4,7-dimethyl-3,4-dihydro-2,7-naphthyridine-1,6(2H,7H)-dione (144.8 mg, 100%) which was used without further purification. MS (apci, m/z)=496.2 (M+H).

Step 7. Preparation of 8-((4-bromo-2-fluorophenyl)amino)-2-(2-hydroxyethoxy)-4,7-dimethyl-3,4-dihydro-2,7-naphthyridine-1,6(2H,7H)-dione. A mixture of 8-((4-bromo-2-fluorophenyl)amino)-2-(2-(tert-butoxy)ethoxy)-4,7-dimethyl-3,4-dihydro-2,7-naphthyridine-1,6(2H,7H)-dione (144.8 mg, 0.292 mmol) in TFA (5 mL) was stirred for 2 hours at 25° C. The mixture was concentrated, dissolved in MeOH (10 mL) and treated with NaHCO$_3$ solid (73 mg, 0.876 mmol). After stirring for 30 minutes, DCM (50 mL) was added. The mixture was filtered, concentrated and purified by prep HPLC (Prep HPLC condition: column: Waters xbridge 150*25 mm 10 um; mobile phase: water (0.05% ammonia hydroxide v/v)-ACN; B %: 24%-64%, FlowRate (ml/min): 25). Clean fractions were lyophilized to afford 8-((4-bromo-2-fluorophenyl)amino)-2-(2-hydroxyethoxy)-4,7-dimethyl-3,4-dihydro-2,7-naphthyridine-1,6(2H,7H)-dione (34.8 mg, 27%). $^1$H NMR (400 MHz, MeOD) δ 7.38 (d, 1H), 7.26 (d, 1H), 6.82 (t, 1H), 6.02 (s, 1H), 3.98 (t, 2H), 3.82 (dd, 1H), 3.66 (t, 2H), 3.64-3.50 (m, 1H), 3.12 (s, 3H), 3.09-3.08 (m, 1H), 1.29 (d, 3H) ppm. MS (apci, m/z)=440.1 (M+H).

Example 69

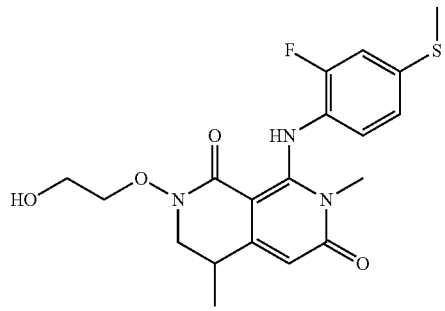 [SMILES: CSc1ccc(Nc2c3c(cc(=O)n2C)C(C)CN(OCCO)C3=O)c(F)c1]

8-((2-fluoro-4-(methylthio)phenyl)amino)-2-(2-hydroxyethoxy)-4,7-dimethyl-3,4-dihydro-2,7-naphthyridine-1,6(2H,7H)-dione Prepared according to Example 68, substituting 2-fluoro-4-(methylthio)aniline in place of 4-bromo-2-fluoroaniline in step 6 to afford 8-((2-fluoro-4-(methylthio)phenyl)amino)-2-(2-hydroxyethoxy)-4,7-dimethyl-3,4-dihydro-2,7-naphthyridine-1,6(2H,7H)-dione (27.5 mg, 23%). $^1$H NMR (400 MHz, MeOD) δ 7.16 (d, 1H), 7.10 (d, 1H), 6.99 (t, 1H), 6.07 (s, 1H), 4.05 (t, 2H), 3.91 (dd, 1H), 3.76 (t, 2H), 3.60 (dd, 1H), 3.21 (s, 3H), 3.19-3.15 (m, 1H), 2.50 (s, 3H), 1.40 (d, 3H) ppm. MS (apci, m/z)=408.2 (M+H).

Example 70

Preparation of anhydrous crystalline 8-((2-fluoro-4-(methylthio)phenyl)amino)-2-(2-hydroxyethoxy)-7-methyl-3,4-dihydro-2,7-naphthyridine-1,6(2H,7H)-dione, Form 1

Phosphoric acid (37.4 g, 25.8 mL, 14.8 molar, 50 Eq. 382 mmol) was added to a stirred solution of 2-(2-(tert-butoxy)ethoxy)-8-((2-fluoro-4-(methylthio)phenyl)amino)-7-methyl-3,4-dihydro-2,7-naphthyridine-1,6(2H,7H)-dione, which may be prepared according to any of the methods disclosed herein (3.43 g, 1 Eq. 7.63 mmol) in acetonitrile (ACN) under Air. The mixture was warmed to 60° C. and stirred for 15 minutes after which LCMS indicated complete reaction. The reaction was cooled to 0° C. and treated with K$_3$PO$_4$ (382 mL, 1M, 382 mmol). The mixture was extracted with ethyl acetate (3×100 mL). The combined organic layers were washed with brine (50 mL), dried over sodium sulfate, filtered, and concentrated in vacuo to afford a bright yellow foam. The crude residue was purified over 80 g silica cartridge, eluting with a gradient of 0% to 15% methanol in dichloromethane (DCM) at first, then increased to 20% methanol in DCM to afford the product as a bright yellow foam (2.17 g). This was dissolved in DCM (50 mL), treated with Norit CA1 activated charcoal (600 mg) and stirred for 15 min. The mixture was filtered through GF paper and the residue concentrated to afford a bright yellow foam. This procedure was repeated using Darco G-60 activated charcoal to afford the product as a pale pink foam. This material was treated with 2-propanol (20 mL) and DCM (5 mL) added to fully solubilize. The mixture was concentrated, during which solids began to form but material became an oil once fully concentrated. The residue was treated with 2-propanol (10 mL) and warmed to 40° C. upon which a thick precipitate appeared. The mixture cooled to room temperature and diluted with cold 2-propanol (5 mL) to facilitate stirring. The mixture was then filtered and 15 mL of cold 2-propanol used for rinsing and washing to afford crystalline anhydrous 8-((2-fluoro-4-(methylthio)phenyl)amino)-2-(2-hydroxyethoxy)-7-methyl-3,4-dihydro-2,7-naphthyridine-1,6(2H,7H)-dione, Form 1 (1.61 g, 4.09 mmol, 53.6%) as an off-white solid after drying in vacuo. FIG. 1 depicts a powder X-ray diffraction pattern of crystalline anhydrous 8-((2-fluoro-4-(methylthio)phenyl)amino)-2-(2-hydroxyethoxy)-7-methyl-3,4-dihydro-2,7-naphthyridine-1,6(2H,7H)-dione, Form 1 prepared according to this method, wherein the PXRD analysis was conducted using the Instrument Methods described in Example 77.

Example 71

Preparation of seed crystals of crystalline anhydrous 8-((2-fluoro-4-(methylthio)phenyl)amino)-2-(2-hydroxyethoxy)-7-methyl-3,4-dihydro-2,7-naphthyridine-1,6(2H,7H)-dione, Form 2

Step 1: Methyl 4-bromo-2-((2-fluoro-4-(methylthio)phenyl)amino)-1-methyl-6-oxo-1,6-dihydropyridine-3-carboxylate (prepared according to any of the methods described herein) (1.0 equiv. 7.5 kg), XPhos (0.075 equiv) and MeThF (10 volumes) were added to a reactor and the reaction was degassed. Pd (II) acetate (0.015 equiv.) was charged to the reactor and reaction was degassed. (Z)-2-(2-ethoxyvinyl)-4,4,5,5-tetramethyl-1,3,2-dioxaborolane (0.8 equiv) and sparged 45 wt % KOH solution (4 equiv.) were charged to the reactor. The reaction mixture was heated at 50° C. for 1 hour before additional (Z)-2-(2-ethoxyvinyl)-4,4,5,5-tetramethyl-1,3,2-dioxaborolane (0.3 equiv) was added, and heating was continued for another hour. The reaction mixture was washed with water (2 volumes) followed by 1M acetic acid (2 equiv.), then stirred with SiliaMetS® thiol (SiliCycle Inc., Quebec City, Quebec, Canada) (0.3 g/g) at 50° C. for 18 hours before filtering. The filter cake was washed with MeTHF (5 volumes). The organic layer was concentrated to 3 volumes and a small portion was removed and cooled to generate seed crystals. The seed crystals were charged back to the reactor and allowed to stir for 1 hour at 50° C. before slowly cooling to 30° C. MeTHF/heptane 1:4 (5 volumes) was then slowly charged to the reactor and the mixture was stirred for 1 hour. the mixture was then slowly cooled to 10° C. and allowed to stir for 18 hours before filtering. The filter cake was washed with MeTHF/heptane 1:1 (5 volumes). The solids were then dried in the vacuum oven to afford methyl 4-[(Z)-2-ethoxyethenyl]-2-[2-fluoro-4-(methylsulfanyl)anilino]-1-methyl-6-oxo-1,6-dihydropyridine-3-carboxylate Step 2: Methyl 4-[(Z)-2-ethoxyethenyl]-2-[2-fluoro-4-(methylsulfanyl)anilino]-1-methyl-6-oxo-1,6-dihydropyridine-3-carboxylate (5.0 g, 12.5 mmol) was combined with 2-methyltetrahydrofuran (20 volumes) and O-(2-(tert-butoxy)ethyl)hydroxylamine hydrochloride (1.3 equiv., 16.3 mmol) and heated to approximately 75° C. The resulting mixture cooled to 20° C. Borane-pyridine complex (2.0 eq, 25.0 mmol) was added as well as HCl in cyclopentyl methyl ether (CPME) (3M, 1.3 eq, 16.3 mmol). The resulting mixture was stirred at 20° C. for 45 min then heated to 60° C. After stirring overnight, the mixture was cooled to 20° C., and quenched with HCl (1M, 30 mL). During this time, some bubbling and exotherm was observed. After the off gassing appeared to be complete, (~5 minutes), the organic layer was separated, washed with water (8 vol), and concentrated to approximately 6 volumes via reduced pressure distillation. At this time, phosphoric acid (14.6M, 15 eq, 187 mmol) was added and the mixture stirred at 65° C. After stirring overnight, the mixture was cooled to 20° C. and diluted with 2-methyltetrahydrofuran (7 vol). A solution of potassium hydroxide (11.5M, 20 eq) was added slowly. After stirring for approximately 10 minutes, the layers were allowed to separate. The organic phase was washed with water (10 volumes) before concentrating to approximately 5 volumes with reduced pressure distillation to afford a solution of 8-((2-fluoro-4-(methylthio)phenyl)amino)-2-(2-hydroxyethoxy)-7-methyl-3,4-dihydro-2,7-naphthyridine-1,6(2H,7H)-dione in 2-methyltetrahydrofuran. Cyclopentyl methyl ether (2 vol) was warmed to approximately 40° C. before adding the solution of 8-((2-fluoro-4-(methylthio)phenyl)amino)-2-(2-hydroxyethoxy)-7-methyl-3,4-dihydro-2,7-naphthyridine-1,6(2H,7H)-dione. The mixture was stirred for 1 hour. During this time a solid precipitated. The solvent was exchanged to CPME (approximately 8 volumes) via reduced pressure distillation and the resulting suspension stirred at 15° C. for 2 hours. The resulting solid was collected and dried at 45° C. under vacuum to provide crystalline anhydrous 8-((2-fluoro-4-(methylthio)phenyl)amino)-2-(2-hydroxyethoxy)-7-methyl-3,4-dihydro-2,7-naphthyridine-1,6(2H,7H)-dione, Form 2. The crystalline form was confirmed by PXRD analysis using the Instrument Methods described in Example 77.

Example 72

Preparation of crystalline anhydrous 8-((2-fluoro-4-(methylthio)phenyl)amino)-2-(2-hydroxyethoxy)-7-methyl-3,4-dihydro-2,7-naphthyridine-1,6(2H,7H)-dione, Form 2

Methyl 4-[(Z)-2-ethoxyethenyl]-2-[2-fluoro-4-(methylsulfanyl)anilino]-1-methyl-6-oxo-1,6-dihydropyridine-3-carboxylate, prepared as described in Example 71, Step 1 (2.0 g, 5.0 mmol) was combined with 2-Methyltetrahydrofuran (20 volumes) and heated to approximately 75° C. O-(2-(tert-butoxy)ethyl)hydroxylamine hydrochloride (1.3 eq, 6.50 mmol) was added to the mixture and the resulting mixture cooled to 20° C. Borane-pyridine complex (2.0 eq, 10.0 mmol) was added as well as HCl in cyclopentyl methyl ether (CPME) (3M, 1.3 eq, 6.5 mmol). The resulting mixture was stirred at 60° C. After stirring overnight, the mixture was cooled to 20° C., quenched with HCl (1M, 12 mL). During this time, some bubbling and exotherm was observed. After the reaction appeared to be complete, (~5 minutes), the organic layer was separated, washed with water (8 vol), and concentrated to approximately 6 volumes via reduced pressure distillation. At this time, phosphoric acid (14.6M, 15 eq, 75.0 mmol) was added and the mixture stirred at 65° C. After stirring overnight, the mixture was cooled to 20° C. and diluted with 2-methyltetrahydrofuran (7 volumes). A solution of potassium hydroxide (11.5M, 20 eq) was added slowly. After stirring for approximately 10 minutes, the layers were allowed to separate. The organic phase was washed with water (10 mL) before concentrating to approximately 5 vol with reduced pressure distillation. The mixture was then heated up to 50° C. with and cyclopentyl methyl ether (2 vol) added. Seeds of crystalline anhydrous 8-((2-fluoro-4-(methylthio)phenyl)amino)-2-(2-hydroxyethoxy)-7-methyl-3,4-dihydro-2,7-naphthyridine-1,6(2H,7H)-dione, Form 2 (prepared as described in Example 71) were added at this time and the resulting suspension cooled to 30° C. Solvent was exchanged to cyclopentyl methyl ether (approximately 9 volumes) via reduced pressure distillation and the resulting suspension stirred at 40° C. for 1 hour. The mixture was cooled to 20° C. and stirred overnight. The resulting solid was collected and washed with cyclopentyl methyl ether (4 volumes) and dried at 45° C. under vacuum to provide crystalline anhydrous 8-((2-fluoro-4-(methylthio)phenyl)amino)-2-(2-hydroxyethoxy)-7-methyl-3,4-dihydro-2,7-naphthyridine-1,6(2H,7H)-dione, Form 2. FIG. 2 depicts a powder X-ray diffraction pattern of crystalline anhydrous 8-((2-fluoro-4-(methylthio)phenyl)amino)-2-(2-hydroxyethoxy)-7-methyl-3,4-dihydro-2,7-naphthyridine-1,6(2H,7H)-dione, Form 2 prepared according to this method, wherein the PXRD analysis was conducted using the Instrument Methods described in Example 77.

Example 73

Preparation of Seed Crystals of Crystalline Monohydrate 8-((2-fluoro-4-(methylthio)phenyl)amino)-2-(2-hydroxyethoxy)-7-methyl-3,4-dihydro-2,7-naphthyridine-1,6(2H,7H)-dione, Form 3

Into a reactor was charged 2-methyltetrahydrofuran (20 volumes) of methyl 4-[(Z)-2-ethoxyethenyl]-2-[2-fluoro-4-

(methylsulfanyl)anilino]-1-methyl-6-oxo-1,6-dihydropyridine-3-carboxylate, prepared as described in Example 71, Step 1 (5.0 kg; limiting reagent—all subsequent chargers based on this quantity), and O-(2-(tert-butoxy)ethyl)hydroxylamine hydrochloride (2.89 kg). The subsequent mixture was heated to 70° C. After the reaction was complete, the mixture was cooled to 20° C. and borane-pyridine (8M, 3.3 L) and HCl in CPME (3M, 5.95 L) were added. The mixture was stirred at 20° C. After reduction was complete, the mixture was heated to 65° C. until cyclization was complete. The reaction was cooled to 25° C., quenched with 1 M HCl (6 volumes) and washed with water (8 volumes). The organic layer was concentrated to approximately 7 volumes. Phosphoric acid (13.1 L) was charged and the resulting mixture heated to 60° C. until deprotection was complete. The reaction with quenched with aqueous 45 wt. % potassium hydroxide (22.8 L) dissolved in water (7 volumes) and then washed with water (10 volumes). The organic was then filtered through a spec free filter. At a reaction temperature of 45° C., the organic layer was concentrated to approximately 5 volumes and the water content measured with KF and adjusted to 5% water. Approximately 5% of the reaction mixture was removed and cooled to 20° C. affording a slurry, which was charged back to the reactor to seed the bulk. After stirring at 45° C. for three hours, the solvent was exchanged to CPME (8 volumes) with between 5%-10% residual 2-MeTHF and KF of at least 0.5%. The reaction was then cooled to 15° C. over 3 hours and granulated for 8 hours. The solids were collected and the washed with CPME (4 volumes). The solids were dried under vacuum to remove residual solvent. The drying process dehydrated the solid form to crystalline anhydrous 8-((2-fluoro-4-(methylthio)phenyl)amino)-2-(2-hydroxyethoxy)-7-methyl-3,4-dihydro-2,7-naphthyridine-1,6(2H,7H)-dione, Form 2. The resulting crystalline anhydrous 8-((2-fluoro-4-(methylthio)phenyl)amino)-2-(2-hydroxyethoxy)-7-methyl-3,4-dihydro-2,7-naphthyridine-1,6(2H,7H)-dione, Form 2 was then rehydrated in an oven (without vacuum) at 25-40° C. with trays of water. The final solids became rehydrated to afford crystalline monohydrate 8-((2-fluoro-4-(methylthio)phenyl)amino)-2-(2-hydroxyethoxy)-7-methyl-3,4-dihydro-2,7-naphthyridine-1,6(2H,7H)-dione, Form 3 based on KF and PXRD analysis, wherein the PXRD analysis was conducted using the Instrument Methods described in Example 77.

Example 74

Preparation of Crystalline Monohydrate 8-((2-fluoro-4-(methylthio)phenyl)amino)-2-(2-hydroxyethoxy)-7-methyl-3,4-dihydro-2,7-naphthyridine-1,6(2H,7H)-dione, Form 3 by Seeded Crystallization Into a reactor was charged 2-MeTHF (6 volumes, 19 L) and water (0.27 volumes, 0.87 L). Amorphous 8-((2-fluoro-4-(methylthio)phenyl)amino)-2-(2-hydroxyethoxy)-7-methyl-3,4-dihydro-2,7-naphthyridine-1,6(2H,7H)-dione, prepared according to Example 6, Method A or B (3.22 kg) was added and the mixture heated to 65° C. During this time the solid dissolved and a solution was obtained. The mixture was cooled to 45° C. and the seeds of crystalline monohydrate 8-((2-fluoro-4-(methylthio)phenyl)amino)-2-(2-hydroxyethoxy)-7-methyl-3,4-dihydro-2,7-naphthyridine-1,6(2H,7H)-dione, Form 3 as prepared in Example 73 were added. The mixture was stirred for approximately 2 hours before slowly charging heptane (4 volumes) over 3 hours. The mixture was cooled to 15° C. over 4 hours and stirred for at least 2 hours. The solids were then collected and washed with 50:50 heptane/2-MeTHF (4 volumes, 13 L). The solids were dried under vacuum to remove residual solvent. The drying process dehydrated the solid form to crystalline anhydrous 8-((2-fluoro-4-(methylthio)phenyl)amino)-2-(2-hydroxyethoxy)-7-methyl-3,4-dihydro-2,7-naphthyridine-1,6(2H,7H)-dione, Form 2. The resulting crystalline anhydrous 8-((2-fluoro-4-(methylthio)phenyl)amino)-2-(2-hydroxyethoxy)-7-methyl-3,4-dihydro-2,7-naphthyridine-1,6(2H,7H)-dione, Form 2 was then rehydrated in an oven (without vacuum) at 25-40° C. with trays of water. After sitting in the oven for 8-24 hours, the solid had rehydrated afford crystalline monohydrate 8-((2-fluoro-4-(methylthio)phenyl)amino)-2-(2-hydroxyethoxy)-7-methyl-3,4-dihydro-2,7-naphthyridine-1,6(2H,7H)-dione, Form 3 based on KF and PXRD analysis.

Example 75

Alternative Preparation of Crystalline Monohydrate 8-((2-fluoro-4-(methylthio)phenyl)amino)-2-(2-hydroxyethoxy)-7-methyl-3,4-dihydro-2,7-naphthyridine-1,6(2H,7H)-dione, Form 3

Amorphous 8-((2-fluoro-4-(methylthio)phenyl)amino)-2-(2-hydroxyethoxy)-7-methyl-3,4-dihydro-2,7-naphthyridine-1,6(2H,7H)-dione, prepared according to Example 6, Method A or B (404.88 mg) was combined with 2-propanol (1.50 mL, 3.7 Volumes) with magnetic stirring. The mixture was heated to 60° C. During this time, the mixture became homogenous, dark red and all solids dissolved. Water (2.5 mL, 6.2 volumes) was added and the mixture allowed to cool to room temperature and stir for 2 hours. During this time, a solid precipitated, the mixture became quite thick. A larger stir bar was added at this time. An aliquot was taken for analysis with PXRD and the mixture was allowed to stir at room temperature. After stirring overnight, the solid was collected and washed with 9:1 2-propanol:water (2×1.00 mL). Dried in preheated oven at 50° C. with pan of water for 3 hours followed by sitting overnight uncapped on the bench. 371 mg, 91% recovery. The isolated material was determined to be crystalline monohydrate 8-((2-fluoro-4-(methylthio)phenyl)amino)-2-(2-hydroxyethoxy)-7-methyl-3,4-dihydro-2,7-naphthyridine-1,6(2H,7H)-dione, Form 3 by PXRD analysis. FIG. 3 depicts a powder X-ray diffraction pattern of crystalline monohydrate 8-((2-fluoro-4-(methylthio)phenyl)amino)-2-(2-hydroxyethoxy)-7-methyl-3,4-dihydro-2,7-naphthyridine-1,6(2H,7H)-dione, Form 3 prepared according to this method, wherein the PXRD analysis was conducted using the Instrument Methods described in Example 77.

Example 76

Moisture Sorption Analysis of Crystalline Monohydrate 8-((2-fluoro-4-(methylthio)phenyl)amino)-2-(2-hydroxyethoxy)-7-methyl-3,4-dihydro-2,7-naphthyrdine-1,6(2H,7H)-dione, Form 3

Water sorption and desorption studies were conducted on automated vapor sorption analyzer (TA instruments Q5000 SA). The microbalance was calibrated using a 100 mg standard weight. The relative humidity sensor was calibrated at 5.0, 11.3, 32.8, 52.8, 75.3, and 84.3% RH (25° C.) using saturated salt solutions. Approximately 10-20 mg of crystalline monohydrate 8-((2-fluoro-4-(methylthio)phenyl)amino)-2-(2-hydroxyethoxy)-7-methyl-3,4-dihydro-2,7-naphthyrdine-1,6(2H,7H)-dione, Form 3 was placed in the quartz sample holder and dried at ≤3% relative humidity (RH) at 25° C. The RH was then progressively increased from 0% to 40% RH in increments of 5% followed by a decrease to a final RH of 0% in 5% RH increments. A maximum equilibration time of 120 minutes was used for all steps. The weight gain at each of the % RH steps is based on the weight after the initial drying step at 0% RH. The weight change of the sample was not used to assess equilibrium and instead all steps were programed to be 120 minutes. After data collection was complete, data analysis was performed using commercially available TA universal analysis software and Microsoft Excel.

Figure 5:
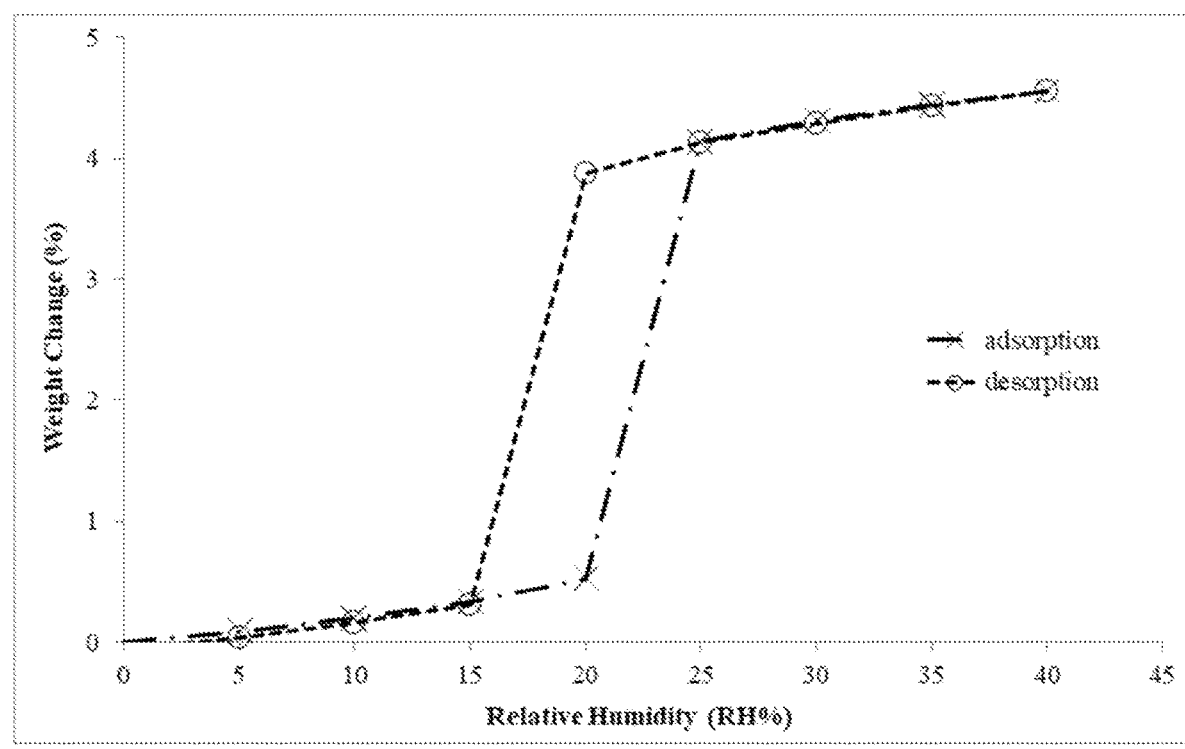
FIG. 5 depicts a sorption isotherm of crystalline monohydrate 8-((2-fluoro-4-(methylthio)phenyl)amino)-2-(2-hydroxyethoxy)-7-methyl-3,4-dihydro-2,7-naphthyrdine-1,6 (2H,7H)-dione, Form 3.

FIG. 5 depicts the sorption isotherm of crystalline monohydrate 8-((2-fluoro-4-(methylthio)phenyl)amino)-2-(2-hydroxyethoxy)-7-methyl-3,4-dihydro-2,7-naphthyridine-1,6 (2H,7H)-dione, Form 3. As shown in FIG. 5, crystalline monohydrate 8-((2-fluoro-4-(methylthio)phenyl)amino)-2-(2-hydroxyethoxy)-7-methyl-3,4-dihydro-2,7-naphthyridine-1,6(2H,7H)-dione, Form 3 dehydrates to crystalline anhydrous 8-((2-fluoro-4-(methylthio)phenyl)amino)-2-(2-hydroxyethoxy)-7-methyl-3,4-dihydro-2,7-naphthyridine-1,6(2H,7H)-dione, Form 2 at 15% RH and ° C. as confirmed by PXRD analysis. Crystalline anhydrous 8-((2-fluoro-4-(methylthio)phenyl)amino)-2-(2-hydroxyethoxy)-7-methyl-3,4-dihydro-2,7-naphthyridine-1,6(2H,7H)-dione, Form 2 rehydrates to crystalline monohydrate 8-((2-fluoro-4-(methylthio)phenyl)amino)-2-(2-hydroxyethoxy)-7-methyl-3,4-dihydro-2,7-naphthyridine-1,6(2H,7H)-dione, Form 3 at 25% RH at 25° C. as confirmed by PXRD analysis. Based on this analysis, crystalline anhydrous 8-((2-fluoro-4-(methylthio)phenyl)amino)-2-(2-hydroxyethoxy)-7-methyl-3,4-dihydro-2,7-naphthyridine-1,6(2H,7H)-dione, Form 2 is stable below 10% RH at 25° C., and crystalline monohydrate 8-((2-fluoro-4-(methylthio)phenyl)amino)-2-(2-hydroxyethoxy)-7-methyl-3,4-dihydro-2,7-naphthyridine-1,6(2H,7H)-dione, Form 3 is stable above 30% RH at 25° C.

Example 77

General Procedures for Solid Form Analyses by PXRD

Instrument Methods

Powder X-ray diffraction analysis of anhydrous crystalline 8-((2-fluoro-4-(methylthio)phenyl)amino)-2-(2-hydroxyethoxy)-7-methyl-3,4-dihydro-2,7-naphthyrdine-1,6 (2H,7H)-dione, Form 1, anhydrous crystalline 8-((2-fluoro-4-(methylthio)phenyl)amino)-2-(2-hydroxyethoxy)-7-methyl-3,4-dihydro-2,7-naphthyridine-1,6(2H,7H)-dione, Form 2, and amorphous 8-((2-fluoro-4-(methylthio)phenyl) amino)-2-(2-hydroxyethoxy)-7-methyl-3,4-dihydro-2,7-naphthyrdine-1,6(2H,7H)-dione Form 4 was conducted using a Rigaku MiniFlex 6G Diffractometer equipped with a Cu radiation source. The sample was prepared using a silicon low background sample holder (2 mm×0.5 mm well). Diffracted radiation was detected by a D/teX Ultra2 detector. The X-ray tube voltage and amperages were set to 40 kV and 15 mA respectively. Data was collected in the Miniflex goniometer at the Cu wavelength from 3.0 to 45.0° 2-Theta using a step with of 0.02° and a step speed of 2.00°/minute. The incident slit box was set to 1.25° and the length limiting slit was set at 10 mm. The sample was rotated at 10 RPM during collection. The data was exported to *txt file using Rigaku software SmartLab Studio II and analyzed with EVA diffract plus software. As shown by Example 76, anhydrous Form 2 rehydrates to monohydrate Form 3 at 25% RH at 25° C. Therefore, the analysis of anhydrous Form 2 by PXRD was conducted at approximately 25° C. and at relative humidity below 10%.

Powder X-ray diffraction analysis of crystalline monohydrate 8-((2-fluoro-4-(methylthio)phenyl)amino)-2-(2-hydroxyethoxy)-7-methyl-3,4-dihydro-2,7-naphthyridine-1,6 (2H,7H)-dione, Form 3 was conducted using a Bruker AXS D8 Endeavor diffractometer equipped with a Cu radiation source. The divergence slit was set at 10 mm continuous illumination. Diffracted radiation was detected by a PSD-Lynx Eye detector, with the detector PSD opening set at 4.11 degrees. The X-ray tube voltage and amperage were set to 40 kV and 40 mA respectively. Data was collected at the Cu wavelength (CuKα=1.5418λ) in the Theta-Theta goniometer from 3.0 to 40.0 degrees 2-Theta. A step size of 0.02 degrees and a step time of 0.3 second was used. The antiscatter screen was set to a fixed distance of 1.5 mm. Samples were rotated during data collection. Samples were prepared by placing them in a silicon low background sample holder and rotated during collection. Data were collected using Bruker DIFFRAC Plus software and analysis was performed by EVA diffract plus software. The PXRD data file was not processed prior to peak searching. Using the peak search algorithm in the EVA software, peaks selected with a threshold value of 1 were used to make preliminary peak assignments. To ensure validity, adjustments were manually made; the output of automated assignments was visually checked, and peak positions were adjusted to the peak maximum. Peaks with relative intensity of a 3% were generally chosen. Typically, the peaks which were not resolved or were consistent with noise were not selected. A typical error associated with the peak position from PXRD stated in USP up to +/−0.2° 2-Theta (USP-941). As shown by Example 76, monohydrate Form 3 dehydrates to anhydrous Form 2 at 15% RH and 25° C. Accordingly, the PXRD analysis of monohydrate Form 3 with PXRD was conducted at approximately 25° C. and at relative humidity above 30%.

PXRD Peak Picking Parameters

Using the peak search algorithm in the EVA software, peaks selected with a threshold value of 1 were used to make preliminary peak assignments. To ensure validity, adjustments were manually made; the output of automated assignments was visually checked, and peak positions were adjusted to the peak maximum. Peaks with relative intensity of a 3% were generally chosen. Typically, the peaks which were not resolved or were consistent with noise were not selected. A typical error associated with the peak position from PXRD stated in USP up to +/−0.2° 2-Theta (USP-941).

It will be apparent to those skilled in the art that various modifications and variations may be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All references cited herein, including patents, patent applications, papers, textbooks, and the like, and the references cited therein, to the extent that they are not already, are hereby incorporated by reference in their entireties. In the event that one or more of the incorporated literature and similar materials differs from or contradicts this application, including but not limited to defined terms, term usage, described techniques, or the like, this application controls.

Incorporated by reference herein in the entirety for all purposes is the content of U.S. Provisional Patent Application No. 63/168,456 filed Mar. 31, 2021 and U.S. Provisional Patent Application No. 63/309,346 filed Feb. 11, 2022.

We claim:
1. A compound of Formula I:

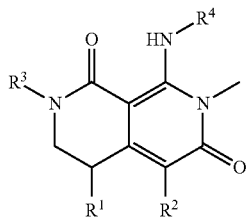

I or a pharmaceutically acceptable salt thereof, wherein:
$R^1$ is H, Br, C1-C6 alkyl or phenyl;
$R^2$ is H, halogen or $CH_3$—;
$R^3$ is H, hydroxyC1-C6 alkyl-, hydroxyC1-C6 alkoxy-, C1-C6 alkoxy, fluoroC1-C6 alkoxy, C3-C6 cycloalkyl, or (C3-C6 cycloalkyl)C1-C6 alkoxy-; and
$R^4$ is phenyl substituted with 1, 2 or 3 substituents independently selected from halogen, C1-C6 alkyl, C1-C6 alkylthio, fluoroC1-C6 alkylthio, fluoroC1-C6 alkyl, C1-C6 alkoxy, fluoroC1-C6 alkoxy, C3-C6 cycloalkyl, and C1-C6 alkyl-C(=O)—.

2. A compound according to claim 1 or a pharmaceutically acceptable salt thereof, wherein $R^1$ is H.

3. A compound according to claim 1 or a pharmaceutically acceptable salt thereof, wherein $R^2$ is H.

4. A compound according to claim 1 or a pharmaceutically acceptable salt thereof, wherein $R^2$ is $CH_3$—.

5. A compound according to claim 1 or a pharmaceutically acceptable salt thereof, wherein $R^3$ is hydroxyC1-C6 alkyl-.

6. A compound according to claim 1 or a pharmaceutically acceptable salt thereof, wherein $R^4$ is phenyl substituted with 1 or 2 substituents independently selected from halogen, C1-C6 alkyl, C1-C6 alkylthio, fluoroC1-C6 alkylthio, fluoroC1-C6 alkyl, C1-C6 alkoxy, fluoroC1-C6 alkoxy, C3-C6 cycloalkyl, and C1-C6 alkyl-C(=O)—.

7. A compound according to claim 1 or a pharmaceutically acceptable salt thereof, wherein $R^4$ is phenyl substituted with 1 or 2 substituents independently selected from halogen and C1-C6 alkylthio.

8. A compound of Formula II:

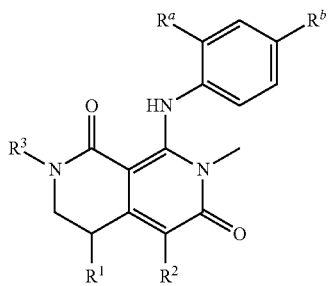

II or a pharmaceutically acceptable salt thereof, wherein
$R^1$ is H, Br, C1-C6 alkyl or phenyl;
$R^2$ is H, halogen or $CH_3$—;
$R^3$ is H, hydroxyC1-C6 alkyl-, hydroxyC1-C6 alkoxy-, C1-C6 alkoxy, fluoroC1-C6 alkoxy, C3-C6 cycloalkyl, or (C3-C6 cycloalkyl)C1-C6 alkoxy-; and
$R^a$ and $R^b$ are independently selected from halogen, C1-C6 alkyl, C1-C6 alkylthio, fluoroC1-C6 alkylthio, fluoroC1-C6 alkyl, C1-C6 alkoxy, fluoroC1-C6 alkoxy, C3-C6 cycloalkyl, and C1-C6 alkyl-C(=O)—.

9. A compound according to claim 8 or a pharmaceutically acceptable salt thereof, wherein $R^a$ is halogen.

10. A compound according to claim 9 or a pharmaceutically acceptable salt thereof, wherein $R^b$ is halogen, C1-C6 alkyl, C1-C6 alkylthio, or fluoroC1-C6 alkoxy.

11. A compound according to claim 10 or a pharmaceutically acceptable salt thereof, wherein $R^b$ is C1-C6 alkylthio.

12. A compound according to claim 11 or a pharmaceutically acceptable salt thereof, wherein $R^1$ is H.

13. A compound according to claim 12 or a pharmaceutically acceptable salt thereof, wherein $R^2$ is H.

14. A compound according to claim 13 or a pharmaceutically acceptable salt thereof, wherein $R^3$ is hydroxyC1-C6 alkoxy-.

15. A compound according to claim 1, selected from:
8-((4-bromo-2-fluorophenyl)amino)-2-cyclopropyl-7-methyl-3,4-dihydro-2,7-naphthyridine-1,6(2H,7H)-dione;
8-((4-bromo-2-fluorophenyl)amino)-2-(cyclopropylmethoxy)-7-methyl-3,4-dihydro-2,7-naphthyridine-1,6(2H,7H)-dione;
8-((4-bromo-2-fluorophenyl)amino)-2-ethoxy-7-methyl-3,4-dihydro-2,7-naphthyridine-1,6(2H,7H)-dione;
2-cyclopropyl-8-((2-fluoro-4-(methylthio)phenyl)amino)-7-methyl-3,4-dihydro-2,7-naphthyridine-1,6(2H,7H)-dione;
2-cyclopropyl-8-((2-fluoro-4-iodophenyl)amino)-7-methyl-3,4-dihydro-2,7-naphthyridine-1,6(2H,7H)-dione;
8-((2-fluoro-4-(methylthio)phenyl)amino)-2-(2-hydroxyethoxy)-7-methyl-3,4-dihydro-2,7-naphthyridine-1,6(2H,7H)-dione;
8-((4-bromo-2-fluorophenyl)amino)-2-(2-hydroxyethoxy)-7-methyl-3,4-dihydro-2,7-naphthyridine-1,6(2H,7H)-dione;
8-((2-fluoro-4-iodophenyl)amino)-2-(2-hydroxyethoxy)-7-methyl-3,4-dihydro-2,7-naphthyridine-1,6(2H,7H)-dione;
8-((2-chloro-4-iodophenyl)amino)-2-(2-hydroxyethoxy)-7-methyl-3,4-dihydro-2,7-naphthyridine-1,6(2H,7H)-dione;
8-((4-bromo-2-chlorophenyl)amino)-2-(2-hydroxyethoxy)-7-methyl-3,4-dihydro-2,7-naphthyridine-1,6(2H,7H)-dione;
8-((4-bromo-2,3-difluorophenyl)amino)-2-(2-hydroxyethoxy)-7-methyl-3,4-dihydro-2,7-naphthyridine-1,6(2H,7H)-dione;
8-((4-bromo-3-chloro-2-fluorophenyl)amino)-2-(2-hydroxyethoxy)-7-methyl-3,4-dihydro-2,7-naphthyridine-1,6(2H,7H)-dione;
8-((2-fluoro-4-(trifluoromethyl)phenyl)amino)-2-(2-hydroxyethoxy)-7-methyl-3,4-dihydro-2,7-naphthyridine-1,6(2H,7H)-dione;
8-((4-ethyl-2-fluorophenyl)amino)-2-(2-hydroxyethoxy)-7-methyl-3,4-dihydro-2,7-naphthyridine-1,6(2H,7H)-dione;

8-((4-cyclopropyl-2-fluorophenyl)amino)-2-(2-hydroxyethoxy)-7-methyl-3,4-dihydro-2,7-naphthyridine-1,6(2H,7H)-dione;

8-((2-fluoro-4-methoxyphenyl)amino)-2-(2-hydroxyethoxy)-7-methyl-3,4-dihydro-2,7-naphthyridine-1,6(2H,7H)-dione;

8-((2-fluoro-4-((trifluoromethyl)thio)phenyl)amino)-2-(2-hydroxyethoxy)-7-methyl-3,4-dihydro-2,7-naphthyridine-1,6(2H,7H)-dione;

8-((2-fluoro-4-isopropylphenyl)amino)-2-(2-hydroxyethoxy)-7-methyl-3,4-dihydro-2,7-naphthyridine-1,6(2H,7H)-dione;

8-((2-chloro-4-cyclopropylphenyl)amino)-2-(2-hydroxyethoxy)-7-methyl-3,4-dihydro-2,7-naphthyridine-1,6(2H,7H)-dione;

8-((4-acetyl-2-fluorophenyl)amino)-2-(2-hydroxyethoxy)-7-methyl-3,4-dihydro-2,7-naphthyridine-1,6(2H,7H)-dione;

8-((2-chloro-4-(methylthio)phenyl)amino)-2-(2-hydroxyethoxy)-7-methyl-3,4-dihydro-2,7-naphthyridine-1,6(2H,7H)-dione;

8-((4-(difluoromethoxy)-2-fluorophenyl)amino)-2-(2-hydroxyethoxy)-7-methyl-3,4-dihydro-2,7-naphthyridine-1,6(2H,7H)-dione;

8-((2-chloro-4-ethylphenyl)amino)-2-(2-hydroxyethoxy)-7-methyl-3,4-dihydro-2,7-naphthyridine-1,6(2H,7H)-dione;

8-((2-fluoro-4-(trifluoromethoxy)phenyl)amino)-2-(2-hydroxyethoxy)-7-methyl-3,4-dihydro-2,7-naphthyridine-1,6(2H,7H)-dione;

8-((4-((difluoromethyl)thio)-2-fluorophenyl)amino)-2-(2-hydroxyethoxy)-7-methyl-3,4-dihydro-2,7-naphthyridine-1,6(2H,7H)-dione;

8-((4-bromo-2-fluorophenyl)amino)-2-isopropoxy-7-methyl-3,4-dihydro-2,7-naphthyridine-1,6(2H,7H)-dione;

8-((2-fluoro-4-iodophenyl)amino)-2-isopropoxy-7-methyl-3,4-dihydro-2,7-naphthyridine-1,6(2H,7H)-dione;

2-ethoxy-8-((2-fluoro-4-iodophenyl)amino)-7-methyl-3,4-dihydro-2,7-naphthyridine-1,6(2H,7H)-dione;

8-((2-fluoro-4-iodophenyl)amino)-2-methoxy-7-methyl-3,4-dihydro-2,7-naphthyridine-1,6(2H,7H)-dione;

2-(tert-butoxy)-8-((2-fluoro-4-iodophenyl)amino)-7-methyl-3,4-dihydro-2,7-naphthyridine-1,6(2H,7H)-dione;

(S)-8-((2-fluoro-4-iodophenyl)amino)-2-(2-hydroxypropoxy)-7-methyl-3,4-dihydro-2,7-naphthyridine-1,6(2H,7H)-dione;

(R)-8-((2-fluoro-4-iodophenyl)amino)-2-(2-hydroxypropoxy)-7-methyl-3,4-dihydro-2,7-naphthyridine-1,6(2H,7H)-dione;

(S)-8-((4-bromo-2-fluorophenyl)amino)-2-(2-hydroxypropoxy)-7-methyl-3,4-dihydro-2,7-naphthyridine-1,6(2H,7H)-dione;

(R)-8-((4-bromo-2-fluorophenyl)amino)-2-(2-hydroxypropoxy)-7-methyl-3,4-dihydro-2,7-naphthyridine-1,6(2H,7H)-dione;

(R)-8-((4-bromo-2-fluorophenyl)amino)-2-(2-hydroxypropoxy)-5,7-dimethyl-3,4-dihydro-2,7-naphthyridine-1,6(2H,7H)-dione;

8-((4-bromo-2-fluorophenyl)amino)-2-(2-hydroxyethoxy)-5,7-dimethyl-3,4-dihydro-2,7-naphthyridine-1,6(2H,7H)-dione;

8-((4-bromo-2-fluorophenyl)amino)-5-chloro-2-(2-hydroxyethoxy)-7-methyl-3,4-dihydro-2,7-naphthyridine-1,6(2H,7H)-dione;

5-chloro-8-((2-fluoro-4-iodophenyl)amino)-2-(2-hydroxyethoxy)-7-methyl-3,4-dihydro-2,7-naphthyridine-1,6(2H,7H)-dione;

8-((4-bromo-2-fluorophenyl)amino)-5-fluoro-2-(2-hydroxyethoxy)-7-methyl-3,4-dihydro-2,7-naphthyridine-1,6(2H,7H)-dione;

8-((2-fluoro-4-iodophenyl)amino)-2-(2-hydroxyethoxy)-5,7-dimethyl-3,4-dihydro-2,7-naphthyridine-1,6(2H,7H)-dione;

8-((2-fluorophenyl)amino)-2-(2-hydroxyethoxy)-5-iodo-7-methyl-3,4-dihydro-2,7-naphthyridine-1,6(2H,7H)-dione;

5-bromo-8-((4-bromo-2-fluorophenyl)amino)-2-(2-hydroxyethoxy)-7-methyl-3,4-dihydro-2,7-naphthyridine-1,6(2H,7H)-dione;

4-bromo-8-((2-fluorophenyl)amino)-2-(2-hydroxyethoxy)-5,7-dimethyl-3,4-dihydro-2,7-naphthyridine-1,6(2H,7H)-dione;

8-((4-ethyl-2-fluorophenyl)amino)-2-(2-hydroxyethoxy)-5,7-dimethyl-3,4-dihydro-2,7-naphthyridine-1,6(2H,7H)-dione;

8-((4-cyclopropyl-2-fluorophenyl)amino)-2-(2-hydroxyethoxy)-5,7-dimethyl-3,4-dihydro-2,7-naphthyridine-1,6(2H,7H)-dione;

8-((4-bromo-2-fluorophenyl)amino)-7-methyl-3,4-dihydro-2,7-naphthyridine-1,6(2H,7H)-dione;

8-((4-bromo-2-fluorophenyl)amino)-5,7-dimethyl-3,4-dihydro-2,7-naphthyridine-1,6(2H,7H)-dione;

8-((2-fluoro-4-iodophenyl)amino)-5,7-dimethyl-3,4-dihydro-2,7-naphthyridine-1,6(2H,7H)-dione;

8-((4-iodo-2-fluorophenyl)amino)-7-methyl-3,4-dihydro-2,7-naphthyridine-1,6(2H,7H)-dione;

8-((2-fluoro-4-(methylthio)phenyl)amino)-7-methyl-3,4-dihydro-2,7-naphthyridine-1,6(2H,7H)-dione;

8-((4-ethyl-2-fluorophenyl)amino)-7-methyl-3,4-dihydro-2,7-naphthyridine-1,6(2H,7H)-dione;

8-((4-cyclopropyl-2-fluorophenyl)amino)-7-methyl-3,4-dihydro-2,7-naphthyridine-1,6(2H,7H)-dione;

8-((4-(difluoromethoxy)-2-fluorophenyl)amino)-7-methyl-3,4-dihydro-2,7-naphthyridine-1,6(2H,7H)-dione;

8-((2-fluoro-4-propylphenyl)amino)-7-methyl-3,4-dihydro-2,7-naphthyridine-1,6(2H,7H)-dione;

8-((2-fluoro-4-(methylthio)phenyl)amino)-5,7-dimethyl-3,4-dihydro-2,7-naphthyridine-1,6(2H,7H)-dione;

8-((4-ethyl-2-fluorophenyl)amino)-5,7-dimethyl-3,4-dihydro-2,7-naphthyridine-1,6(2H,7H)-dione;

8-((4-cyclopropyl-2-fluorophenyl)amino)-5,7-dimethyl-3,4-dihydro-2,7-naphthyridine-1,6(2H,7H)-dione;

8-((4-(difluoromethoxy)-2-fluorophenyl)amino)-5,7-dimethyl-3,4-dihydro-2,7-naphthyridine-1,6(2H,7H)-dione;

8-((4-bromo-2-chlorophenyl)amino)-7-methyl-3,4-dihydro-2,7-naphthyridine-1,6(2H,7H)-dione;

8-((4-bromo-2-fluorophenyl)amino)-2-(2-hydroxyethyl)-7-methyl-3,4-dihydro-2,7-naphthyridine-1,6(2H,7H)-dione;

8-((2-fluoro-4-(methylthio)phenyl)amino)-2-(2-hydroxyethoxy)-5,7-dimethyl-3,4-dihydro-2,7-naphthyridine-1,6(2H,7H)-dione;

8-((4-(difluoromethoxy)-2-fluorophenyl)amino)-2-(2-hydroxyethoxy)-5,7-dimethyl-3,4-dihydro-2,7-naphthyridine-1,6(2H,7H)-dione;

2-(2,2-difluoroethoxy)-8-((2-fluoro-4-(methylthio)phenyl)amino)-7-methyl-3,4-dihydro-2,7-naphthyridine-1,6(2H,7H)-dione;

8-((4-bromo-2-fluorophenyl)amino)-7-methyl-4-phenyl-3,4-dihydro-2,7-naphthyridine-1,6(2H,7H)-dione;

8-((2-fluoro-4-(methylthio)phenyl)amino)-7-methyl-4-phenyl-3,4-dihydro-2,7-naphthyridine-1,6(2H,7H)-dione;

8-((4-bromo-2-fluorophenyl)amino)-4,7-dimethyl-3,4-dihydro-2,7-naphthyridine-1,6(2H,7H)-dione;

8-((2-fluoro-4-(methylthio)phenyl)amino)-4,7-dimethyl-3,4-dihydro-2,7-naphthyridine-1,6(2H,7H)-dione;

8-((4-bromo-2-fluorophenyl)amino)-2-(2-hydroxyethoxy)-4,7-dimethyl-3,4-dihydro-2,7-naphthyridine-1,6(2H,7H)-dione; and 8-((2-fluoro-4-(methylthio)phenyl)amino)-2-(2-hydroxyethoxy)-4,7-dimethyl-3,4-dihydro-2,7-naphthyridine-1,6(2H,7H)-dione;

or a pharmaceutically acceptable salt thereof.

16. A pharmaceutical composition, comprising a compound according to claim 1 or a pharmaceutically acceptable salt thereof, and at least one pharmaceutically acceptable excipient.

17. A pharmaceutical composition, comprising a compound according to claim 8 or a pharmaceutically acceptable salt thereof, and at least one pharmaceutically acceptable excipient.

18. A method of treating a MEK-associated tumor, comprising administering to a subject in need thereof a therapeutically effective amount of a compound of Formula I:

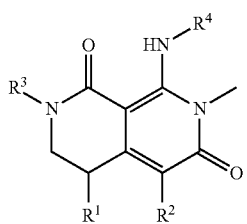

I or a pharmaceutically acceptable salt thereof, wherein:
$R^1$ is H, Br, C1-C6 alkyl or phenyl;
$R^2$ is H, halogen or $CH_3$—;
$R^3$ is H, hydroxyC1-C6 alkyl-, hydroxyC1-C6 alkoxy-, C1-C6 alkoxy, fluoroC1-C6 alkoxy, C3-C6 cycloalkyl, or (C3-C6 cycloalkyl)C1-C6 alkoxy-; and
$R^4$ is phenyl substituted with 1, 2 or 3 substituents independently selected from halogen, C1-C6 alkyl, C1-C6 alkylthio, fluoroC1-C6 alkylthio, fluoroC1-C6 alkyl, C1-C6 alkoxy, fluoroC1-C6 alkoxy, C3-C6 cycloalkyl, and C1-C6 alkyl-C(=O)—.

19. The method according to claim 18, wherein the tumor has a BRAF V600 mutation selected from V600E, V600K, V600D, V600R and V600S.

20. The method according to claim 19, wherein the tumor has a BRAF V600E mutation.

21. The method according to claim 19, wherein the tumor is a CNS tumor.

22. The method according to claim 21, wherein the CNS tumor is an intracranial tumor.

23. The method according to claim 22, wherein the intracranial tumor is a brain cancer.

24. The method according to claim 23, wherein the brain cancer is a metastatic brain cancer.

25. The method according to claim 24, wherein the metastatic brain cancer is selected from melanoma, colorectal cancer, non-small cell lung cancer, thyroid cancer, and ovarian cancer.

26. The method according to claim 18, wherein the compound is 8-((2-fluoro-4-(methylthio)phenyl)amino)-2-(2-hydroxyethoxy)-7-methyl-3,4-dihydro-2,7-naphthyridine-1,6(2H,7H)-dione having the structure:

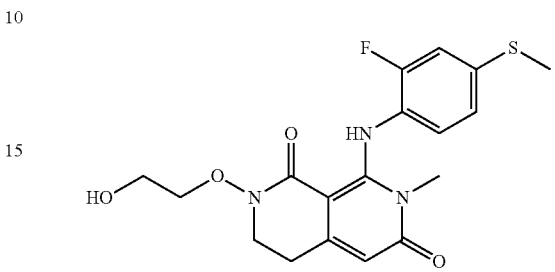

or a pharmaceutically acceptable salt thereof.

27. The method according to claim 21, wherein the compound is 8-((2-fluoro-4-(methylthio)phenyl)amino)-2-(2-hydroxyethoxy)-7-methyl-3,4-dihydro-2,7-naphthyridine-1,6(2H,7H)-dione having the structure:

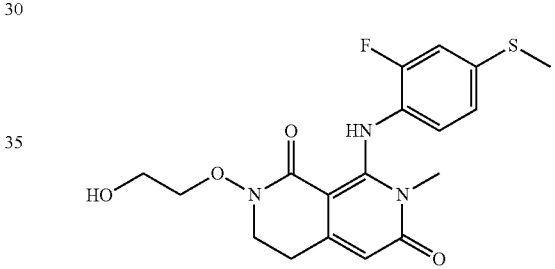

or a pharmaceutically acceptable salt thereof.

28. The method according to claim 24, wherein the compound is 8-((2-fluoro-4-(methylthio)phenyl)amino)-2-(2-hydroxyethoxy)-7-methyl-3,4-dihydro-2,7-naphthyridine-1,6(2H,7H)-dione having the structure:

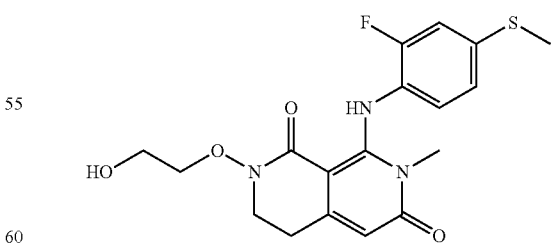

or a pharmaceutically acceptable salt thereof.

29. The method according to claim 25, wherein the compound is 8-((2-fluoro-4-(methylthio)phenyl)amino)-2-(2-hydroxyethoxy)-7-methyl-3,4-dihydro-2,7-naphthyridine-1,6(2H,7H)-dione having the structure:

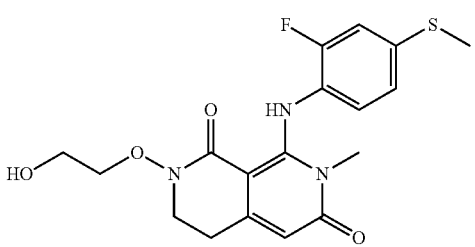 [SMILES: CSc1ccc(Nc2c3c(cc(=O)n2C)CCN(OCCO)C3=O)c(F)c1]

or a pharmaceutically acceptable salt thereof.

30. The method according to claim 21, wherein the CNS tumor is intracranial LMD or extracranial LMD.

31. The method according to claim 30, wherein the LMD is from melanoma metastases, colorectal cancer metastases, or non-small cell lung cancer metastases.

32. The method according to claim 30, wherein the compound is 8-((2-fluoro-4-(methylthio)phenyl)amino)-2-(2-hydroxyethoxy)-7-methyl-3,4-dihydro-2,7-naphthyridine-1,6(2H,7H)-dione having the structure:

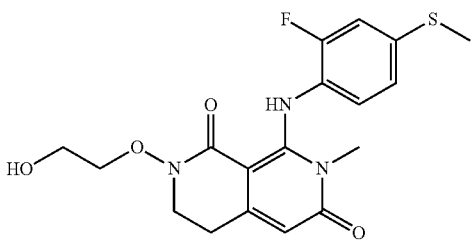 [SMILES: CSc1ccc(Nc2c3c(cc(=O)n2C)CCN(OCCO)C3=O)c(F)c1]

or a pharmaceutically acceptable salt thereof.

33. The method according to claim 22, wherein the intracranial tumor is a primary tumor.

34. The method according to claim 33, wherein the primary brain tumor is a malignant tumor.

35. The method according to claim 34, wherein the primary brain tumor is a Grade 2 glioma, a Grade 3 glioma or a Grade 4 glioma.

36. The method according to claim 33, wherein the compound is 8-((2-fluoro-4-(methylthio)phenyl)amino)-2-(2-hydroxyethoxy)-7-methyl-3,4-dihydro-2,7-naphthyridine-1,6(2H,7H)-dione having the structure:

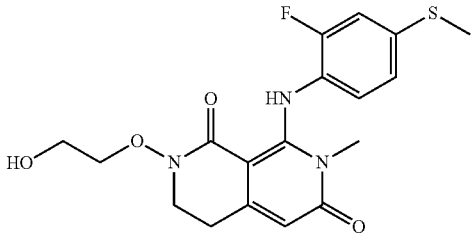 [SMILES: CSc1ccc(Nc2c3c(cc(=O)n2C)CCN(OCCO)C3=O)c(F)c1]

or a pharmaceutically acceptable salt thereof.

37. The method according to claim 33, wherein the primary brain tumor is a benign tumor.

38. The method according to claim 18, wherein the tumor has a BRAF fusion.

39. The method according to claim 38, wherein the tumor has a BRAF fusion selected from KIAA11549-BRAF, MKRN1-BRAF, TRIM24-BRAF, AGAP3-BRAF, ZC3HAV1-BRAF, AKAP9-BRAF, CCDC6-BRAF, AGK-BRAF, EPS15-BRAF, NUP214-BRAF, ARMC10-BRAF, BTF3L4-BRAF, GHR-BRAF, ZC3HAV1-BRAF, ZNF767-BRAF, CCDC91-BRAF, DYNC112-BRAF, ZKSCAN1-BRAF, GTF2I-BRAF, MZT1-BRAF, RAD18-BRAF, CUX1-BRAF, SLC12A7-BRAF, MYRIP-BRAF, SND1-BRAF, NUB1-BRAF, KLHL7-BRAF, TANK-BRAF, RBMS3-BRAF, STRN3-BRAF, STK35-BRAF, ETFA-BRAF, SVOPL-BRAF, and JHDM1D-BRAF.

40. The method according to claim 39, wherein the tumor is breast carcinoma, colorectal carcinoma, esophageal carcinoma, glioma, head and neck carcinoma, lung carcinoma, melanoma, pancreatic carcinoma, prostatic carcinoma, sarcoma, thyroid carcinoma, unknown primary carcinoma, pleura mesothelioma, rectum adenocarcinoma, uterus endometrial carcinoma, or ovary serous carcinoma.

41. The method according to claim 39, wherein the compound is 8-((2-fluoro-4-(methylthio)phenyl)amino)-2-(2-hydroxyethoxy)-7-methyl-3,4-dihydro-2,7-naphthyridine-1,6(2H,7H)-dione having the structure:

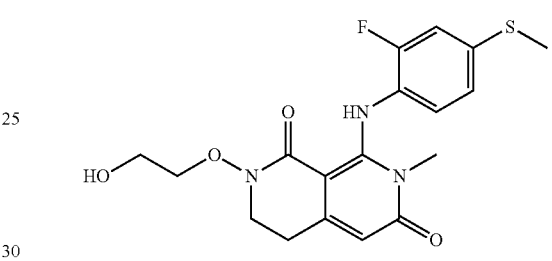

or a pharmaceutically acceptable salt thereof.

42. The method according to claim 18, wherein the tumor is a BRAF wild-type tumor.

43. The method according to claim 26, wherein the method further comprises administering one or more additional anticancer therapies.

44. The method according to claim 43, wherein the additional anticancer therapy is selected from one or more anticancer agents.

45. The method according to claim 44, where in the anticancer agent is a BRAF inhibitor.

46. The method according to claim 45, wherein the BRAF inhibitor is encorafenib or a pharmaceutically acceptable salt thereof.

47. The method according to claim 45, wherein the BRAF inhibitor is selected from:
  N-(3-((3,5-dimethyl-4-oxo-3,4-dihydroquinazolin-6-yl)amino)-2,4-difluorophenyl)propane-1-sulfonamide;
  N-(2-chloro-3-((3,5-dimethyl-4-oxo-3,4-dihydroquinazolin-6-yl)amino)phenyl)-3-fluoropropane-1-sulfonamide;
  N-(2-chloro-3-((3,5-dimethyl-4-oxo-3,4-dihydroquinazolin-6-yl)amino)-4,5-difluorophenyl)propane-1-sulfonamide;
  N-(2-chloro-3-((3,5-dimethyl-4-oxo-3,4-dihydroquinazolin-6-yl)amino)-4-fluorophenyl)propane-1-sulfonamide;
  N-(2-chloro-3-((3,5-dimethyl-4-oxo-3,4-dihydroquinazolin-6-yl)amino)-4-fluorophenyl)-3-fluoropropane-1-sulfonamide;
  N-(2-chloro-4-fluoro-3-((5-methyl-3-(methyl-d3)-4-oxo-3,4-dihydroquinazolin-6-yl)amino)-phenyl)-3-fluoropropane-1-sulfonamide;
  N-{2-chloro-3-[(3,5-dimethyl-4-oxo-3,4-dihydroquinazolin-6-yl)oxy]-4-fluorophenyl}propane-1-sulfonamide;

N-(3-chloro-4-((3,5-dimethyl-4-oxo-3,4-dihydroquinazolin-6-yl)oxy)-5-fluoropyridin-2-yl)propane-1-sulfonamide; and N-{2-chloro-3-[(3,5-dimethyl-4-oxo-3,4-dihydroquinazolin-6-yl)oxy]-4-fluorophenyl}-3-fluoropropane-1-sulfonamide;

or a pharmaceutically acceptable salt thereof.

48. The method according to claim 47, wherein the BRAF inhibitor is N-(2-chloro-3-((3,5-dimethyl-4-oxo-3,4-dihydroquinazolin-6-yl)amino)-4-fluorophenyl)-3-fluoropropane-1-sulfonamide or a pharmaceutically acceptable salt thereof.

49. The method according to claim 45, wherein the BRAF inhibitor is selected from:

N-(2-chloro-4-fluoro-3-((5-fluoro-3-methyl-4-oxo-3,4-dihydroquinazolin-6-yl)amino)phenyl)-2-azabicyclo[2.1.1]hexane-2-sulfonamide, (R)—N-(2-chloro-4-fluoro-3-((5-fluoro-3-methyl-4-oxo-3,4-dihydroquinazolin-6-yl)amino)phenyl)-3-fluoropyrrolidine-1-sulfonamide, and N-(2-chloro-3-((5-chloro-3-methyl-4-oxo-3,4-dihydroquinazolin-6-yl)amino)-4-fluorophenyl)-3-fluoroazetidine-1-sulfonamide, or a pharmaceutically acceptable salt thereof.

50. The method according to claim 49, wherein the BRAF inhibitor is N-(2-chloro-3-((5-chloro-3-methyl-4-oxo-3,4-dihydroquinazolin-6-yl)amino)-4-fluorophenyl)-3-fluoroazetidine-1-sulfonamide, or a pharmaceutically acceptable salt thereof.

51. The method according to claim 44, wherein the anticancer agent is a SHP2 inhibitor.

52. The method according to claim 51, wherein the SHP2 inhibitor is (S)-1'-(6-((2-amino-3-chloropyridin-4-yl)thio)-1,2,4-triazin-3-yl)-1,3-dihydrospiro[indene-2,4'-piperidin]-1-amine or a pharmaceutically acceptable salt thereof.

53. The method according to claim 18, wherein the subject is a human.

* * * * *